(12) United States Patent
Mandell et al.

(10) Patent No.: US 12,365,939 B2
(45) Date of Patent: Jul. 22, 2025

(54) COMPOSITIONS, SYSTEMS, AND METHODS FOR DETECTING EVENTS USING TETHERS ANCHORED TO OR ADJACENT TO NANOPORES

(71) Applicant: Illumina, Inc., San Diego, CA (US)

(72) Inventors: Jeffrey G. Mandell, La Jolla, CA (US); Kevin L. Gunderson, Encinitas, CA (US); Jens H. Gundlach, Seattle, WA (US)

(73) Assignee: Illumina, Inc., San Diego, CA (US)

( * ) Notice: Subject to any disclaimer, the term of this patent is extended or adjusted under 35 U.S.C. 154(b) by 827 days.

(21) Appl. No.: 17/675,264

(22) Filed: Feb. 18, 2022

(65) Prior Publication Data

US 2022/0251641 A1 Aug. 11, 2022

Related U.S. Application Data

(62) Division of application No. 16/520,083, filed on Jul. 23, 2019, now Pat. No. 11,254,981, which is a
(Continued)

(51) Int. Cl.
*C12Q 1/6869* (2018.01)
*G01N 27/447* (2006.01)

(52) U.S. Cl.
CPC ..... *C12Q 1/6869* (2013.01); *G01N 27/44743* (2013.01); *G01N 27/44791* (2013.01)

(58) Field of Classification Search
CPC ............ C12Q 1/6869; C12Q 1/6883; C12Q 2525/197; C12Q 2565/607;
(Continued)

(56) References Cited

U.S. PATENT DOCUMENTS 6,015,714 A 1/2000 Baldarelli et al.
7,057,026 B2 6/2006 Barnes et al.
(Continued)

FOREIGN PATENT DOCUMENTS

WO 91/06678 5/1991
WO 04/018497 3/2004
(Continued)

OTHER PUBLICATIONS

Wilson ("Electronic Control of DNA Polymerase Binding and Unbinding to Single DNA Molecules") ACS Nano 2009, 3, 4, 995-1003 (Year: 2009).*
(Continued)

*Primary Examiner* — Jennifer Wecker
*Assistant Examiner* — Jonathan Bortoli
(74) *Attorney, Agent, or Firm* — Gavrilovich, Dodd & Lindsey LLP

(57) ABSTRACT

Compositions, systems, and methods for detecting events are provided. A composition can include a nanopore including a first side, a second side, and an aperture extending through the first and second sides; and a permanent tether including head and tail regions and an elongated body disposed there between. The head region can be anchored to or adjacent to the first or second side of the nanopore. The elongated body including a reporter region can be movable within the aperture responsive to a first event occurring adjacent to the first side of the nanopore. For example, the reporter region is translationally movable toward the first side responsive to the first event, then toward the second side, then toward the first side responsive to a second event. The first event can include adding a first nucleotide to a polynucleotide. The second event can include adding a second nucleotide to the polynucleotide.

15 Claims, 37 Drawing Sheets

Specification includes a Sequence Listing.

Related U.S. Application Data division of application No. 15/625,100, filed on Jun. 16, 2017, now Pat. No. 10,364,463, which is a division of application No. 14/728,721, filed on Jun. 2, 2015, now Pat. No. 9,708,655.

(60) Provisional application No. 62/157,371, filed on May 5, 2015, provisional application No. 62/007,248, filed on Jun. 3, 2014.

(58) Field of Classification Search
CPC ........ C12Q 2565/631; C12Q 2600/158; C12Q 2600/178; G01N 27/44743; G01N 27/44791
See application file for complete search history.

(56) References Cited

U.S. PATENT DOCUMENTS

| | | | |
|---|---|---|---|
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,771,903 | B2 | 8/2010 | Zhang et al. |
| 7,816,503 | B2 | 10/2010 | Milton et al. |
| 8,133,672 | B2 | 3/2012 | Bjornson et al. |
| 8,652,779 | B2 | 2/2014 | Turner et al. |
| 8,673,550 | B2 | 3/2014 | Gundlach et al. |
| 8,999,716 | B2 | 4/2015 | Gundlach et al. |
| 9,017,937 | B1 | 4/2015 | Turner et al. |
| 9,027,947 | B2 | 4/2015 | Turner et al. |
| 2008/0108082 | A1 | 5/2008 | Rank et al. |
| 2009/0298072 | A1 | 12/2009 | Ju et al. |
| 2011/0174625 | A1 | 7/2011 | Akeson et al. |
| 2011/0312529 | A1 | 12/2011 | He et al. |
| 2012/0142016 | A1* | 6/2012 | Ronaghi ................ B82Y 15/00 435/7.1 |
| 2013/0146457 | A1 | 6/2013 | Gundlach et al. |
| 2013/0240359 | A1 | 9/2013 | Turner et al. |
| 2014/0051069 | A1 | 2/2014 | Jayasinghe et al. |
| 2014/0087474 | A1 | 3/2014 | Huber et al. |
| 2014/0134616 | A1 | 5/2014 | Davis et al. |
| 2015/0031024 | A1* | 1/2015 | Olsen .................. C12Q 1/6869 435/287.2 |
| 2015/0068904 | A1* | 3/2015 | Bruce .................. G01N 27/447 530/358 |
| 2015/0119259 | A1* | 4/2015 | Ju ........................ C12Q 1/6869 435/6.1 |
| 2015/0337366 | A1* | 11/2015 | Davis ............... G01N 33/48721 435/6.19 |

FOREIGN PATENT DOCUMENTS

| | | |
|---|---|---|
| WO | 07/123744 | 11/2007 |
| WO | 12/142174 | 10/2012 |
| WO | 12/164270 | 12/2012 |
| WO | 13/057495 | 4/2013 |
| WO | 13/153359 | 10/2013 |
| WO | 14/066902 | 5/2014 |
| WO | 15/126494 | 8/2015 |

OTHER PUBLICATIONS

Bentley et al., "Accurate whole human genome sequencing using reversible terminator chemistry", Nature, 456:53-59 (2008).
Bonnac et al., "Synthesis and 0-phosphorylation of 3,3,4,4-tetrafluoroaryl-C-nucleoside analogues," Org Biomol Chem 8(6): 1445-1454 (2010).
Butler et al., "Single-molecule DNA detection with an engineered MspA protein nanopore," Proc. Natl. Acad. Sci. 105: 20647-20652 (2008).
Cabello-Aguilar et al., "Slow translocation of polynucleotides and their discrimination by a-hemolysin inside a single track-etched nanopore designed by atomic layer deposition.," Nanoscale 5: 9582-9586 (2013).
Chavanne, Franz, International Search Report for PCT/US2015/033749 dated Jan. 29, 2016 (9 pages).
Chavanne, Franz, Written Opinion of the International Searching Authority for PCT/US2015/033749 dated Jan. 29, 2016 (11 pages).
Clarke et al., "Continuous base identification for single-molecule nanopore DNA sequencing," Nature Nanotechnology 4: 265-270 (2009).
Dahl et al., "Dynamics oftranslocation and substrate binding in individual complexes formed with active site mutants of {phi}29 DNA polymerase," J Biol Chem 289(10): 6350-6361 (2014).
Dekker, "Solid-state nanopores," Nature Nanotechnology 2: 209-215 (2007).
Derrington et al., "Nanopore DNA sequencing with MspA," PNAS 107:16060-16065 (2010).
Du, Ning, Intellectual Property Office of Singapore, Office Action, 11201609692S, dated Jan. 4, 2018.
Franceschini, L. et al., "A nanopore machine promotes the vectorial transport of DNA across membranes," Nature Communications, vol. 4, p. 2415, Sep. 12, 2013.
Garaj et al., "Graphene as a subnanometre trans-electrode membrane," Nature 467: 190-193 (2010).
Garalde et al., "Distinct complexes of DNA polymerase I (Klenow fragment) for base and sugar discrimination during nucleotide substrate selection," J. Biol. Chem. 286: 14480-14492 (2011).
Gill et al., "DNA polymerase activity at the single-molecule level," Biochem. Soc. Trans. 39: 595-599 (2011).
Hall et al., "Hybrid pore formation by directed insertion of a-haemolysin into solid-state nanopores," Nature Nanotechnology 5: 874-877 (2010).
Howorka et al., "Kinetics of duplex formation for individual DNA strands within a single protein nanopore," PNAS 98: 12996-13301 (2001).
Howorka et al., "Probing distance and electrical potential within a protein pore with tethered DNA," Biophysical Journal 83: 3202-3210 (2002).
Howorka et al., "Sequence-specific detection of individual DNA strands using engineered nanopores," Nature Biotechnology 19: 636-639 (2001).
Hurt et al., "Specific nucleotide binding and rebinding to individual DNA polymerase complexes captured on a nanopore," JACS 131: 3772-3778 (2009).
Invitation to Pay Additional Fees in PCT/US2015/033749, dated Oct. 29, 2015 (8 pages).
Ivankin et al., "Label-free optical detection of biomolecular translocation through nanopore arrays," ACSNano 8 (10): 10774-10781 (2014).
Johnson et al., "Processive DNA synthesis observed in a polymerase crystal suggests a mechanism for the prevention offrameshift mutations," Proc. Natl. Acad. Sci. USA 100: 3895-3900 (2003).
Johnson, "The kinetic and chemical mechanism of high-fidelity DNA polymerases," Biochim Biophys Acta 1804(5): 1041-1048 (2010).
Kim et al., "Detecting single-abasic residues within a DNA strand immobilized in a biological nanopore using an integrated CMOS sensor," Sens. Actuators B Chem. 177: 1075-1082 (2012).
Kowalczyk et al., "Single-molecule transport across an individual biomimetic nuclear pore complex", Nature Nanotechnology, 6(7): 433-438 (2011).
Kulkarni, G. S. and Z. Zhong, "Detection beyond the Debye screening length in a high-frequency nanoelectronic biosensor," Nano Lett 12(2): 719-723 (2012).
Kulkarni, G. S. and Z. Zhong, "Fabrication of carbon nanotube high-frequency nanoelectronic biosensor for sensing in high ionic strength solutions," J Vis Exp(77) (2013).
Kumar et al., "PEG-labeled nucleotides and nanopore detection for single molecule DNA sequencing by synthesis," Scientific Reports 2: 684 (2012).
Kumar et al., "Terminal phosphate labeled nucleotides: synthesis, applications, and linker effect on incorporation by DNA polymerases," Nucleosides, Nucleotides, and Nucleic Acids 24: 401-408 (2005).

(56) References Cited

OTHER PUBLICATIONS

Lee et al., "Synthesis and reactivity of novel gamma-phosphate modified ATP analogues," Bioorganic & Medicinal Chemistry Letters 19: 3804-3807 (2009).

Lieberman et al., "Kinetic mechanism of translocation and dNTP binding in individual DNA polymerase complexes," J Am Chem Soc 135(24): 9149-9155 (2013).

Manrao et al., "Nucleotide discrimination with DNA immobilized in the MspA nanopore," PLos ONE 6: e25723, 7 pages, (2011).

Markiewicz et al., "Single-molecule microscopy reveals new insights into nucleotide selection by DNA polymerase I," Nucleic Acids Res. 40: 7975-7984 (2012).

Merchant et al., "DNA translocation through graphene nanopores," Nano Letters 10:2915-2921 (2010).

Mulder et al., "Nucleotide modification at the gamma-phosphate leads to the improved fidelity of HIV-1 reverse transcriptase," Nucleic Acids Research 33: 4865-4873 (2005).

Olsen et al., "Electronic measurements of single-molecule processing by DNA polymerase I (Kienow fragment).," J Am Chem Soc 135(21): 7855-7860 (2013).

Osmanovic et al., "Bistable collective behavior of polymers tethered in a nanopore", arxiv.org, Cornell University Library, 201 Olin Library Cornell University Ithaca, NY 14853, XP080525258 (Jul. 17, 2012).

Patel et al., "Getting a grip on how DNA polymerases function," Nature Structural Biology 8: 656-659 (2001).

Santoso Yet al., "Conformational transitions in DNA polymerase I revealed by single-molecule FRET," Proc Natl Acad Sci US A. Jan. 12, 2010;107(2):715-20.

Schneider et al., "DNA translocation through graphene nanopores," Nano Letters 10: 3163-3167 (2010).

Sood et al., "Terminal phosphate-labeled nucleotides with improved substrate properties for homogeneous nucleic acid assays," J Am Chem Soc 127(8): 2394-2395 (2005).

Torella et al., "Identifying molecular dynamics in single-molecule FRET experiments with burst variance analysis," Biophysics J. 100: 1568-1577 (2011).

Wang et al., -Single-molecule DNA detection using a novel SPI protein nanopore, Chem. Commun., 19:1741-1743, 2013.

Wilson et al., "Electronic Control of DNA Polymerase Binding and Unbinding to Single DNA Molecules," ACS Nano, 3(4): 995-1003, Apr. 1, 2009.

Xia et al., "Alteration in the cavity size adjacent to the active site of RB69 DNA polymerase changes its conformational dynamics," Nucl. Acids Res., 41(19):9077-9089 (2013).

\* cited by examiner

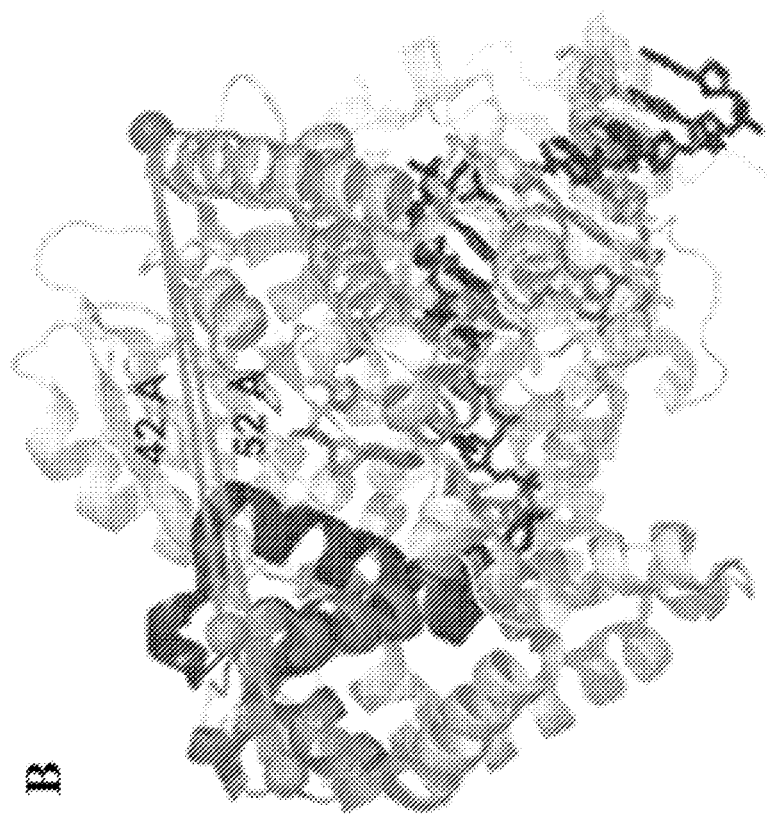
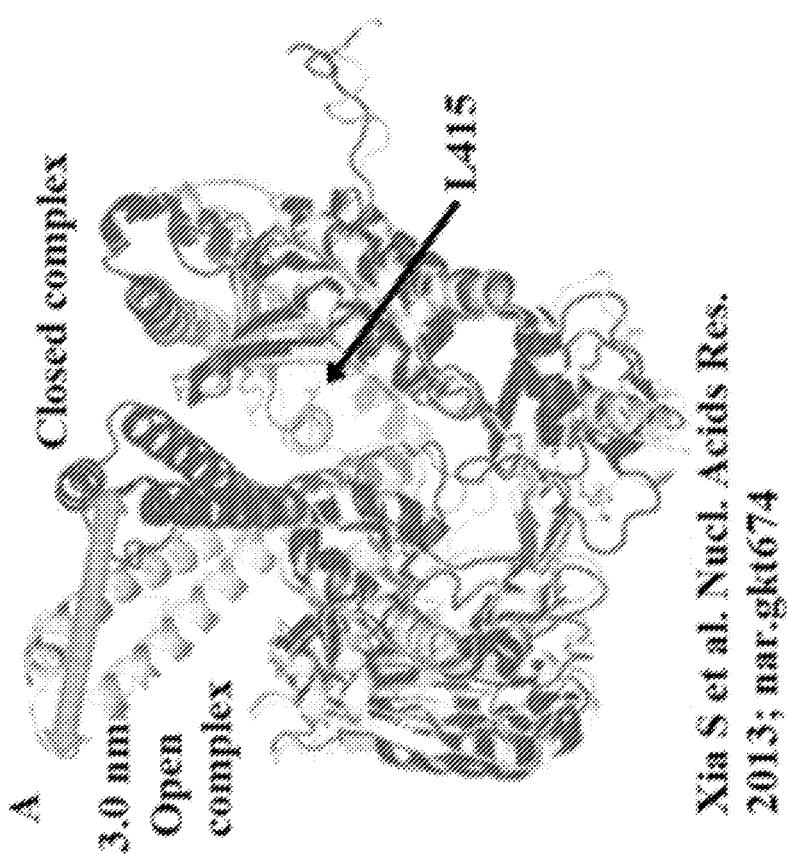
FIG. 6A
FIG. 6B

△ = 5'-CCCAT-3'      (A)
◇ = 5'-CCCATA-3'     (T)
□ = 5'-CCCATAT-3'    (C)
○ = 5'-CCCATATA-3'   (G)

```
            1011        1015        1014        1013   1012
Mal-3'-GGGTATATTTTTTXTTTTTTTTTT-5' Phos
    5'-CCCAT-3'      (A)  Tm < 10 °C
    5'-CCCATA-3'     (T)  Tm < 10 °C
    5'-CCCATAT-3'    (C)  Tm < 10 °C
    5'-CCCATATA-3'   (G)  Tm ~ 12 °C
```

Tether sequence: 5' Phos-TTTTTTTTTTNTTTTTTTATATGGG-3' (maleimide)

Panel A

| Tag Sequence: | 5'-CCCAT-3' |
|---|---|
| Best match # base pairs: | 5 |
| Best delta G (kcal/mole): | -9.57 |
| Hyb: | 5'-TTTTTTTTTTNTTTTTTTATATGGG<br>                                  \|\|\|\|\|<br>3'-                                    TACCC<br>(1A) |

| Tag Sequence: | 5'-CCCAT-3' |
|---|---|
| Second-best match # base pairs: | 2 |
| Best delta G (kcal/mole): | -3.07 |
| Hyb: | 5'-TTTTTTTTTTNTTTTTTTATATGGG<br>                                  \|\|<br>3'-                                    TACCC<br>(1B) |

FIG. 11A

Panel B

| Tag Sequence: | 5'-CCCATA-3' |
|---|---|
| Best match # base pairs: | 6 |
| Best delta G (kcal/mole): | -10.53 |
| Hyb: | 5'-TTTTTTTTTTNTTTTTTTATATGGG<br>                                 \|\|\|\|\|\|<br>3'-                                   ATACCC<br>(2A) |

| Tag Sequence: | 5'-CCCATA-3' |
|---|---|
| Best match # base pairs: | 3 |
| Best delta G (kcal/mole): | >-3.20 |
| Hyb: | 5'-TTTTTTTTTTNTTTTTTTATATGGG<br>                                \|\|\|<br>3'-                                    ATACCC<br>(2B) |

FIG. 11B

Stem-1: 5'-CCCAT-3'
Stem-2: 5'-ATGGG-3'
Loop: $T_{10}$
Full sequence: 5'-CCC ATT TTT TTT TTT ATG GG-3'

Mfold (from IDT DNA) used to predict stem melting temperature with the following parameters:
- Temp: 25°C
- $Na^+$ concentration: 50 mM
- $Mg^{2+}$ concentration: 2 mM
- Suboptimality: 50%

The most stable predicted structure is shown in (C)
- Delta G (kcal/mole): -2.54
- Delta H (kcal/mole): -34
- Delta S (cal/$K^{-1}$$mole^{-1}$): -105.53
- Tm: 49°C

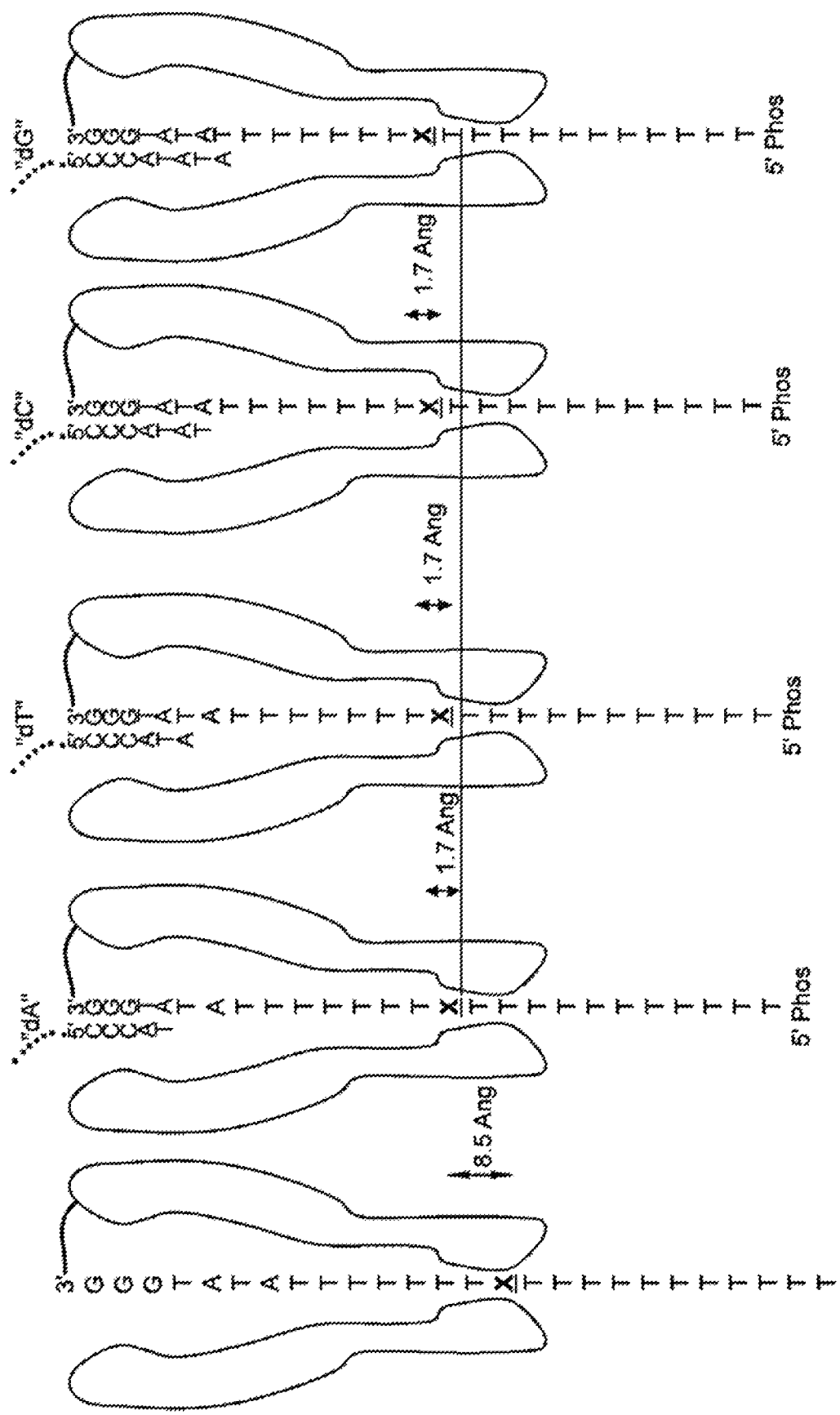

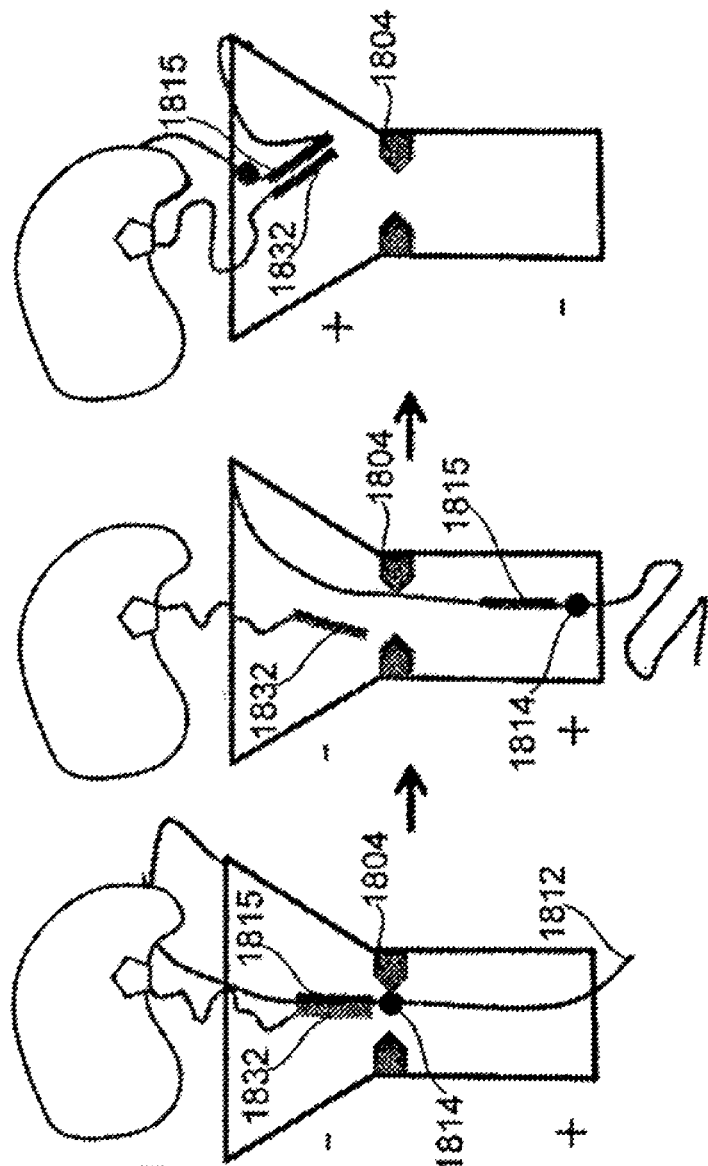

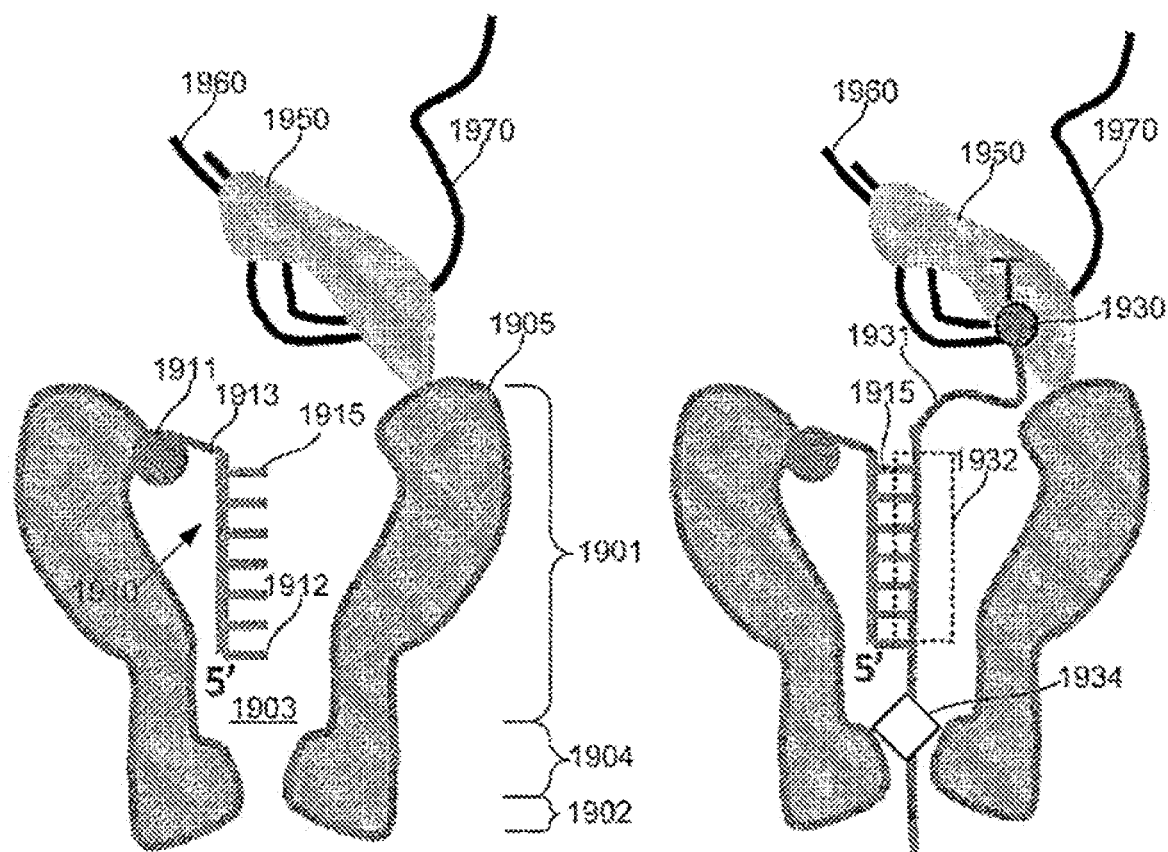
FIG. 19A
FIG. 19B
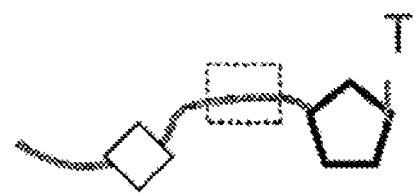
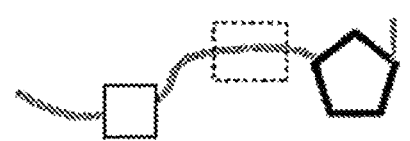
FIG. 19C

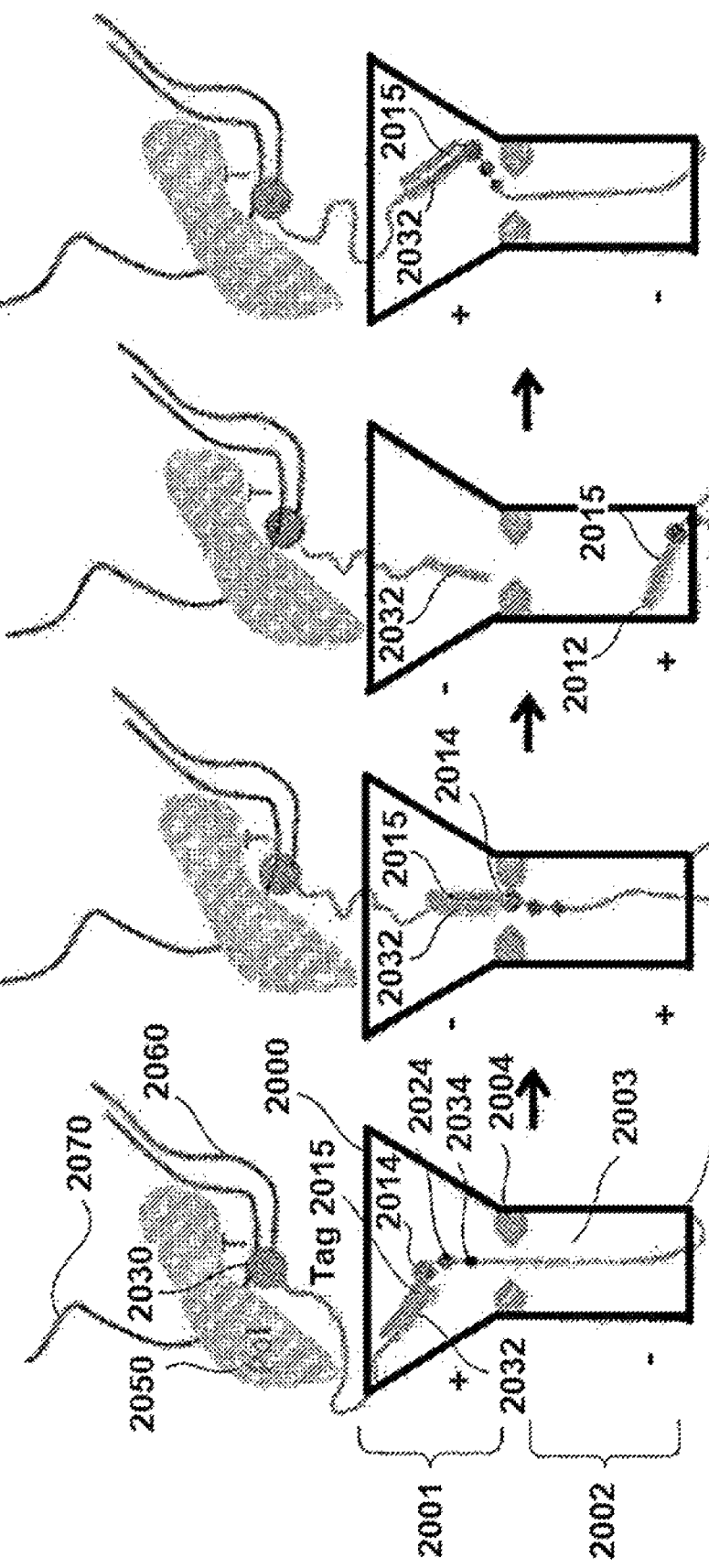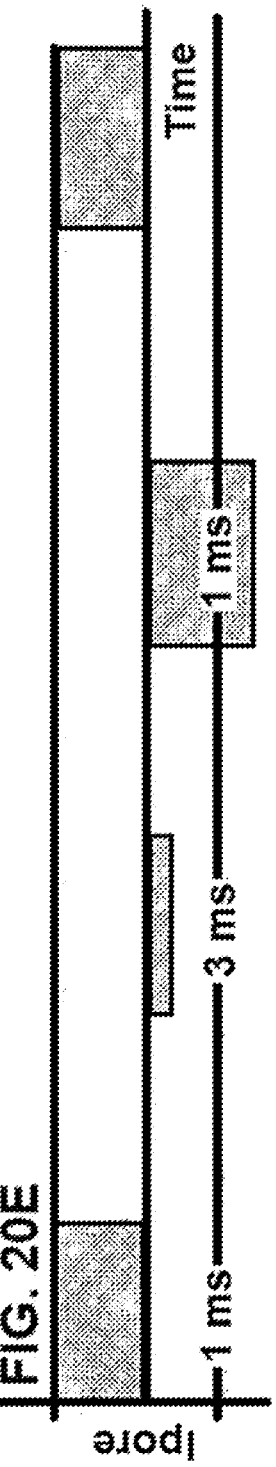

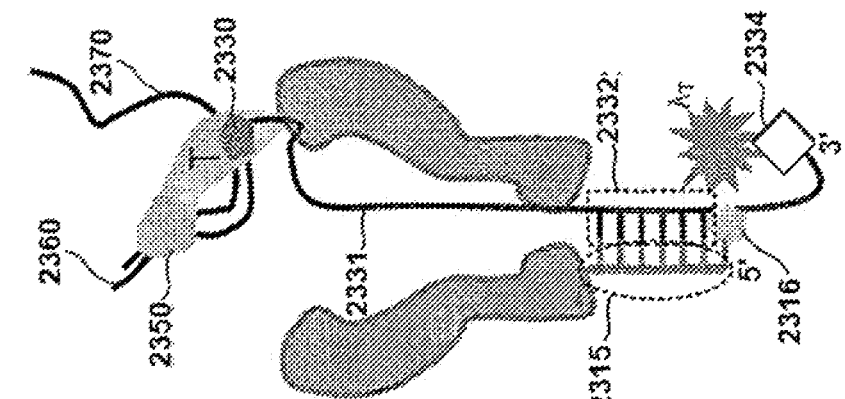
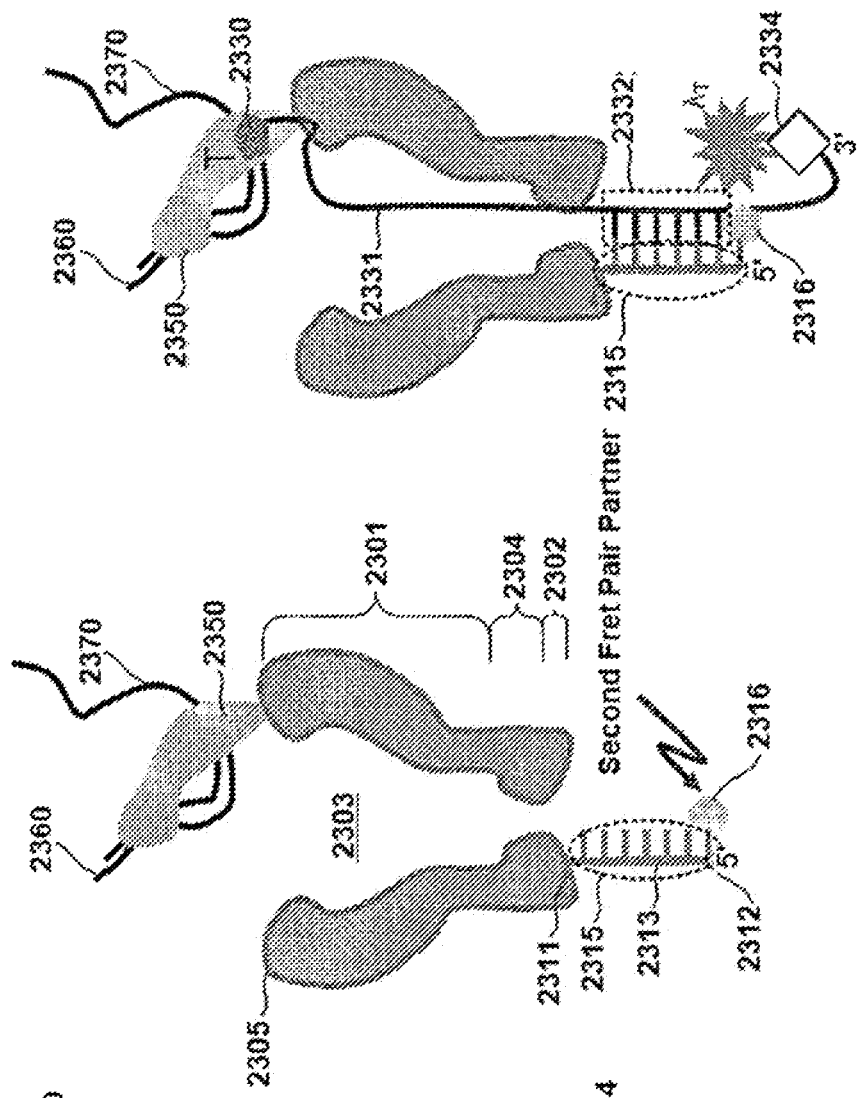
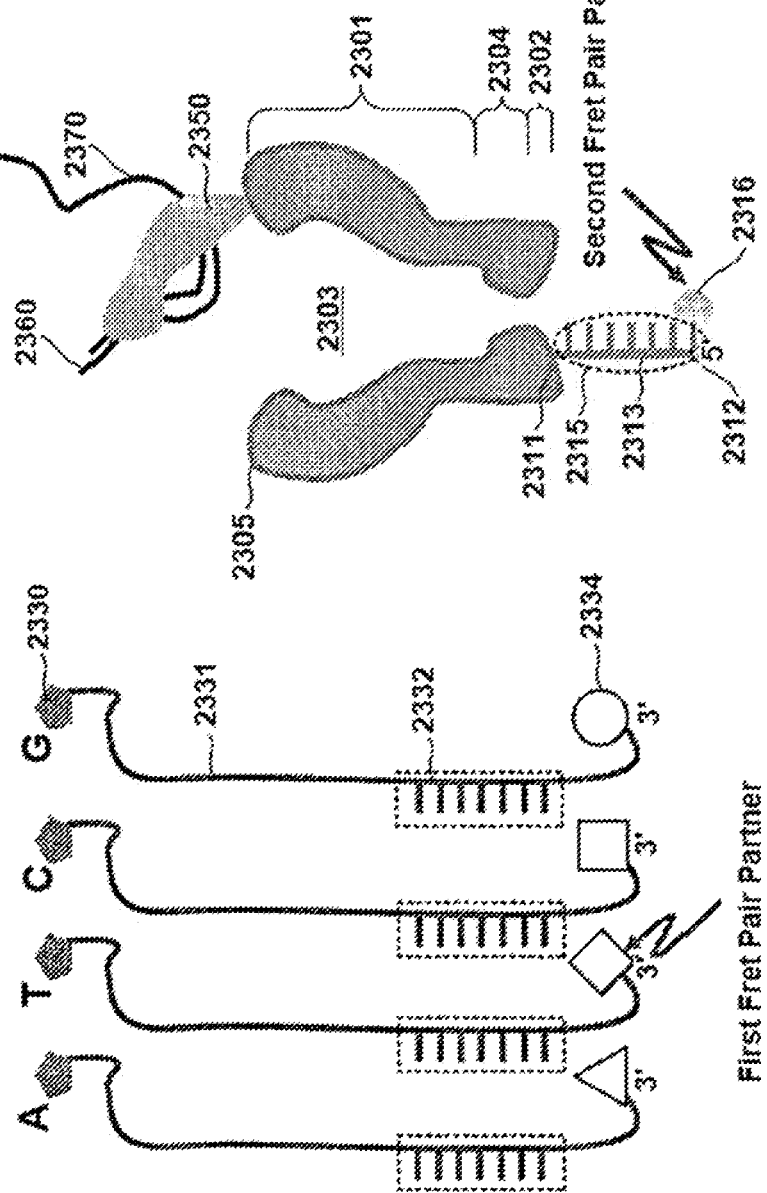
FIG. 23A
FIG. 23B
FIG. 23C

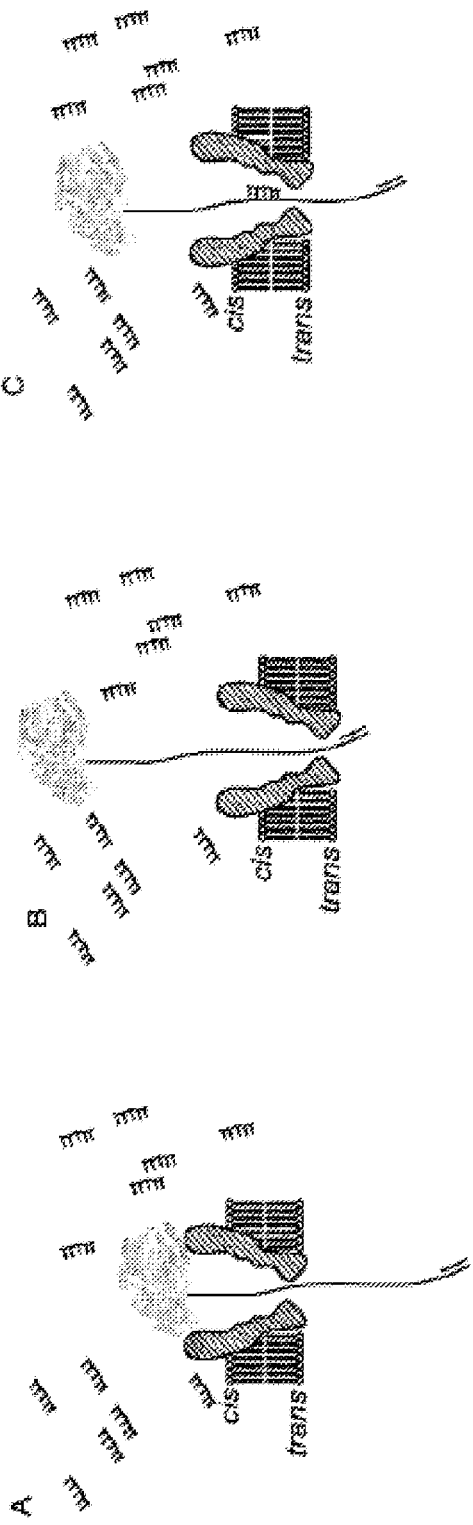

| | Reaction Parameters | | | Tag Dwell Time (usec) |
|---|---|---|---|---|
| Reaction Scheme | $ED_n+dNTP \underset{K_1}{\rightleftharpoons} ED_ndNTP$ open | $ED_ndNTP \underset{k_{-2}}{\overset{k_2}{\rightleftharpoons}} FD_ndNTP$ closed | $FD_ndNTP \underset{k_{-3}}{\overset{k_3}{\rightleftharpoons}} FD_{n+1}PP_i$ closed $\overset{fast}{\longrightarrow} ED_{n+1}+PP_i$ open | $1/(k_2+k_3)$ |
| Perfect Match Nucleotide | $ED_n+dNTP \underset{28\ \mu M}{\rightleftharpoons} ED_ndNTP$ open | $ED_ndNTP \underset{1.6\ s^{-1}}{\overset{660\ s^{-1}}{\rightleftharpoons}} FD_ndNTP$ closed | $FD_ndNTP \overset{360\ s^{-1}}{\rightleftharpoons} FD_{n+1}PP_i$ closed $\overset{fast}{\longrightarrow} ED_{n+1}+PP_i$ open | 2760 |
| Mismatch Nucleotide | $ED_n+dNTP \underset{200\ \mu M}{\rightleftharpoons} ED_ndNTP$ open | $ED_ndNTP \underset{420\ s^{-1}}{\overset{220\ s^{-1}}{\rightleftharpoons}} GD_ndNTP$ mismatch | $GD_ndNTP \overset{0.3\ s^{-1}}{\rightleftharpoons} GD_{n+1}PP_i$ mismatch $\overset{fast}{\longrightarrow} ED_{n+1}+PP_i$ open | 2380 |

FIG. 25

COMPOSITIONS, SYSTEMS, AND METHODS FOR DETECTING EVENTS USING TETHERS ANCHORED TO OR ADJACENT TO NANOPORES

CROSS-REFERENCE TO RELATED APPLICATIONS

This application is a continuation of U.S. application Ser. No. 16/520,083, filed Jul. 23, 2019, which is a divisional of and claims the benefit of U.S. application Ser. No. 15/625,100, filed Jun. 16, 2017, which is a divisional and claims the benefit of U.S. application Ser. No. 14/728,721, filed Jun. 2, 2015, which claims the benefit of U.S. Prov. Appl. No. 62/157,371, filed May 5, 2015 and U.S. Prov. Appl. No. 62/007,248, filed Jun. 3, 2014, the entire contents of each of which are incorporated by reference herein.

SEQUENCE LISTING

The instant application contains a Sequence Listing which has been submitted electronically in ASCII format and is hereby incorporated by reference in its entirety. Said ASCII copy, created on Feb. 18, 2022, is named Sequence-Listing.txt and is 1,972 bytes in size.

FIELD

This application generally relates to detecting molecular events, such as the motion of a molecule or a portion of that molecule.

BACKGROUND

A significant amount of academic and corporate time and energy has been invested into detecting events, such as the motion of a molecule or a portion of that molecule, particularly where the molecule is DNA or an enzyme that binds DNA, such as a polymerase. For example, Olsen et al., "Electronic Measurements of Single-Molecule Processing by DNA Polymerase I (Klenow Fragment)," JACS 135: 7855-7860 (2013), the entire contents of which are incorporated by reference herein, discloses bioconjugating single molecules of the Klenow fragment (KF) of DNA polymerase I into electronic nanocircuits so as to allow electrical recordings of enzymatic function and dynamic variability with the resolution of individual nucleotide incorporation events. Or, for example, Hurt et al., "Specific Nucleotide Binding and Rebinding to Individual DNA Polymerase Complexes Captured on a Nanopore," JACS 131: 3772-3778 (2009), the entire contents of which are incorporated by reference herein, discloses measuring the dwell time for complexes of DNA with the KF atop a nanopore in an applied electric field. Or, for example, Kim et al., "Detecting single-abasic residues within a DNA strand immobilized in a biological nanopore using an integrated CMOS sensor," Sens. Actuators B Chem. 177: 1075-1082 (2012), the entire contents of which are incorporated by reference herein, discloses using a current or flux-measuring sensor in experiments involving DNA captured in a α-hemolysin nanopore. Or, for example, Garalde et al., "Distinct Complexes of DNA Polymerase I (Klenow Fragment) for Based and Sugar Discrimination during Nucleotide Substrate Selection," J. Biol. Chem. 286: 14480-14492 (2011), the entire contents of which are incorporated by reference herein, discloses distinguishing KF-DNA complexes on the basis of their properties when captured in an electric field atop an α-hemolysin pore. Other references that disclose measurements involving α-hemolysin include the following, all to Howorka et al., the entire contents of which are incorporated by reference herein: "Kinetics of duplex formation for individual DNA strands within a single protein nanopore," PNAS 98: 12996-13301 (2001); "Probing Distance and Electrical Potential within a Protein Pore with Tethered DNA," Biophysical Journal 83: 3202-3210 (2002); and "Sequence-specific detection of individual DNA strands using engineered nanopores," Nature Biotechnology 19: 636-639 (2001).

U.S. Pat. No. 8,652,779 to Turner et al., the entire contents of which are incorporated by reference herein, discloses compositions and methods of nucleic acid sequencing using a single polymerase enzyme complex including a polymerase enzyme and a template nucleic acid attached proximal to a nanopore, and nucleotide analogs in solution. The nucleotide analogs include charge blockade labels that are attached to the polyphosphate portion of the nucleotide analog such that the charge blockade labels are cleaved when the nucleotide analog is incorporated into a growing nucleic acid. According to Turner, the charge blockade label is detected by the nanopore to determine the presence and identity of the incorporated nucleotide and thereby determine the sequence of a template nucleic acid. U.S. Patent Publication No. 2014/0051069 to Jayasinghe et al., the entire contents of which are incorporated by reference herein, is directed to constructs that include a transmembrane protein pore subunit and a nucleic acid handling enzyme.

However, previously known compositions, systems, and methods such as described by Olsen, Hurt, Kim, Garalde, Howorka, Turner, and Jayasinghe may not necessarily be sufficiently robust, reproducible, or sensitive and may not have sufficiently high throughput for practical implementation, e.g., demanding commercial applications such as genome sequencing in clinical and other settings that demand cost effective and highly accurate operation. Accordingly, what is needed are improved compositions, systems, and methods for detecting events.

SUMMARY

Embodiments of the present invention provide compositions, systems, and methods for detecting events using tethers anchored to or adjacent to nanopores.

Under one aspect, a composition includes a nanopore including a first side, a second side, and an aperture extending through the first and second sides; and a permanent tether including a head region, a tail region, and an elongated body disposed therebetween. The head region can be anchored to or adjacent to the first side or second side of the nanopore. The elongated body including a reporter region can be movable within the aperture responsive to a first event occurring adjacent to the first side of the nanopore. In one non-limiting example, the head region can be anchored to a molecule, such as a protein, disposed on the first side or second side of the nanopore.

In some embodiments, the reporter region is translationally movable within the aperture responsive to the first event. Additionally, or alternatively, the reporter region can be rotationally movable within the aperture responsive to the first event. Additionally, or alternatively, the reporter region can be conformationally movable within the aperture responsive to the first event.

In some embodiments, the head region is anchored to or adjacent to the first side or second side of the nanopore via a covalent bond. The head region can be anchored to the first side of the nanopore. The tail region can extend freely toward the second side of the nanopore.

In some embodiments, the reporter region is translationally movable toward the first side of the nanopore responsive to the first event. The reporter region can be translationally movable toward the second side after the first event. The reporter region further can be translationally movable toward the first side responsive to a second event occurring adjacent to the first side of the nanopore, the second event being after the first event. The reporter region further can be translationally movable toward the second side after the second event. In some embodiments, the first event includes adding a first nucleotide to a polynucleotide. In embodiments that include a second event, the second event can include adding a second nucleotide to the polynucleotide.

An electrical or flux blockade characteristic of the reporter region can be different than an electrical or flux blockade characteristic of another region of the elongated body.

A system can include a composition and measurement circuitry configured to measure a first current or flux through the aperture or to measure a first optical signal while the reporter region is moved responsive to the first event.

In some embodiments, the composition further includes a protein disposed adjacent to the first side of the nanopore, and the first event includes a first conformational change of the protein. The protein is generally not a native component of a nanopore.

In some embodiments, the head region is anchored to the protein. The first conformational change can move the head region, and the movement of the head region can translationally move the reporter region.

In some embodiments, the protein is in contact with the first side of the nanopore. In some embodiments, the protein can be anchored to or adjacent to the first side of the nanopore.

In some embodiments, the protein includes an enzyme. For example, the enzyme can include a polymerase. The first conformational change can occur responsive to the polymerase acting upon a first nucleotide. In some embodiments, the first conformational change moves the head region, and the movement of the head region translationally moves the reporter region. The first nucleotide can be identifiable based on a measured magnitude or time duration, or both, of a change in a current or flux through the aperture or a first optical signal responsive to the translational movement of the reporter region.

The reporter region further can be translationally movable responsive to a second conformational change of the polymerase occurring responsive to the polymerase acting upon a second nucleotide. In some embodiments, the first nucleotide is identifiable based on a measured magnitude or time duration, or both, of a first change in a current or flux through the aperture or a first optical signal responsive to the translational movement of the reporter region responsive to the first conformational change. The second nucleotide can be identifiable based on a measured magnitude or time duration, or both, of a second change in the current or flux through the aperture or a second optical signal responsive to the translational movement of the reporter region responsive to the second conformational change. In some embodiments, the first and second nucleotides are individually distinguishable from one another based on the first and second changes in the current or flux or based on the first and second optical signals.

In some embodiments, the composition further includes a polymerase disposed adjacent to the first side of the nanopore, and the first event includes the polymerase acting upon a first nucleotide. The first nucleotide can include an elongated tag including a moiety that interacts with the tether. The interaction of the moiety with the tether can translationally move the reporter region.

In some embodiments, the elongated body of the tether can include a synthetic polymer. In some embodiments, the tether includes a first oligonucleotide. An abasic nucleotide of the first oligonucleotide can define the reporter region. Additionally, or alternatively, the moiety can include a second oligonucleotide that hybridizes to the first oligonucleotide. The hybridization of the second oligonucleotide to the first oligonucleotide can shorten the tether by a first amount. In some embodiments, the first nucleotide is identifiable based on a measured magnitude or time duration, or both, of change in a current or flux through the aperture or an optical signal responsive to the shortening of the tether by the first amount. In some embodiments, the reporter region further is translationally movable toward the first side responsive to the polymerase acting upon a second nucleotide. The second nucleotide can include a third oligonucleotide that hybridizes to the first oligonucleotide. The hybridization of the third oligonucleotide to the first oligonucleotide can shorten the tether by a second amount. In some embodiments, the first nucleotide is identifiable based on a measured magnitude or time duration, or both, of a first change in a current or flux through the aperture or a first optical signal responsive to the shortening of the tether by the first amount. In embodiments that include a second nucleotide, the second nucleotide can be identifiable based on a measured magnitude or time duration, or both, of a second change in the current or flux through the aperture or a second optical signal responsive to the shortening of the tether by the second amount. In some embodiments, the first and second nucleotides are individually distinguishable from one another based on the first and second changes in the current or flux or based on the first and second optical signals.

In some embodiments, the head region is anchored to the first side of the nanopore. In some embodiments, the polymerase is in contact with the first side of the nanopore. In some embodiments, the polymerase is anchored to or adjacent to the first side of the nanopore.

Some embodiments further include a polymerase disposed on the first side, the head region being anchored to the polymerase. Some embodiments further include a first nucleotide and first and second polynucleotides each in contact with the polymerase, the polymerase configured to add the first nucleotide to the first polynucleotide based on a sequence of the second polynucleotide. In some embodiments, the polymerase is modified so as to delay release of pyrophosphate responsive to addition of the first nucleotide to the first polynucleotide. In some embodiments, the polymerase includes a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, the polymerase includes a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, the polymerase includes a modified recombinant Φ29 DNA polymerase having at least one amino acid substitution or combination of substitutions selected from the group consisting of E375Y, K512Y, T368F, A484E, A484Y, N387L, T372Q, T372L, K478Y, I370W, F198W, and L381A.

In some embodiments, the composition further includes a polymerase disposed on the first side, the head region being anchored to the polymerase. Some embodiments further include a first nucleotide and first and second polynucleotides each in contact with the polymerase, the polymerase configured to add the first nucleotide to the first polynucleotide based on a sequence of the second polynucleotide. In some embodiments, the first nucleotide is coupled to a reversible terminator that inhibits the polymerase from adding a second nucleotide to the first polynucleotide. In some embodiments, the reversible terminator is cleavable by exposure to light or heat. In some embodiments, the reversible terminator is cleavable by absorption of heat from the light. In some embodiments, the reversible terminator is cleavable by a photochemical reaction induced by the light. In some embodiments, the reversible terminator is cleavable by reaction with a chemical agent. In some embodiments, the composition further includes a source of the chemical agent. In some embodiments, the reversible terminator is disposed on the first side, and the source of the chemical agent is disposed on the second side such that the chemical agent moves from the second side to the first side through the aperture. In some embodiments, the reversible terminator includes azidomethyl ($CH_2N_3$), and the chemical agent includes THP.

In some embodiments, an apparatus includes such a composition, wherein the composition is present in a flow cell and the flow cell is configured to replenish reagents that are in contact with the polymerase.

Under another aspect, a method includes providing a nanopore including a first side, a second side, and an aperture extending through the first and second sides; and providing a permanent tether including a head region, a tail region, and an elongated body disposed therebetween. The head region can be anchored to or adjacent to the first or second side of the nanopore, and the elongated body can include a reporter region. The method can include moving the reporter within the aperture responsive to a first event occurring adjacent to the first side of the nanopore.

In some embodiments, the reporter region is translationally moved within the aperture responsive to the first event. Additionally, or alternatively, the reporter region can be rotationally moved within the aperture responsive to the first event. Additionally, or alternatively, the reporter region is conformationally moved within the aperture responsive to the first event.

In some embodiments, the head region is anchored to or adjacent to the first side or second side of the nanopore via a covalent bond. In some embodiments, the head region is anchored to the first side of the nanopore. In some embodiments, the tail region extends freely toward the second side of the nanopore.

In some embodiments, the reporter region is translationally moved toward the first side of the nanopore responsive to the first event. Some embodiments further include translationally moving the reporter region toward the second side after the first event. Some embodiments further include translationally moving the reporter region toward the first side responsive to a second event occurring adjacent to the first side of the nanopore, the second event being after the first event. Some embodiments further include translationally moving the reporter region toward the second side after the second event. In some embodiments, the first event includes adding a first nucleotide to a polynucleotide. In some embodiments, the second event includes adding a second nucleotide to the polynucleotide.

In some embodiments, an electrical or flux blockade characteristic of the reporter region is different than an electrical or flux blockade characteristic of another region of the elongated body.

The method further can include measuring a first current or flux through the aperture or a first optical signal while the reporter region is moved responsive to the first event.

In some embodiments, a protein is disposed adjacent to the first side of the nanopore, and the first event includes a first conformational change of the protein. The head region can be anchored to the protein. The first conformational change can move the head region, and the movement of the head region can translationally move the reporter region.

In some embodiments, the protein is in contact with the first side of the nanopore. In some embodiments, the protein is anchored to or adjacent to the first side of the nanopore.

In some embodiments, the protein includes an enzyme. For example, the enzyme can include a polymerase. The first conformational change can occur responsive to the polymerase acting upon a first nucleotide. In some embodiments, the first conformational change moves the head region, and the movement of the head region translationally moves the reporter region. Some embodiments further include identifying the first nucleotide based on a measured magnitude or time duration, or both, of a change in a current or flux through the aperture or an optical signal responsive to the translational movement of the reporter region.

Some embodiments further include translationally moving the reporter region responsive to a second conformational change of the polymerase occurring responsive to the polymerase acting upon a second nucleotide. Some embodiments further include identifying the first nucleotide based on a measured magnitude or time duration, or both, of a first change in a current or flux through the aperture or a first optical signal responsive to the translational movement of the reporter region responsive to the first conformational change. Some embodiments further include identifying the second nucleotide based on a measured magnitude or time duration, or both, of a second change in the current or flux through the aperture or a second optical signal responsive to the translational movement of the reporter region responsive to the second conformational change. In some embodiments, the first and second nucleotides are individually distinguishable from one another based on the first and second changes in the current or flux or based on the first and second optical signals.

Some embodiments include disposing a polymerase adjacent to the first side of the nanopore, and the first event can include the polymerase acting upon a first nucleotide. The first nucleotide can include an elongated tag including a moiety that interacts with the tether. The interaction of the moiety with the tether can translationally move the reporter region.

In some embodiments, the elongated body of the tether includes a synthetic polymer. In some embodiments, the tether includes a first oligonucleotide. In some embodiments, an abasic nucleotide of the first oligonucleotide defines the reporter region. In some embodiments, the moiety includes a second oligonucleotide that hybridizes to the first oligonucleotide. The hybridization of the second oligonucleotide to the first oligonucleotide can shorten the tether by a first amount. Some embodiments further include identifying the first nucleotide based on a measured magnitude or time duration, or both, of a change in a current or flux through the aperture or an optical signal responsive to the shortening of the tether by the first amount. Some embodiments also include translationally moving the reporter region toward the first side responsive to the polymerase acting upon a second nucleotide. The second nucleotide can include a third oligonucleotide that hybridizes to the first oligonucleotide. The hybridization of the third oligonucleotide to the first oligonucleotide can shorten the tether by a second amount. Some embodiments further include identifying the first nucleotide based on a measured magnitude or time duration, or both, of a first change in a current or flux through the aperture or a first optical signal responsive to the shortening of the tether by the first amount. Some embodiments also include identifying the second oligonucleotide based on a measured magnitude or time duration, or both, of a second change in the current or flux through the aperture or a second optical signal responsive to the shortening of the tether by the second amount. The first and second nucleotides can be individually distinguishable from one another based on the first and second changes in the current or flux or based on the first and second optical signals.

In some embodiments, the head region is anchored to the first side of the nanopore. In some embodiments, the polymerase is in contact with the first side of the nanopore. In some embodiments, the polymerase is anchored to or adjacent to the first side of the nanopore.

In some embodiments, the method includes disposing a polymerase on the first side, the head region being anchored to the polymerase. In some embodiments, the method further includes contacting the polymerase with a first nucleotide and with first and second polynucleotides, the polymerase adding the first nucleotide to the first polynucleotide based on a sequence of the second polynucleotide. In some embodiments, the polymerase is modified so as to delay release of pyrophosphate responsive to addition of the first nucleotide to the first polynucleotide. In some embodiments, the polymerase includes a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, the polymerase includes a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, the polymerase includes a modified recombinant Φ29 DNA polymerase having at least one amino acid substitution or combination of substitutions selected from the group consisting of E375Y, K512Y, T368F, A484E, A484Y, N387L, T372Q, T372L, K478Y, I370W, F198W, and L381A.

In some embodiments, polymerase is disposed on the first side, the head region being anchored to the polymerase. In some embodiments, the method further includes contacting the polymerase with a first nucleotide and with first and second polynucleotides, the polymerase adding the first nucleotide to the first polynucleotide based on a sequence of the second polynucleotide. In some embodiments, the first nucleotide is coupled to a reversible terminator, the method further including inhibiting, by the reversible terminator, the polymerase from adding a second nucleotide to the first polynucleotide. In some embodiments, the method further includes cleaving the reversible terminator by exposure to light or heat. Some embodiments include cleaving the reversible terminator by absorption of heat from the light. Some embodiments include cleaving the reversible terminator by a photochemical reaction induced by the light. Some embodiments include cleaving the reversible terminator by reaction with a chemical agent. Some embodiments include providing a source of the chemical agent. Some embodiments include flowing fluid past the polymerase to remove the chemical agent. Some embodiments include supplying new reagents to the polymerase by fluid flow. In some embodiments, the reversible terminator is disposed on the first side and the source of the chemical agent is disposed on the second side, the method including moving the chemical agent from the second side to the first side through the aperture. In some embodiments, the reversible terminator includes azidomethyl ($CH_2N_3$), and the chemical agent includes THP.

Under yet another aspect, a composition includes a nanopore including a first side, a second side, and an aperture extending through the first and second sides; and a permanent tether including a head region, a tail region, and an elongated body disposed therebetween. The head region can be anchored to or adjacent to the first side or second side of the nanopore, and the elongated body can include a moiety. A polymerase can be disposed adjacent to the first side of the nanopore. The composition also can include a first nucleotide including a first elongated tag. The first elongated tag can include a first moiety that interacts with the moiety of the tether responsive to the polymerase acting upon the first nucleotide.

In some embodiments, the head region is anchored to or adjacent to the first side or second side of the nanopore via a covalent bond. For example, in some embodiments, the head region is anchored to the first side of the nanopore. In some embodiments, the tail region extends freely toward the second side of the nanopore. In some embodiments, the tail region is movable between the first and second side of the nanopore responsive to an applied voltage. Or, for example, in some embodiments, the head region is anchored to the second side of the nanopore. In some embodiments, the tail region extends freely toward the first side of the nanopore. In some embodiments, the tail region is movable between the first and second side of the nanopore responsive to an applied voltage.

The polymerase can be in contact with the first side of the nanopore. The polymerase can be anchored to or adjacent to the first side of the nanopore.

In some embodiments, the interaction between the first moiety and the moiety of the tether defines a duplex. The nanopore further can include a constriction disposed between the first and second sides. The anchoring of the head region to or adjacent to the first or second side of the nanopore, or to the polymerase, can inhibit movement of the duplex through the constriction. Alternatively, or additionally, the duplex can be sufficiently large as to inhibit movement of the duplex through the constriction.

In some embodiments, the first elongated tag of the first nucleotide further includes a first reporter region. Optionally, the first reporter region can be configured to be disposed within the aperture responsive to the first moiety interacting with the moiety of the tether. A system can include any such composition and measurement circuitry configured to measure a current or flux through the aperture or an optical signal while the first reporter region is disposed within the aperture. The current or flux or optical signal can be based on an electrical or flux blockade characteristic of the first reporter region, and the first nucleotide can be identifiable based on the current or flux or optical signal.

In some embodiments, a composition further includes a second nucleotide including a second elongated tag, the second elongated tag including a second moiety that interacts with the moiety of the tether responsive to the polymerase acting upon the second nucleotide. The second elongated tag further can include a second reporter region. In some embodiments, the second reporter region is configured to be disposed within the aperture responsive to the second moiety interacting with the moiety of the tether. A system can include any such composition and measurement circuitry configured to measure a first current or flux through the aperture or a first optical signal while the first reporter region is disposed within the aperture and a second current or flux through the aperture or a second optical signal while the second reporter region is disposed within the aperture. The first current or flux or the first optical signal can be based on a first electrical or flux blockade characteristic of the first reporter region. The first nucleotide can be identifiable based on the first current or flux or the first optical signal. The second current or flux or the second optical signal can be based on a second electrical or flux blockade characteristic of the second reporter region. The second nucleotide can be identifiable based on the second current or flux or the second optical signal. The first and second nucleotides can be individually distinguishable from one another based on the first and second currents or fluxes or the first and second optical signals.

In some embodiments of the present compositions, the first elongated tag is cleavable from the first nucleotide responsive to the polymerase acting upon the first nucleotide, and the second elongated tag is cleavable from the second nucleotide responsive to the polymerase acting upon the second nucleotide.

In some embodiments, the elongated body of the tether includes a synthetic polymer. In some embodiments, the moiety of the tether includes a first oligonucleotide. In some embodiments, the first moiety includes a second oligonucleotide that hybridizes to the first oligonucleotide. An abasic nucleotide of the second oligonucleotide can define the reporter region. In some embodiments, the second moiety includes a third oligonucleotide that hybridizes to the first oligonucleotide. In some embodiments, the first moiety and the second moiety are the same as one another.

In some embodiments, the elongated body of the tether further includes a reporter region. The reporter region can be disposed at a predefined location relative to the first moiety responsive to the interaction of the first moiety with the moiety of the tether. The reporter region can be translationally movable within the aperture responsive to a first applied voltage. In some embodiments, the nanopore further including a constriction disposed between the first and second sides. The reporter region can be translationally movable to a first predetermined location relative to the constriction responsive to the first applied voltage.

An electrical or flux blockade characteristic of the reporter region can be different than an electrical or flux blockade characteristic of another region of the elongated body.

A system can include such a composition and measurement circuitry configured to measure a current or flux through the aperture or an optical signal while the reporter region is disposed at the first predetermined location. The current or flux or optical signal can be based on the electrical or flux blockade characteristic of the reporter region and the first predetermined location of the reporter region, and the first nucleotide can be identifiable based on the current or flux or optical signal.

In some embodiments, the first moiety and the moiety of the tether are dissociable responsive to the first applied voltage. The moiety of the tether can be translationally movable through the constriction responsive to dissociation of the first moiety and the moiety of the tether. In some embodiments, the first moiety interacts with the moiety of the tether responsive to a second applied voltage subsequent to the first applied voltage. In some embodiments, the composition further includes a second nucleotide including a second elongated tag, the second elongated tag including a second moiety that interacts with the moiety of the tether responsive to the polymerase acting upon the second nucleotide. The reporter region can be disposed at a predetermined location relative to the second moiety responsive to the interaction of the second moiety with the moiety of the tether. In some embodiments, the reporter region is translationally movable within the aperture responsive to a second applied voltage. In some embodiments, the nanopore further includes a constriction disposed between the first and second sides. The reporter region can be translationally movable to a second location relative to the constriction responsive to the second applied voltage.

An electrical or flux blockade characteristic of the reporter region can be different than an electrical or flux blockade characteristic of another region of the elongated body.

A system can include such a composition and measurement circuitry configured to measure a first current or flux through the aperture or a first optical signal while the reporter region is disposed at the first location responsive to the first applied voltage, and to measure a second current or flux through the aperture or a second optical signal while the reporter region is disposed at the second location responsive to the second applied voltage. The first current or flux or first optical signal can be based on the electrical or flux blockade characteristic of the reporter region and the first predetermined location of the reporter region. The first nucleotide can be identifiable based on the first current or flux or first optical signal. The second current or flux or second optical signal can be based on the electrical or flux blockade characteristic of the reporter region and the second predetermined location of the reporter region. The second nucleotide can be identifiable based on the second current or flux or second optical signal. In some embodiments, the first and second nucleotides are individually distinguishable from one another based on the first current or flux and the second current or flux or based on the first and second optical signals. In some embodiments, the first and second voltages have the same magnitude as one another, and the second voltage is subsequent to the first voltage.

In some embodiments of the present compositions, the first elongated tag is cleavable from the first nucleotide responsive to the polymerase acting upon the first nucleotide, and the second elongated tag is cleavable from the second nucleotide responsive to the polymerase acting upon the second nucleotide.

In some embodiments, the elongated body of the tether includes a synthetic polymer. In some embodiments, the moiety of the tether includes a first oligonucleotide. An abasic nucleotide of the first oligonucleotide can define the reporter region. The first moiety can include a second oligonucleotide that hybridizes to the first oligonucleotide. The second moiety can include a third oligonucleotide that hybridizes to the first oligonucleotide. The first moiety and the second moiety can be different than one another. The reporter region can be translationally movable within the aperture responsive to the polymerase acting upon the first nucleotide. Alternatively, or additionally, the reporter region can be rotationally movable within the aperture responsive to the polymerase acting upon the first nucleotide. Alternatively, or additionally, the reporter region can be conformationally movable within the aperture responsive to the polymerase acting upon the first nucleotide.

In some embodiments, the elongated body of the tether includes a synthetic polymer. In some embodiments, the moiety of the tether includes a first oligonucleotide. An abasic nucleotide of the first oligonucleotide can define the reporter region. The first moiety can include a second oligonucleotide that hybridizes to the first oligonucleotide. The hybridization of the second oligonucleotide to the first oligonucleotide can shorten the tether by a first amount. The first nucleotide can be identifiable based on a measured magnitude or time duration, or both, of change in a current or flux through the aperture or an optical signal responsive to the shortening of the tether by the first amount.

In some embodiments, the first elongated tag of the first nucleotide further includes a first fluorescent resonant energy transfer (FRET) pair partner, and the tether further includes a second FRET pair partner. The first FRET pair partner and the second FRET pair partner can interact with one another responsive to the polymerase acting upon the first nucleotide. A first wavelength emitted responsive to the interaction between the first FRET pair partner and the second FRET pair partner is detectable. The composition further can include a second nucleotide including a second elongated tag, the second elongated tag including a third fluorescent resonant energy transfer (FRET) pair partner. A system can include such a composition. The third FRET pair partner and the second FRET pair partner can interact with one another responsive to the polymerase acting upon the second nucleotide. The system can include an optical detection system configured to detect a second wavelength emitted responsive to the interaction between the third FRET pair partner and the second FRET pair partner. The first and second nucleotides can be individually distinguishable from one another based on the first and second wavelengths.

In some embodiments, the composition further includes first and second polynucleotides in contact with the polymerase, the polymerase configured to add the first nucleotide to the first polynucleotide based on a sequence of the second polynucleotide. In some embodiments, the polymerase is modified so as to delay release of pyrophosphate responsive to addition of the first nucleotide to the first polynucleotide. In some embodiments, the polymerase includes a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, the polymerase includes a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, the polymerase includes a modified recombinant Φ29 DNA polymerase having at least one amino acid substitution or combination of substitutions selected from the group consisting of E375Y, K512Y, T368F, A484E, A484Y, N387L, T372Q, T372L, K478Y, I370W, F198W, and L381A.

In some embodiments, the first moiety and the moiety of the tether are configured to hybridize with one another so as to form a hairpin structure. A system can include such a composition and a voltage source configured to apply a voltage across the first and second sides. The first moiety and the moiety of the tether can be configured to dehybridize from one another responsive to the voltage in a two-step process.

In some embodiments, the first elongated tag further includes a second moiety, the composition further including a third moiety anchored to or adjacent to the first side or second side of the nanopore, the second moiety and the third moiety interacting responsive to addition of the first nucleotide to the first polynucleotide. A system can include such a composition and a voltage source configured to apply a voltage across the first and second sides. In some embodiments, the first moiety and the moiety of the tether are configured to separate from one another responsive to the voltage in a first process, and the second moiety and the third moiety are configured to separate from one another responsive to the voltage in a second process.

In some embodiments, the composition further includes first and second polynucleotides in contact with the polymerase, the polymerase configured to add the first nucleotide to the first polynucleotide based on a sequence of the second polynucleotide. In some embodiments, the first elongated tag further includes a reversible terminator that inhibits the polymerase from adding a second nucleotide to the first polynucleotide. In some embodiments, the reversible terminator is cleavable by exposure to light or heat. In some embodiments, the reversible terminator is cleavable by absorption of heat from the light. In some embodiments, the reversible terminator is cleavable by a photochemical reaction induced by the light. In some embodiments, the reversible terminator is cleavable by reaction with a chemical agent. Some embodiments further include a source of the chemical agent. In some embodiments, the reversible terminator is disposed on the first side, and the source of the chemical agent is disposed on the second side such that the chemical agent moves from the second side to the first side through the aperture. In some embodiments, the reversible terminator includes azidomethyl ($CH_2N_3$), and the chemical agent includes THP.

In some embodiments, an apparatus includes such a composition, wherein the composition is present in a flow cell and the flow cell is configured to replenish reagents that are in contact with the polymerase.

Under still another aspect, a method includes providing a nanopore including a first side, a second side, and an aperture extending through the first and second sides; and providing a permanent tether including a head region, a tail region, and an elongated body disposed therebetween. The head region can be anchored to or adjacent to the first side or second side of the nanopore, and the elongated body can include a moiety. The method further can include providing a polymerase disposed adjacent to the first side of the nanopore, and providing a first nucleotide including a first elongated tag, the first elongated tag including a moiety. The method further can include acting upon the first nucleotide with the polymerase; and interacting the first moiety with the moiety of the tether responsive to the polymerase acting upon the first nucleotide.

In some embodiments, the head region is anchored to or adjacent to the first side or second side of the nanopore via a covalent bond. For example, in some embodiments, the head region is anchored to the first side of the nanopore. In some embodiments, the tail region extends freely toward the second side of the nanopore. Some embodiments include moving the tail region between the first and second side of the nanopore responsive to an applied voltage. Or, for example, in some embodiments, the head region is anchored to the second side of the nanopore. In some embodiments, the tail region extends freely toward the first side of the nanopore. Some embodiments include moving the tail region between the first and second side of the nanopore responsive to an applied voltage.

In some embodiments, the polymerase is in contact with the first side of the nanopore. In some embodiments, the polymerase is anchored to or adjacent to the first side of the nanopore.

In some embodiments, the interaction between the first moiety and the moiety of the tether defines a duplex. The nanopore further can include a constriction disposed between the first and second sides. The method further can include inhibiting movement of the duplex through the constriction via the anchoring of the head region to or adjacent to the first or second side of the nanopore. Additionally, or alternatively, the duplex can be sufficiently large as to inhibit movement of the duplex through the constriction.

In some embodiments, the first elongated tag of the first nucleotide further includes a first reporter region. Some embodiments include disposing the first reporter region within the aperture responsive to the first moiety interacting with the moiety of the tether. Some embodiments further include measuring a current or flux through the aperture or an optical signal while the first reporter region is disposed within the aperture. In some embodiments, the current or flux or optical signal is based on an electrical or flux blockade characteristic of the first reporter region, and the first nucleotide is identifiable based on the current or flux or optical signal. Some embodiments further include providing a second nucleotide including a second elongated tag, the second elongated tag including a second moiety, acting upon the second nucleotide with the polymerase, and interacting the second moiety with the moiety of the tether responsive to the polymerase acting upon the second nucleotide. The second elongated tag further can include a second reporter region. Some embodiments include disposing the second reporter region within the aperture responsive to the second moiety interacting with the moiety of the tether. Some embodiments include measuring a first current or flux through the aperture or a first optical signal while the first reporter region is disposed within the aperture and measuring a second current or flux through the aperture or a second optical signal while the second reporter region is disposed within the aperture. In some embodiments, the first current or flux or the first optical signal is based on a first electrical or flux blockade characteristic of the first reporter region, the first nucleotide is identifiable based on the first current or flux or first optical signal, the second current or flux or the second optical signal is based on a second electrical or flux blockade characteristic of the second reporter region, and the second nucleotide is identifiable based on the second current or flux or second optical signal. In some embodiments, the first and second nucleotides are individually distinguishable from one another based on the first current or flux and second current or flux or first and second optical signals. Some embodiments further include cleaving the first elongated tag from the first nucleotide responsive to the polymerase acting upon the first nucleotide, and cleaving the second elongated tag from the second nucleotide responsive to the polymerase acting upon the second nucleotide.

In some embodiments, the elongated body of the tether includes a synthetic polymer. In some embodiments, the moiety of the tether includes a first oligonucleotide. In some embodiments, the first moiety includes a second oligonucleotide that hybridizes to the first oligonucleotide. In some embodiments, an abasic nucleotide of the second oligonucleotide defines the reporter region. In some embodiments, the second moiety includes a third oligonucleotide that hybridizes to the first oligonucleotide. In some embodiments, the first moiety and the second moiety are the same as one another. In some embodiments, the elongated body of the tether further includes a reporter region. Some embodiments further include disposing the reporter region at a predefined location relative to the first moiety responsive to the interaction of the first moiety with the moiety of the tether. Some embodiments further include translationally moving the reporter region within the aperture responsive to a first applied voltage. The nanopore further can include a constriction disposed between the first and second sides. The reporter region can be translationally moved to a first predetermined location relative to the constriction responsive to the first applied voltage. An electrical or flux blockade characteristic of the reporter region can be different than an electrical or flux blockade characteristic of another region of the elongated body. Some embodiments further include measuring a current or flux through the aperture or an optical signal while the reporter region is disposed at the first predetermined location. In some embodiments, the current or flux or optical signal is based on the electrical or flux blockade characteristic of the reporter region and the first predetermined location of the reporter region, and the first nucleotide is identifiable based on the current or flux or optical signal. Some embodiments further include dissociating the first moiety and the moiety of the tether responsive to the first applied voltage. Some embodiments include translationally moving the moiety of the tether through the constriction responsive to dissociation of the first moiety and the moiety of the tether. Some embodiments include interacting the first moiety with the moiety of the tether responsive to a second applied voltage subsequent to the first applied voltage.

In some embodiments, the method further includes providing a second nucleotide including a second elongated tag, the second elongated tag including a second moiety that interacts with the moiety of the tether responsive to the polymerase acting upon the second nucleotide. The method can include disposing the reporter region at a predetermined location relative to the second moiety responsive to the interaction of the second moiety with the moiety of the tether. The method can include translationally moving the reporter region within the aperture responsive to a second applied voltage. The nanopore further can include a constriction disposed between the first and second sides. The reporter region can be translationally moved to a second location relative to the constriction responsive to the second applied voltage. An electrical or flux blockade characteristic of the reporter region can be different than an electrical or flux blockade characteristic of another region of the elongated body. Some embodiments further include measuring a first current or flux through the aperture or a first optical signal while the reporter region is disposed at the first location responsive to the first applied voltage, and measuring a second current or flux or a second optical signal through the aperture while the reporter region is disposed at the second location responsive to the second applied voltage. In some embodiments, the first current or flux or first optical signal is based on the electrical or flux blockade characteristic of the reporter region and the first predetermined location of the reporter region. The first nucleotide can be identifiable based on the first current or flux or first optical signal. The second current or flux or second optical signal can be based on the electrical or flux blockade characteristic of the reporter region and the second predetermined location of the reporter region. The second nucleotide can be identifiable based on the second current or flux or second optical signal. In some embodiments, the first and second nucleotides are individually distinguishable from one another based on the first current or flux and second current or flux or based on the first and second optical signals. The first and second voltages can have the same magnitude as one another, and the second voltage can be subsequent to the first voltage. In some embodiments, the first elongated tag is cleavable from the first nucleotide responsive to the polymerase acting upon the first nucleotide, and the second elongated tag is cleavable from the second nucleotide responsive to the polymerase acting upon the second nucleotide.

In some embodiments, the elongated body of the tether includes a synthetic polymer. In some embodiments, the moiety of the tether includes a first oligonucleotide. An abasic nucleotide of the first oligonucleotide can define the reporter region. The first moiety can include a second oligonucleotide that hybridizes to the first oligonucleotide. The second moiety can include a third oligonucleotide that hybridizes to the first oligonucleotide. The first moiety and the second moiety can be different than one another.

In some embodiments, the reporter region is translationally movable within the aperture responsive to the polymerase acting upon the first nucleotide. Additionally, or alternatively, the reporter region can be rotationally movable within the aperture responsive to the polymerase acting upon the first nucleotide. Additionally, or alternatively, the reporter region can be conformationally movable within the aperture responsive to the polymerase acting upon the first nucleotide.

The elongated body of the tether can include a synthetic polymer. The moiety of the tether can include a first oligonucleotide. An abasic nucleotide of the first oligonucleotide can define the reporter region. The first moiety can include a second oligonucleotide that hybridizes to the first oligonucleotide. The hybridization of the second oligonucleotide to the first oligonucleotide can shorten the tether by a first amount. The first nucleotide can be identifiable based on a measured magnitude or time duration, or both, of change in a current or flux through the aperture or an optical signal responsive to the shortening of the tether by the first amount.

In some embodiments, the first elongated tag of the first nucleotide further includes a first fluorescent resonant energy transfer (FRET) pair partner, and the tether further includes a second FRET pair partner. The first FRET pair partner and the second FRET pair partner can interact with one another responsive to the polymerase acting upon the first nucleotide. The method further can include detecting a first wavelength emitted responsive to the interaction between the first FRET pair partner and the second FRET pair partner. The method further can include providing a second nucleotide including a second elongated tag, the second elongated tag including a third fluorescent resonant energy transfer (FRET) pair partner. The third FRET pair partner and the second FRET pair partner can interact with one another responsive to the polymerase acting upon the second nucleotide. The method further can include detecting a second wavelength emitted responsive to the interaction between the third FRET pair partner and the second FRET pair partner. The first and second nucleotides can be individually distinguishable from one another based on the first and second wavelengths.

In some embodiments, the method further includes disposing a polymerase on the first side, the head region being anchored to the polymerase. In some embodiments, the method further includes contacting the polymerase with a first nucleotide and with first and second polynucleotides, the polymerase adding the first nucleotide to the first polynucleotide based on a sequence of the second polynucleotide. In some embodiments, the polymerase is modified so as to delay release of pyrophosphate responsive to addition of the first nucleotide to the first polynucleotide. In some embodiments, the polymerase includes a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, the polymerase includes a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, the polymerase includes a modified recombinant Φ29 DNA polymerase having at least one amino acid substitution or combination of substitutions selected from the group consisting of E375Y, K512Y, T368F, A484E, A484Y, N387L, T372Q, T372L, K478Y, 137W, F198W, and L381A.

In some embodiments, the first moiety and the moiety of the tether hybridize with one another so as to form a hairpin structure. In some embodiments, the method further includes applying a voltage across the first and second sides. In some embodiments, the first moiety and the moiety of the tether dehybridize from one another responsive to the voltage in a two-step process.

In some embodiments, the first elongated tag further includes a second moiety, a third moiety anchored to or adjacent to the first side or second side of the nanopore, the second moiety and the third moiety interacting responsive to addition of the first nucleotide to the first polynucleotide. In some embodiments, the method further includes applying a voltage across the first and second sides. In some embodiments, the first moiety and the moiety of the tether separate from one another responsive to the voltage in a first process, and the second moiety and the third moiety separate from one another responsive to the voltage in a second process.

In some embodiments, the method includes disposing a polymerase on the first side, the head region being anchored to the polymerase. Some embodiments include contacting the polymerase with a first nucleotide and with first and second polynucleotides, the polymerase adding the first nucleotide to the first polynucleotide based on a sequence of the second polynucleotide. In some embodiments, the first elongated tag includes a reversible terminator, the method further including inhibiting, by the reversible terminator, the polymerase from adding a second nucleotide to the first polynucleotide. Some embodiments include cleaving the reversible terminator by exposure to light or heat. Some embodiments include cleaving the reversible terminator by absorption of heat from the light. Some embodiments include cleaving the reversible terminator by a photochemical reaction induced by the light. Some embodiments include cleaving the reversible terminator by reaction with a chemical agent. Some embodiments include providing a source of the chemical agent. In some embodiments, the reversible terminator is disposed on the first side and the source of the chemical agent is disposed on the second side, the method including moving the chemical agent from the second side to the first side through the aperture. In some embodiments, the reversible terminator includes azidomethyl ($CH_2N_3$), and the chemical agent includes THP.

Some embodiments include flowing fluid past the polymerase to remove the chemical agent. Some embodiments further include supplying new reagents to the polymerase by fluid flow.

Under another aspect, a composition includes a nanopore including a first side, a second side, and an aperture extending through the first and second sides. The composition also can include a permanent tether including a head region, a tail region, and an elongated body disposed therebetween, the head region being anchored to a polymerase, the elongated body including a moiety. The polymerase can be disposed adjacent to the first side of the nanopore. The composition also can include a first nucleotide including a first elongated tag, the first elongated tag including a first moiety that interacts with the moiety of the tether responsive to the polymerase acting upon the first nucleotide.

In some embodiments, the tail region includes a first nucleic acid. Some embodiments further include a second nucleic acid to which the first nucleic acid is hybridized. In some embodiments, the head region is disposed on the first side of the nanopore, and the tail region is disposed on the second side. In some embodiments, the head region is anchored to the polymerase. In some embodiments, the interaction between the first nucleic acid and the second nucleic acid defines a duplex. In some embodiments, the nanopore further includes a constriction disposed between the first and second sides. In some embodiments, the duplex is sufficiently large as to inhibit movement of the duplex through the constriction. In some embodiments, the tether including the duplex inhibits separation of the polymerase from the nanopore.

Under another aspect, a system includes such a composition and measurement circuitry configured to measure a current or flux through the constriction or an optical signal. In some embodiments, the current or flux or optical signal is based on the first moiety, and the first nucleotide is identifiable based on the current or flux or optical signal. In some embodiments, the first elongated tag or the elongated body further includes a reporter region, the current or flux or optical signal is based on the reporter region being disposed within the aperture, and the first nucleotide is identifiable based on the current or flux or optical signal.

Under another aspect, a method includes providing a nanopore including a first side, a second side, and an aperture extending through the first and second sides. The method also can include providing a permanent tether including a head region, a tail region, and an elongated body disposed therebetween, the head region being anchored to a polymerase, the elongated body including a moiety. The method also can include providing the polymerase disposed adjacent to the first side of the nanopore. The method also can include providing a first nucleotide including a first elongated tag, the first elongated tag including a moiety. The method also can include acting upon the first nucleotide with the polymerase. The method also can include interacting the first moiety with the moiety of the tether responsive to the polymerase acting upon the first nucleotide.

In some embodiments, the tail region includes a first nucleic acid. Some embodiments further include hybridizing a second nucleic acid to the first nucleic acid. Some embodiments further include disposing the head region on the first side of the nanopore and disposing the tail region on the second side. Some embodiments further include anchoring the head region to the polymerase. In some embodiments, the interaction between the first nucleic acid and the second nucleic acid defines a duplex. In some embodiments, the nanopore further includes a constriction disposed between the first and second sides. Some embodiments further include inhibiting, by a size of the duplex, movement of the duplex through the constriction. Some embodiments further include including inhibiting, by the tether including the duplex, separation of the polymerase from the nanopore. Some embodiments further include measuring a current or flux through the constriction or an optical signal. In some embodiments, the current or flux or optical signal is based on the first moiety, the method further including identifying the first nucleotide based on the current or flux or optical signal. In some embodiments, the first elongated tag or the elongated body further includes a reporter region, wherein the current or flux or optical signal is based on the reporter region being disposed within the aperture, the method further including identifying the first nucleotide based on the current or flux or optical signal.

Under another aspect, a method of making a nanopore sequencing device includes providing a chamber including a first liquid medium separated from a second liquid medium by a nanopore, the nanopore including a first side in contact with the first liquid medium, a second side in contact with the second liquid medium, and an aperture extending through the first and second sides. The method also can include providing a polymerase to the first liquid medium, wherein the polymerase includes a tether, the tether including a head region, a tail region, and an elongated body disposed therebetween, the head region being anchored to the polymerase. The method also can include providing a capture moiety to the second liquid medium. The method also can include applying a current or flux through the nanopore to translocate the tail region of the tether through the nanopore. The method also can include binding the capture moiety to the tail region of the tether, thereby retaining the tether in the nanopore.

In some embodiments, the tether includes a nucleic acid. In some embodiments, the tail region includes a nucleic acid. In some embodiments, the capture moiety includes a nucleic acid that is complementary to the nucleic acid of the tail region. In some embodiments, the capture moiety binds covalently to the tail region. In some embodiments, the capture moiety binds non-covalently to the tail region.

BRIEF DESCRIPTION OF DRAWINGS

FIGS. 6A-6B schematically illustrate exemplary conformational changes of a polymerase.

FIGS. 11A-11D illustrate exemplary calculations of interactions between a tether and moieties, according to some embodiments of the present invention. Sequence disclosed as SEQ ID NO: 5.

FIGS. 13A-13E schematically illustrate interactions between an exemplary tether and moieties of respective nucleotides, according to some embodiments of the present invention. Sequences disclosed as SEQ ID NO: 5.

FIGS. 18A-18D schematically illustrate a composition including a tether anchored to or adjacent to a nanopore and configured for use in detecting action of a polymerase upon a nucleotide using a change in electrical or flux blockade potential across the nanopore, according to some embodiments of the present invention.

FIG. 18E illustrates an exemplary signal that can be generated during use of a composition such as illustrated in FIGS. 18A-18D, according to some embodiments of the present invention.

FIGS. 19A-19B schematically illustrate a composition including a tether anchored to or adjacent to a nanopore and configured for use in detecting action of a polymerase upon a nucleotide that includes an elongated tag including a reporter region, according to some embodiments of the present invention.

FIG. 19C schematically illustrate exemplary nucleotides including elongated tags including respective reporter regions and moieties that can bond to an exemplary tether during use in detecting action of a polymerase upon the nucleotides, according to some embodiments of the present invention.

FIGS. 20A-20D schematically illustrate a composition including a tether anchored to or adjacent to a nanopore and configured for use in detecting action of a polymerase upon a first nucleotide using a change in applied voltage across the nanopore, according to some embodiments of the present invention.

FIG. 20E illustrates an exemplary signal that can be generated during use of a composition such as illustrated in FIGS. 20A-20D, according to some embodiments of the present invention.

FIGS. 21A-21D schematically illustrate the composition of FIGS. 20A-20D configured for use in detecting action of the polymerase upon a second nucleotide using a second change in applied voltage across the nanopore, according to some embodiments of the present invention.

FIG. 21E illustrates an exemplary signal that can be generated during use of a composition such as illustrated in FIGS. 21A-21D, according to some embodiments of the present invention.

FIG. 23A schematically illustrates exemplary nucleotides including elongated tags including respective reporter regions and moieties that can bond to an exemplary tether during use in detecting action of a polymerase upon the nucleotides, according to some embodiments of the present invention.

FIG. 23B schematically illustrates a composition including a tether anchored to or adjacent to a nanopore and configured for use in detecting action of a polymerase upon a first nucleotide based on an interaction between the tether and a reporter region of a nucleotide, according to some embodiments of the present invention.

FIG. 23C schematically illustrates a detectable interaction between one of the reporter regions of FIG. 23A with the tether of FIG. 23B during action of a polymerase upon a first nucleotide, according to some embodiments of the present invention.

FIGS. 24A-24C illustrate an exemplary protein-DNA tether conjugate captured in an MspA nanopore and locked into place using a trans-side lock oligonucleotide, and FIG. 24D illustrates an exemplary duplex signal versus time that can be generated using the conjugate illustrated in FIGS. 24A-24C, according to some embodiments of the present invention. An oligonucleotide complementary to a region of the DNA tether was then added to the cis side. Voltage was cycled between 120 mV and −60 mV with approximately a 200 msec period. (A) The conjugate upon the application of forward voltage. Signal is seen (D-2402). (B). The conjugate upon the application of the negative voltage. Signal is seen (D-2400). (C) Upon hybridization of an oligonucleotide conjugate that is pulled up to the pore constriction. The exemplary signal is seen prior to stripping (D-2401). After stripping, the system returns to the state shown in FIG. 24A while the voltage is still at 120 mV, resulting in signal D-2402. Data in FIG. 24D was filtered with a 2 KHz low-pass filter for visual clarity.

FIG. 25 illustrates exemplary reaction parameters, e.g., rate constants and dwell times, for reaction schemes in which a nucleotide respectively being acted upon by a polymerase is a match or a mismatch (adapted from Johnson, "The kinetic and chemical mechanism of high-fidelity DNA polymerases," Biochim Biophys Acta 1804(5): 1041-1048 (2010), the entire contents of which are incorporated by reference herein).

DETAILED DESCRIPTION

Figure 1A:
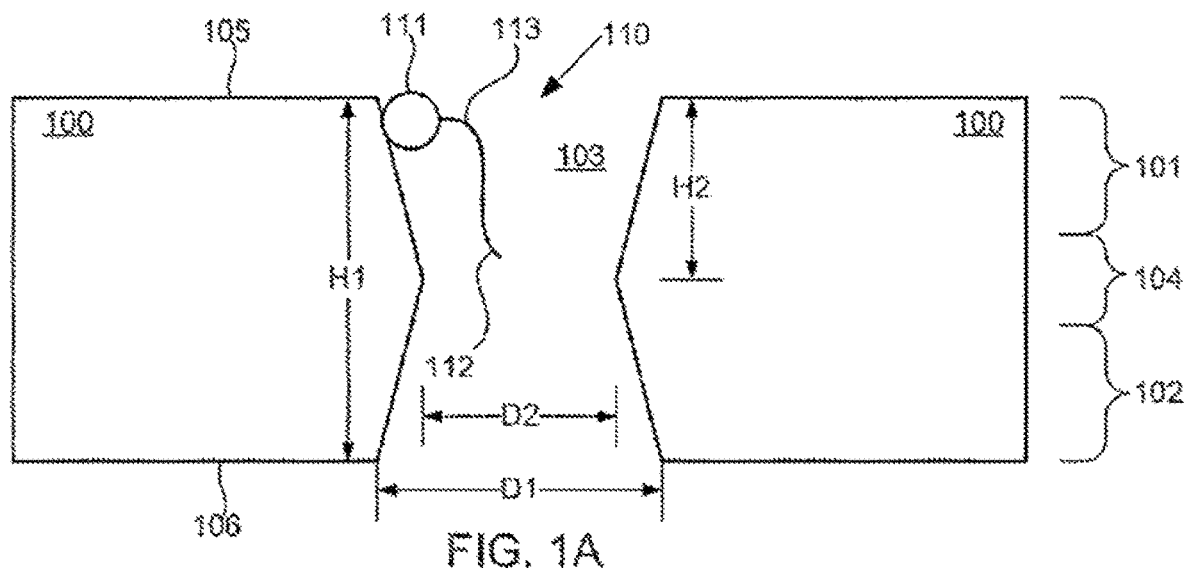
FIGS. 1A-1M schematically illustrate compositions including various configurations of tethers anchored to or adjacent to nanopores, according to some embodiments of the present invention.

Embodiments of the present invention provide compositions, systems, and methods for detecting events using tethers anchored to or adjacent to nanopores.

More specifically, the present compositions, systems, and methods suitably can be used to detect events, such as motion of a molecule or a portion thereof, in a manner that is robust, reproducible, sensitive, and has high throughput. For example, the present compositions can include a nanopore and a permanent tether that is anchored to, or adjacent to, the nanopore. The nanopore can include first and second sides and an aperture that extends through the first and second sides. The permanent tether can include head and tail regions and an elongated body disposed therebetween. At least one of the head and tail regions of the tether is anchored to, or adjacent to, the first or second side of the nanopore. The tether can include one or more features that facilitates detection of an event that occurs adjacent to the nanopore, e.g., on the first or second side of the nanopore.

For example, in some embodiments, the elongated body of the tether can include a reporter region, e.g., a region that facilitates detection or characterization of the tether using a suitable detection technique or apparatus. The reporter region can be movable (e.g., translationally, conformationally, or rotationally movable or a combination thereof) within the aperture responsive to an event that occurs adjacent to the first side of the nanopore. The movements of the reporter region are measurable, and information about the event is interpretable based on the measurements of the movements. Additionally, the reporter region can be configured so as to be repeatedly movable, e.g., responsive to different events. Such events can be different from one another, and can occur in any sequence. In particular embodiments, the events occur in a series of cycles such as occurs in the synthesis of a polymer by sequential addition of monomers, or in the degradation of a polymer by sequential removal of monomers. Particularly useful polymers are nucleic acids containing nucleotide monomers. Information about each event is individually determinable based on measurement of the movement of the reporter region responsive to that event. For example, a magnitude or a time duration, or both, of a signal based on the movement of the reporter region can be individually correlated to each event.

One example of an event that can be detected using the present compositions, systems, and methods is a conformational change of a molecule that disposed adjacent to the first side of the nanopore. Another example of an event that can be detected using the present compositions, systems, and methods is the interaction of one molecule with another molecule. It should be appreciated that a molecule's interaction with another molecule can cause, but need not necessarily cause, a conformational change in one or both of the molecules. Additionally, a conformational change of a molecule can be, but need not necessarily be, responsive to that molecule's interaction with another molecule. The present compositions, systems, and methods can be suitably configured so as to detect any such interaction, or any such conformational change, or a combination of an interaction and conformational change.

Tethers having other characteristics also can be suitably used to detect events. For example, the elongated body of the tether can include a moiety that interacts with a first molecule. The event can include action upon the first molecule by a second molecule. The tether can include a reporter region that is movable (e.g., translationally, conformationally, or rotationally movable or a combination thereof) responsive to the interaction between the moiety of the tether and the first molecule. Alternatively, the reporter region of the tether can be disposed at a location within the aperture that is based upon the interaction between the moiety of the tether and the first molecule. As still another alternative, the first molecule, rather than the tether, can include a reporter region. The presence of such a reporter region can be detectable responsive to interaction between the moiety of the tether and the first molecule, or detectable responsive to any other suitable stimulus. Additionally, the present compositions can be used to stabilize other molecules. For example, the tether's interaction with another molecule can stabilize that molecule, e.g., temporarily retain that molecule or a portion thereof within or adjacent to a nanopore.

Other configurations readily can be envisioned based on the teachings provided herein.

First, some terms used herein will be briefly explained. Then, some exemplary compositions, exemplary systems including measurement circuitry (e.g., electrical or optical measurement circuitry) that can be used with the present compositions, exemplary methods that can be used with the present compositions, and some specific examples of compositions that can be used during such methods, will be described.

Exemplary Terms

As used herein, the term "pore" is intended to mean a structure that includes an aperture that permits molecules to cross therethrough from a first side of the pore to a second side of the pore. That is, the aperture extends through the first and second sides of the pore. Molecules that can cross through an aperture of a pore can include, for example, ions or water-soluble molecules such as nucleic acids, proteins, nucleotides, and amino acids. The pore can be disposed within a barrier. When at least a portion of the aperture of a pore has a width of 100 nm or less, e.g., 10 nm or less, or 2 nm or less, the pore can be, but need not necessarily be, referred to as a "nanopore." Optionally, a portion of the aperture can be narrower than one or both of the first and second sides of the pore, in which case that portion of the aperture can be referred to as a "constriction." Alternatively or additionally, the aperture of a pore, or the constriction of a pore (if present), or both, can be greater than 0.1 nm, 0.5 nm, 1 nm, 10 nm or more. A pore can include multiple constrictions, e.g., at least two, or three, or four, or five, or more than five constrictions.

As used herein, a "barrier" is intended to mean a structure that normally inhibits passage of molecules from one side of the barrier to the other side of the barrier. The molecules for which passage is inhibited can include, for example, ions or water soluble molecules such as nucleic acids, proteins, nucleotides, and amino acids. A pore can be disposed within a barrier, and the aperture of the pore can permit passage of molecules from one side of the barrier to the other side of the barrier. Barriers include membranes of biological origin, and non-biological barriers such as solid state membranes.

As used herein, "tether" is intended to mean an elongated member having a head region, a tail region, and an elongated body therebetween. A tether can include a molecule. A tether can be, but need not necessarily be, in an elongated state, e.g., can include an elongated molecule. For example, an elongated body of a tether can have secondary or tertiary configurations such as hairpins, folds, helical configurations, or the like. Tethers can include polymers such as polynucleotides or synthetic polymers. Tethers can have lengths (e.g., measured in a stretched or maximally extended state) ranging, for example, from about 5 nm to about 500 nm, e.g., from about 10 nm to about 100 nm. Tethers can have widths ranging, for example, from about 1 nm to about 50 nm, e.g., from about 2 nm to about 20 nm. Tethers can be linear or branched. A tether can be considered to be "permanent" when it is not removed from a composition set forth herein under the conditions in which the composition is used, for example, in a detection method. A tether that is used in a cyclic or repeated reaction can also be considered "permanent" when there is no net change in position of the tether from one cycle to the next or from one reaction to a repeat of the reaction. It will be understood that the position of a permanent tether may change during an individual cycle or reaction even though there is no net change in position across the cycles or reactions.

As used herein, a "head region" of a tether is intended to mean a functional group of the tether that is attached to another member. Such attachment can be formed via a chemical bond, e.g., via a covalent bond, hydrogen bond, ionic bond, dipole-dipole bond, London dispersion forces, or any suitable combination thereof. In one embodiment, such attachment can be formed through hybridization of a first oligonucleotide of the head region to a second oligonucleotide of another member. Alternatively, such attachment can be formed using physical or biological interactions, e.g., an interaction between a first protein structure of the head region and a second protein structure of the other member that inhibits detachment of the head region from the other member. Exemplary members to which a head region of a tether can be attached include a pore, e.g., the first or second side of the pore, a barrier in which the pore is disposed, and a molecule, such as a protein, disposed on either the first or second side of the pore. If the head region of the tether is attached to another member that is disposed on either the first or second side of the pore, the head region of the tether can be said to be adjacent to the pore. The head region can be, but need not necessarily be, located at an end of the tether.

As used herein, "anchored" is intended to mean an attachment between a first member and a second member that is permanent, e.g., is sufficiently stable as to be useful for detecting an event or, e.g., is movable but undergoes no net movement under the conditions in which the attached members are used. In some embodiments, such a permanent attachment is normally irreversible under the conditions in which the attached members are used, for example, in a detection method. In other embodiments, such a permanent attachment is reversible but persists for at least the period of time in which it is used for detecting an event. For example, a tether can be permanently attached to or adjacent to a pore during use of the tether to detect an event, and can be subsequently removable or replaceable with another tether. Covalent bonds are only one example of an attachment that suitably can be used to anchor a first member to a second member. Other examples include duplexes between oligonucleotides, peptide-peptide interactions, and streptavidin-biotin or streptavidin-desthiobiotin.

As used herein, a "tail region" of a tether is intended to mean a portion of the tether that is disposed distally from the head region. The tail region can extend freely away from the head region, e.g., can be unattached to any other member. The tail region alternatively can be attached. Such attachment can be formed via a chemical bond, e.g., via a covalent bond, hydrogen bond, ionic bond, dipole-dipole bond, London dispersion forces, or any suitable combination thereof. In one embodiment, such attachment can be formed through hybridization of a first oligonucleotide of the tail region to a second nucleotide of another member. Alternatively, such attachment can be formed using physical or biological interactions e.g., an interaction between a first protein structure of the tail region and a second protein structure of the other member that inhibits detachment of the tail region from the other member. Any member to which the tail region is attached can be, but need not necessarily be, the same member to which the head region is attached. The tail region can be, but need not necessarily be, located at an end of the tether.

As used herein, an "elongated body" is intended to mean a portion of a member, such as a tether, that is sufficiently long and narrow to be disposed within at least a portion of an aperture of a pore. When an elongated body is attached to a nucleotide being acted upon, such an elongated body can be referred to as an "elongated tag" so as to facilitate distinction from an elongated body of a tether. An elongated body can be formed of any suitable material of biological origin or nonbiological origin, or a combination thereof. In one example, the elongated body includes a polymer. Polymers can be biological or synthetic polymers. Exemplary biological polymers that suitably can be included within an elongated body include polynucleotides, polypeptides, polysaccharides, polynucleotide analogs, and polypeptide analogs. Exemplary polynucleotides and polynucleotide analogs suitable for use in an elongated body include DNA, enantiomeric DNA, RNA, PNA (peptide-nucleic acid), morpholinos, and LNA (locked nucleic acid). Exemplary synthetic polypeptides can include charged amino acids as well as hydrophilic and neutral residues. Exemplary synthetic polymers that suitably can be included within an elongated body include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(w-alkenoic acid esters), poly(alkyl methacrylates), and other polymeric chemical and biological linkers such as described in Hermanson, Bioconjugate Techniques, third edition, Academic Press, London (2013). Additionally, an elongated body optionally can include a moiety that can interact with another moiety. Such moieties can include biological polymers DNA, RNA, PNA, LNA, morpholinos, or enantiomeric DNA, for example. Regions of the elongated body can be charged or neutral depending on the particular implementation of the reporter readout.

As used herein, a "reporter region" is intended to mean a moiety that is, upon relatively small movements, detectable using a suitable detection method or system. Such movements can be approximately 10 nm or less, or approximately 5 nm or less, or approximately 2 nm or less, or approximately 1 nm or less, or approximately 0.5 nm or less, or approximately 0.2 nm or less, or even approximately 0.1 nm or less, and can be detected using the reporter region and a suitable detection method or system. The moiety can have a detectable physical, chemical, electrical, optical, or biological property or other suitable flux blockade property. For example, the moiety can have an optical property that facilitates optical detection or characterization. Optical properties include fluorescence and generation of a Raman signal. In one illustrative example, the moiety is a fluorescent resonance energy transfer (FRET) donor or acceptor that interacts with a corresponding FRET acceptor or donor so as to emit light of a particular wavelength that can be detected. The donor and acceptor can be considered to be FRET pair partners. Or, for example, the moiety can have an electrical or flux blockade property. Electrical or flux blockade properties include electrostatic charge, e.g., a positive charge, or a negative charge. Or, for example, the moiety can have a physical property. Physical properties include the volume and shape of the moiety. In one illustrative example, movement of the moiety within the aperture causes a measurable change in current or flux through an aperture, or an optional constriction therein, by modulating a blockage current or flux through the aperture or constriction. Or, for example, the moiety can have a chemical or biological property that facilitates chemical or biological detection. Chemical or biological properties include presence of a chemical or biological group, e.g., a radioactive group or a group having enzymatic activity. One or more electrical, physical, chemical, biological, or other flux blockade properties of the moiety can provide a measurable change in current through an aperture or constriction, a measurable change in flux of molecules through an aperture or constriction, or an optical signal. In one illustrative example, movement of the moiety within an aperture causes a measurable change in a current through an aperture or constriction, or causes a measurable change in flux of molecules through an aperture or constriction, which change in flux can be electrically, chemically, biologically, or optically detectable. An abasic nucleotide is one nonlimiting example of a moiety the movement of which can cause a measurable change in a current through an aperture or constriction or a measurable change in flux of molecules through an aperture or constriction.

As used herein, an "event" is intended to mean an action having an associated effect. In the present context, an action can include, but is not limited to, the motion of a molecule or a portion of that molecule, and the effect can be any result of such motion. "Motion" or "movement" can be translational, rotational, or conformational, or a combination thereof. An exemplary effect of such motion can include the movement of a reporter region within a nanopore aperture or constriction. For example, an event can include the translational motion of a molecule, or a rotational change of a molecule, or a conformational change of a molecule. Or, for example, an event can include an interaction between a first molecule and a second molecule. An exemplary effect associated with such an event can be a conformational change of the first molecule, of the second molecule, or of both the first and second molecules. An event also can include the concerted action of multiple molecules, or any portion of such concerted action. For example, an event can include a molecule entering an active site on a protein, and the protein experiencing a conformational change when acting upon the molecule. An event also can include, but is not limited to, a chemical change to a molecule or a portion of that molecule, and the effect can be any associated result of such a chemical change. Chemical changes can include removing a portion of the molecule, adding the molecule to another molecule, a first molecule binding or debinding from another molecule, modifying the molecule or a portion thereof, and formation or cleavage of a chemical bond, e.g., during polynucleotide synthesis, and the like. For example, an event can include adding a nucleotide to a polynucleotide, or hybridizing or dehybridizing two oligonucleotides. An event optionally can include both motion and chemical change of one or more molecules. Exemplary effects of any such events can include the movement of a reporter region within a pore aperture or constriction or a reporter region becoming disposed in a particular location within a nanopore aperture or constriction. As nonlimiting, purely illustrative examples, an event can include one or more of: a polymerase testing a nucleotide, the polymerase rejecting a nucleotide if the nucleotide is a mismatch to the next nucleotide in a polynucleotide that is being sequenced, the polymerase excising a nucleotide from a polynucleotide using exonuclease activity, and the polymerase excising a nucleotide from a polynucleotide using pyrophosphorylysis. FIG. 25 illustrates exemplary reaction parameters, e.g., rate constants and dwell times, for reaction schemes in which a nucleotide respectively being acted upon by a polymerase is a match or a mismatch (adapted from Johnson, "The kinetic and chemical mechanism of high-fidelity DNA polymerases," Biochim Biophys Acta 1804(5): 1041-1048 (2010), the entire contents of which are incorporated by reference herein). Polymerases such as T7 Pol typically discriminate between match and mismatch nucleotides based on a combination of increased binding affinity for the correct match nucleotide (e.g., approximately 10-fold preference correct vs. mismatch), greatly reduced catalytic rate for mismatch nucleotide (e.g., approximately 1000-fold slower for mismatch), and a greatly increased off-rate for the mismatch nucleotide from the closed catalytic state (e.g., approximately 300-fold faster for mismatch).

As used herein, a "conformational change" is intended to mean a change in shape of a molecule (e.g., a change in relative atomic coordinates of a molecule). Such a conformational change can include a portion of a molecule moving relative to another portion of the molecule. The chemical reactivity of a portion of the molecule can change responsive to the relative motion of that portion, or another portion, of the molecule. A molecule can undergo a conformational change responsive to a stimulus. Such a stimulus can include, but is not limited to, changes to or forces applied to the molecule, interactions with other molecules, or environmental factors. Changes to or forces applied to the molecule can include a physical force applied to the molecule or a portion thereof, an electrical field applied to the molecule, or a chemical reaction with the molecule or a portion thereof, or a combination thereof, e.g., binding of a substrate, catalysis, and/or release of a product. Interactions with other molecules can include the presence of another molecule, a concentration of another molecule, an action by or upon another molecule, or a combination thereof. An exemplary interaction with another molecule includes hybridization of two oligonucleotides, or a polymerase acting upon a nucleotide. Environmental factors can include a change in pH or a change in temperature, or a combination thereof.

As used herein, the term "nucleotide" is intended to mean a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

The term "nucleotide" also is intended to encompass any "nucleotide analogue" which is a type of nucleotide that includes a modified nucleobase, sugar and/or phosphate moiety compared to naturally occurring nucleotides. Exemplary modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

Exemplary nucleotides modified at a phosphate moiety include, for example, the nucleotide analogues described by Lee et al., "Synthesis and reactivity of novel γ-phosphate modified ATP analogues," Bioorganic & Medicinal Chemistry Letters 19: 3804-3807 (2009); Kumar et al, "PEG-labeled nucleotides and nanopore detection for single molecule DNA sequencing by synthesis," Scientific Reports 2: 684 (2012); Kumar et al., "Terminal phosphate labeled nucleotides: synthesis, applications, and linker effect on incorporation by DNA polymerases," Nucleosides, Nucleotides, and Nucleic Acids 24: 401-408 (2005), and Mulder et al., "Nucleotide modification at the γ-phosphate leads to the improved fidelity of HIV-1 reverse transcriptase," Nucleic Acids Research 33: 4865-4873 (2005), the entire contents of which are incorporated by reference herein. Lee et al. describes certain exemplary γ-phosphate modified ATP analogues having the following structures:

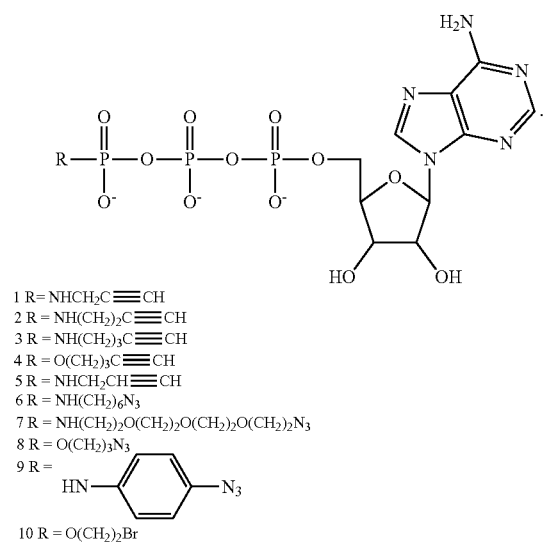

Kumar et al. (2012) discloses different length PEG-coumarin tags which can be attached to the terminal phosphate of dNTP or NTP (dNTP/NTP) or to the terminal phosphate of tetraphosphate nucleotides (dN4P/4P). Exemplary lengths include, for example, coumarin-$PEG_{16}$-dN4P/N4P, coumarin-$PEG_{20}$-dN4P/N4P, coumarin-$PEG_{24}$-dN4P/N4P, and coumarin-$PEG_{36}$-dN4P/N4P. Kumar et al. (2005) discloses tetra- and penta-phosphate-modified nucleotides including dyes attached with or without linkers. As described in Kumar et al. (2005) exemplary dyes attached without linkers include DDAO, RESORUFIN, COUMARINS, alkyl-XANTHENES, nitrophenol, hydroxy-indole, ELF, and BBT; exemplary dyes attached via linkers include R110, REG, TAMRA, ROX, Cy dyes, and ET dyes; and exemplary linkers include diaminopropane, diaminoheptane, diaminododecane, EEA, PAP, diaminocyclohexane, diamino-xylene, and penta-lysine. Mulder et al. discloses chemically modified nucleotides including 1-aminonaphthalene-5-sulfonate (ANS) attached to the γ-phosphate of a nucleotide, e.g., γ-P-aminonaphthalene-5-sulfonate deoxy or ribonucleotides (dNTP or NTP) such as ANS-ATP, ANS-CTP, ANS-GTP, and ANS-TTP and/or the deoxy forms of these or other nucleotides.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. The precise sequence of nucleotides in a polynucleotide can be known or unknown. The following are exemplary examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "hybridize" is intended to mean noncovalently binding a first polynucleotide to a second polynucleotide. The strength of the binding between the first and second polynucleotides increases with the complementarity between those polynucleotides.

As used herein, the term "protein" is intended to mean a molecule that includes, or consists of, a polypeptide that is folded into a three-dimensional structure. The polypeptide includes moieties that, when folded into the three-dimensional structure, impart the protein with biological activity.

As used herein, the term "enzyme" is intended to mean a molecule that catalytically modifies another molecule. Enzymes can include proteins, as well as certain other types of molecules such as polynucleotides. Examples of enzymes that also are proteins include polymerases, exonucleases and helicases.

As used herein, a "polymerase" is intended to mean an enzyme having an active site that assembles polynucleotides by polymerizing nucleotides into polynucleotides. A polymerase can bind a primed single stranded polynucleotide template, and can sequentially add nucleotides to the growing primer to form a polynucleotide having a sequence that is complementary to that of the template.

Exemplary Compositions

Some exemplary compositions including various configurations of tethers anchored to or adjacent to nanopores now will be described with reference to FIGS. 1A-1M. Under one aspect, a composition includes a nanopore including a first side, a second side, and an aperture extending through the first and second sides; and a permanent tether including a head region, a tail region, and an elongated body disposed therebetween. The head region can be anchored to or adjacent to the first side or second side of the nanopore.

For example, FIG. 1A schematically illustrates a cross-section of an exemplary composition that includes nanopore 100 and permanent tether 110. Nanopore 100 includes first side 101, second side 102, aperture 103, and optional constriction 104. Permanent tether 110 includes head region 111, tail region 112, and elongated body 113. In the embodiment illustrated in FIG. 1A, head region 111 is anchored to first side 101 of nanopore 100, tail region 112 is disposed on first side 101 of nanopore 100 and extends freely toward second side 102 of nanopore 100, and elongated body 113 is movable within aperture 103 of nanopore 100. However, nanopore 100 or tether 110, or both, can have different configurations than illustrated in FIG. 1A, such as exemplified herein.

Head region 111, tail region 112, and elongated body 113 of tether 110 can include any suitable material or combination of materials. For example, head region 111 can be configured so as to be anchored to first side 101 via a chemical bond, e.g., via a covalent bond, hydrogen bond, ionic bond, dipole-dipole bond, London dispersion forces, or any suitable combination thereof. For example, head region 111 can include a first moiety that is bonded, e.g., covalently, to a second moiety of first side 101. Exemplary covalent bonds that can anchor head region 111 to first side 101 include carbon-carbon bonds, carbon-nitrogen bonds, carbon-oxygen bonds, oxygen-oxygen bonds, sulfur-sulfur bonds, phosphorus-oxygen bonds, phosphorus-sulfur bonds, amide bonds, thioether bonds, hydrazide bonds, carbon-sulfur bonds, and bonds that result from the reaction of oxyamine with carbonyls (aldehydes and ketones), of Staudinger reagent pairs such as phosphine and azides, or click chemistry pairs such as azides and alkynes. However, the attachment need not be covalent. For example, such attachment can be formed through hybridization of a first oligonucleotide of the head region to a second nucleotide of another member. Alternatively, such attachment can be formed using physical or biological interactions, e.g., an interaction between a first protein structure of the head region and a second protein structure of another member that inhibits detachment of the head region from the other member. For example, head region 111 can include a first alpha helix and first side 101 can include a second alpha helix that locks to head region 111 so as to inhibit dissociation of head region 111 from first side 101. Interactions between receptors and ligands are also useful, examples of which include avidin-biotin, or analogs thereof antibody-epitope; lectin-carbohydrate, and the like.

Elongated body 113 can be attached, e.g., covalently bonded, to head region 111, and tail region 112 can define an end of elongated body 113 that is distal from head region 111. Elongated body 113 can include any suitable material of biological origin or a nonbiological origin, or a combination thereof. As described in greater detail below, elongated body 113 optionally can include one or more reporter regions that facilitate detection or movement of the elongated body, or can include one or more moieties that interact with other molecules, or can include one or more of such reporter regions and one or more of such moieties. Other regions of elongated body 113 can be substantially inert, so as to inhibit interaction of such regions with other molecules in a manner that otherwise can cause movement of elongated body 113 relative to such molecules or relative to nanopore 100. Exemplary biological materials that can be included within elongated body 113 include biological polymers such as polynucleotides, polypeptides, polysaccharides, and analogs of the aforementioned. Exemplary synthetic polymers that suitably can be included within elongated body 113 include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(w-alkenoic acid esters), poly(alkyl methacrylates), and other polymeric chemical and biological linkers such as described in Hermanson et al., mentioned further above.

Nanopore 100 can have any suitable configuration that permits anchoring of head region 111 to first side 101 of nanopore 100. In some embodiments, nanopore 100 can be a biological pore, solid state pore, or a biological and solid state hybrid pore. A biological pore is intended to mean a pore that is made from one or more materials of biological origin. "Biological origin" refers to material derived from or isolated from a biological environment such as an organism or cell, or a synthetically manufactured version of a biologically available structure. Biological pores include, for example, polypeptide pores and polynucleotide pores.

A polypeptide pore is intended to mean a pore that is made from one or more polypeptides. The one or more polypeptides can include a monomer, a homopolymer or a heteropolymer. Structures of polypeptide pores include, for example, an α-helix bundle pore and a β-barrel pore as well as all others well known in the art. Exemplary polypeptide pores include α-hemolysin, *Mycobacterium smegmatis* porin A, gramicidin A, maltoporin, OmpF, OmpC, PhoE, Tsx, F-pilus, SP1, mitochondrial porin (VDAC), Tom40, outer membrane phospholipase A, and *Neisseria* autotransporter lipoprotein (NaIP). "*Mycobacterium smegmatis* porin A (MspA)" is a membrane porin produced by Mycobacteria, allowing hydrophilic molecules to enter the bacterium. MspA forms a tightly interconnected octamer and transmembrane beta-barrel that resembles a goblet and includes a central constriction. For further details regarding α-hemolysin, see U.S. Pat. No. 6,015,714, the entire contents of which are incorporated by reference herein. For further details regarding SP1, see Wang et al., Chem. Commun., 49:1741-1743, 2013, the entire contents of which are incorporated by reference herein. For further details regarding MspA, see Butler et al., "Single-molecule DNA detection with an engineered MspA protein nanopore," Proc. Natl. Acad. Sci. 105: 20647-20652 (2008) and Derrington et al., "Nanopore DNA sequencing with MspA," Proc. Natl. Acad. Sci. USA, 107:16060-16065 (2010), the entire contents of both of which are incorporated by reference herein. Other pores include, for example, the MspA homolog from *Norcadia farcinica*, and lysenin. For further details regarding lysenin, see PCT Publication No. WO 2013/153359, the entire contents of which are incorporated by reference herein.

A polynucleotide pore is intended to mean a pore that is made from one or more nucleic acid polymers. A polynucleotide pore can include, for example, a polynucleotide origami.

A solid state pore is intended to mean a pore that is made from one or more materials of non-biological origin. "Solid-state" refers to materials that are not of biological origin. A solid-state pore can be made of inorganic or organic materials. Solid state pores include, for example, silicon nitride pores, silicon dioxide pores, and graphene pores.

A biological and solid state hybrid pore is intended to mean a hybrid pore that is made from materials of both biological and non-biological origins. Materials of biological origin are defined above and include, for example, polypeptides and polynucleotides. A biological and solid state hybrid pore includes, for example, a polypeptide-solid state hybrid pore and a polynucleotide-solid state pore.

It should be appreciated that different types of nanopores can have different dimensions than one another in multiple respects. For example, as illustrated in FIG. 1A, nanopore 100 can be characterized as having a first dimension H1 defining a thickness of nanopore 100, e.g., a thickness between outer surface 105 of first side 101 and outer surface 106 of second side 102, adjacent to aperture 103. In embodiments in which nanopore 100 includes optional constriction 104, nanopore 100 also can be characterized as having a second dimension H2 defining a constriction depth, e.g., a depth between outer surface 105 of first side 101 and the narrowest portion of constriction 104, adjacent to aperture 103. Nanopore 100 also can be characterized as having a first diameter D1 defining a diameter of aperture 103, e.g., a diameter of aperture 103 at the aperture's widest point. In embodiments in which nanopore 100 includes optional constriction 104, nanopore 100 also can be characterized as having a second diameter D2 defining a constriction diameter, e.g., a diameter of constriction 104 at the constriction's narrowest point. It should be appreciated that such dimensions of nanopore 100 should not be construed as limiting, and that other dimensions of nanopore 100 can be suitably defined. For example, first dimension H1 of nanopore 100 can vary along the lateral dimension, e.g., if nanopore 100 includes a relatively thin barrier in which a relatively thick pore is disposed, such as illustrated in FIG. 1K. Or, for example, in embodiments in which nanopore 100 includes optional constriction 104, second dimension H2 of nanopore 100 can vary depending on the relative location of constriction 104 to outer surface 105 of first side 101. That is, optional constriction 104 can be located disposed at any suitable location within nanopore 100, and indeed can even be disposed distal to first outer surface 105 or outer surface 106 of second side 102. FIGS. 1J and 1K, discussed in greater detail below, illustrate non-limiting, exemplary locations of optional constriction 104. Aperture 103 and optional constriction 104 need not necessarily be perfectly circular, and still can be characterized as having an approximate diameter or using any other suitable dimensions. Moreover, nanopore 100 can include multiple constrictions, each of which suitably can be characterized using appropriate dimensions.

In some embodiments, first dimension H1 of nanopore 100 is about 100 nm or smaller, or about 50 nm or smaller, or about 20 nm or smaller, or about 10 nm or smaller, or about 5 nm or smaller, or about 2 nm or smaller. For example, H1 can be between about 2 nm and about 100 nm, or between about 5 nm and about 50 nm, or between about 10 nm and about 20 nm. In embodiments that include optional constriction 104, second dimension H2 of nanopore 100 is about 100 nm or smaller, or about 50 nm or smaller, or about 20 nm or smaller, or about 10 nm or smaller, or about 5 nm or smaller, or about 2 nm or smaller, or about 1 nm or smaller. For example, H2 can be between about 1 nm and about 100 nm, or between about 2 nm and about 50 nm, or between about 5 nm and about 20 nm. Illustratively, H1 can be between about 5 nm and about 50 nm, and H2 (if applicable) can be between about 1 nm and about 5 nm. In one exemplary embodiment, H1 is about 10 nm and H2 is about 5 nm. In another exemplary embodiment, H1 is about 10 nm and H2 is about 6 nm. In another exemplary embodiment, H1 is about 10 nm and H2 is about 7 nm. In another exemplary embodiment, H1 is about 10 nm and H2 is about 8 nm. In another exemplary embodiment, H1 is about 10 nm and H2 is about 9 nm. In another exemplary embodiment, H1 is about 10 nm and H2 is about 10 nm. In another exemplary embodiment, H1 is about 5 nm and H2 is about 2 nm. In another exemplary embodiment, H1 is about 5 nm and H2 is about 3 nm. In another exemplary embodiment, H1 is about 5 nm and H2 is about 4 nm. In another exemplary embodiment, H1 is about 5 nm and H2 is about 5 nm. The terms "approximately" and "about" are intended to mean within 10% above or below the stated value.

In some embodiments, first diameter D1 of aperture 103 of nanopore 100 is about 100 nm or smaller, or about 50 nm or smaller, or about 20 nm or smaller, or about 10 nm or smaller, or about 5 nm or smaller, or about 2 nm or smaller. For example, D1 can be between about 2 nm and about 100 nm, or between about 5 nm and about 50 nm, or between about 10 nm and about 20 nm. In embodiments including optional constriction 104, second diameter D2 of constriction 104 of nanopore 100 is about 100 nm or smaller, or about 50 nm or smaller, or about 20 nm or smaller, or about 10 nm or smaller, or about 5 nm or smaller, or about 2 nm or smaller, or about 1 nm or smaller. For example, D2 can be between about 1 nm and about 100 nm, or between about 2 nm and about 50 nm, or between about 5 nm and about 20 nm. Illustratively, D1 can be between about 5 nm and about 50 nm, and D2 (if applicable) can be between about 1 nm and about 5 nm.

In one illustrative embodiment, D1 is about 5 to 10 nm, and D2 is about 1 to 1.2 nm. In another illustrative embodiment, D1 is about 5 to 10 nm, and D2 is about 1.2 to 1.4 nm. In yet another illustrative embodiment, D1 is about 5 to 10 nm, and D2 is about 1.4 to 1.6 nm. In yet another illustrative embodiment, D1 is about 5 to 10 nm, and D2 is about 1.6 to 1.8 nm. In yet another illustrative embodiment, D1 is about 5 to 10 nm, and D2 is about 1.8 to 2.0 nm. In exemplary embodiments where the pore is MspA, D1 can be, for example, about 4.8 nm, D2 can be, for example, about 1.1 to 1.2 nm, H1 can be, for example, about 9.6 nm, and H2 can be, for example, about 7.9 to 8.1 nm. In exemplary embodiments where the pore is α-hemolysin, D1 can be, for example, about 2.6 nm, D2 can be, for example, about 1.4 to 1.5 nm, H1 can be, for example, about 10 nm, and H2 can be, for example, about 5 nm. Other suitable combinations of dimensions suitably can be selected for other types of pores.

The characteristics of permanent tether 110 can be suitably selected based on one or more of the dimensions of nanopore 100. For example, elongated body 113 of tether 110 can have a width selected based on D1 or D2 (if applicable), or both D1 and D2 (if applicable). For example, the width of elongated body 113 can be selected such that elongated body 113 is movable within aperture 103 responsive to an event or other stimulus, e.g., elongated body 113 has a width that is smaller than first diameter D1 of aperture 103. In embodiments that include optional constriction 104, the width of elongated body 113 also can be selected such that at least a portion of elongated body 113 is movable adjacent to constriction 104, e.g., has a width that is equal to, or smaller than, second diameter D2. Optionally, in embodiments that include constriction 104, the width of elongated body 113 also can be selected such that at least a portion of elongated body 113 is movable through constriction 104, e.g., has a width that is sufficiently smaller than second diameter D2 to permit movement of elongated body 113 through constriction 104, e.g., responsive to an event or other stimulus. If nanopore 100 includes multiple constrictions (not specifically illustrated), then the width of elongated body 113 can be selected such that elongated body 113 is movable through some or all of such constrictions as appropriate.

The length of elongated body 113 of tether 110 can be selected based on H1 or H2 (if applicable), or both H1 and H2 (if applicable). For example, the length of elongated body 113 can be selected so as to be shorter than H1, so that tail region 112 would not extend beyond outer surface 106 of the second side 102 of nanopore 100 even if elongated body 113 were fully extended through constriction 104 toward second side 102. Or, for example, in embodiments including optional constriction 104, the length of elongated body 113 can be selected so as to be shorter than H2, so that tail region 112 would not extend beyond constriction 104 of nanopore 100 even if elongated body 113 were fully extended toward second side 103. In other embodiments, the length of elongated body 113 can be selected so as to be longer than H1, so that tail region 112 would extend beyond outer surface 106 of the second side 102 of nanopore 100 if elongated body 113 were fully extended through constriction 104 toward second side 102. Or, for example, in embodiments that include optional constriction 104, the length of elongated body 113 can be selected so as to be longer than H2, so that tail region 112 would extend beyond constriction 104 of nanopore 100 if elongated body 113 were fully extended toward second side 103.

The length of elongated body 113 can be selected so as to permit relatively free movement of elongated body 113 within aperture 103, at least on first side 101 of nanopore 100, substantially without steric hindrance or other interference caused by the elongated body itself. That is, elongated body 113 can be configured so as to occupy only a portion of the volume of aperture 103 on first side 101 of nanopore 100, e.g., so as to occupy less than 50% of the volume of aperture 103 on first side 101 of nanopore 100, or less than 20% of the volume of aperture 103 on first side 101 of nanopore 100, or less than 10% of the volume of aperture 103 on first side 101 of nanopore 100, or less than 5% of the volume of aperture 103 on first side 101 of nanopore 100, or less than 1% of the volume of aperture 103 on first side 101 of nanopore 100. Additionally, in the embodiment illustrated in FIG. 1A, tail region 112 of tether 110 can be unattached to nanopore 100 or to any other member, thus permitting relatively free movement of the entirety of elongated body 113 relative to head region 111.

Although FIG. 1A illustrates one exemplary arrangement of the components of nanopore 100 and permanent tether 110, it should be understood that other arrangements suitably can be used. For example, head region 111 of permanent tether 110 instead can be anchored to second side 102. Or, for example, head region 111 of permanent tether 110 instead can be anchored adjacent to either first side 101 or second side 102 of nanopore 100. Or, for example, tail region 112 of permanent tether 110 instead can be disposed on second side 102 of nanopore 100. Or, for example, tail region 112 of permanent tether 110 instead can be anchored to either the first side 101 or second side 102 of nanopore 100. Or, for example, elongated body 113 of permanent tether 110 can include a reporter region, or a moiety that can bond to another molecule, or both a reporter region and a moiety that can bond to another molecule. Some of such combinations of features are described herein, but it should be appreciated that all such combinations of features are contemplated and readily can be envisioned based on the teachings herein.

Figure 1B:
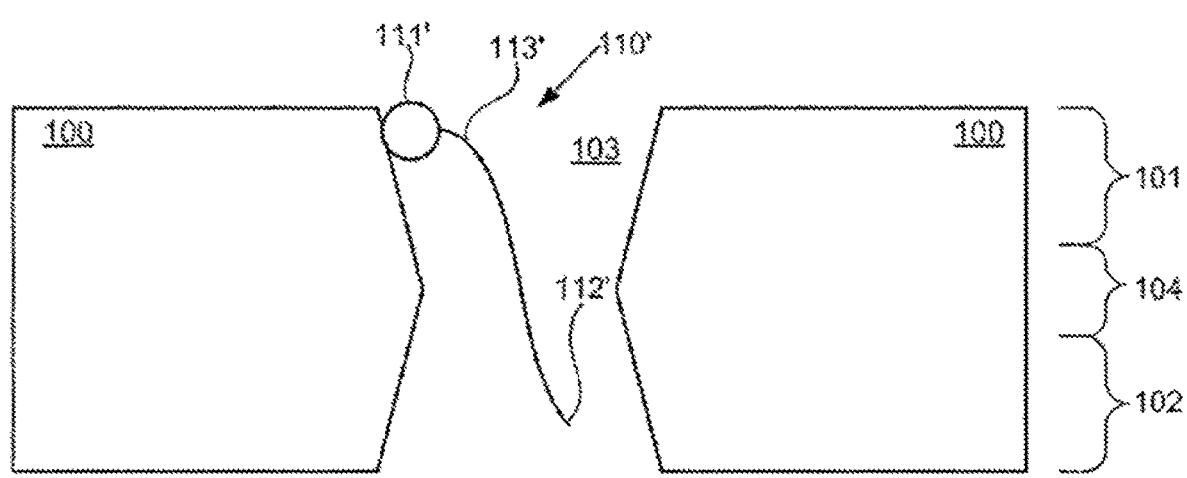

For example, FIG. 1B illustrates an alternative composition that includes nanopore 100 and alternative tether 110' having head region 111', tail region 112', and elongated body 113'. Head region 111' is anchored to first side 101 of nanopore 100. Tail region 112' extends freely toward second side 102 of nanopore 100 in a manner analogous to that illustrated in FIG. 1A, except that elongated body 113' is sufficiently long that tail region 112' can be disposed on second side 102 of nanopore 100. Constriction 104 is optional.

Under another aspect, a composition includes a nanopore including a first side, a second side, and an aperture extending through the first and second sides; and a permanent tether including a head region, a tail region, and an elongated body disposed therebetween. The head region can be anchored to or adjacent to the first side or second side of the nanopore. The elongated body including a reporter region can be movable within the aperture responsive to a first event occurring adjacent to the first side of the nanopore. The reporter region can be translationally movable within the aperture responsive to the first event. Additionally, or alternatively, the reporter region can be rotationally movable within the aperture responsive to the first event. Additionally, or alternatively, the reporter region can be conformationally movable within the aperture responsive to the first event.

Figure 1C:
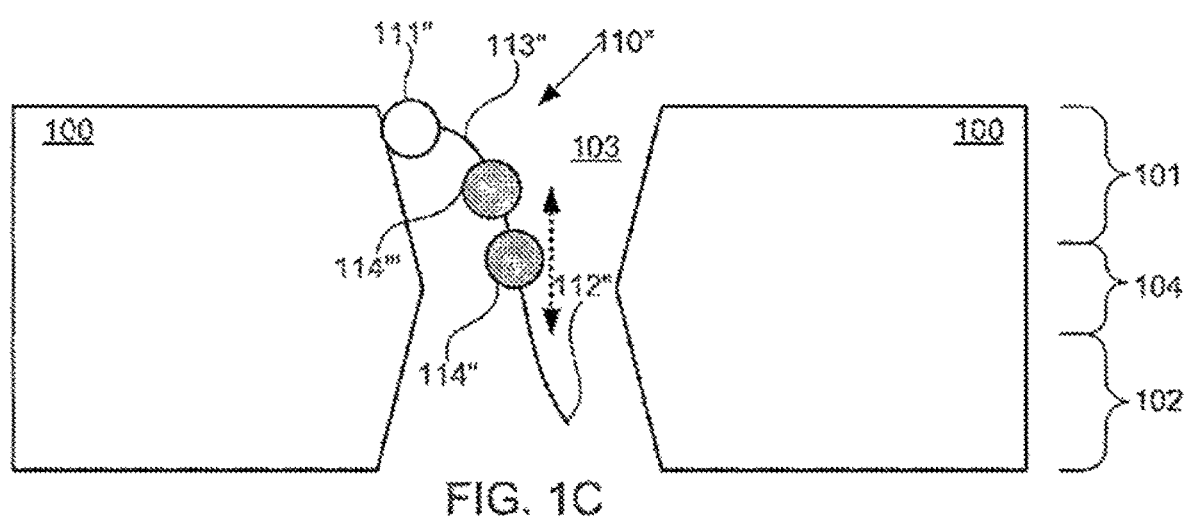

For example, FIG. 1C illustrates an alternative composition that includes nanopore 100 and alternative tether 110" having head region 111", tail region 112", and elongated body 113". Head region 111" is anchored to first side 101 of nanopore 100. Tail region 112" extends freely toward second side 102 of nanopore 100, and elongated body 113" is sufficiently long that tail region 112" can be disposed on second side 102 of nanopore 100. Additionally, elongated body 113" includes a first reporter region 114", which facilitates measurement of the translational, rotational, or conformational movement of elongated body 113", e.g., movement relative to optional constriction 104 in embodiments that include such a constriction. For example, first reporter region 114" can have a different physical, chemical, optical, electrical, biological, or other suitable flux blockade property than one or more other regions of elongated body 113". Translational, rotational, or conformational movement of first reporter region 114", represented in FIG. 1C by the dashed arrow, can be detectable using one or more techniques described herein, known in the art, or yet to be developed. Optionally, elongated body 113" can include more than one reporter region, e.g., can include second reporter region 114'". Elongated body 113" can include any suitable number of reporter regions, e.g., one, or two, or three, or four, or five, or more than five reporter regions. Each such reporter region can be the same as each other reporter region. Alternatively, each such reporter region can be different than each other reporter region. Or, some reporter regions can be the same as one another, while other reporter regions can be different than one another.

In certain embodiments, first reporter region 114" and optional second reporter region 114'" are translationally movable toward first side 101 of nanopore 100 responsive to a first event. First reporter region 114" and optional second reporter region 114'" also can be translationally movable toward second side 102 of nanopore 100 after the first event. First reporter region 114" and optional second reporter region 114'" also can be translationally movable toward first side 101 of nanopore 100 responsive to a second event after the first event, and again translationally movable toward second side 102 of nanopore 100 after the second event. The first or second event, or both, can occur adjacent to the first side of the nanopore. In embodiments that include optional constriction 104, first reporter region 114" can be disposed at a location along elongated body 113" that is selected such that, based upon elongated body 113" being fully or partially extended, first reporter region 114" is positionable adjacent to or within constriction 104. Additionally, optional second reporter region 114'" can be disposed at a location along elongated body 113" that is selected such that, based upon elongated body 113" being fully or partially extended, second reporter region 114" is positionable adjacent to or within constriction 104. In some embodiments, first reporter region 114'" is positionable adjacent to or within constriction 104 responsive to a first event, and second reporter region 114'" is positionable adjacent to or within constriction 104 responsive to a second event, and the first and second events are distinguishable from one another based on detecting whether the first reporter region 114" or the second reporter region 114'" is disposed adjacent to or within constriction 104. In one illustrative, non-limiting example, elongated body 113" includes a polynucleotide that includes one or more abasic nucleotides that define first reporter region 114" and optional second reporter region 114'" along a portion of the length of elongated body 113". An abasic nucleotide can be detected within an aperture of a nanopore as described, for example, in Wilson, "Electronic Control of DNA Polymerase Binding and Unbinding to Single DNA Molecules Tethered in a Nanopore," Ph.D. Thesis, University of California Santa Cruz (2009), the entire contents of which are incorporated by reference herein. Illustratively, movement or presence of one or more abasic nucleotides or other suitable reporter region(s) 114", 114'" can cause a measurable change in a current through aperture 103 or constriction 104, a measurable change in flux of molecules through aperture 103 or constriction 104, or an optical signal. For example, a change in a flux of molecules through aperture 103 or construction 104 can be detected electrically, chemically, biologically, or optically.

Figure 1D:
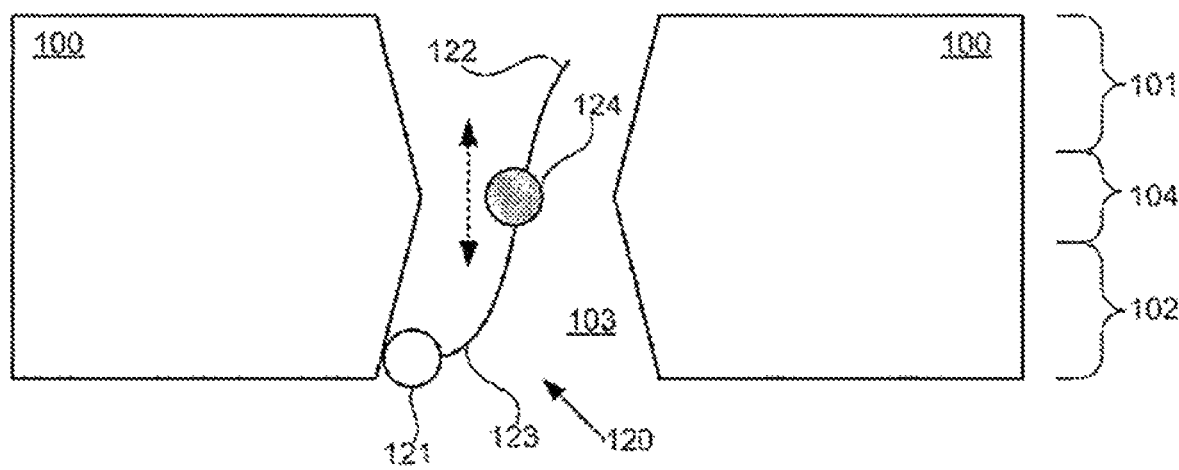

As another example, FIG. 1D illustrates an alternative composition that includes nanopore 100 and alternative tether 120 having head region 121, tail region 122, and elongated body 123. Head region 121 is anchored to second side 102 of nanopore 100. Tail region 122 extends freely toward first side 101 of nanopore 100, and elongated body 123 is sufficiently long that tail region 122 can be disposed on first side 101 of nanopore 100. However, it should be appreciated that tail region 122 instead can be disposed on second side 102 of nanopore 100, e.g., that elongated body 123 is of such a length that tail region 122 is disposed on second side 102 of nanopore 100 even if elongated body 123 is fully extended. Additionally, elongated body 123 includes reporter region 124, which facilitates measurements of translational, rotational, or conformational movement (or a combination thereof) of elongated body 124, e.g., as represented in FIG. 1D by the dashed arrow. In certain embodiments, reporter region 124 is translationally movable toward first side 101 of nanopore 100 responsive to a first event or other stimulus, and translationally movable toward second side 102 of nanopore 100 after the first event or other stimulus. Reporter region 124 also can be translationally movable toward first side 101 of nanopore 100 responsive to a second event or other stimulus after the first event or other stimulus, and again movable toward second side 102 of nanopore 100 after the second event or other stimulus. The first or second event, or both, can occur adjacent to the first side of the nanopore. The stimulus can include, for example, an applied voltage across nanopore 100. In embodiments that include optional constriction 104, reporter region 124 can in some embodiments be movable adjacent to or even through constriction 104, e.g., responsive to an event or other stimulus. It should be appreciated that elongated body 123 need not necessarily include reporter region 124.

Figure 1E:
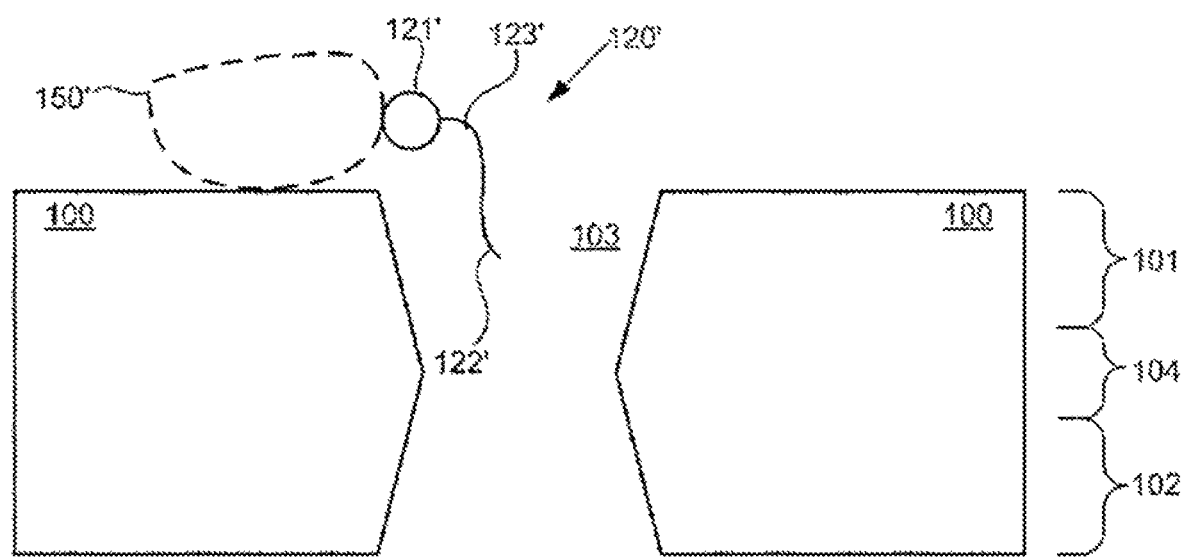

As another example, FIG. 1E illustrates an alternative composition that includes nanopore 100 and alternative tether 120' having head region 121', tail region 122', and elongated body 123'. Head region 121' is anchored adjacent to first side 101 of nanopore 100, e.g., is anchored to another member 150' that can have, but need not necessarily have, a substantially fixed position relative to nanopore 100, and can be disposed adjacent to nanopore 100. Tail region 122' extends freely toward second side 102 of nanopore 100 in a manner analogous to that illustrated in FIG. 1A. In the embodiment illustrated in FIG. 1E, tail region 122' is disposed on first side 101 of nanopore 100, e.g., elongated body 123' has a length selected such that tail region 122' is disposed on first side 101 of nanopore 100 even if elongated body 123' is fully extended. It should be appreciated that elongated body 123' instead can be sufficiently long that tail region 122' can be disposed on second side 102 of nanopore 100. Constriction 104 is optional. Head region 121' instead can be anchored to another member (not illustrated) disposed adjacent to second side 102 of nanopore 100.

Figure 1F:
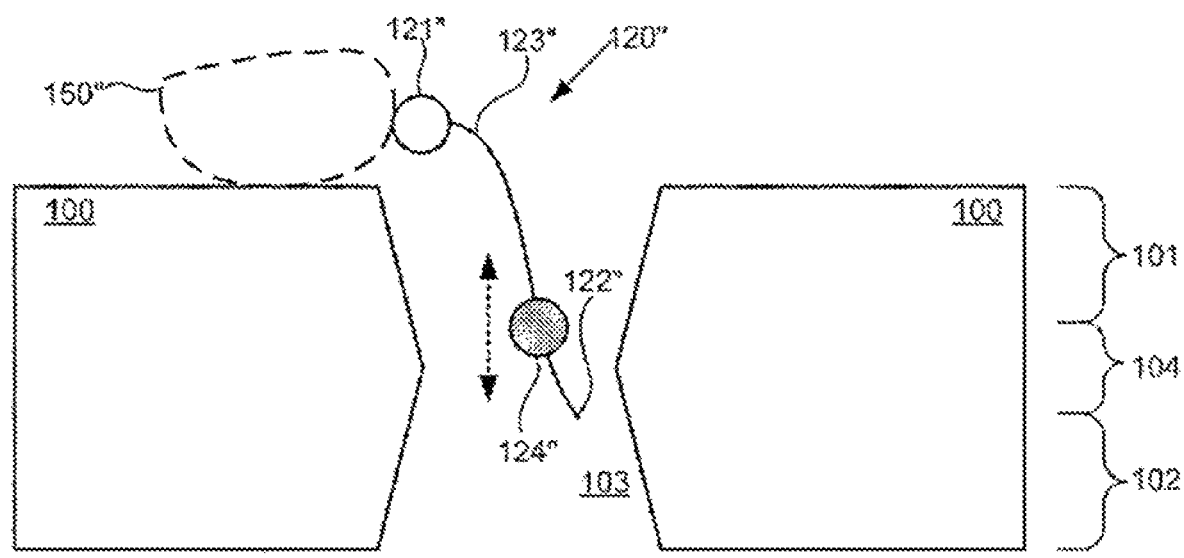

As another example, FIG. 1F illustrates an alternative composition that includes nanopore 100 and alternative tether 120" having head region 121", tail region 122", and elongated body 123". Head region 121" is anchored adjacent to first side 101 of nanopore 100, e.g., is anchored to another member 150" that can have, but need not necessarily have, a substantially fixed position relative to nanopore 100, and can be disposed adjacent to nanopore 100. Tail region 122" extends freely toward second side 102 of nanopore 100, and elongated body 123" is sufficiently long that tail region 122" can be disposed on second side 102 of nanopore 100. Additionally, elongated body 123" includes reporter region 124", which facilitates measurement of translational, rotational, or conformational movement of elongated body 113", e.g., as represented in FIG. 1F by the dashed arrow. In certain embodiments, reporter region 124" is translationally movable toward first side 101 of nanopore 100 responsive to a first event, and translationally movable toward second side 102 of nanopore after the first event. Reporter region 124" also can be translationally movable toward first side 101 of nanopore 100 responsive to a second event after the first event, and again translationally movable toward second side 102 of nanopore 100 after the second event. The first or second event, or both, can occur adjacent to the first side of the nanopore. In embodiments that include constriction 104, reporter region 124" can be translationally movable adjacent to or even through constriction 104, e.g., responsive to an event or other stimulus. Head region 121" instead can be anchored to another member (not illustrated) disposed adjacent to second side 102 of nanopore 100.

Figure 1G:
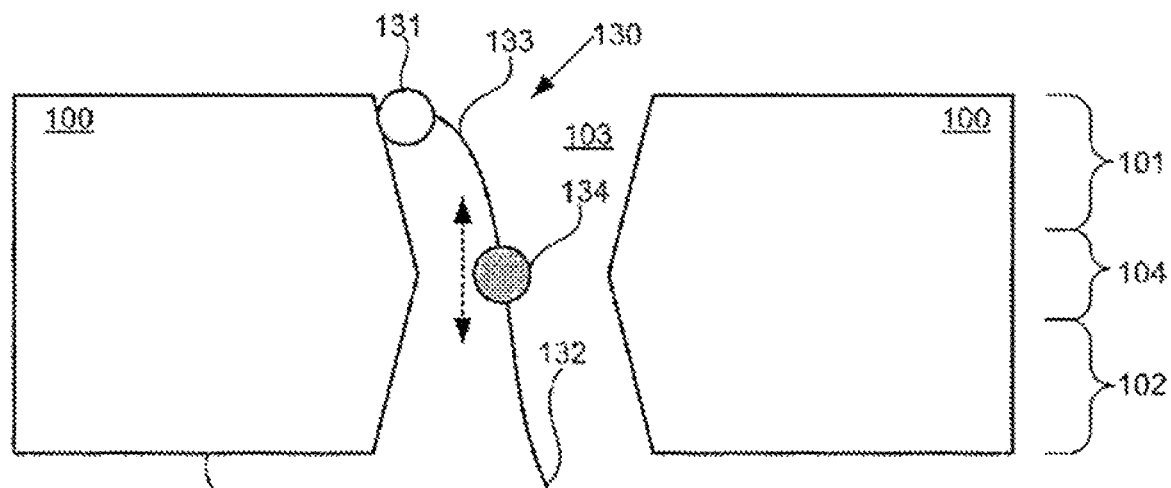

The lengths of the present elongated bodies suitably can be varied such that the present tail regions can be disposed at any suitable location relative to nanopore 100. For example, FIG. 1G illustrates an alternative composition that includes nanopore 100 and alternative tether 130 having head region 131, tail region 132, and elongated body 133. Head region 131 is anchored to first side 101 of nanopore 100. Tail region 132 extends freely toward second side 102 of nanopore 100, and elongated body 133 is sufficiently long that tail region 132 can be disposed beyond second side 102 of nanopore 100, e.g., beyond outer surface 106 of second side 102. Optionally, elongated body 133 also includes reporter region 134. Head region 131 instead can be anchored to second side 102 of nanopore 100, or adjacent to either the first side 101 or second side 102 of nanopore 100.

Figure 1H:
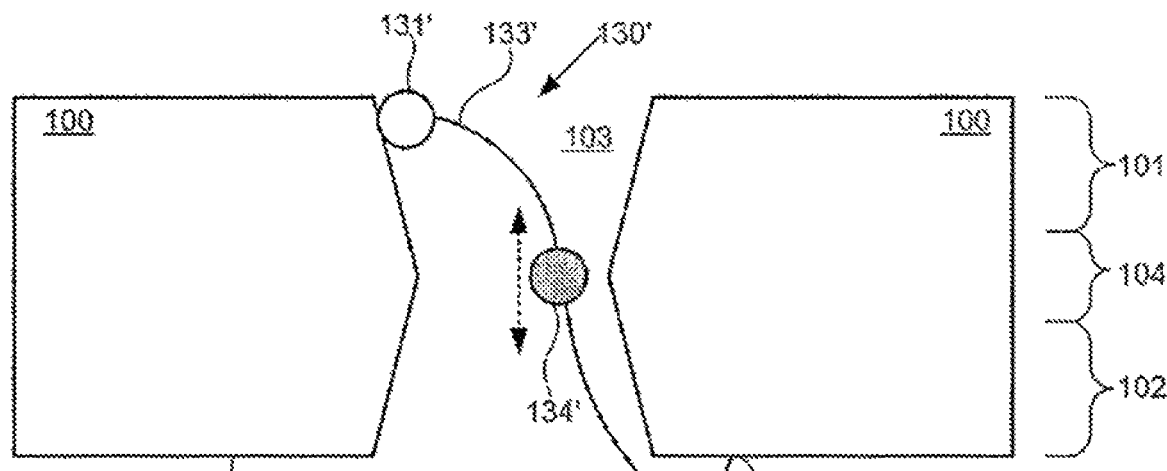

Additionally, the present tail regions need not necessarily extend freely, but instead can be attached to any suitable member. For example, FIG. 1H illustrates an alternative composition that includes nanopore 100 and alternative tether 130' having head region 131', tail region 132', and elongated body 133'. Head region 131' is anchored to first side 101 of nanopore 100, although head region 131' instead can be anchored adjacent to first side 101 of nanopore 100. Tail region 132' extends through aperture 103 of nanopore 100, and is anchored on second side 102 of nanopore 100, e.g., is anchored to outer surface 106 of second side 102, although tail region 132' instead can be anchored adjacent to second side 102 of nanopore 100. Elongated body 133' is sufficiently long to permit attachment of head region 131' to or adjacent to first side 101 of nanopore 100 and attachment of tail region 132' to or adjacent to second side 102 of nanopore 100. Optionally, elongated body 133 also includes reporter region 134'. Alternatively, head region 131' can be attached to, or adjacent to, second side 102 of nanopore 100 and tail region 132' can be attached to, or adjacent to, first side 101 of nanopore 100.

Figure 1I:
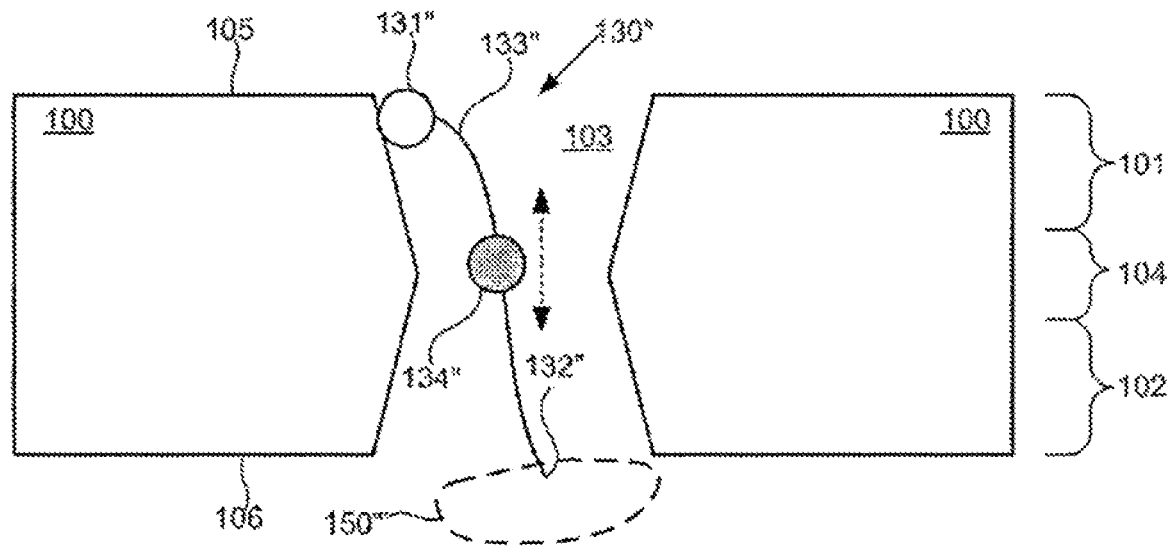
Figure 1J:
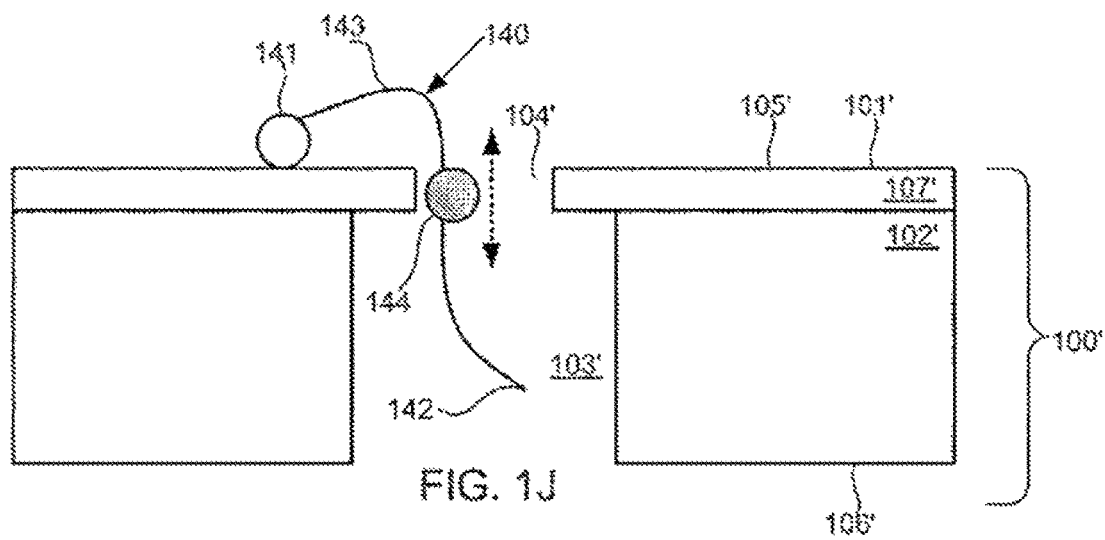
Figure 1K:
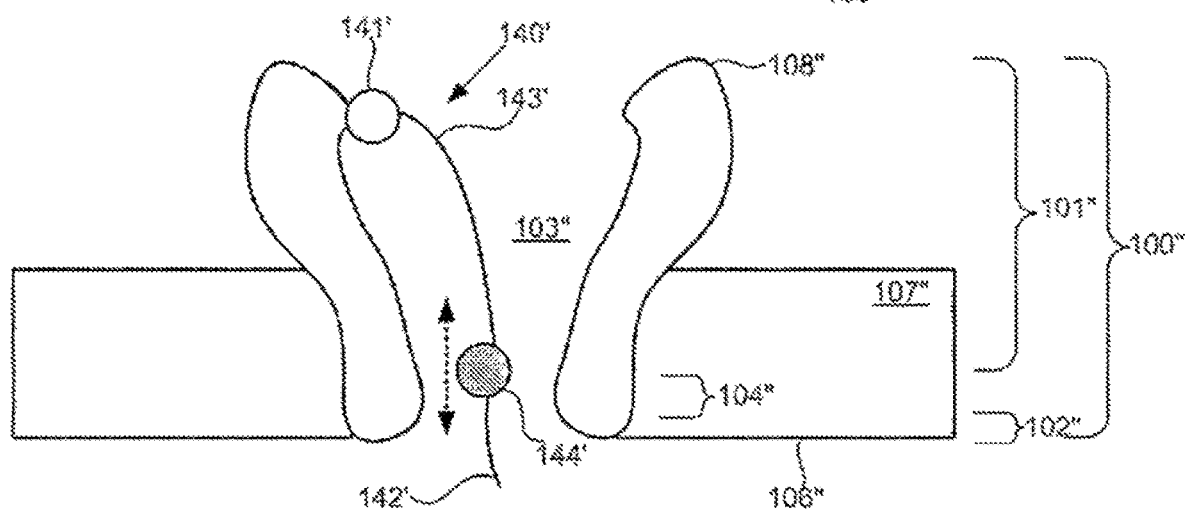

As another example, FIG. 1I illustrates an alternative composition that includes nanopore 100 and alternative tether 130" having head region 131", tail region 132", and elongated body 133". Head region 131" is anchored to first side 101 of nanopore 100, although head region 131" instead can be anchored adjacent to first side 101 of nanopore 100. Tail region 132" extends through aperture 103 of nanopore 100, and is attached adjacent to or beyond second side 102 of nanopore 100, e.g., is anchored to another member 150''' that is disposed adjacent to, or beyond, outer surface 106 of second side 102. Alternatively, member 150''' can be fully or partially disposed within aperture 103. Elongated body 133" is sufficiently long to permit attachment of head region 131" to or adjacent to first side 101 of nanopore 100 and attachment of tail region 132" to member 150''', e.g., adjacent to or beyond second side 102 of nanopore 100, or within aperture 103. Optionally, elongated body 133 also includes reporter region 134". Alternatively, head region 131" can be attached to or adjacent to second side 102 of nanopore 100 and tail region 132" can be attached adjacent to or beyond first side 101 of nanopore 100, e.g., can be anchored to another member (not illustrated) that is disposed adjacent to, or beyond, outer surface 105 of first side 101.

It should be appreciated that any suitable type of nanopore and any suitable type of permanent tether can be used in the embodiments illustrated in FIGS. 1A-1I. For example, as noted further above, the nanopore can include a biological pore, solid state pore, or a biological and solid state hybrid pore. FIG. 1J illustrates an exemplary composition that includes solid state nanopore 100' and tether 140 having head region 141, tail region 142, and elongated body 143. Nanopore 100' includes first side 101' and second side 102' that can include any suitable solid state material or combination of solid state materials. First side 101' can be defined by layer 107' that includes one or more solid state materials, and is disposed upon second side 102', which can include one or more solid state materials. Exemplary solid state materials suitable for use in first side 101' or second side 102', or both, include silicon (Si), silicon nitride (SiN or $SiN_x$), graphene, and silicon oxide ($SiO_2$ or $SiO_x$). In the illustrated embodiment, aperture 103' can be defined through second side 102', and constriction 104' can be defined through layer 107'. However, it should be appreciated that layer 107' and second side 102' can have any suitable configurations so as to define an aperture and a constriction region. Head region 141 is anchored to outer surface 105' of first side 101' of nanopore 100', although head region 141 instead can be anchored adjacent to first side 101' of nanopore 100', or can be anchored to or adjacent to second side 102' of nanopore 100'. In the embodiment illustrated in FIG. 1J, tail region 142 extends freely toward second side 102' of nanopore 100', and elongated body 143 is sufficiently long that tail region 142 can be disposed on second side 102' of nanopore 100'. Alternatively, tail region 142 can extend freely toward, or can be attached to, adjacent to, or beyond, either of the first side 101' or second side 102' of nanopore 100'. Optionally, elongated body 143 also includes reporter region 144. For further details regarding solid state nanopores, see the following references, the entire contents of each of which are incorporated by reference herein: Dekker, "Solid-state nanopores," Nature Nanotechnology 2: 209-215 (2007); Schneider et al., "DNA Translocation through Graphene Nanopores," Nano Letters 10: 3163-3167 (2010); Merchant et al. Nano Letters 10:2915-2921 (2010); and Garaj et al., "Graphene as a subnanometre trans-electrode membrane," Nature 467: 190-193 (2010).

As another example, FIG. 1K illustrates an exemplary composition that includes biological or biological and solid state hybrid nanopore 100" and tether 140' having head region 141', tail region 142', and elongated body 143'. Nanopore 100" includes barrier 107" and biological pore 108" disposed within barrier 107". Biological pore 108" includes aperture 103" defined therethrough, and one or more constrictions 104". Biological pores include, for example, polypeptide pores and polynucleotide pores. Barrier 107" can include a membrane of biological origin, or a solid state membrane. Membranes of biological origin include lipid bilayers. Solid state membranes include silicon and graphene. Head region 141' of tether 140' is anchored to or adjacent to first side 101" of nanopore 100". For example, in the embodiment illustrated in FIG. 1K, head region 141' is anchored to biological pore 108" on the first side 101" of nanopore 100", e.g., covalently bonded to a moiety on biological pore 108" on first side 101". Head region 141' instead can be anchored adjacent to first side 101" of nanopore 100", e.g., can be anchored to a member that is adjacent to biological pore 108" on first side 101", or can be anchored to or adjacent to second side 102" of nanopore 100". Tail region 142' extends freely toward second side 102" of nanopore 100", and elongated body 143' is sufficiently long that tail region 142' can be disposed on or beyond second side 102" of nanopore 100", e.g., beyond outer surface 106" of barrier 107". Alternatively, tail region 142' can extend freely toward, or can be attached to, adjacent to, or beyond, either of the first side 101" or second side 102" of nanopore 100". Optionally, elongated body 143' also includes reporter region 144'. For further details regarding exemplary hybrid nanopores and the preparation thereof, see the following references, the entire contents of each of which are incorporated by reference herein: Hall et al., "Hybrid pore formation by directed insertion of alpha hemolysin into solid-state nanopores," Nature Nanotechnology 5: 874-877 (2010), and Cabello-Aguilar et al., "Slow translocation of polynucleotides and their discrimination by α-hemolysis inside a single track-etched nanopore designed by atomic layer deposition," Nanoscale 5: 9582-9586 (2013).

Figure 1L:
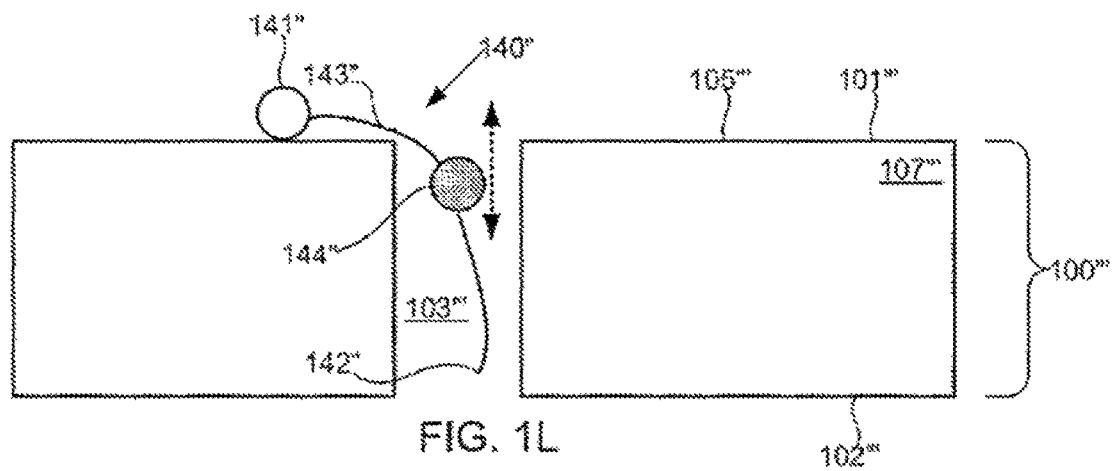

Note that in any of the embodiments described herein, the nanopore need not necessarily include the optional constriction. For example, FIG. 1L illustrates an exemplary composition that includes alternative nanopore 100''' and tether 140" having head region 141", tail region 142", and elongated body 143". Nanopore 100''' includes first side 101''' and second side 102''' that can include any suitable solid state material or combination of solid state materials. First side 101''' and second side 102''' can be defined by layer 107''' that includes one or more solid state materials. Exemplary solid state materials suitable for use in layer 107''' include silicon (Si), silicon nitride (SiN or $SiN_x$), graphene, silicon oxide ($SiO_2$ or $SiO_x$), or a combination thereof. In the illustrated embodiment, aperture 103''' can be defined through first and second sides 101''', 102''', and can lack a constriction region. Head region 141" of tether 140" is anchored to outer surface 105''' of first side 101''' of nanopore 100''', although head region 141" instead can be anchored adjacent to first side 101''' of nanopore 100''', or can be anchored to or adjacent to second side 102''' of nanopore 100'. In the embodiment illustrated in FIG. 1L, tail region 142" extends freely toward second side 102''' of nanopore 100''', and elongated body 143" is sufficiently long that tail region 142" can be disposed on second side 102''' of nanopore 100'''. Alternatively, tail region 142" can extend freely toward, or can be attached to, adjacent to, or beyond, either of the first side 101''' or second side 102''' of nanopore 100'''.

Optionally, elongated body 143" also includes reporter region 144". Reporter region 144" can facilitate measurement of translational, rotational, or conformational movement of elongated body 143". In one exemplary embodiment, dimension D1 of aperture 103" suitably is selected so as to facilitate the use of reporter region to measure movement of elongated body 143". For example, aperture 103" can be sufficiently narrow so as to measurably interact with reporter region 144" responsive to movement of reporter region 144". As one example, reporter region 144" has an electrical or flux blockade characteristic, and aperture 103" is has a width selected such that movement of reporter region 144" causes a detectable change in current or flux through aperture 103" under an applied voltage across nanopore 100'''. For example, nucleotides that are larger (such as A and G) can result in more blockage when they are disposed in an aperture, e.g., disposed in the constriction of MspA, as compared with T, which is smaller. Exemplary ranges of blockage currents or fluxes in terms of % of open pore current or flux include 0 to 10%, 10% to 20%, 20% to 30%, 30% to 40%, 40% to 50%, 60% to 70%, 70% to 80%, 80% to 90%, and 90% to 100%. In one exemplary embodiment, the range is between 20% and 70% for MspA in 300 mM KCL with a 180 mV bias and an open pore current of 110 pA.

Figure 1M:
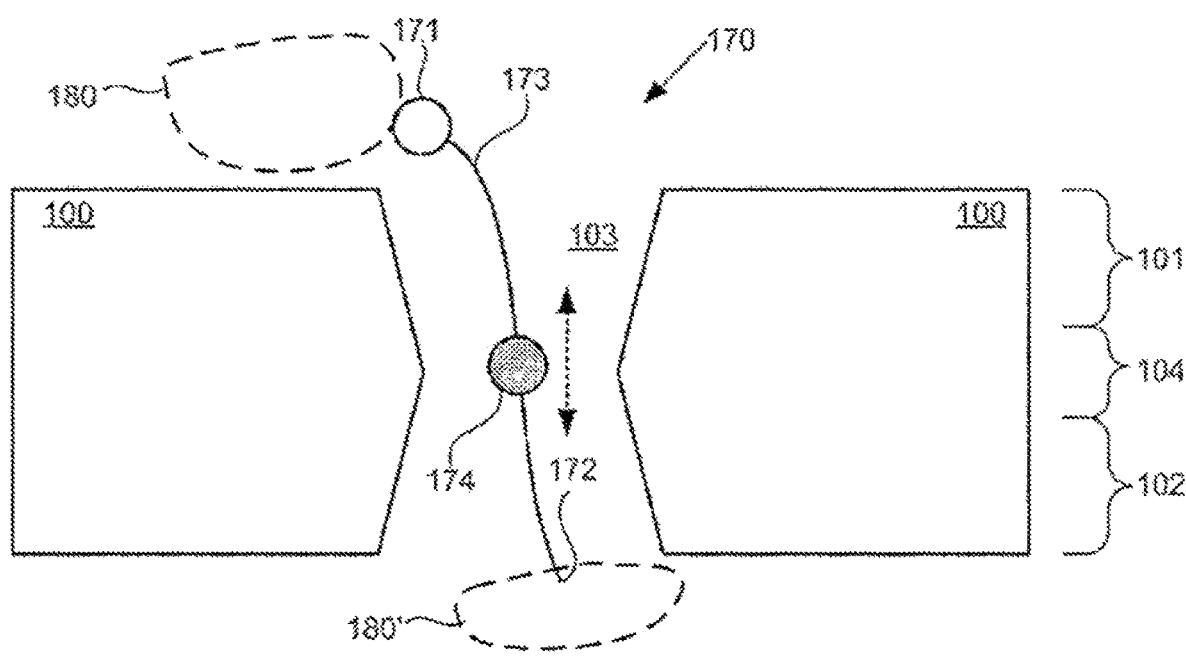

In yet another example, FIG. 1M illustrates an alternative composition that includes nanopore 100 and alternative tether 170 having head region 171, tail region 172, and elongated body 173. Head region 171 is anchored adjacent to first side 101 of nanopore 100, e.g., is anchored to another member 180 that optionally may have, but need not necessarily have, a substantially fixed position relative to nanopore 100. Tail region 172 extends through aperture 103 of nanopore 100, and is attached adjacent to or beyond second side 102 of nanopore 100, e.g., is anchored to another member 180' that is disposed within aperture 103 or is disposed adjacent to, or beyond, the outer surface of second side 102. Elongated body 173 is sufficiently long to permit attachment of head region 171 to member 180 and attachment of tail region 172 to member 180'. Optionally, member 180 is sufficiently large as to be unable to physically pass through the entirety of aperture 103. Additionally, or alternatively, member 180' is sufficiently large as to be unable to physically pass through the entirety of aperture 203. Accordingly, the attachment of head region 171 to member 180 and attachment of tail region 172 to member 180' can retain tether 170 in nanopore 100, can retain member 180 on first side 101 of nanopore 100, and can retain member 180' on second side 102 of nanopore 100, even if members 180 and 180' are not respectively attached to first side 101 or second side 102 of nanopore 100. Accordingly, head region 171 can be considered to be anchored adjacent to first side 101 regardless of whether member 180 is attached to first side 101. In one example, the composition illustrated in FIG. 1M can be prepared by attaching head region 171 to member 180, followed by disposing tail region 172 on second side 102, followed by attaching tail region 172 to member 180'. In another example, the composition illustrated in FIG. 1M can be prepared by attaching tail region 172 to member 180', followed by disposing head region 171 on first side 101, followed by attaching head region 171 to member 180. Any suitable attachment, including those described elsewhere herein, can be used. In one non-limiting, purely illustrative embodiment, first member 180 can include a polymerase, and second member 180' can include a nucleic acid that hybridizes to a nucleic acid of tail region 172. In one example, an exemplary preparation of such a composition, and an exemplary use of such a composition to detect action of the polymerase upon a nucleotide, are described in greater detail herein with reference to FIGS. 22A-22D.

Additionally, elongated body 173 optionally includes reporter region 174, which facilitates measurement of translational, rotational, or conformational movement of elongated body 173, e.g., as represented in FIG. 1M by the dashed arrow. In certain embodiments, reporter region 174 is translationally movable toward first side 101 of nanopore 100 responsive to a first event, and translationally movable toward second side 102 of nanopore 100 after the first event. Reporter region 174 also can be translationally movable toward first side 101 of nanopore 100 responsive to a second event after the first event, and again translationally movable toward second side 102 of nanopore 100 after the second event. The first or second event, or both, can occur adjacent to the first side of the nanopore. In embodiments that include constriction 104, reporter region 174 can be translationally movable adjacent to or even through constriction 104, e.g., responsive to an event or other stimulus.

Additionally, note that in any of the foregoing examples, as well as other compositions not specifically illustrated, the elongated body of the tether optionally can include a moiety that interacts with a molecule. Such interaction can, for example, cause a change in the relative position of a reporter region so as to measurably indicate the presence of the molecule, or can stabilize the molecule in a particular position relative to the constriction of the nanopore. Some non-limiting examples of such moieties, and uses thereof, are provided further herein.

Additionally, it should be appreciated that a head group of a tether can be attached to a nanopore in any number of ways. For example, well-known bioconjugate chemistry such as described by Hermanson, mentioned above, can be used. In illustrative embodiments, the nanopore includes a chemical moiety for forming an attachment such as a cysteine, or a peptide linker such as a SpyTag. Further information regarding spytags and use thereof to form attachments can be found, for example, in the following references, the entire contents of each of which are incorporated by reference herein: Zakeri et al., "Peptide tag forming a rapid covalent bond to a protein, through engineering a bacterial adhesin," Proc. Nat. Acad. Sci. USA 109: E690-E697 (2012), and Fierer et al., "SpyLigase peptide-peptide ligation polymerases affibodies to enhance magnetic cancer cell capture," Proc. Nat. Acad. Sci. USA 111: E1176-E1181 (2014).

Moreover, it should be appreciated that another member (to which the head group of the tether can be attached) can be attached to or adjacent to a nanopore in any number of ways. For example, the head group of a tether can be attached to another member, then the other member can be loaded onto or adjacent to the nanopore, and the other member then can be attached to or adjacent to the nanopore using a suitable attachment. In one nonlimiting, purely illustrative example, the head group of a tether can be attached to a polymerase, then the polymerase can be loaded onto or adjacent to the nanopore, and the polymerase then can be attached to or adjacent to the nanopore using a suitable attachment, such as a covalent bioconjugated linker between the tether and the nanopore. In this manner, the tether can be attached to the polymerase, and both the tether and the polymerase can be attached to the nanopore via a linkage on the tether. Examples of such linkers include: NETS-esters, isocyanates, and isothicyanate linker conjugation to amines, maleimides to cysteines, Click-chemistry with azides to alkynes, use of fusion tags such as Halotag, Spycatcher-Spytag, and other similar protein-protein bioconjugation methods. For further information about exemplary linkages that can be used, see the following references, the entire contents of each of which are incorporated by reference herein: Hermanson, Bioconjugate Techniques, 2nd Ed., Elsevier, 2008; Zakeri et al., "Peptide tag forming a rapid covalent bond to a protein, through engineering a bacterial adhesin," PNAS 109(12): E691-E697 (2012); and Liu et al., "Specific Enzyme Immobilization Approaches and Their Application with Nanomaterials," Topics in Catalysis 55(16-18): 1146-1156 (2012).

Exemplary Systems

Figure 2A:
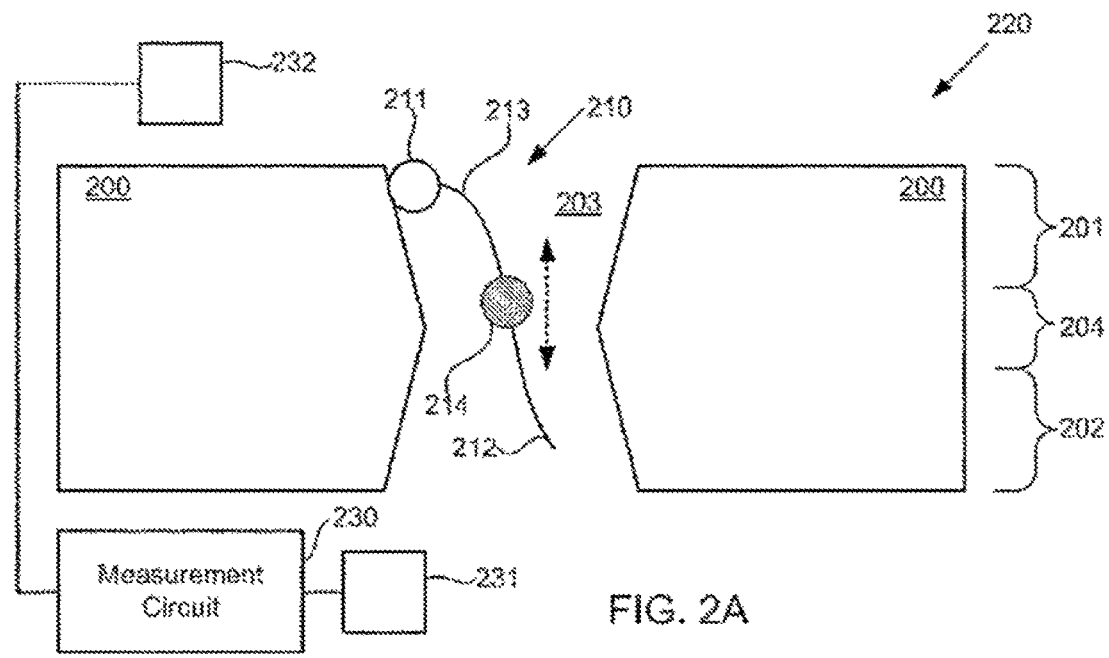
FIG. 2A schematically illustrates a system including measurement circuitry configured to measure movement of a reporter region within the aperture of a nanopore, according to some embodiments of the present invention.

Exemplary systems for detecting events using tethers anchored to or adjacent to nanopores now will be described with reference to FIGS. 2A-2C. FIG. 2A schematically illustrates a system including measurement circuitry (e.g., electrical or optical measurement circuitry) configured to measure movement or presence of a reporter region within the aperture of a nanopore. System 220 includes nanopore 200, permanent tether 210, and measurement circuit 230. Nanopore 200 includes first side 201, second side 202, aperture 203, and optionally also includes constriction 204. Permanent tether 210 includes head region 211, tail region 212, and elongated body 213. In the embodiment illustrated in FIG. 2A, head region 211 is anchored to first side 201 of nanopore 200, tail region 212 is disposed on second side 201 of nanopore 200 and extends freely toward second side 202 of nanopore 100 or is attached to another member, and elongated body 213 is movable through aperture 203 of nanopore 200. However, nanopore 200 or tether 210, or both, can have different configurations than illustrated in FIG. 2A, such as exemplified herein. For example, head region 211 can be anchored to or adjacent to nanopore 200, for example, using a thioether or amide linkage. In one illustrative, nonlimiting example, a thioether linkage can be created by a maleimide group on tether 211 that reacts with a reduced thiol group in a cysteine residue on or adjacent to nanopore 200. Introduction of a maleimide group into tether 211 can be readily achieved using methods well known in the art. Illustratively, head region 211 can be attached to another member (e.g., a polymerase) disposed on or adjacent to first side 201 of nanopore 200 in a manner analogous to that described above with reference to FIGS. 1F and 1M, or tail region 212 can be attached to another member (e.g., a nucleic acid) disposed on second side 202 of nanopore 200 (e.g., within aperture 203) in a manner analogous to that described above with reference to FIGS. 1I and 1M, or both head region 211 can be attached to another member (e.g., a polymerase) disposed on or adjacent to first side 201 of nanopore 200 and tail region 212 can be attached to another member (e.g., a nucleic acid) disposed on second side 202 of nanopore 200 (e.g., within aperture 203) in a manner analogous to that described above with reference to FIG. 1M. Optionally, one or both of such members can be sufficiently large as to be unable to pass entirely through aperture 203 of nanopore 200.

Additionally, elongated body 213 can include reporter region 214 that facilitates measurement of translational, rotational, or conformational movement or presence (or a combination thereof) of elongated body 213 using measurement circuit 230. For example, reporter region 214 can have a different physical, chemical, electrical, optical, biological, or other suitable flux blockade property than one or more other regions of elongated body 213. In some embodiments, measurement circuit 230 can be configured to optically, electrically, chemically, or biologically detect movement of reporter region 214 relative to constriction 204, e.g., as represented in FIG. 2A by the dashed arrow. For example, a system can include a composition and measurement circuitry configured to measure current or flux through the aperture or an optical signal while the reporter region of a tether is moved responsive to an event. In one illustrative example, nanopore 200 and tether 210 can be immersed in a conductive fluid, e.g., an aqueous salt solution. Measurement circuit 230 can be in communication with first electrode 231 and second electrode 232, and can be configured to apply a voltage between first electrode 231 and second electrode 232 so as to impose a voltage across nanopore 200. Either a direct-current (DC) or an alternating-current (AC) voltage suitably can be used. In some embodiments, measurement circuit 230 further can be configured to use first electrode 231 and second electrode 232 to measure the magnitude of a current or flux through aperture 203. In some embodiments, measurement circuit 230 further can include an optical, biological, or chemical sensor respectively configured to optically, biologically, or chemically sense the magnitude of a molecular flux through aperture 203. Exemplary optical sensors include CCDs and photodiodes. In some embodiments, measurement circuit 230 includes one or more agents that chemically or biologically react with the molecular flux through aperture 203 so as to generate an optically detectable signal.

For example, reporter region 214 can have a different physical property than some or all other regions of elongated body 213. For example, reporter region 214 can cause a differential blockage current or flux through aperture 203 as compared to other regions of elongated body 213. Additionally, or alternatively, reporter region 214 can have a different electrical or flux blockade property than some or all other regions of elongated body 213. For example, reporter region 214 can include an electrostatic charge, while some or all other regions of elongated body 213 can include a different electrostatic charge, or can be uncharged (e.g., can be electrically neutral). Or, for example, reporter region 214 can be uncharged, while some or all other regions of elongated body 213 can include an electrostatic charge. Or, for example, reporter region 214 can have a physical property. Physical properties include the volume and shape of reporter region 214. In one illustrative example, movement of reporter region 214 within aperture 203 causes a measurable change in current or flux through the aperture, or optional constriction 204 therein, by modulating a blockage current or flux through the aperture or constriction. Or, for example, reporter region 214 can have a chemical or biological property that facilitates chemical or biological detection. Chemical or biological properties include presence of a chemical or biological group, e.g., a radioactive group or a group having enzymatic activity.

One or more electrical, physical, chemical, optical, biological, or other flux blockade properties of reporter region 214 can provide a measurable change in current through aperture 203 or constriction 204, a measurable change in flux of molecules through aperture 203 or constriction 204, or an optical signal. In one illustrative example, movement or presence of reporter region 214 within aperture 203 causes a measurable change in a current through aperture 203 or constriction 204, or causes a measurable change in flux of molecules through aperture 203 or constriction 204, which change in flux can be electrically, chemically, biologically, or optically detectable. For example, presence or movement of reporter region 214 within aperture 203 or constriction 204 can cause an ionic current blockade or a molecular flux blockade, which can be detected optically, electrically, chemically, or biologically. Illustratively, a gradient of a molecule on the trans side can create a natural molecular flux that can be partially blocked by reporter region 214. Measurement circuitry 230 can be configured to measure such a molecular flux non-electrically (e.g., optically) using fluxes of luminescent (e.g., fluorescent or chemiluminescent molecules, or fluxes of reagents that become chemiluminescent in the presence of other reagents. For example, $Ca^{2+}$ can flux from one side of the nanopore to the other side where it encounters a calcium sensitive dye, such as Fluo-2, Fluo-4, Fluo-8, or the like, to induce fluorescence. Other reagent pairs that can be used include, but are not limited to, luminol and oxidants, calcium and aequorin, or ATP and luciferase, to name a few. For further details regarding optical detection of molecular fluxes through an aperture or constriction, see Ivankin et al., "Label-Free Optical Detection of Biomolecular Translocation through Nanopore Arrays," ACSNano 8(10): 10774-10781 (2014), the entire contents of which are incorporated by reference herein.

Illustratively, the magnitude of the current or flux through aperture 203 or optical signal can measurably change responsive to movement of reporter region 214 within aperture 203, and the time period for such a measurable change in the current or flux or optical signal is based on the duration of the reporter region's change in position. In one illustrative, non-limiting example, elongated body 213 includes a polynucleotide that includes one or more abasic nucleotides that define reporter region 214.

In one illustrative embodiment, nanopore 200 is a biological nanopore to which tether 211 is attached using a thioether linkage. Non-limiting examples of biological nanopores include MspA and alpha hemolysin. Reporter region 214 of tether 211 can include one or more abasic residues configured to be positioned within or adjacent to one or more constrictions 204 of the biological nanopore. Movement of one or more properly positioned abasic residues through a constriction of either pore can result in a readily detectable signal, e.g., a detectable change in current or flux through the constriction(s) 204 or an optical signal. Biological nanopores such as MspA and alpha hemolysin usefully can include constrictions that can serve to focus the effect of reporter region 214. For example, MspA includes a single constriction with a diameter of approximately 1.2 nm and a length of approximately 0.5 nm, can provide suitable spatial resolution because the magnitude of the ionic current or flux blockade through the constriction primarily are based on the elongated-body segment threaded through the narrow region (constriction) of the nanopore.

Figure 2B:
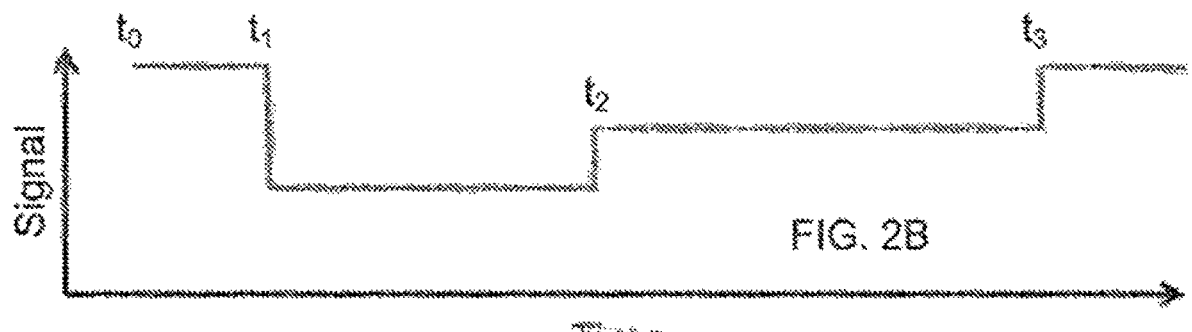
FIG. 2B is a plot of an exemplary signal that can be generated during use of the system of FIG. 2A, according to some embodiments of the present invention.

FIG. 2B is a plot of an exemplary signal (e.g., optical or electrical signal) that system 220 illustrated in FIG. 2A can generate as reporter region 214 translationally, rotationally, or conformationally moves over time, e.g., moves responsive to one or more events or other stimulus. The value (e.g., magnitude) of the signal at time $t_0$ can correspond to a first translational, rotational, or conformational position of reporter region 214 within aperture 203. At time $t_1$, the value (e.g., magnitude) of signal can change to a second value, corresponding to reporter region 214 translationally, rotationally, or conformationally moving to a second position within aperture 203. The time duration between $t_0$ and $t_1$ corresponds to an amount of time that reporter region 214 spent at the first position. At time $t_2$, the value (e.g., magnitude) of signal can change to a third value, corresponding to reporter region 214 translationally, rotationally, or conformationally moving to a third position. The time duration between $t_1$ and $t_2$ corresponds to an amount of time that reporter region 214 spent at the second position before moving to the third position. At time $t_3$, the value (e.g., magnitude) of signal can change to the first value, corresponding to reporter region 214 translationally, rotationally, or conformationally returning to the first position. The time duration between $t_2$ and $t_3$ corresponds to an amount of time that reporter region 214 spent at the third position before returning to the first position. It should be appreciated that the particular values and time periods of the signals illustrated in FIG. 2B are intended to be purely exemplary, and not limiting in any way.

In one illustrative embodiment, reporter region 214 includes an electrostatic charge, and the signal generated by system 220 includes the current or flux through constriction 204 or optical signal. However, it should be understood that measurement circuit 230 can include, or be in communication with, any element or combination of elements that facilitates measurement of any suitable reporter region, and need not necessarily be based on the measurement of current or flux through constriction 204 or an optical signal, or even based on the movement of the reporter region. Additionally, the reporter region 214 need not necessarily be attached to the tether, and instead can be attached to a nucleotide or other molecule being acted upon. The particular properties of the reporter region can be selected based on the particular configuration of measurement circuit 230 so as to facilitate measurement of that reporter region. For example, the reporter region can have an optical property, and measurement circuit 230 can include, or be in communication with, an optical sensor configured to measure the optical property and to generate a signal based on the presence of or movement of the reporter region. In one illustrative embodiment, the reporter region can include a first FRET pair partner, e.g., a FRET donor or acceptor, that interacts with a corresponding second FRET pair partner, e.g., a FRET acceptor or donor, so as to emit light of a particular wavelength that measurement circuit 230 is configured to detect. Or, for example, the reporter region can have a chemical or biological property, and measurement circuit 230 can include, or be in communication with, a chemical or biological sensor configured to measure the chemical or biological property and that generates a signal based on the presence of or movement of the reporter region. As another example, the reporter region can provide a molecular flux blockade that modulates the flux of molecules through the aperture or constriction, which flux can be detected optically, electrically, chemically, or biologically.

In one exemplary embodiment, reporter region 214 can be translationally movable toward first side 201 of nanopore 200 responsive to a first event. The first event can be individually identifiable based on a measured magnitude or time duration, or both, of a signal (e.g., an optical or electrical signal) generated by system 220. For example, the first event can cause reporter region 214 to translationally move to a first location, and the presence of reporter region 214 at the first location causes the signal to have a first magnitude. As such, the signal having the first magnitude correlates to the first event having occurred. Or, for example, the first event can cause reporter region to translationally move to the first location for a first period of time, and the presence of reporter region 214 at the first location causes the signal to have a first time duration. As such, the signal having the first time duration correlates to the first event having occurred. In one specific example, the signal has both a first magnitude and a first time duration, each of which is based on the presence of reporter region 214 at the first location, thus increasing confidence based on the signal in a determination that a conformation change has occurred. Reporter region 214 can remain at the first location following the first event. Alternatively, reporter region 214 can be movable toward second side 202 of nanopore 200 after the first event. For example, reporter region 214 can return to a previous location, or to a different location, after the first event.

Additionally, in some embodiments, reporter region 214 also can be movable toward first side 201 of nanopore 200 responsive to a second event that occurs after the first event. The second event can be individually identifiable based on a measured magnitude or time duration, or both, of a signal (e.g., an optical or electrical signal) generated by system 220. For example, the second event can cause reporter region 214 to move to a second location, and the presence of reporter region 214 at the second location causes the signal to have a second magnitude. As such, the signal having the second magnitude correlates to the second event having occurred. Or, for example, the second event can cause reporter region to move to the second location for a second period of time, and the presence of reporter region 214 at the second location causes the signal to have a second time duration. As such, the signal having the second time duration correlates to the second event having occurred. In one specific example, the signal has both a second magnitude and a second time duration, each of which is based on the presence of reporter region 214 at the second location, thus increasing confidence in a determination based on the signal that a conformation change has occurred. Reporter region 214 can remain at the second location following the second event. Alternatively, reporter region 214 can be movable toward second side 202 of nanopore 200 after the second event. For example, reporter region 214 can return to an original location, or to a different location, after the second event. The first and second events can be individually identifiable and distinguishable from one another based on respective measured magnitudes, or time durations, or both, of the signals (e.g., optical or electrical signals) generated by system 220.

In one non-limiting example, conformational motion can be measured. For example, it is well known that the distance between bases in extended single stranded DNA (ssDNA) can be greater than that in double stranded DNA (dsDNA). For example, a ssDNA tether that is anchored adjacent to the first side of a biological MspA nanopore and is stretched due to an applied electric field can have inter-base distances of about 4.9 Angstroms per base. Double stranded DNA (dsDNA), on the other hand, has a spacing of about 3.32 Angstroms per base. Tether 211 can include an arbitrary DNA sequence and can be permanently anchored to MspA nanopore 200 such that under the applied force created by the electric field, reporter region 214 that includes one or more abasic residues is disposed at the main MspA constriction. The abasic reporter residue(s) 214 can be flanked by deoxythymidine residues which have a very different blockage current or flux in the MspA pore than the abasic site(s). A conformational change can be induced in the elongated body 213 of the tether 211 by hybridization of a complementary oligonucleotide to the tether. The conformational change results from the conversion of ssDNA to dsDNA due to the inter-base spacing differences between ssDNA and dsDNA. The conformational change occurs within the elongated body 213 which results in movement of the reporter 214 out of the constriction 204 towards the first side, and the movement of deoxythymidine residues into the constriction zone. Due to the different blockage currents or fluxes of these moieties, a change in current or flux signal occurs, which can be readily detected, e.g., electrically or optically. For further details regarding interactions between MspA and ssDNA, see Manrao et al., "Nucleotide Discrimination with DNA Immobilized in the MspA Nanopore," PLos ONE 6: e25723, 7 pages, (2011), the entire contents of which are incorporated by reference herein.

Note that the location of reporter region 214, and the resulting signal generated by system 220, need not necessarily be responsive solely to occurrence of an event, but can be responsive to any suitable stimulus. For example, measurement circuit 230 can be configured to apply a voltage between first electrode 231 and second electrode 232 so as to apply a voltage across nanopore 200, which causes reporter region 214 to translationally move towards a given location, e.g., towards second side 202 of nanopore 200. The occurrence of the event prior to or during such motion can define a location at which reporter region 214 stops (even if transiently), which can define the signal (e.g., an optical or electrical signal) that system 220 generates. Additionally, note that in embodiments such as described above with reference to FIG. 1M, in which head region 211 of tether 210 is attached to a first member and tail region 212 of tether 210 is attached to a second member, neither of which members need be attached to the first or second side of the nanopore, applying a voltage between first electrode 231 and second electrode 232 can cause a corresponding net movement of the tether 210 and the first and second members either towards first electrode 231 or towards second electrode 232. Optionally, one or both of the first and second members is sufficiently large as to be unable to pass fully through aperture 203 of nanopore 200. For example, based upon application of a first appropriate voltage between first electrode 231 and second electrode 232, tether 210 and the first and second members attached thereto can move towards first electrode 231, which movement can cause the first member (attached to head region 211 in a manner analogous to that illustrated in FIG. 1M) to become temporarily lodged in a first location relative to aperture 203, e.g., disposed adjacent to aperture 203 on first side 201 or fully or partially disposed within aperture 203 on first side 201 without passing fully through aperture 203, thus inhibiting further movement of tether 210 and the first and second members towards first electrode 231. Or, for example, based upon application of a second appropriate voltage between first electrode 231 and second electrode 232, tether 210 and the first and second members attached thereto can move towards second electrode 232, which movement can cause the second member (attached to tail region 212 in a manner analogous to that illustrated in FIG. 1M) to become temporarily lodged in a second location relative to aperture 203, e.g., disposed adjacent to aperture 203 on second side 202 or fully or partially disposed within aperture 203 without passing fully through aperture 203, thus inhibiting further movement of tether 210 and the first and second members towards second electrode 232. As such, even if alternating voltages are applied across first electrode 231 and second electrode 232, tether 210 and the first and second members can be retained relative to nanopore 200.

In embodiments that include optional constriction 204, based on the relative width of reporter region 214, the length of elongated body 213, and the diameter of constriction 204 (e.g., dimension D2 illustrated in FIG. 1A), reporter region 214 can in some embodiments be movable adjacent to, into, or even through constriction 204, e.g., responsive to an event or other stimulus. For example, reporter region 214 can be disposed within constriction 204, and then pulled out of constriction 204 toward first side 201 responsive to the event or other stimulus. Or, for example, reporter region 214 can be disposed on second side 202 of nanopore 200, and then pulled through constriction 204 and onto first side 201 of nanopore 200 responsive to the event or other stimulus.

Additionally, note that system 220 suitably can be configured so as to generate signals (e.g., optical or electrical signals) based upon reporter regions that are disposed on members other than on permanent tether 210. For example, tether 210 can interact with another molecule to which a reporter region is attached. Such an interaction can cause the reporter region of the other molecule to move to a location, and the presence of the reporter region at that location can cause the signal generated by system 220 to have a magnitude, or time duration, or both magnitude and time duration, that correlates to the interaction having occurred. For example, an interaction between tether 210 and another molecule can cause a reporter region attached to that molecule to become positioned at a location at which the reporter region is detectable by circuit 230.

It further should be appreciated that an array of nanopores can be provided so as to detect a plurality of events occurring in parallel with one another. For example, FIG. 2C schematically illustrates a plan view of a system 260 including measurement circuitry 240 configured to measure movement of respective reporter regions within the respective apertures of an array of nanopores. A plurality of systems 250, which can be configured analogously to system 220 described above with reference to FIGS. 2A-2B, can be integrally disposed in a common substrate as one another, or can be separately prepared and disposed adjacent to one another. Each system 250 can include nanopore 200, a tether (tether not specifically illustrated), and an addressable electrode 241. Measurement circuit 240 can be configured analogously to measurement circuit 230, can be in electrical communication with each addressable electrode 241 of each system via a suitable communication path, e.g., conductor (communication illustrated for only a single system 250) and with a common electrode 242. Measurement circuit 240 can be configured to selectably apply a voltage across each nanopores 200 by applying a voltage across the addressable electrode 241 of that nanopore and across common electrode 242, and to selectably measure a current or flux through that nanopore or an optical signal at the applied voltage. An event can be detected based on such a current or flux or optical signal, e.g., such as described elsewhere herein. Analogous arrays readily can be envisioned for other types of detection systems, e.g., light, chemical, or biological detection systems.

Exemplary Methods and Exemplary Compositions for Use During Such Methods

Some exemplary methods for detecting events, and exemplary compositions that can be used during such methods, now will be described. Under one aspect, a method includes providing a nanopore including a first side, a second side, and an aperture extending through the first and second sides; and providing a permanent tether including a head region, a tail region, and an elongated body disposed therebetween. The head region can be anchored to or adjacent to the first or second side of the nanopore, and the elongated body can include a reporter region. The method can include moving the reporter within the aperture responsive to a first event occurring adjacent to the first side of the nanopore. In some embodiments, the reporter region is translationally moved within the aperture responsive to the first event. Additionally, or alternatively, the reporter region can be rotationally moved within the aperture responsive to the first event. Additionally, or alternatively, the reporter region is conformationally moved within the aperture responsive to the first event.

Figure 3A:
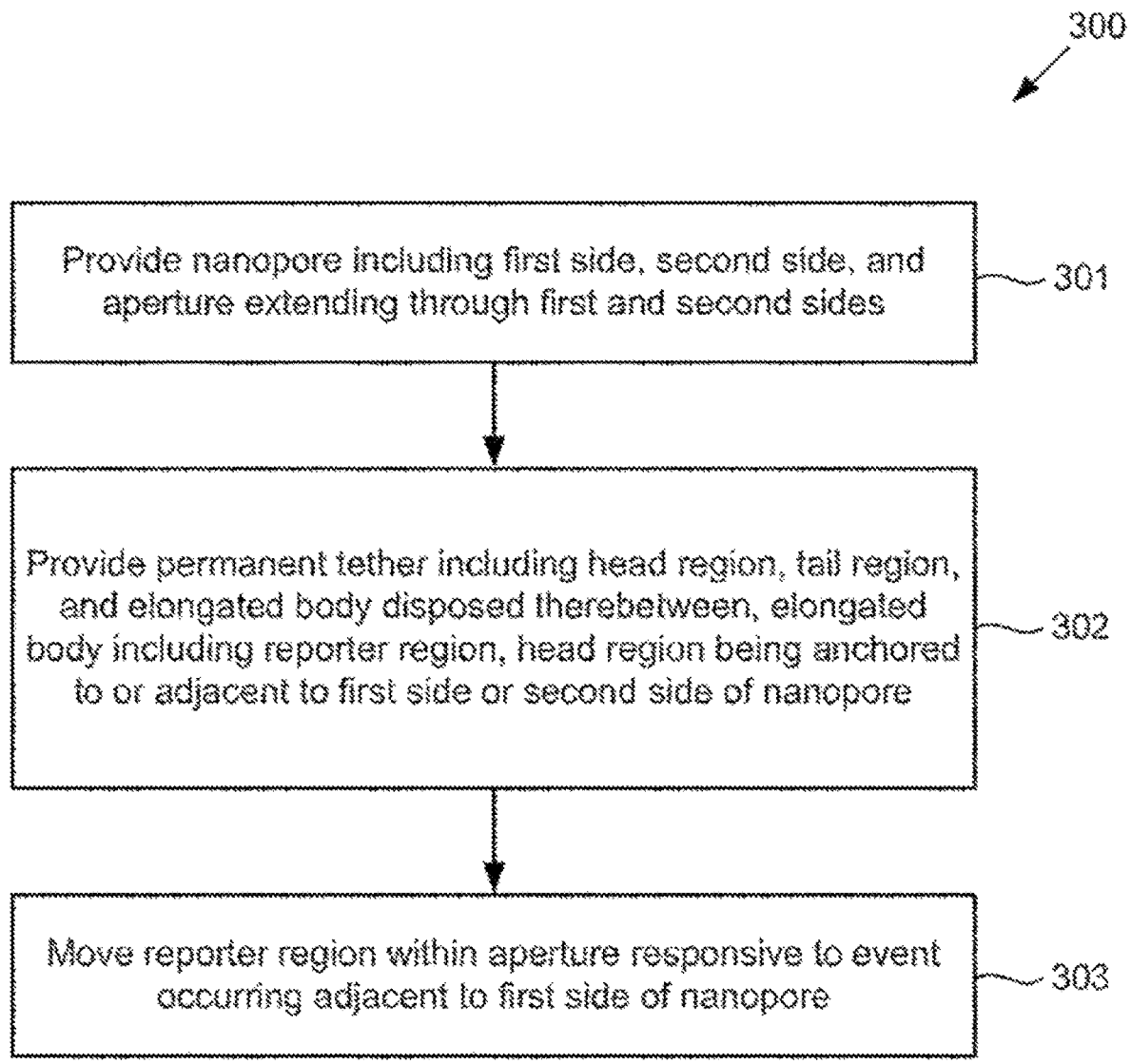
FIG. 3A illustrates a method for detecting an event using a composition including a tether anchored to or adjacent to a nanopore, according to some embodiments of the present invention.

For example, FIG. 3A illustrates an illustrative method 300 for detecting an event using a composition including a tether anchored to or adjacent to a nanopore. Method 300 includes providing a nanopore including a first side, a second side, and an aperture extending through the first and second sides (step 301). The nanopore can have any suitable configuration, e.g., such as described above with reference to FIGS. 1A-1M. For example, nanopore 100 illustrated in FIG. 1A includes first side 101, second side 102, and aperture 103 extending through the first and second sides. Or, for example, nanopore 100' illustrated in FIG. 1J includes first side 101', second side 102', an aperture defined by aperture 103' and constriction 104'. Or, for example, nanopore 100" illustrated in FIG. 1K includes first side 101", second side 102", and aperture 103" extending through the first and second sides, e.g., defined by biological pore 108". Or, for example, nanopore 100''' illustrated in FIG. 1L includes first side 101''', second side 102''', and aperture 103''' extending through the first and second sides, e.g., defined through layer 107'''.

Step 301 also can, but need not necessarily, include preparing the nanopore. For example, step 301 can include defining a barrier and disposing a nanopore on or in the barrier. Methods of preparing nanopores are known in the art. For example, illustrative methods of preparing an MspA nanopore can be found in Butler et al., "Single-molecule DNA detection with an engineered MspA protein nanopore," Proc. Natl. Acad. Sci. 105: 20647-20652 (2008), the entire contents of which are incorporated by reference herein. Or, for example, illustrative methods of preparing an alpha hemolysin nanopore can be found in Howorka et al., "Sequence-specific detection of individual DNA strands using engineered nanopores," Nature Biotechnology 19: 636-639 (2001), and in Clarke et al., "Continuous base identification for single-molecule nanopore DNA sequencing," Nature Nanotechnology 4: 265-270 (2009), the entire contents of both of which are incorporated by reference herein.

Method 300 illustrated in FIG. 3A also includes providing a permanent tether including a head region, a tail region, and an elongated body therebetween, the elongated body including a reporter region, the head region being anchored to or adjacent to the first side or second side of the nanopore (step 302). The tether can have any suitable configuration, such as described above with reference to FIGS. 1A-1M. For example, the elongated body can be of a length that is shorter than a first dimension H1 defining a thickness of the nanopore, e.g., such as illustrated in FIGS. 1A, 1B, and 1J. Or, for example, the elongated body can be of a length that is longer than a first dimension H1 defining a thickness of the nanopore, e.g., such as illustrated in FIGS. 1G and 1K. Or, for example, in embodiments that include a constriction, the elongated body can be of a length that is shorter than a second dimension H2 defining a constriction depth, e.g., such as illustrated in FIG. 1A. Or, for example, in embodiments that include a constriction, the elongated body can be of a length that is longer than a second dimension H2 defining a constriction depth, e.g., such as illustrated in FIGS. 1B, 1G, 1J, and 1K. Or, for example, the reporter region can be disposed at a location along the elongated body that is selected such that, based upon the elongated body being fully or partially extended when the head region is anchored to or adjacent to the nanopore, the reporter region is positionable within the aperture of the nanopore, e.g., adjacent to or within an optional constriction, such as illustrated in FIGS. 1C, 1J, and 1K. Any suitable combination of such features can be used.

Step 302 also can, but need not necessarily, include preparing the tether. For example, step 302 can include defining an elongated body that includes portions thereof defining a head region, tail region, and one or more reporter region(s). For example, as described elsewhere herein, a tether can include DNA. A DNA oligonucleotide of sufficient length can be prepared using procedures well known in the art. For example, oligonucleotides with a 5' or 3' primary amine can be purchased commercially from vendors such as Integrated DNA Technologies, Inc. (Coralville, Iowa). The oligonucleotide can be ordered so as to include one or more abasic moieties, which can be used as one or more reporter regions as described herein. A bifunctional linker, such as sulfo-SMCC (sulfosuccinimidyl-4-(N-maleimidomethyl) cyclohexane-1-carboxylate) that includes an amine reactive group (NHS) and a thiol reaction group (maleimide) can be readily obtained from commercial sources, e.g., from Thermo Fisher Scientific, Inc. (Rockford, Illinois). Such a linker can be reacted with the oligonucleotide under appropriate reaction conditions well known in the art to form a stable amide bond. After purification of the oligonucleotide from the unreacted sulfo-SMCC, the modified oligonucleotide (which is now thiol reactive by virtue of its maleimide group) can be reacted with the nanopore, e.g., protein nanopore. The protein nanopore can be prepared in advance so as to include at least one solvent accessible cysteine residue that has its thiol (SH) group in reduced form. The reduced form can be obtained by incubation with 5 mM tris(2-carboxyethyl)phosphine (TCEP), for example, which is a readily available commercial compound. The modified oligonucleotide can be combined, e.g., in molar excess, with the reduced protein nanopore and under reaction conditions well known in the art, such that the maleimide forms a stable thioether bond. The protein-oligonucleotide conjugate can be purified away from excess unreacted oligonucleotide. In another example, compounds suitable for inclusion in a polyethylene glycol (PEG) based tether, e.g., maleimide-PEG, are readily available from commercial sources, such as Laysan Bio, Inc. (Arab, Alabama). For example, the maleimide can be conjugated to a reduced cysteine thiol in a manner analogous to that described above. A suitable reporter region can be defined within the PEG. In another example, a disulfide bond between an oligonucleotide and an alpha hemolysin nanopore can be prepared in a manner such as described in Howorka et al., "Kinetics of duplex formation for individual DNA strands within a single protein nanopore," PNAS 98: 12996-13301 (2001), the entire contents of which are incorporated by reference herein.

Additionally, or alternatively, step 302 optionally can include anchoring the head region of the tether to or adjacent to the first side or the second side of the nanopore. For example, the head region of the tether can be attached to or adjacent to the first side or the second side of the nanopore using a chemical bond, e.g., a covalent bond, hydrogen bond, ionic bond, dipole-dipole bond, London dispersion forces, or any suitable combination thereof. Or, for example, the head region of the tether can be attached to the first side or the second side of the nanopore using an interaction between a first protein structure on the head region and a second protein structure that is attached to, or adjacent to, the first or second side of the nanopore. For example, the first and second structures can include alpha helices that interlock with one another. The attachment of the head region of the tether to or adjacent to the first or second side of the nanopore can be permanent, such that the head group of the tether is held in a generally fixed position with respect to the first or second side of the nanopore. For example, the head region can be anchored to the first side of the nanopore, e.g., as illustrated in FIGS. 1A, 1J, and 1K. Or, for example, the head region can be anchored to the second side of the nanopore, e.g., as illustrated in FIG. 1D. Or, for example, the head region can be anchored adjacent to the first side of the nanopore, e.g., anchored to a member that is disposed adjacent to, and optionally is attached to, the first side of the nanopore such as illustrated in FIGS. 1E, 1F, and 1M. Note that even if such member moves translationally or conformationally adjacent to the nanopore, the tether anchored thereto still can be considered to be anchored adjacent to the nanopore. Analogously, the head region can be anchored adjacent to the second side of the nanopore or to another member that is disposed adjacent to, and optionally is attached to, the second side of the nanopore (not specifically illustrated).

In one illustrative embodiment, the reduced thiol (—SH) group (also called a sulfhydryl group) of a cysteine residue can be reacted with a tether having a thiol-reactive group. Examples of such groups include maleimide and iodoacetamide. As described in greater detail at www.lifetechnologies.com/us/en/home/references/molecular-probes-the-handbook/thiol-reactive-probes/introduction-to-thiol-modification-and-detection.html #head2, primary thiol-reactive reagents, including iodoacetamides, maleimides, benzylic halides, and bromomethylketones can react by S-alkylation of thiols so as to generate stable thioether products; arylating reagents such as 7-nitrobenz-2,1,3-oxadiazole (NBD) halides can react with thiols or amines by a similar substitution of the aromatic halide by the nucleophile; and because the thiolate anion is a better nucleophile than the neutral thiol, cysteine is more reactive above its pKa. Additionally, as described in greater detail at www.piercenet.com/method/sulfhydryl-reactive-cross-linker-chemistry, sulfhydryl-reactive chemical groups include haloacetyls, maleimides, aziridines, acryloyls, arylating agents, vinylsulfones, pyridyl disulfides, TNB-thiols (2-nitro-5-thiobenzoic acid), and disulfide reducing agents; such groups can conjugate to sulfhydryls via alkylation (e.g., via formation of a thioether bond) or disulfide exchange (e.g., formation of a disulfide bond). Sulfhydryl exchange reactions also suitably can be used. Alternatively, Amines (—NH$_2$) can be targeted. For example, the primary amine of the lysine residue and the polpypeptide N-terminus are relatively reactive. Amine residues can be targeted with N-hydroxysuccinimide esters (NHS esters), which can form a stable amide bond, or imidoester crosslinkers, which can react with primary amines to form amidine bonds. There are many other amine-reactive compounds. For example, as described at [www.]piercenet.com/method/amine-reactive-crosslinker-chemistry, synthetic chemical groups that can form chemical bonds with primary amines include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters; such groups can conjugate to amines, for example, via acylation or alkylation. In still other embodiments, a modified amino acid residue can be used to introduce a novel functionality like an azide or alkyne to be used with click chemistry. For example, thiol or amine reactivities such as described above can be used with linkers that permit the addition of azide or alkyne functionalities to further be used in a click chemistry reaction.

In the embodiment illustrated in FIG. 3A, method 300 includes moving the reporter region within the aperture of the nanopore responsive to an event occurring adjacent to the first side of the nanopore (step 303). Such movement can be translational, rotational, or conformational, or any suitable combination thereof. For example, the event can cause translational movement of the head region toward the first side of the nanopore, and the translational movement of the head region can cause movement of the elongated body, or a portion thereof, and the reporter region toward the first side of the nanopore. Or, for example, the event can cause translational movement of a portion of the elongated body toward the first side of the nanopore, and the translational movement of the portion of the elongated body can cause translational movement of the reporter region toward the first side of the nanopore. In one illustrative embodiment, the reporter region initially is disposed in, or adjacent to, a constriction of the nanopore, the event causes the reporter region to move away from the constriction towards the first side, to a first location.

Optionally, method 300 also includes moving the reporter region toward the second side of the nanopore after the event (not specifically illustrated). For example, after the event, the head region can translationally move toward the second side of the nanopore, and the movement of the head region can cause translational movement of the elongated body, or a portion thereof, and the reporter region toward the second side of the nanopore. Or, for example, after the event, a portion of the elongated body can translationally move toward the second side of the nanopore, and the movement of the portion of the elongated body can cause translational movement of the reporter region toward the second side of the nanopore. Or, for example, a stimulus, such as an applied voltage, can cause translational movement of the reporter region toward the second side of the nanopore. In one illustrative embodiment, after the event, the reporter region translationally moves from a first location to which it had moved responsive to the first event, towards the second side and towards the constriction, and optionally translationally moves adjacent to or into the constriction. As noted above, the reporter region can be repeatedly movable, e.g., translationally, rotationally, or conformationally, within the aperture responsive to different events, thus facilitating detection of each such event.

Figure 3B:
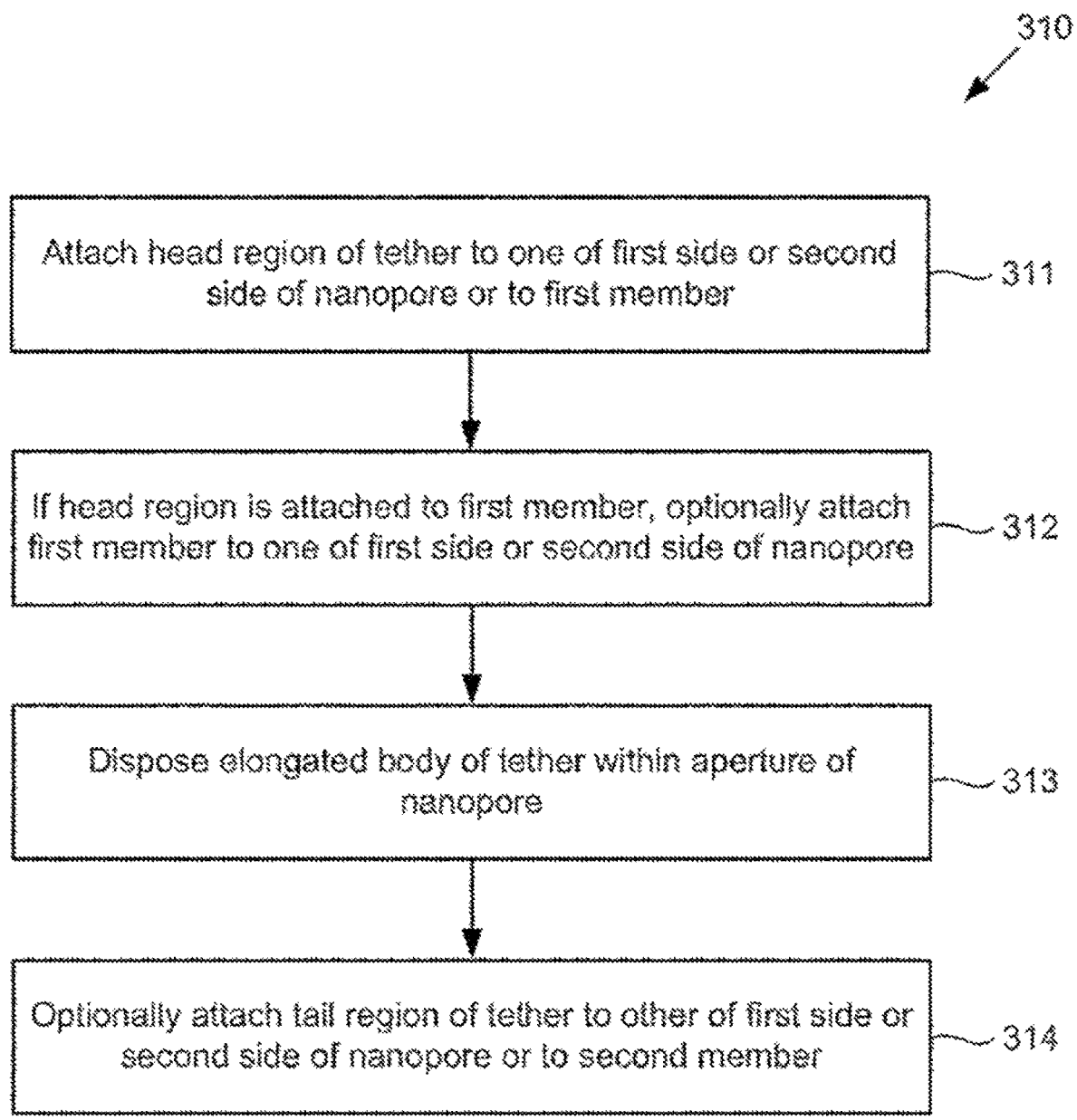
FIG. 3B illustrates a method for preparing a composition including a tether and a polymerase adjacent to a nanopore, according to some embodiments of the present invention.

It should be appreciated that step 302 can be performed, or any other composition provided herein can be prepared, using any suitable combination of steps. For example, FIG. 3B illustrates a method for preparing a composition including a tether and a polymerase adjacent to a nanopore, according to some embodiments of the present invention. Method 310 includes attaching a head region of a tether to one of a first side or a second side of a nanopore or to a first member (311). For example, method 310 can include attaching the head region of the tether directly to the first side or second side of a nanopore, in a manner analogous to that described above with reference to FIGS. 1A-1C, 1D, or 1G-1L using any suitable attachment provided herein or otherwise known in the art. Or, for example, method 310 can include attaching the head region of the tether directly to a first member in a manner analogous to that illustrated in FIGS. 1E, 1F, or 1M using any suitable attachment provided herein or otherwise known in the art.

In embodiments in which the head region of the tether is attached to a first member, method 310 illustrated in FIG. 3B optionally can include attaching the first member to one of the first side or the second side of the nanopore (312). For example, a first member having a head region of a tether attached thereto, such as described above with reference to FIGS. 1E, 1F, or 1M, can be attached to the first side or the second side of the nanopore. Alternatively, a first member having a head region of a tether attached thereto, such as described above with reference to FIGS. 1E, 1F, or 1M, can be disposed adjacent to the first side or the second side of the nanopore without attaching the first member thereto.

Method 310 illustrated in FIG. 3B further can include disposing the elongated body of a tether within an aperture of the nanopore (313). Based on the length of the elongated body, the elongated body can, but need not necessarily, extend all the way through the aperture of the nanopore. For example, in embodiments such as described above with reference to FIGS. 1A, and 1E, the elongated body of the tether optionally can be sufficiently short that the tail region of the tether remains on the same side of a constriction (if present) of the nanopore as is the head region of the tether. Or, for example, in embodiments such as described above with reference to FIGS. 1B-1D, 1F, 1J, or 1L, the elongated body of the tether optionally can be sufficiently long that the tail region of the tether remains disposed within the aperture of the nanopore, and optionally can be sufficiently long that the tail region of the tether is disposed on the other side of a constriction (if present) of the nanopore as is the head region of the tether. Or, for example, in embodiments such as described above with reference to FIGS. 1G-1I, 1K, or 1M, the elongated body of the tether optionally can be sufficiently long that the tail region of the tether can be disposed beyond the other side of the nanopore as is the head region of the tether.

Illustratively, the elongated body of the tether can be disposed within the aperture of the nanopore by applying a suitable directional force to the elongated body of the tether. For example, a voltage can be applied across the nanopore in a manner such as described herein with reference to FIGS. 2A-2C, and the elongated body of the tether can include at least one charged moiety that, based on the voltage, attracts the tail region of the tether towards the side of the nanopore opposite that to which the head region of the tether is attached or at which the head region of the tether is attached to a first member, and causes translocation of the tail region so as to dispose all or a portion of the elongated body of the tether within the aperture of the nanopore. Note that in embodiments in which the head region of the tether is attached to a first member, such a directional force also can bring the first member adjacent to, or fully or partially disposed within, the aperture of the nanopore in a manner such as described herein with reference to FIG. 1M. For example, the attraction of the tail region towards the side of the nanopore opposite that at which the head region of the tether is attached to a first member also can cause translocation of the first member to a position adjacent to, or fully or partially disposed within, the aperture of the nanopore.

Method 310 illustrated in FIG. 3B optionally further can include attaching the tail region of the tether to the other of the first side or second side of the nanopore or to a second member (314). Any suitable attachment such as provided herein, or otherwise known in the art, suitably can be used. For example, method 310 optionally can include attaching the tail region of the tether to the side of the nanopore opposite of that of the head region, such as described above with reference to FIG. 1H. Or, for example, method 310 optionally can include attaching the tail region of the tether to a second member disposed on the side of the nanopore opposite to that of the head region, such as described above with reference to FIGS. 1I or 1M. The second member optionally can be disposed within the aperture of the nanopore. Alternatively, step 314 need not be performed, and method 310 can include allowing the tail region of the tether to extend freely within the aperture of the nanopore, in a manner such as described above with reference to FIGS. 1A-1F, 1J, or 1L, or beyond the aperture of the nanopore, in a manner such as described above with reference to FIGS. 1G or 1K.

Under some conditions, the application of a directional force to the elongated body of a tether can cause translocation of the tail region so as to dispose all of the tether within the aperture of the nanopore. A sufficiently large force can cause a polymerase (or other protein) that is attached to the tether to become temporarily lodged in or on the nanopore. Although not intending to be a limiting with respect to physical configuration, the result can be termed 'corking' of the nanopore by the protein. Corking can be inhibited or avoided by limiting the force on the tether (e.g., applying less than 180 mV across the nanopore), limiting the duration of time that force is applied on the system, or using a sufficiently large protein that the corking interaction is avoided. Alternatively or additionally, a reverse voltage can be applied to the system to reverse the interaction between the protein and nanopore (referred to as 'uncorking'). Another option to inhibit or avoid corking or to facilitate uncorking is to remove charged amino acids from the nanopore opening or complementary charges on the surface of the protein, so as to reduce charge affinity between the two components. It can be further beneficial to add cross links to the structure of the protein (e.g., engineered cysteine pairs that for disulfide crosslinks or chemical crosslinkers), in order to stabilize the globular structure of the protein.

Corking can be observed based on a characteristic current or flux or optical pattern that is distinct from patterns resulting from other configurations of the nanopore system. The distinct pattern can be observed for example, when applying a negative bias to the nanopore system. Accordingly, current or flux or optical patterns can be detected during assembly or use of a system that includes a protein that is localized to a nanopore via tether that is attached to the protein and disposed in the nanopore lumen. Detection of the patterns can be used to monitor assembly (e.g., to avoid corking), guide uncorking, or otherwise optimize desired assembly.

It should be appreciated that the present compositions, systems, and methods suitably can be used to detect many types of events. For example, the present compositions, systems, and methods suitably can be used to detect the motion of a molecule or a portion of that molecule. In one illustrative embodiment, the motion includes a conformational change of the molecule. In another illustrative embodiment, the motion includes an interaction of a molecule with another molecule, such as a first molecule binding another molecule, e.g., a protein binding a nucleotide, or a nucleotide being added to a polynucleotide. Other events can be envisioned.

Figure 4A:
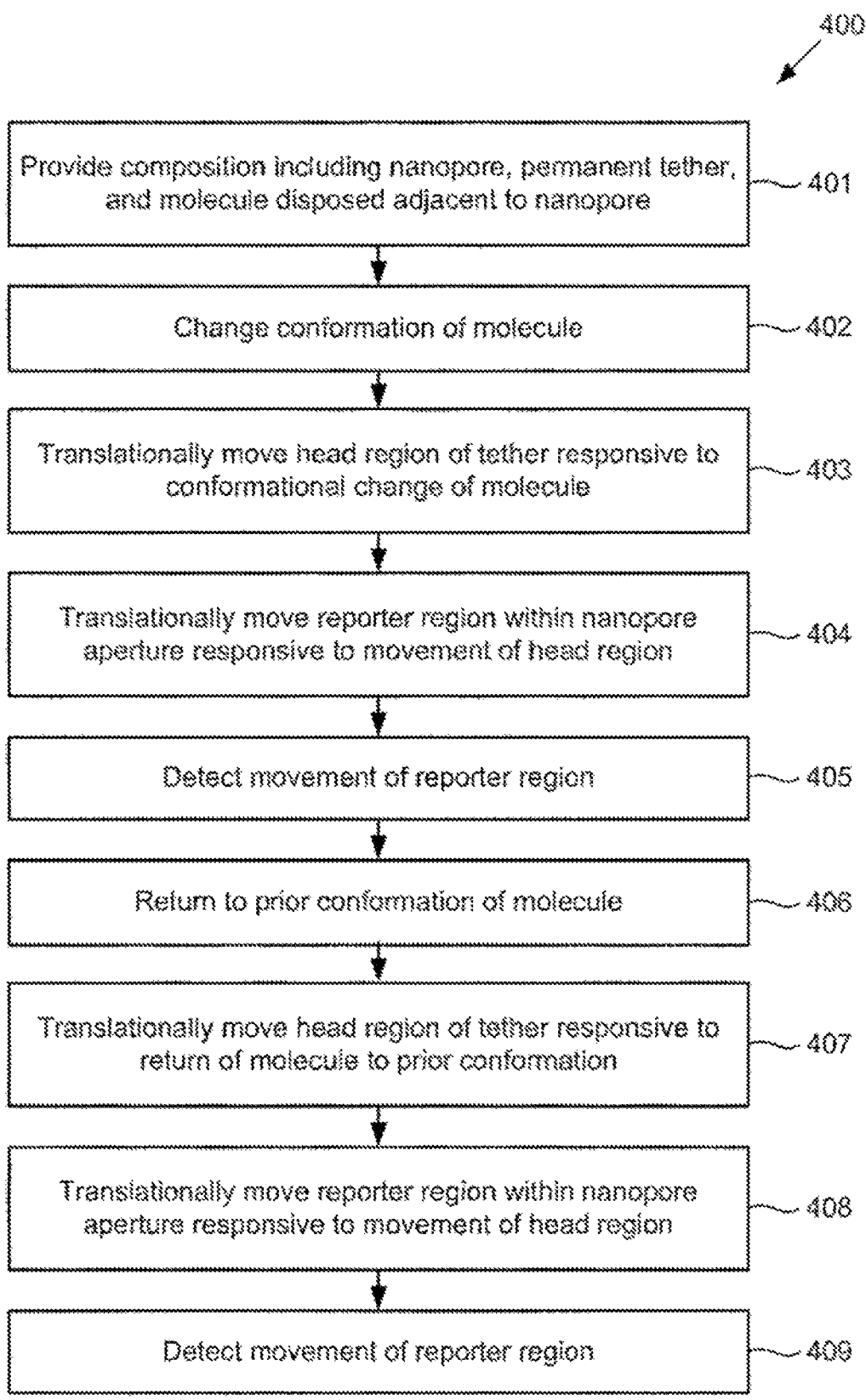
FIG. 4A illustrates a method for detecting a conformational change of a molecule using a composition including a tether anchored to or adjacent to a nanopore, according to some embodiments of the present invention.

Exemplary Methods and Compositions for Detecting Conformational Changes of Molecules FIG. 4A illustrates exemplary method 400 for detecting a conformational change of a molecule using a composition including a tether anchored to or adjacent to a nanopore. It should be appreciated that method 400 suitably can be adapted to detecting conformational changes of many types of molecules, such as proteins and nucleic acids.

Figure 5A:
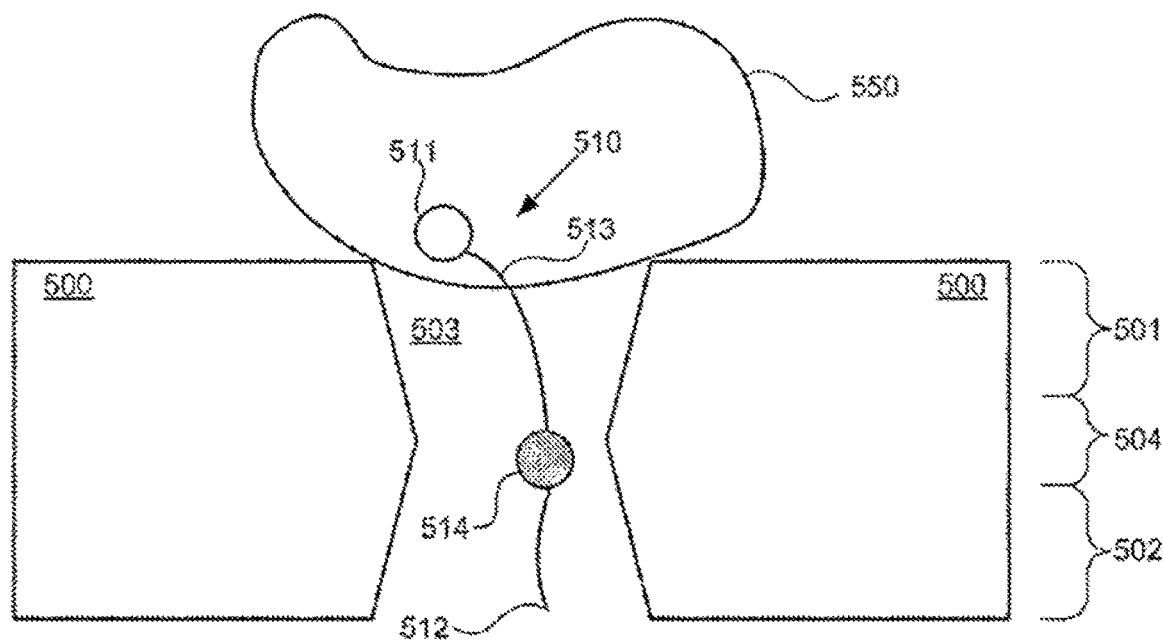
FIGS. 5A-5B schematically illustrate a composition including a tether anchored adjacent to a nanopore and configured for use in detecting a conformational change of a molecule disposed adjacent to the nanopore, according to some embodiments of the present invention.
Figure 5B:
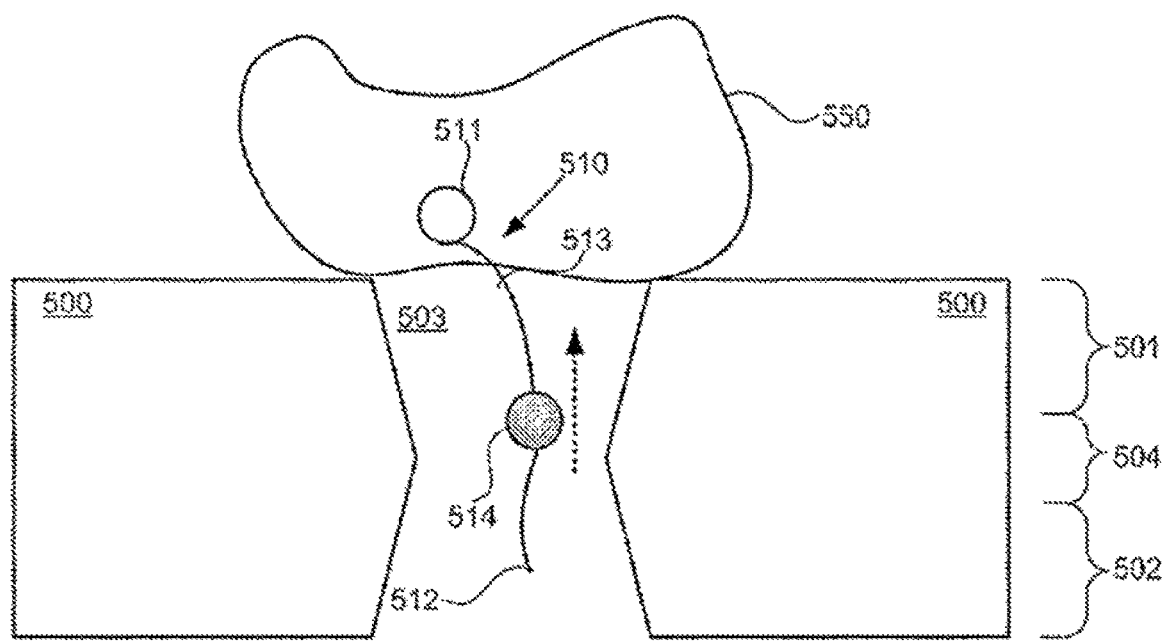

Method 400 illustrated in FIG. 4A includes providing a composition including a nanopore, a permanent tether, and a molecule disposed adjacent to the nanopore (step 401). A composition can include a nanopore including a first side, a second side, and an aperture extending through the first and second sides; and a permanent tether including a head region, a tail region, and an elongated body disposed therebetween. The head region can be anchored to or adjacent to the first side or second side of the nanopore. The elongated body including a reporter region can be movable within the aperture responsive to a first event occurring adjacent to the first side of the nanopore. For example, FIGS. 5A-5B schematically illustrate a composition including a tether anchored adjacent to a nanopore and configured for use in detecting a conformational change of a molecule disposed adjacent to the nanopore. In the exemplary embodiment illustrated in FIG. 5A, the composition can include nanopore 500, permanent tether 510, and molecule 550. Nanopore 500 includes first side 501, second side 502, aperture 503, and optionally also includes constriction 504. Permanent tether 510 includes head region 511, tail region 512, and elongated body 513 disposed therebetween and including reporter region 514 (optionally, one or more additional reporter regions can be provided such as described above with reference to FIG. 1C).

Molecule 550 can be disposed adjacent to first side 501 of nanopore 500. For example, molecule 550 can be in contact with first side 501 of nanopore 500, and optionally can be anchored to or adjacent to the first side of nanopore 500 via any suitable chemical bond, protein-protein interaction, or any other suitable attachment that is normally irreversible. In one illustrative embodiment, molecule 550 includes a protein. One example of a protein suitable for use in method 400 illustrated in FIG. 4A is an enzyme. One example of an enzyme suitable for use in method 400 illustrated in FIG. 4A is a polymerase. Other types of molecules, proteins, or enzymes suitably can be used. In the embodiment illustrated in FIG. 5A, head region 511 of tether 510 is attached to, e.g., anchored to, molecule 550, via any suitable chemical bond, protein-protein interaction, or any other suitable attachment that is permanent. Head region 511 can be attached to any suitable portion of molecule 550 that undergoes a conformational change that can cause movement of reporter region 514 relative to constriction 504. Note that molecule 550 need not necessarily be considered to be part of the inventive composition, but instead can be considered to be in contact with a composition that includes nanopore 500 and permanent tether 510. Additionally, note that molecule 550 can be, but need not necessarily be, attached to or adjacent to nanopore 500. Additionally, note that tail region 512 optionally can be attached to a second molecule (not specifically illustrated) in a manner such as described above with reference to FIGS. 1I and 1M.

Referring again to FIG. 4A, method 400 includes changing the conformation of the molecule (step 402). For example, FIG. 5B schematically illustrates a conformational change to molecule 550 that causes motion of one or more regions of molecule 550 relative to one or more other regions of molecule 550. In one illustrative embodiment in which molecule 550 is a polymerase, the conformational change of the polymerase can be responsive to the polymerase binding a nucleotide. Alternatively, the conformational change of the polymerase can be responsive to the polymerase adding a nucleotide to a polynucleotide. In still other alternative embodiments, the conformational change of the polymerase can be responsive to the polymerase binding to a nucleic acid template, releasing a nucleic acid template, releasing a nucleotide without incorporating it, or excising a nucleotide, or a combination thereof.

Referring again to FIG. 4A, method 400 also includes translationally moving the head region of the tether responsive to the conformational change of the molecule (step 403). For example, FIG. 5B schematically illustrates a conformational change to molecule 550 that moves head region 511. Such movement of region can be, but need not necessarily be, away from nanopore 500. For example, in the embodiment illustrated in FIG. 5B, head region 511 is moved both laterally relative to aperture 503 and away from first side 501 of nanopore 500.

Referring again to FIG. 4A, method 400 also includes translationally moving the reporter region within the nanopore aperture responsive to movement of the head region (step 404). For example, FIG. 5B schematically illustrates a conformational change to molecule 550 that translationally moves head region 511, and the movement of head region 511 translationally moves reporter region 514 toward first side 501, as indicated by the dashed arrow. For example, reporter region 514 can be adjacent to or disposed within optional constriction 504 prior to the conformational change, such as illustrated in FIG. 5A, and can be moved away from optional constriction 504 toward first side 501 responsive to the conformational change. Alternatively, a conformational change to molecule 550 instead can move head region 511 in such a manner that reporter region 514 translationally moves toward second side 502, or undergoes any other suitable translational, rotational, or conformational movement, or a combination thereof, within aperture 503.

Referring back to FIG. 4A, method 400 further includes detecting the movement of the reporter region (step 405). For example, the composition can be in operable communication with a measurement circuit such as described above with reference to FIG. 2A or FIG. 2C. The measurement circuit can be configured to detect the movement of the reporter region within the aperture. In one illustrative embodiment, nanopore 500, tether 510, and molecule 550 can be immersed in a conductive fluid, e.g., an aqueous salt solution. A measurement circuit configured analogously to measurement circuit 230 illustrated in FIG. 2A or measurement circuit 240 illustrated in FIG. 2C can be in communication with first and second electrodes and can be configured to apply a voltage between those electrodes so as to impose a voltage across nanopore 500. The measurement circuit further can be configured to use the electrodes to measure the magnitude of a current or flux through aperture 503 or can include an optical sensor to measure an optical signal. Reporter region 514 can have a different current or flux blockade property, e.g., a different physical, chemical, biological, optical, or electrical property, than some or all other regions of elongated body 513. For example, reporter region 514 can include an electrostatic charge, while some or all other regions of elongated body 513 can include a different electrostatic charge, or can be uncharged (e.g., can be electrically neutral). Or, for example, reporter region can be uncharged, while some or all other regions of elongated body 513 can include an electrostatic charge. The magnitude of the current or flux through aperture 503 or optical signal can measurably change responsive to a change in the position of reporter region 214 relative to constriction 204, and the time period for such a measurable change in the current or flux or optical signal is based on the duration of the reporter region's change in position. In one illustrative, nonlimiting example, elongated body 513 includes a polynucleotide that includes one or more abasic nucleotides that define reporter region 514.

The change in conformation of molecule 550 can be individually identifiable based on a measured (e.g., optically or electrically measured) magnitude or time duration, or both, of a signal generated by such a system. For example, the conformational change can cause reporter region 514 to move to a first location, and the presence of reporter region 514 at the first location causes the signal (e.g., an optical or electrical signal) to have a first magnitude. As such, the signal having the first magnitude correlates to the conformation change having occurred. Or, for example, the conformation change can cause reporter region 514 to move to the first location for a first period of time, and the presence of reporter region 514 at the first location causes the signal to have a first time duration. As such, the signal having the first time duration correlates to the conformation change having occurred. In one specific example, the signal has both a first magnitude and a first time duration, each of which is based on the presence of reporter region 514 at the first location, thus increasing confidence in a determination based on the signal that a conformation change has occurred.

As illustrated in FIG. 4A, method 400 further can include returning to the prior conformation of the molecule (step 406). Method 400 further can include translationally moving the head region of the tether responsive to return of the molecule to the prior confirmation (step 407). Method 400 further can include translationally moving the reporter region of the tether within the nanopore aperture responsive to movement of the head region (step 408). For example, following the conformational change illustrated in FIG. 5B, molecule 550 can return to the molecule's previous conformation, e.g., such as illustrated in FIG. 5A. Such a return can move head region 511 in such a manner that reporter region 514 can translationally move toward second side 502, e.g., to a location adjacent to or within constriction 504. Alternatively, rather than returning to the prior conformation, the molecule instead can change to a different conformation that is different than the prior conformation. Method 400 further can include detecting the movement of the reporter region (step 409). Such detection can be performed analogously as described above with reference to step 406.

It should be appreciated that method 400 illustrated in FIG. 4A suitably can be adapted to detect events other than conformational changes, e.g., to detect translational molecular motions, or combinations of different types of molecular motions. Additionally, it should be appreciated that method 400 illustrated in FIG. 4A suitably can be adapted to detect such events using any suitable combination of translational, rotational, or conformational changes of the reporter region of the tether.

Sequencing by Synthesis Using Exemplary Methods and Compositions Based on Detecting Conformational Changes of a Polymerase It should be appreciated that method 400 illustrated in FIG. 4A suitably can be used to detect any of a variety of conformational changes. In one nonlimiting, illustrative embodiment described below with reference to FIGS. 6A-6D, method 400 can be used to detect the conformational change of a polymerase associated with the polymerase acting upon a nucleotide. Detection of such conformational changes can be used to sequence a first polynucleotide by synthesizing a second polynucleotide that is complementary to the first nucleotide, e.g., using "sequencing by synthesis," or SBS.

Previously known methods for SBS have been developed. For example, single stranded DNA (ssDNA) can pass through a biological nanopore, such as a protein nanopore, that is embedded in a barrier such as a lipid bilayer, responsive to an electrical potential being applied across the nanopore. In what can be referred to as "strand" sequencing, as nucleotides of the ssDNA pass through a pore constriction, combinations of those nucleotides can create unique current or flux blockades corresponding to the identities of nucleotides in the particular combinations pass through the constriction. These strands that are being sequenced are not permanently attached to the pore or to the polymerase. Rather, these strands translocate through the pore such that the net position of the strand changes relative to the pore. However, the extremely rapid translocation rate of ssDNA (~1 nt/pec), as well as the native resolution of the constriction that encompasses a combination of nucleotides, rather than a single nucleotide, can hinder accurate measurement of such current or flux blockades on a nucleotide-by-nucleotide basis. Enzymatic "motors" have been used to slow the translocation speed to a rate which is more compatible with data acquisition (milliseconds per nucleotide). However, such motors when used in strand sequencing configurations can introduce error modes such as skipping, slipping and toggling, which can inhibit reliable detection of nucleotides in the ssDNA. These and other motor-independent error modes that can occur during strand sequencing can result from the "springiness" or elasticity of the ssDNA residing between the motor and the constriction of the nanopore. Such springiness can be a function of the sequence of the ssDNA, and can result in different currents or fluxes for the same combination of nucleotides transiting the constriction if different instances of that combination respectively are surrounded by different ssDNA sequences. Further, because the constriction can be relatively small, e.g., about 2 nt, and Brownian motion is always present, the pore "read head" can be effectively about 4 nucleotides in size, e.g., the constriction reads a combination of about 4 nucleotides at a time, thus making it more difficult to uniquely identify each nucleotide since there are 4^4 (256) currents or fluxes that need to be differentiated from one another.

Accordingly, a need remains for improvements in SBS, e.g., for inexpensive, accurate, long-read, high-throughput compositions, systems, and methods for SBS. SBS using biological nanopores represents one potential solution to this need because of the nanoscale reproducibility and ease of production of these proteins. Taken together, an approach which is motor free (e.g. using nucleic enzymes as a detector that is coupled to a nanopore rather than as a motor that modulates passage of a target strand through a nanopore), more tolerant of Brownian motion, and has single nucleotide resolution can be expected to greatly advance the field of nanopore DNA sequencing.

As noted above, the present methods, compositions, and systems can be used to detect conformational changes in a molecule. Accordingly, the present methods, compositions, and systems can be applied to monitoring conformational changes that a DNA polymerase undergoes as it synthesizes DNA from a template. For example, the polymerase can transition between what is referred to as an "open state," in which the polymerase does not bind a nucleotide, to a "closed state," in which the polymerase binds a nucleotide. See, e.g., Xia et al., "Alteration in the cavity size adjacent to the active site of RB69 DNA polymerase changes its conformational dynamics," Nucl. Acids Res. (2013), nar.gkt674, the entire contents of which are incorporated by reference herein. See also Santoso et al., "Conformational transitions in DNA polymerase I revealed by single-molecule FRET," Proc. Natl. Acad. Sci. USA, 107(2): 715-720 (2010), the entire contents of which are incorporated herein by reference.

Conformational changes on the order of several nanometers are known to occur during the catalytic cycle of nucleotide incorporation as the polymerase transitions from the open to closed state, or as the polymerase switches into editing mode. For example, FIGS. 6A-6B schematically illustrate relatively large polymerase conformation changes (>1 nm) in two different polymerases. FIG. 6A illustrates RB69 polymerase, which exhibits a relatively large conformational change that results in relative movement between the thumb domain and finger domain, undergoing over 3 nm of movement between the open and closed conformations, as described by Xia et al. FIG. 6B illustrates Pol I (Klenow Fragment, or KF), which undergoes conformational changes during nucleotide incorporation as disclosed by Santoso et al. The α-carbon backbone of the polymerase is shown in beige. The DNA template strand is in dark gray, the primer strand in light gray. The terminal base pair at the active site is magenta. According to Santoso, the β carbons of the two side chains were used as fluorophore attachment sites, shown as green and red spheres, to measure conformational changes of the polymerase. The arrows indicate the distance in Angstroms between the green and red CP positions in the open and closed conformations. There also is evidence that the conformational changes of a polymerase can be dependent upon the identity of the nucleotide being incorporated, e.g., such as described in Olsen et al., "Electronic Measurements of Single-Molecule Processing by DNA Polymerase I (Klenow Fragment)," JACS 135: 7855-7860 (2013), the entire contents of which are incorporated by reference herein. In the nanopore embodiments of the present disclosure, the finger domain can be anchored to a nanopore while a tether is attached to the thumb domain. Alternatively, the thumb domain can be anchored to a nanopore while a tether is attached to the finger domain. In either construct, the relative movement that occurs between the finger and thumb domains during polymerase activity can be detected as relative movement between the tether and the nanopore. Attachment chemistries used to attach optical probes (e.g., FRET pairs) in the references cited herein can be used in the nanopore embodiments set forth herein. Other attachment points can be used in a polymerase-nanopore construct so long as conformational changes in the polymerase are reliably transmitted as relative movement between the tether and nanopore.

Using the present composition, a nanopore and a permanent tether can be used to transduce the conformational changes of a polymerase during SBS into an electrical current or flux signature. Note that using the present compositions, systems, and methods, the DNA being sequenced during SBS according to the present methods need not transit the nanopore, and can be sequenced on a nucleotide-by-nucleotide basis, thus distinguishing the method from strand sequencing methods such as mentioned above and such as described in greater detail in U.S. Patent Publication No. 2014/0051096 to Jeyasinghe et al., the entire contents of which are incorporated by reference herein.

Figure 6C:
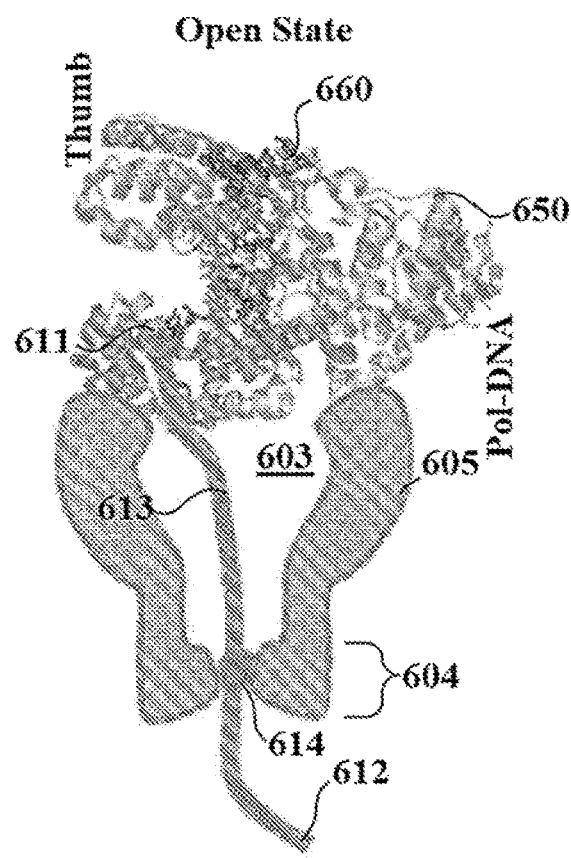
FIGS. 6C-6D schematically illustrate a composition including a tether anchored to a polymerase disposed adjacent to a nanopore and configured for use in detecting a conformational change of the polymerase responsive to action of the polymerase upon a nucleotide, according to some embodiments of the present invention.
Figure 6D:
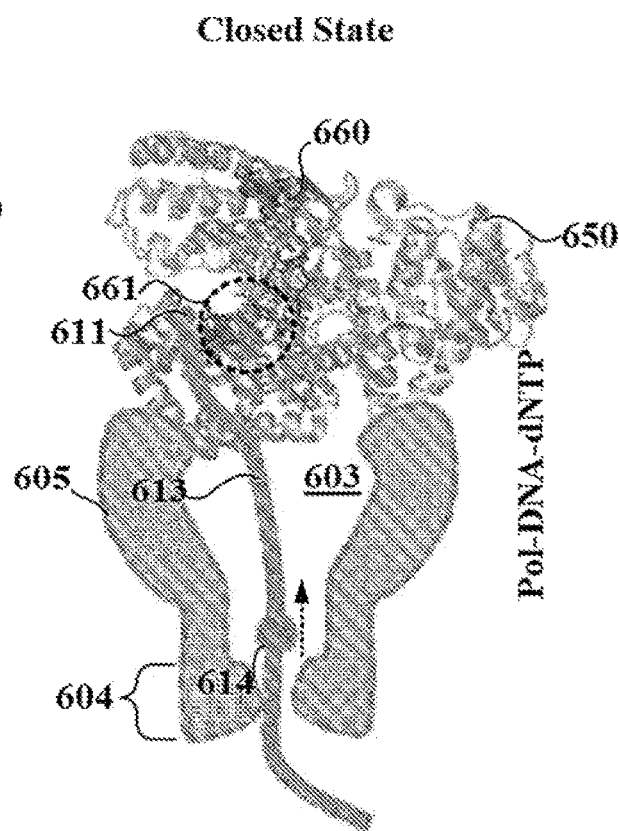

More specifically, FIGS. 6C-6D schematically illustrate an exemplary composition including a permanent tether anchored to a polymerase disposed adjacent to a nanopore and configured for use in detecting a conformational change of the polymerase responsive to binding of a nucleotide. The nanopore includes biological pore 605, which can be disposed in a barrier (not specifically illustrated), e.g., a membrane of biological origin such as a lipid bilayer, or a solid state membrane. Biological pore 605 includes aperture 603 and constriction 604. The permanent tether includes head region 611, tail region 612, elongated body 613, and reporter region 614. Optionally, tail region 612 can be attached to a second member (not specifically illustrated) in a manner analogous as described with reference to FIGS. 1F and 1M. Polymerase 650 is disposed adjacent to biological pore 605, and optionally can be attached to biological pore 605.

Polymerase 650 is configured to receive a template polynucleotide, e.g., circular or linear ssDNA to be sequenced, to synthesize a polynucleotide having a complementary sequence to that of the ssDNA by sequentially receiving, binding, and adding nucleotides to the polynucleotide in accordance with the sequence of the ssDNA. Head region 611 of the permanent tether is anchored to a location of polymerase 650 that undergoes a conformational change, e.g., responsive to receiving a nucleotide, binding a nucleotide, or adding a nucleotide to polynucleotide 660, and that moves reporter region 614 to a sufficiently different location relative to constriction 604 so as to produce a signal from which an identity of that polynucleotide can be individually determined. For example, head region 611 can be attached to a finger region of the polymerase, or a thumb of the polymerase. Exemplary attachment points in the finger and thumb regions of polymerases and chemistries for attaching moieties to these points are set forth in U.S. Patent Publication No. 2011/0312529 A1, the entire contents of which are incorporated by reference herein. For further details on the structure and function of family A and B polymerases, see Patel et al., "Getting a grip on how DNA polymerases function," Nature Structural Biology 8: 656-659 (2001), the entire contents of which are incorporated by reference herein. For further details on the structure and function of polymerases such as Pol I, see the following references, the entire contents of each of which are incorporated by reference herein: Olsen et al., "Electronic measurements of Single-Molecule Processing by DNA Polymerase I (Klenow Fragment," JACS 135: 7855-7860 (2013); Torella et al., "Identifying molecular dynamics in single-molecule FRET experiments with burst variance analysis," Biophysics J. 100: 1568-1577 (2011); Santoso et al., "Conformational transitions in DNA polymerase I revealed by single-molecule FRET," Proc. Natl. Acad. Sci. USA, 107(2): 715-720 (2010), Markiewicz et al., "Single-molecule microscopy reveals new insights into nucleotide selection by DNA polymerase I," Nucleic Acids Res. 40: 7975-7984 (2012); Gill et al., "DNA Polymerase activity at the single-molecule level," Biochem. Soc. Trans. 39: 595-599 (2011), and Johnson et al., "Processive DNA synthesis observed in a polymerase crystal suggests a mechanism for the prevention of frameshift mutations," Proc. Natl. Acad. Sci. USA 100: 3895-3900 (2003). Any two residues or domains that are known from the above references (or other references cited herein) to undergo a change in relative position during polymerase activity can serve as attachment points to a nanopore and tether respectively in an embodiment of the present invention.

Figure 2C:
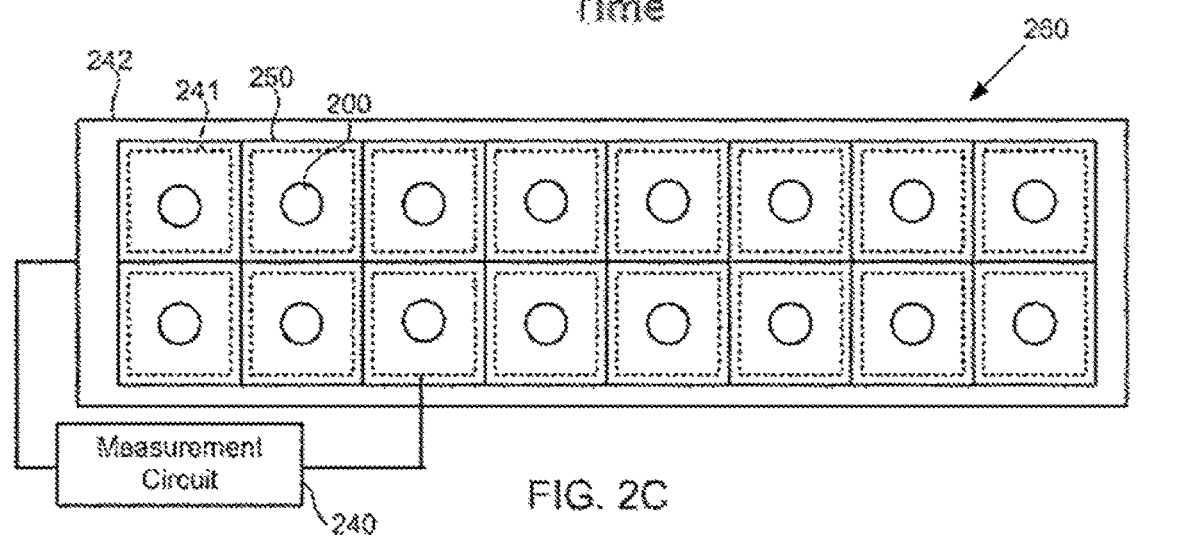
FIG. 2C schematically illustrates a plan view of a system including measurement circuitry configured to measure movement of respective reporter regions within the respective apertures of an array of nanopores, according to some embodiments of the present invention.

In one example, a voltage can be applied across the nanopore 605, e.g., using measurement circuit 230 and electrodes 231, 232 such as described further above with reference to FIG. 2A, or measurement circuit 240 and electrodes 241, 242 such as described further above with reference to FIG. 2C. Reporter region 614 or elongated body 613 includes an electrostatic charge that, responsive to the applied voltage, causes elongated body 613 to extend through constriction 604 such that reporter region 614 is disposed within or adjacent to constriction 604. Optionally, the applied voltage can cause elongated body 613 to become taut. As the protein domains of polymerase 650 move, e.g., change conformation, such movements can impose a force on head region 611, which imposes a force on elongated body 613, which imposes a force on reporter region 614, resulting in translational movement of reporter region 614 within aperture 603, e.g., movement relative to constriction 604. As a result, a conformational change of polymerase 650 can be translated or transduced into a measurable change in current or flux through aperture 603, which also can be referred to as a blockade current or flux. In one illustrative embodiment, reporter region 614 is constructed using one or more modified nucleotides. For example, abasic nucleotides typically generate a 70 pA blockade current compared to residues that include bases, such as dT residues that generate only a 20 pA blockade current under conditions that include 10 mM 4-(2-hydroxyethyl)-1-piperazineethanesulfonic acid) (HEPES) buffer, pH 8.0, 300 mM KCl, 1 mM $MgCl_2$, 1 mM DL-dithiothreitol (DTT), MspA M2 mutant pore (D90N, D91N, D93N, D118R, D134R & E139K), 180 mV across a 1,2-diphytanoyl-sn-glycero-3-phosphocholine (DPhPC) bilayer.

Movements of one or more abasic residues on the order, e.g., of just a few Angstroms, can cause easily detectable changes in current or flux, e.g., of from one to tens of pAs. Because some polymerases move on the order of nanometers, and a single base in the tether corresponds to about 0.5 nanometers, it is anticipated that tether movements resulting from conformational changes in the polymerase to which the tether is anchored can be generated and readily transduced into currents or fluxes. Because the identity of the nucleotide influences both the magnitude of the conformational change as well as the time spent in the open state, unique current or flux signatures can be generated that individually identify nucleotides as they bind to or reside in the active site of the polymerase. Additionally, these unique current or flux signatures can individually indicate whether or not a nucleotide is complementary or not to a next nucleotide in a polynucleotide being sequenced. For further details regarding differences in polymerase conformation and kinetics between match and mismatch nucleotides, see the following references, the entire contents of each of which are incorporated by reference herein: Freudenthal et al., "New structural snapshots provide molecular insights into the mechanism of high fidelity DNA synthesis," DNA Repair, doi:10.2016/j.dnarep/2015.04.007 (available online Apr. 30, 2015); Freudenthal et al., "Watching a DNA polymerase in action," Cell Cycle 13: 691-692, doi:10.4161/cc.27789 (2014); and Freudenthal et al., "Observing a DNA polymerase choose right from wrong," Cell 154: 157-168, doi:10.1016/j.cell.2013.05.048 (2013).

For example, as illustrated in FIG. 6D, a conformation change of polymerase 650 from the open state to the closed state can translate to an "up" movement of reporter region 614 to a first location within aperture 603, and a conformation change of polymerase 650 from the closed state to the open state can translate to a "down" movement of reporter region 614 to a second location within aperture 603, resulting in detectable changes in the blockade current or flux that can be correlated to individual nucleotides.

For example, a first conformational change of polymerase 650 can occur responsive to the polymerase binding a first nucleotide, e.g., nucleotide 661 illustrated in FIG. 6D. The first nucleotide can be individually identifiable based on a measured (e.g., optically or electrically measured) magnitude or time, or both, of a first current or flux through the constriction. For example, reporter region 614 can move towards the polymerase responsive to the first conformational change, causing a change in current or flux through constriction 604. Additionally, a second conformational change of polymerase 650 can occur responsive to the polymerase binding a second nucleotide. The second conformational change can differ from the first conformational change, e.g., in magnitude or in time. The second nucleotide can be individually identifiable based on a measured (e.g., optically or electrically measured) magnitude or time, or both, of a second current or flux through the constriction. For example, reporter region 614 can move towards the polymerase responsive to the second conformational change, causing a change in current or flux through constriction 604.

Alternatively, or additionally, a first conformational change of polymerase 650 can occur responsive to the polymerase adding a first nucleotide, e.g., nucleotide 661 illustrated in FIG. 6D, to a polynucleotide, e.g., polynucleotide 660. The first nucleotide can be individually identifiable based on a measured (e.g., optically or electrically measured) magnitude or time, or both, of a first current or flux through the constriction. For example, reporter region 614 can translationally move towards at least a portion of polymerase 650 responsive to the first conformational change, causing a change in current or flux through constriction 604. Additionally, a second conformational change of polymerase 650 can occur responsive to the polymerase adding a second nucleotide to the polynucleotide. The second conformational change can differ from the first conformational change, e.g., in magnitude or in time. The second nucleotide can be individually identifiable, and distinguishable from the first nucleotide, based on a measured (e.g., optically or electrically measured) magnitude or time, or both, of a second current or flux through the constriction. For example, reporter region 614 can translationally move towards at least a portion of polymerase 650 responsive to the second conformational change, causing a change in current or flux through constriction 604.

As noted above, the magnitude or time duration, or both, of the polymerase's conformational change(s) can be based on the particular nucleotide that the polymerase receives, binds, and adds to a polynucleotide. Table 1 lists exemplary single molecule kinetic parameters that were measured for Klenow fragment processing of templates using current changes in a SWNT attached to a single polymerase and reported by Olsen et al. In Table 1, $\tau_{lo}$ corresponds to the duration of time spent in the polymerase's closed conformation, no corresponds to the mean-normalized variance for $\tau_{lo}$, $\tau_{hi}$ corresponds to the duration of time spent in the polymerase's open conformation, $r_{hi}$ corresponds to the mean-normalized variance for $\tau_{hi}$, and the rate corresponds to the rate of processing, e.g., how quickly the polymerase adds the nucleotide to the template. Olson et al., reports that the average magnitude H is a proxy for the extent of mechanical closure by the enzyme. For the present systems, methods, and compositions, the value H can be considered to be the extent of conformational change between two reference points on the polymerase, as measured in units of distance.

TABLE 1

("Template" sequences disclosed as SEQ ID NOS 1-4, respectively, in order of appearance)

| Template | Nucleotide | τlo (ms) | rlo | τhi (ms) | rhi | H (nA) | rate (1/s) |
|---|---|---|---|---|---|---|---|
| poly(dT)$_{42}$ | dATP | 0.33 ± 0.08 | 0.85 ± 0.09 | 71.4 ± 1.4 | 0.95 ± 0.08 | 6.94 | 14.4 ± 2.9 |
| poly(dA)$_{42}$ | dTTP | 0.42 ± 0.09 | 0.83 ± 0.06 | 63.7 ± 1.1 | 0.96 ± 0.06 | 4.90 | 16.0 ± 2.9 |
| poly(dG)$_{42}$ | dCTP | 0.32 ± 0.07 | 0.78 ± 0.05 | 39.0 ± 5.6 | 0.98 ± 0.06 | 2.53 | 26.2 ± 4.4 |
| poly(dC)$_{42}$ | dGTP | 0.33 ± 0.05 | 0.78 ± 0.05 | 38.0 ± 5.8 | 1.03 ± 0.07 | 2.40 | 28.5 ± 3.5 |

$^a$Average values ± standard deviation.
doi: 10.1021/ja311603r J Am Chem Soc. 2013 135: 7855-7860

Using the compositions, methods, and systems provided herein, a signal that correlates to the time duration of the open state $\tau_{hi}$, the magnitude of conformational change H, and rate of processing together can be used to indicate a unique signature for each base. Incorporation rates can also be greatly changed by the selective use modified nucleotides, such as alpha- or gamma thiol nucleotides. See, for example, U.S. Patent Publication No. 2011/0312529 to He et al., the entire contents of which are incorporated by reference herein.

In one illustrative embodiment, the template DNA is circularized and polymerase 650 is a strand-displacing polymerase (such as Phi29). In this manner, the template can be sequenced multiple times in a rolling circle mode such as known in the art. Such an embodiment also can inhibit inadvertently pulling the template DNA into or through constriction 604, because only ssDNA can translocate. Any stray ssDNA that may find its way through constriction 604 (or if a linear template is used) is expected to transit rapidly and is expected to manifest as noise in the signal. Alternatively, one can employ a positively charged reporter region 614 under reverse polarity such that only the reporter region is drawn into the constriction 604, whereas negatively charged DNA will be repelled.

In some embodiments, polymerase 650 optionally can be attached, e.g., anchored, to the mouth of biological pore 605. This can be accomplished using cysteine/thiol conjugation chemistry, for example. Such a conjugation can provide that polymerase 650 is anchored in a reproducible and stable orientation that can enhance the transfer of conformational motion of the polymerase 650 to translational motion of reporter region 614. However, conjugation of the polymerase to the pore need not be required. For example, the force exerted by the tether responsive to the applied voltage can be sufficient to hold the polymerase in place. In other embodiments, polymerase 650 is not attached to biological pore 605, and tail region 612 can be attached to another member (such as an oligonucleotide) so as to retain polymerase 650 at pore 605.

Additionally, note that a rapid AC current can be used instead of a DC current in order to produce the requisite electric field. This has the advantage of inhibiting AgCl electrode depletion and lengthening the time the device can run.

It also should be understood that this approach can be extended to the analysis of any enzyme or protein that undergoes conformational changes. As such, the present systems, methods, and compositions can be considered to provide "nanopore force spectroscopy," and represent a tool that can be used to elucidate enzyme kinetics at the single molecule level, and can become an important tool in biochemistry research, analytical detection methods and clinical diagnostics.

Exemplary Methods and Compositions for Detecting Action of a Polymerase Upon a Nucleotide Techniques other than measurement of a conformational change alternatively can be used to detect events. For example, even if a particular event can involve a conformational change of a molecule, such as described above, such an event alternatively, or additionally, can be detected on another basis. For example, a method can include providing a nanopore including a first side, a second side, and an aperture extending through the first and second sides; and providing a permanent tether including a head region, a tail region, and an elongated body disposed therebetween. The head region can be anchored to or adjacent to the first side or second side of the nanopore, and the elongated body can include a moiety. The method further can include providing a polymerase disposed adjacent to the first side of the nanopore, and providing a first nucleotide including a first elongated tag, the first elongated tag including a moiety. The method further can include acting upon the first nucleotide with the polymerase; and interacting the first moiety with the moiety of the tether responsive to the polymerase acting upon the first nucleotide.

Figure 4B:
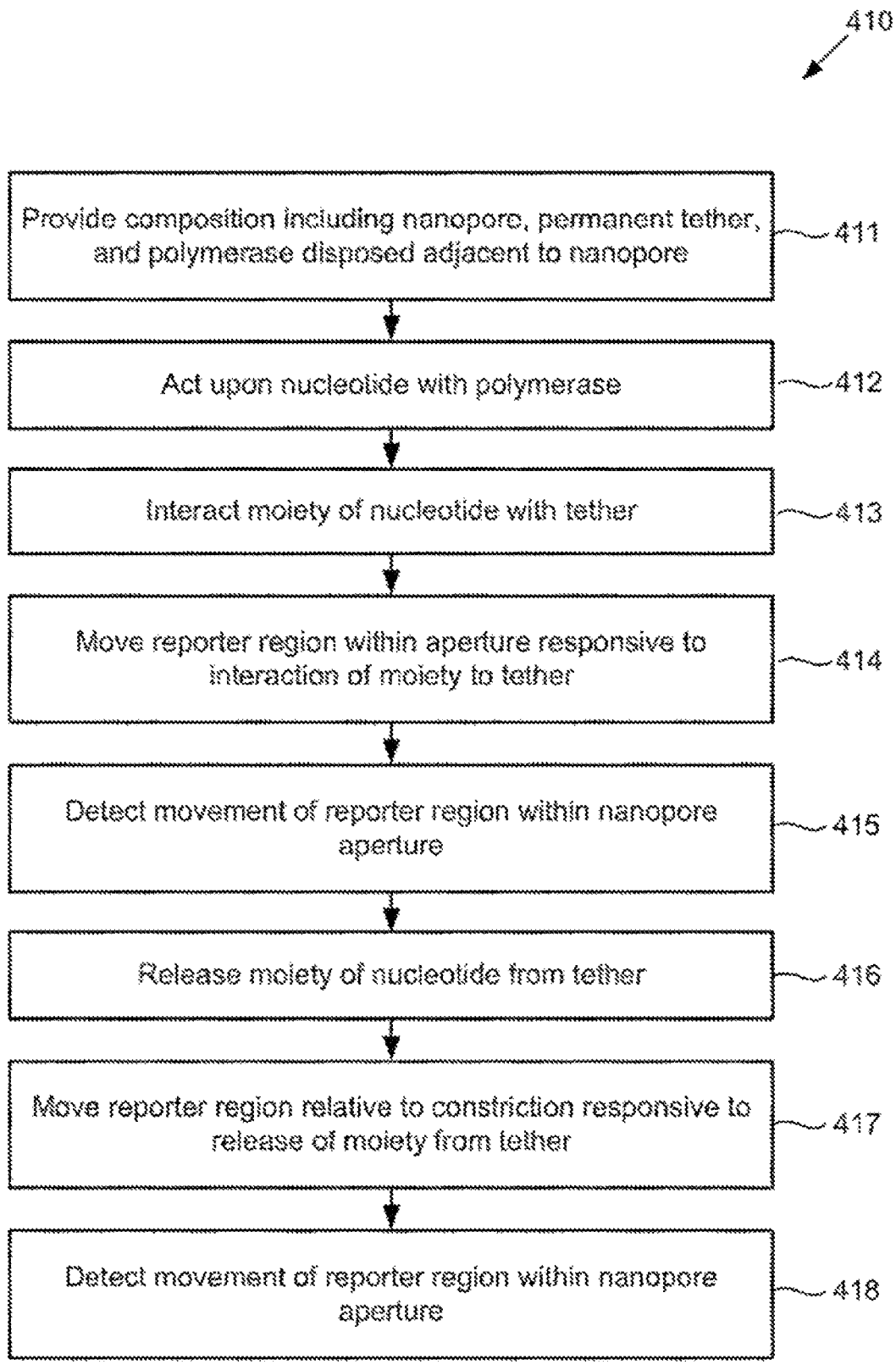
FIG. 4B illustrates a method for detecting action of a polymerase upon a nucleotide using a composition including a tether anchored to or adjacent to a nanopore, according to some embodiments of the present invention.

In one illustrative example, FIG. 4B illustrates a method for detecting action of a polymerase upon a nucleotide using a composition including a tether anchored to or adjacent to a nanopore, according to some embodiments of the present invention.

Figure 7A:
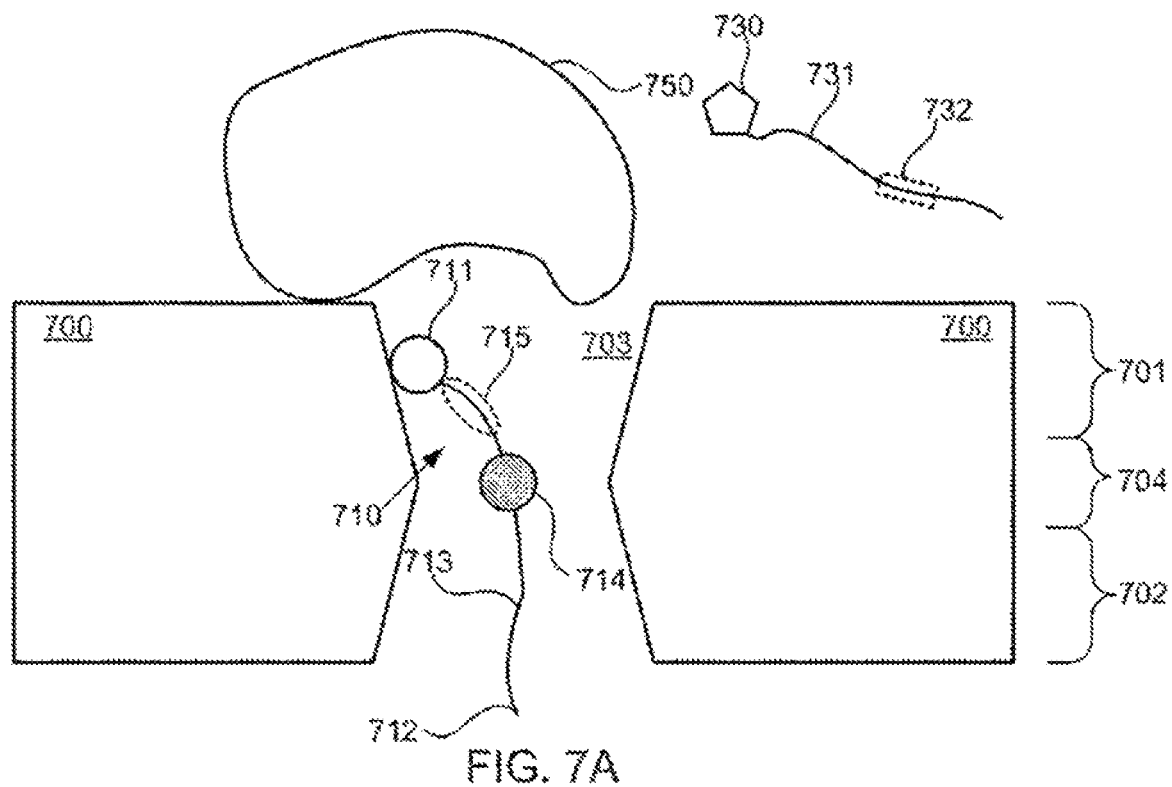
FIGS. 7A-7B schematically illustrate a composition including a tether anchored to or adjacent to a nanopore and configured for use in detecting action of a protein upon a nucleotide, according to some embodiments of the present invention.
Figure 7B:
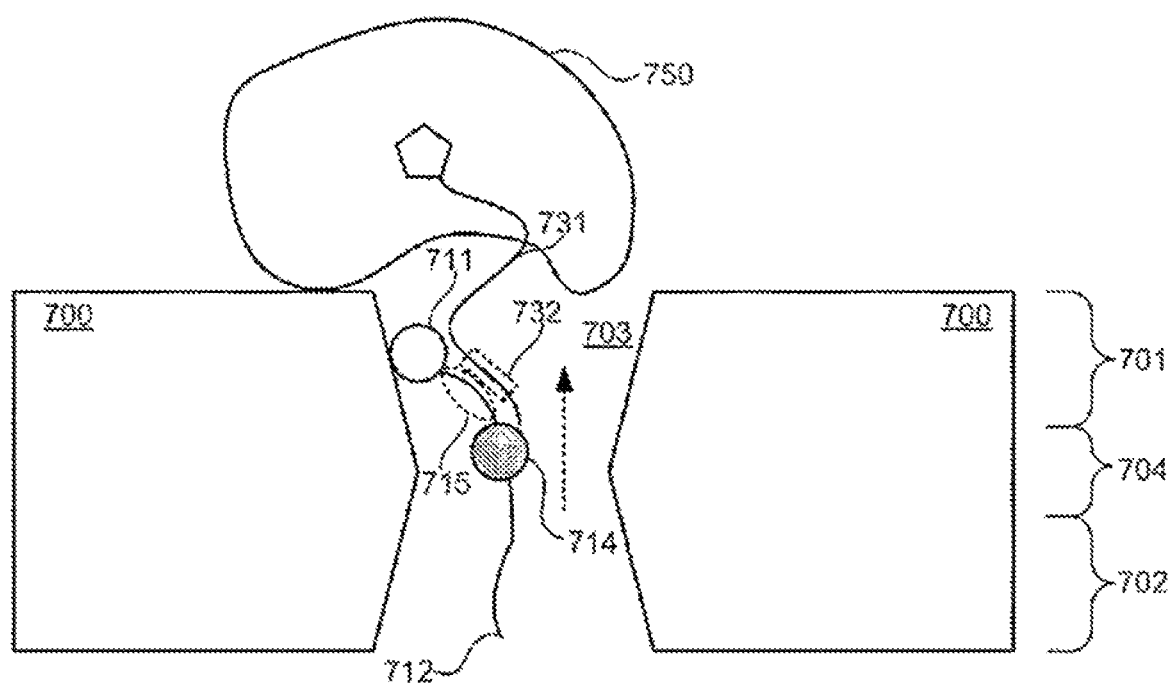

Method 410 illustrated in FIG. 4B includes providing a composition including a nanopore, a permanent tether, and a polymerase disposed adjacent to the nanopore (step 411). For example, FIGS. 7A-7B schematically illustrate a composition including a tether anchored to or adjacent to a nanopore and configured for use in detecting binding of a nucleotide by a protein disposed adjacent to the nanopore. In the exemplary embodiment illustrated in FIG. 7A, the composition can include nanopore 700, permanent tether 710, and polymerase 750. Nanopore 700 includes first side 701, second side 702, aperture 703, and optionally also includes constriction 704. Permanent tether 710 includes head region 711, tail region 712, and elongated body 713 disposed therebetween and including reporter region 714 (optionally, one or more additional reporter regions can be provided such as described above with reference to FIG. 1C). Polymerase 750 is disposed adjacent to first side 701 of nanopore 700. For example, polymerase 750 can be in contact with first side 701 of nanopore 700, and optionally can be anchored to or adjacent to the first side of nanopore 700 via any suitable chemical bond, protein-protein interaction, or any other suitable attachment that is normally irreversible. Optionally, tail region 712 can be anchored to another member in a manner analogous to that described with reference to FIGS. 1I and 1M.

In the embodiment illustrated in FIG. 7A, head region 711 of tether 710 is attached to, e.g., anchored to, first side 701 of nanopore 700, via any suitable chemical bond, protein-protein interaction, or any other suitable attachment that is normally irreversible. Head region 711 can be attached to any suitable portion of nanopore 700 that places reporter region 714 within aperture 703 and places elongated tag 713 sufficiently close to polymerase 750 so as to interact with nucleotides that can be acted upon by polymerase 750, and optionally also places reporter region 714 adjacent to or within constriction 704. For example, nucleotide 730 can include an elongated tag 731 including moiety 732 that interacts with tether 710. In an illustrative embodiment, elongated tag 713 of tether 710 can include a moiety 715 with which moiety 732 of tag can interact. Moiety 715 can be located at any suitable position along elongated tag 713, e.g., can be located adjacent to head region 711 such as illustrated in FIG. 7A, or can be adjacent to tail region 712, adjacent to reporter region 714, between head region 711 and reporter region 714, or between tail region 712 and reporter region 714. Note that polymerase 750 or nucleotide 730, or both, can be, but need not necessarily be, considered to be part of the composition, but instead can be considered to be in contact with a composition that includes nanopore 700 and permanent tether 710.

Referring again to FIG. 4B, method 410 includes acting upon a nucleotide with the polymerase (step 412). For example, FIG. 7B schematically illustrates binding of nucleotide 730 by polymerase 750, but it should be understood that polymerase 750 can act upon nucleotide 730 in a variety of ways, e.g., by adding nucleotide 730 to a polynucleotide, excising nucleotide 730 from an existing polynucleotide (e.g. via exonuclease activity or pyrophosphorolysis activity), or sampling nucleotide 730, e.g., transiently interacting with nucleotide 730 without binding it. It is anticipated that the dwell time of a nucleotide being acted upon by a polymerase can be approximately 1 msec or longer, or 10 msec or longer, or 20 msec or longer, or 50 msec or longer. The nucleotide can be modified so as to even further extend such dwell time, e.g., to 50 msec or longer, or 100 msec or longer.

Method 410 illustrated in FIG. 4B also includes interacting a moiety of the nucleotide with the tether (step 413). For example, in the embodiment illustrated in FIG. 7B, polymerase 750 acting upon nucleotide 730 can bring moiety 732 of nucleotide 730 into sufficiently close proximity to moiety 715 that the moieties interact with one another, e.g., bond with one another. Such an interaction can be reversible, e.g., can include formation of a hydrogen bond, ionic bond, dipole-dipole bond, London dispersion forces, reversible covalent bond, or any suitable combination thereof.

Referring again to FIG. 4B, method 410 also includes moving the reporter region relative to the constriction responsive to the interaction of the nucleotide's moiety with the tether (step 414). For example, FIG. 7B schematically illustrates that the interaction between moiety 732 of nucleotide 730 and moiety 715 of tether 710 can translationally move reporter region 714 toward first side 701, as indicated by the dashed arrow. For example, reporter region 714 can be disposed at a particular location within aperture 703 prior to the interaction, e.g., disposed adjacent to or within optional constriction 704 prior to the interaction, such as illustrated in FIG. 7A, and can be translationally moved within aperture 703 responsive to interaction between moiety 732 and tether 710, e.g., can be translationally moved away from constriction 704 toward first side 701. Alternatively, interaction between moiety 732 and tether 710 can move head region 711 in such a manner that reporter region 714 moves toward second side 702. It should be appreciated that interaction between moiety 732 and tether 710 suitably can cause any type of detectable movement of reporter region 714 within aperture 703, e.g., any detectable combination of translational, conformational, or rotational movement of reporter region 714.

Referring back to FIG. 4B, method 410 further includes detecting the movement of the reporter region within the nanopore aperture (step 415). For example, the composition can be in operable communication with a measurement circuit such as described above with reference to FIG. 2A or FIG. 2C. The measurement circuit can be configured to detect the movement of the reporter region within the nanopore aperture, e.g., relative to the constriction. In one illustrative embodiment, nanopore 700, tether 710, and polymerase 750 can be immersed in a conductive fluid, e.g., an aqueous salt solution. A measurement circuit configured analogously to measurement circuit 230 illustrated in FIG. 2A or measurement circuit 240 illustrated in FIG. 2C can be in communication with first and second electrodes and can be configured to apply a voltage between those electrodes so as to apply a voltage across nanopore 700. The measurement circuit further can be configured to use the electrodes to measure the magnitude of a current or flux through aperture 703. Reporter region 714 can have a different electrical property than some or all other regions of elongated body 713. For example, reporter region 714 can include an electrostatic charge, while some or all other regions of elongated body 713 can include a different electrostatic charge, or can be uncharged (e.g., can be electrically neutral). Or, for example, reporter region 714 can be uncharged, while some or all other regions of elongated body 713 can include an electrostatic charge. The magnitude of the current or flux through aperture 703 can measurably change responsive to translational, rotational, or conformational movement of reporter region 714 within the aperture, e.g., responsive to translational movement of reporter region 714 relative to optional constriction 704, and the time period for such a measurable change in the current or flux can be based on the duration of the reporter region's movement. In one illustrative, nonlimiting example, elongated body 713 includes a polynucleotide that includes one or more abasic nucleotides that define reporter region 714.

The action of polymerase 750 upon nucleotide 730 can be individually identifiable based on a measured magnitude or time duration, or both, of a signal (e.g., optical or electrical signal) generated by such a system. For example, the action of polymerase 750 upon nucleotide 730 can cause reporter region 714 to translationally move to a first location within aperture 703, and the presence of reporter region 714 at the first location causes the signal to have a first magnitude. As such, the signal having the first magnitude correlates to the action of polymerase 750 upon nucleotide 730 having occurred. Note that motions of reporter region 714 other than translational motion can be detectable, e.g., conformational motion or rotational motion, a combination of different types of motion.

As illustrated in FIG. 4B, method 410 further can include releasing the moiety of the nucleotide from the tether (step 416). For example, as polymerase 750 illustrated in FIG. 7B incorporates nucleotide 730 into a polynucleotide, polymerase 750 can cleave elongated tag 731. Such cleaving can cause dissociation of moieties 732 and 715. Method 410 further can include moving the reporter region of the tether responsive to release of the moiety from the tether (step 417). For example, responsive to release of moiety 732 from moiety 715 illustrated in FIG. 7B, reporter region 714 can move translationally toward second side 702, e.g., to a location adjacent to or within constriction 704. Method 410 further can include detecting the movement of the reporter region within the aperture (step 418). Such detection can be performed analogously as described above with reference to step 415. Note that motions of reporter region 714 other than translational motion can be detectable, e.g., conformational motion or rotational motion.

Sequencing by Synthesis Using Exemplary Methods and Compositions Based on Detecting Action of Polymerases Upon Nucleotides It should be appreciated that method 410 illustrated in FIG. 4B suitably can be used to detect the action of one type of molecule upon any other suitable type of molecule having a moiety attached thereto.

In one nonlimiting, illustrative embodiment described below with reference to FIGS. 8A-14, method 410 can be used to detect a polymerase's action upon a nucleotide. Detection of such action can be used to sequence a first polynucleotide by synthesizing a second polynucleotide that is complementary to the first nucleotide, e.g., using "sequencing by synthesis" (SBS).

Under one aspect, a composition can include a nanopore including a first side, a second side, and an aperture extending through the first and second sides; and a permanent tether including a head region, a tail region, and an elongated body disposed therebetween. The head region can be anchored to or adjacent to the first side or second side of the nanopore, and the elongated body can include a moiety. A polymerase can be disposed adjacent to the first side of the nanopore. The composition also includes a first nucleotide including a first elongated tag. The first elongated tag includes a first moiety that interacts with the moiety of the tether responsive to the polymerase acting upon the first nucleotide.

Figure 8A:
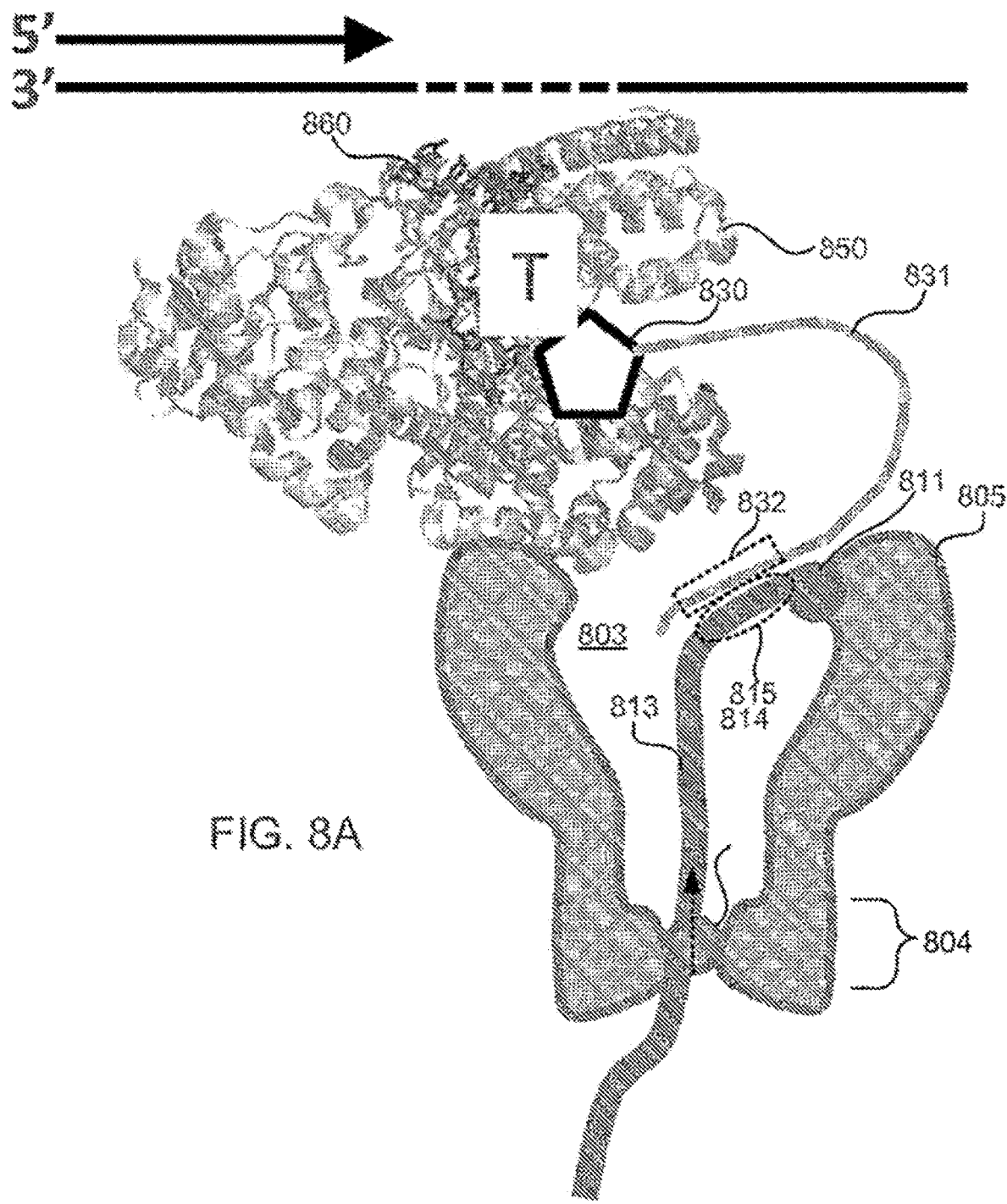
FIG. 8A schematically illustrates a composition including a tether anchored to a nanopore and configured for use in detecting action of a polymerase upon a nucleotide, according to some embodiments of the present invention.

In one illustrative example, FIG. 8A schematically illustrates an exemplary composition including a tether anchored to a nanopore and configured for use in detecting action of a polymerase upon a nucleotide. The nanopore includes biological pore 805, which can be disposed in a barrier (not specifically illustrated), e.g., a membrane of biological origin such as a lipid bilayer, or a solid state membrane. Biological pore 805 includes aperture 803 and constriction 804, although it should be understood that biological pore 805 suitably can include no constriction, or multiple constrictions. The permanent tether includes head region 811, elongated body 813, and reporter region 814. Polymerase 850 is disposed adjacent to, and in contact with, biological pore 805, and optionally can be anchored to biological pore 805 via a physical or chemical linkage (e.g., using click chemistry or a cysteine-maleimide bond). Polymerase 850 is configured to receive a template polynucleotide 860, e.g., circular or linear ssDNA to be sequenced, to synthesize a polynucleotide having a complementary sequence to that of the ssDNA by sequentially acting upon nucleotides, e.g., binding nucleotides, adding the nucleotides to a polynucleotide in accordance with the sequence of the ssDNA, excising the nucleotides from an existing polynucleotide, or by sampling the nucleotides, e.g., transiently interacting with the nucleotides without binding them. Head region 811 can be anchored to any suitable portion of nanopore 800 that places reporter region 814 within aperture 803, e.g., adjacent to or within constriction 804 and places elongated body 813 sufficiently close to polymerase 850 so as to interact with nucleotides that can be acted upon by polymerase 850. For example, nucleotide 830 can include an elongated tag 831 including moiety 832 that interacts with moiety 815 of the tether. The template DNA to be sequenced and the primer for the complementary polynucleotide to be sequenced are represented in FIG. 8A by the black lines (the broken line indicating a relatively long distance).

In one example, a voltage can be applied across the nanopore 805, e.g., using measurement circuit 230 and electrodes 231, 232 such as described further above with reference to FIG. 2A, or measurement circuit 240 and electrodes 241, 242 such as described further above with reference to FIG. 2C. Reporter region 814 or elongated body 813 includes an electrostatic charge that, responsive to the applied voltage, causes elongated body 813 to extend through aperture 803, optionally such that reporter region 814 is disposed within or adjacent to constriction 804. Optionally, the applied voltage can cause elongated body 813 to become taut. Responsive to polymerase 805 acting upon nucleotide 830, moiety 832 of nucleotide 830 can interact with, e.g., reversibly bond to, moiety 815 of tether 832. Such interaction can impose a force on reporter region 814 resulting in movement of reporter region 814 within aperture 803, e.g., translational movement. As a result, the action of polymerase 850 upon nucleotide 830 can be translated or transduced into a measurable change in current or flux through constriction 804, which also can be referred to as a blockade current or flux. Additionally, the force exerted on tether by the applied voltage can be expected to pull on the pore rather than the polymerase, and thus is not expected to significantly disrupt polymerase activity.

In one illustrative embodiment, moiety 815 includes a first oligonucleotide, and moiety 832 includes a second oligonucleotide that is complementary to the first oligonucleotide, e.g., that hybridizes to the first oligonucleotide responsive to the action of polymerase 850 upon nucleotide 830. The hybridization of the second oligonucleotide to the first oligonucleotide can cause a change in the length of the elongated body 813 of tether 810, which in turn can move reporter region 814 to a predetermined location. The action of polymerase 850 upon nucleotide 830 can be individually detected based on a measured (e.g., optically or electrically measured) magnitude or time duration, or both, of a current or flux through aperture 803. In one illustrative embodiment, moiety 815 includes a first oligonucleotide, and moiety 832 includes a second oligonucleotide that is complementary to the first oligonucleotide, e.g., that hybridizes to the first oligonucleotide. The hybridization of the second oligonucleotide to the first oligonucleotide can shorten the elongated body 813 of tether 810 by a predetermined amount, which in turn can move reporter region 814 to a predetermined location within aperture 803. The binding of the nucleotide can be individually detected based on a measured (e.g., optically or electrically measured) magnitude or time duration, or both, of a current or flux through aperture 803.

Figure 8B:
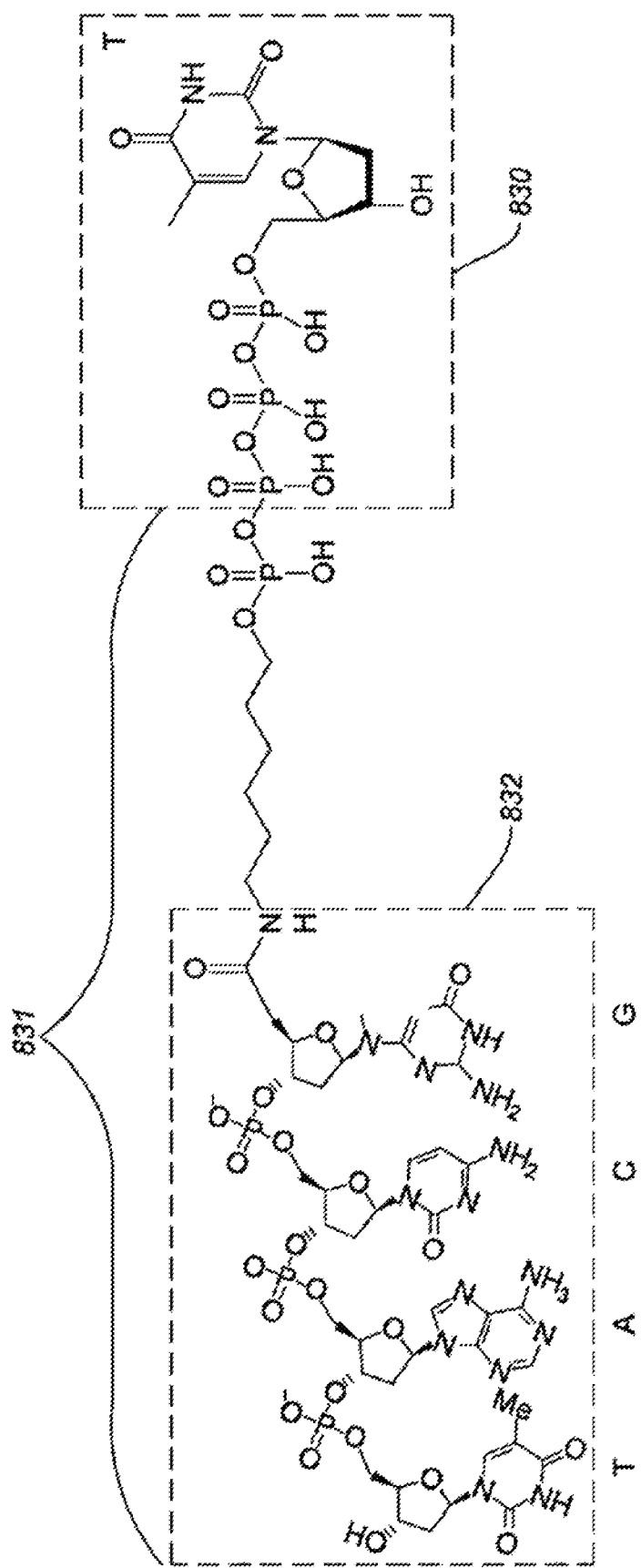
FIG. 8B schematically illustrates an exemplary nucleotide including an elongated tag including a moiety that interacts with the tether of FIG. 8A during use in detecting action of a polymerase upon the nucleotide, according to some embodiments of the present invention.

For example, FIG. 8B schematically illustrates an exemplary nucleotide including an elongated tag including a moiety that interacts with the tether of FIG. 8A during use in detecting action of a polymerase upon the nucleotide. As illustrated in FIG. 8B, elongated tag 831 of nucleotide 830, e.g., T, can include an oligonucleotide moiety 832 attached to the gamma phosphate of the nucleotide 830, e.g., via a delta phosphate linkage. Oligonucleotide moiety 832 can include any suitable sequence of nucleotides selected to hybridize to a corresponding sequence of nucleotides within moiety 815 of the tether. For example, oligonucleotide moiety 832 illustrated in FIG. 8B can include the exemplary sequence 5' GCAT 3', and moiety 815 can include the complementary sequence 5' ATGC 3'. Referring again to FIG. 8A, the action of polymerase 805 upon nucleotide 830 can maintain moiety 832 in relatively close proximity to moiety 815 of the tether, resulting in a transient increase in the local concentration of oligonucleotide moiety 832 that can induce hybridization between moieties 832 and 815 preferentially to moieties that are attached to nucleotides not presently being acted upon by polymerase 805. The resulting hybridization causes movement of the tether, e.g., conformational movement resulting in a shortening of elongated body 813 that can move reporter region 814 relative to constriction 804. Polymerase 850 can cleave elongated tag 831 upon incorporating nucleotide 830 into a polynucleotide, responsive to which moiety 832 can dissociate from moiety 815.

The conformational change in the tether can be induced by the creation of double stranded DNA (dsDNA) from ssDNA that respectively is included within moieties 815 and 832. For example, ssDNA is longer than dsDNA by about 1.5 Angstroms per nucleotide, which is within the resolution limits of the present systems, e.g., system 220 illustrated in FIG. 2A or system 250 illustrated in FIG. 2C. Each nucleotide can include a corresponding oligonucleotide moiety 832 that is selected to create a different length of dsDNA upon hybridization of moiety 832 with moiety 815, thus shortening the tether by a distance that corresponds to the nucleotide being acted upon by polymerase 850. In some embodiments, the formula for the amount of shortening of a fully taut tether, such as a tether extended across the pore responsive to an applied voltage, can be expressed as:

$$D_s = N^*(L_{ss} - L_{ds}) \tag{1}$$

where N is the number of bases that are hybridized, $D_s$ is the distance by which the tether shortens, $L_{ss}$ is the length between nucleotides in ssDNA (approximately 5 Angstroms), and $L_{ds}$ is the length between nucleotides in dsDNA (approximately 3.3 Angstroms).

Figure 9A:
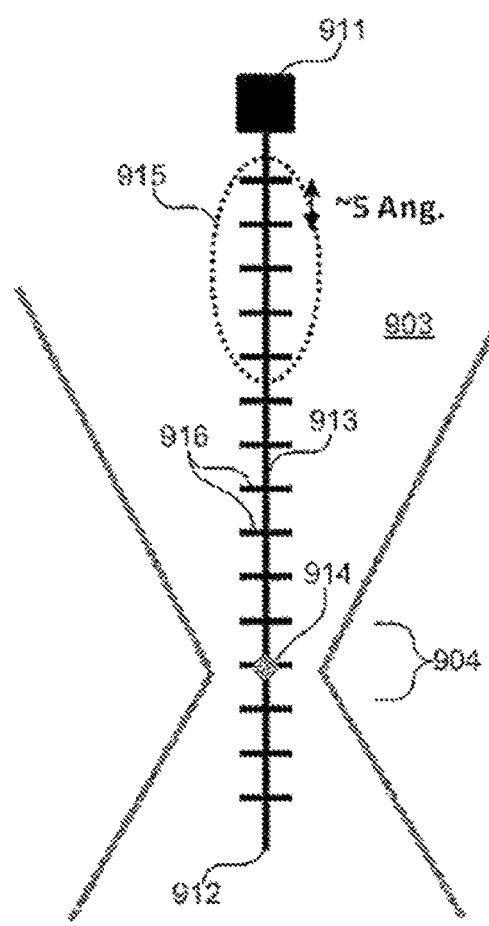
FIGS. 9A-9B schematically illustrate movement of an exemplary tether responsive to hybridization with a moiety of an elongated tag of an exemplary nucleotide during use in detecting action of a polymerase upon the nucleotide, according to some embodiments of the present invention.
Figure 9B:
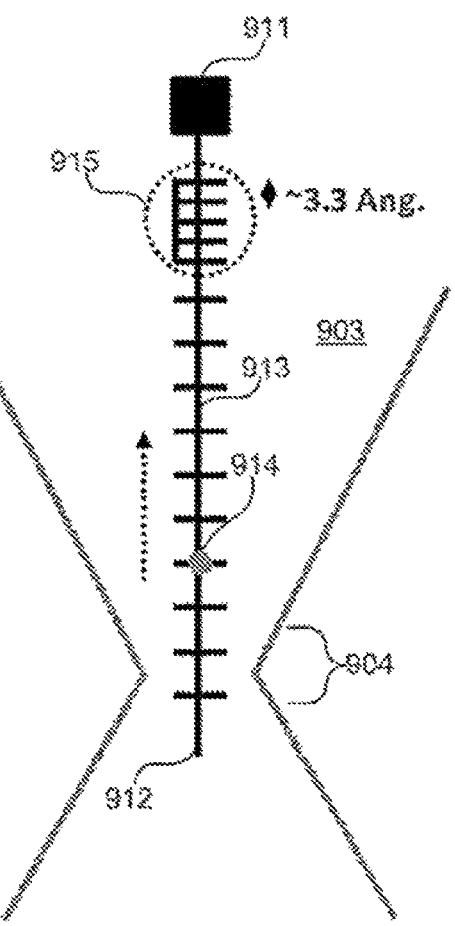

FIGS. 9A-9B schematically illustrate a conformational change, e.g., shortening, of an exemplary tether responsive to hybridization with a moiety of an elongated tag of an exemplary nucleotide during use in detecting action of a polymerase upon the nucleotide. Head region 911 of the tether is anchored to nanopore 900 optionally including constriction 904, and elongated body 913 extends through aperture 903, e.g., such that reporter region 914 is disposed within, or adjacent to, constriction 914. In the embodiment illustrated in FIGS. 9A-9B, elongated body 913 includes a polynucleotide such as ssDNA, the nucleotides of which are represented by horizontal bars 916. Reporter region 914 includes one or more abasic sites of the polynucleotide, e.g., ssDNA. Moiety 915 includes a sequence of nucleotides that is selected so as to hybridize with a corresponding moiety, e.g., a complementary sequence of nucleotides, of an elongated tag of a nucleotide being acted upon by polymerase 900 (nucleotide being acted upon, and elongated tag thereof, not specifically illustrated in FIGS. 9A-9B).

As illustrated in FIG. 9A, prior to binding of moiety 915 to the corresponding moiety of the nucleotide being acted upon, nucleotides 916 are spaced apart from one another by approximately 5 Angstroms. As illustrated in FIG. 9B, responsive to moiety 915 interacting with, e.g., hybridizing to, the corresponding moiety of the nucleotide being acted upon, e.g., responsive to the moieties forming a double stranded DNA duplex, the spacing between nucleotides 916 within moiety 915 decreases to about 3.3 Angstroms. The short, black vertical line in FIG. 9B indicates a 5-base hybridization event, which shortens the tether and moves reporter region 914 to a new location. Duplexes of 6, 7 or 8 bases can be even shorter than represented in FIG. 9B, as discussed further below.

Figures 10A, 10B, 10C:
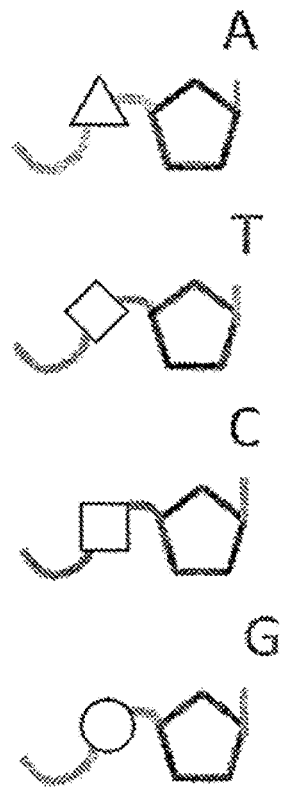
FIGS. 10A-10B schematically illustrate exemplary nucleotides including elongated tags including respective moieties that can interact with an exemplary tether during use in detecting action of a polymerase upon the nucleotides, according to some embodiments of the present invention.
FIG. 10C schematically illustrates an exemplary tether and moieties that can interact with the tether during use in detecting action of a polymerase upon a nucleotide, according to some embodiments of the present invention. Sequence disclosed as SEQ ID NO: 5.

Each different type of nucleotide can include a corresponding elongated tag that is attached to its gamma phosphate in a manner analogous to that illustrated in FIG. 8B, or otherwise suitably attached. For example, FIGS. 10A-10B schematically illustrate exemplary nucleotides including elongated tags including respective moieties that interact with an exemplary tether during use in detecting binding of the nucleotide by a polymerase disposed adjacent to a nanopore. As shown in FIG. 10A, the A, T, C, and G nucleotides can include respectively elongated tags that include different moieties than one another, e.g., as respectively represented by the triangle, diamond, square, and circle. The particular moieties can be suitably selected so as to interact with, e.g., hybridize to, a corresponding moiety of the permanent tether, and to induce different respective conformational changes to the tether. FIG. 10B illustrates nonlimiting examples of moieties that can be included in the elongated tags illustrated in FIG. 10A. Each such moiety can interact with, e.g., hybridize with, a different, respective portion of a corresponding moiety of the permanent tether, so as to induce a different, respective conformational change of the tether.

For example, FIG. 10C schematically illustrates an exemplary tether that includes head region 1011, tail region 1012, and elongated body 1013 that includes reporter region 1014 and moiety 1015. Head region 1011 can include a chemical linker such as a 3' maleimide ("Mal") group for conjugation to a cysteine (Cys) residue on the pore. Tail region 1012 can include a 5' phosphate group ("phos") that is charged and thus assists with feeding the tether through the aperture of the pore responsive to an applied voltage. Elongated body 1013 can include a polymer, e.g., a polynucleotide such as illustrated in FIG. 10C, or any other suitably polymer, such as a biological polymer or a synthetic polymer. Reporter region 1014 includes one or more abasic nucleotides denoted as "X", and in one exemplary embodiment can be located about 14-15 bases from the maleimide, which can be about the distance H2 from the pore mouth to the pore constriction for certain nanopore types. Moiety 1015 can include a sequence of nucleotides, e.g., GGGTATAT, with which each of the moieties attached to the A, T, C, and G nucleotides to be acted upon can interact, e.g., hybridize, differently than one another.

Note that the moieties illustrated in FIGS. 10A-10C are intended to be purely exemplary, and not limiting of the invention. However, the moieties attached to the nucleotides to be acted upon can be selected so as satisfy one or more of the following parameters, and optionally all of the following parameters:

1. Moieties attached to different types of nucleotides than one another can interact with the moiety of the tether in a manner that is distinguishable from one another, e.g., via measurement of current or flux through the pore constriction.
2. The stability of a duplex between the moiety of the nucleotide and the corresponding moiety of the tether is sufficiently low that such moieties attached to "free" nucleotides (nucleotides that are not being acted upon by the polymerase and thus transiently interact with the tether) interact only briefly with the moiety of the tether, e.g., for less than 1 msec. For example, the stability of the duplex between the moiety of the nucleotide and the moiety of the tether can be expressed as the Tm, or melting temperature, of the duplex. The system operational temperature is expected to be about 20° C., or room temperature. Moieties that are about 5-8 nucleotides long are expected have Tm<12° C., which can provide sufficiently low stability at room temperature that moieties attached to "free" nucleotides will interact only briefly with the moiety of the tether.
3. The stability of a duplex between the moiety of the nucleotide and the corresponding moiety of the tether is sufficiently high that when the nucleotide is acted upon and held in place by the polymerase for the several milliseconds (1 to 30 msec, for example) during incorporation, such action increases the effective concentration of the moiety of the nucleotide relative to the moiety of the tether, which drives the reaction between the moieties forward and increases stability such that the effective Tm of the duplex is greater than 20° C. (or the anticipated operational temperature of the system), e.g., is greater than 30° C., or greater than 40° C., or greater than 50° C.
4. The length of the elongated tag of the nucleotide being acted upon, e.g., the length between the moiety and the gamma phosphate, can be sufficiently long that when the moiety is stably hybridized to the corresponding moiety of the tether, there is substantially no force on the nucleotide. If this length is too short, the tether can impose a force on the elongated tag of the nucleotide, which is expected to result in reduced polymerase efficiency.

For further information about hybridizing oligonucleotides to one another, see U.S. Pat. No. 8,652,779 to Turner et al., the entire contents of which are incorporated by reference herein. According to Turner et al., at such a size scale, an oligonucleotide should sample its configuration space about 100-fold faster than a polymerase can incorporate a nucleotide. Applying such a principle to the present compositions, it is believed to be likely that the moiety of the nucleotide being acted upon will readily "find," and interact with, the corresponding moiety of the tether, and also will dissociate from the tether after the moiety is cleaved from the nucleotide being acted upon.

Note that in the exemplary moieties illustrated in FIG. 10C, each moiety attached to a nucleotide being acted upon has only a single matching hybridization with the corresponding tether moiety 1015 that includes between 5 to 8 bases. While other hybridization options exist that do not cause complete hybridization, such options can be anticipated to be significantly less stable than the full-length options.

Figures 11C, 11D:
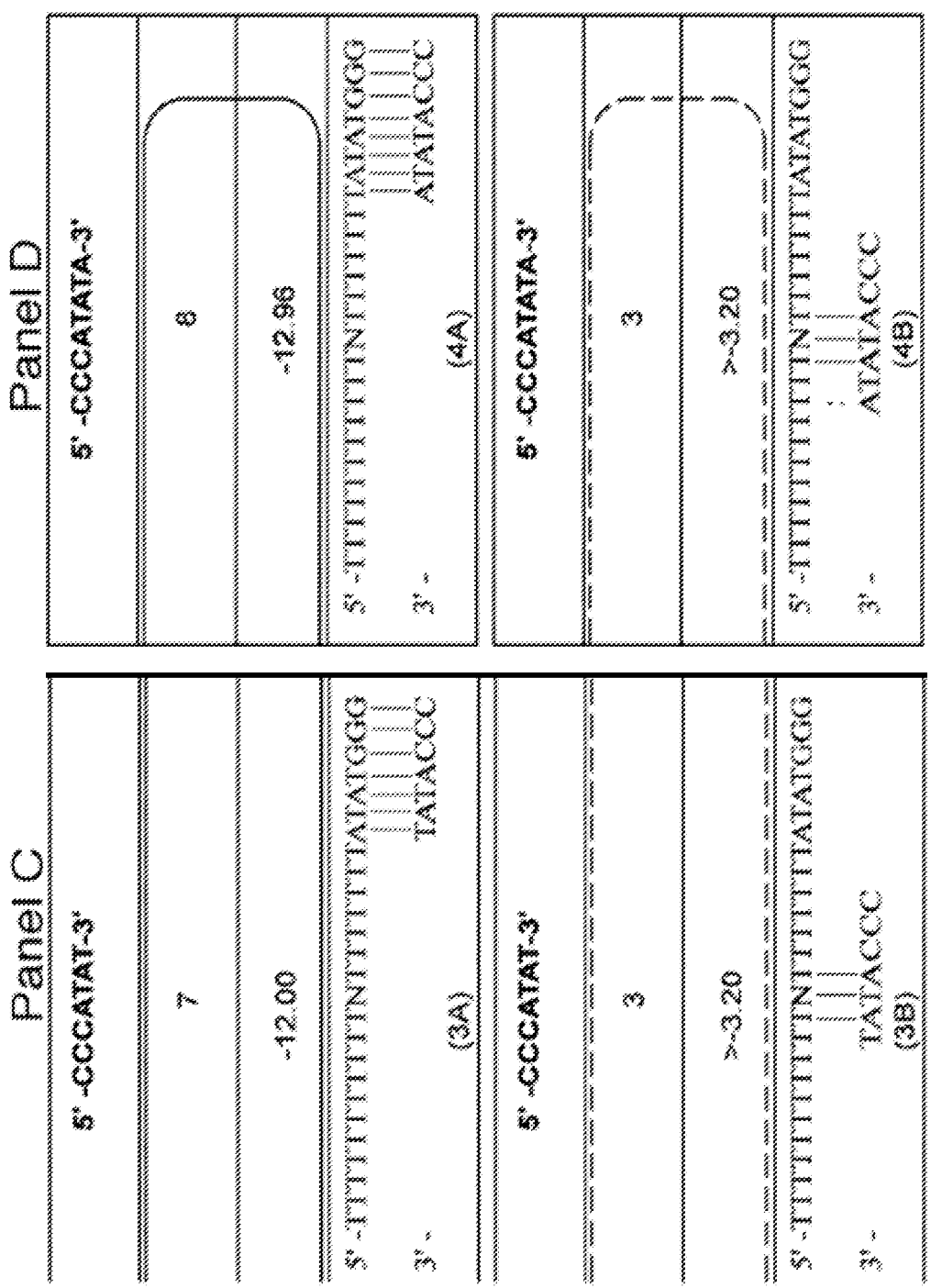

FIGS. 11A-11D illustrate exemplary calculations of interactions between a tether and moieties. Hybridization options are shown for each moiety with their predicted free energies, based upon the assumption of two freely diffusing oligonucleotides in the presence of 50 mM NaCl and 2 mM $Mg^{2+}$, a divalent ion that is known to increase Tm and can be used at this concentration for polymerase activity. The "tether sequence" illustrated above FIGS. 11A-11D corresponds to the sequence of the tether, and the "tag sequences" illustrated in FIGS. 11A-11D correspond to exemplary sequences of moieties that respectively can be attached to a nucleotide. The moiety (tag sequence) illustrated in FIG. 11A is five base pairs long, while the moiety (tag sequence) illustrated in FIG. 11B is six base pairs long and is similar to the moiety illustrated in FIG. 11A but includes one additional base, A, on the 3' end. The moiety (tag sequence) in FIG. 11C is seven base pairs long and is similar to the moiety illustrated in FIG. 11B but includes one additional base, T, on the 3' end. The moiety (tag sequence) in FIG. 11D is eight base pairs long and is similar to the moiety illustrated in FIG. 11C but includes one additional base, A, on the 3' end.

The calculated difference in free energy ($\Delta G$) is respectively illustrated for the best match (solid box) and second best match (dashed box) hybridizations between the primary sequence and the different secondary sequences, based on the assumption that the primary sequence and the respective secondary sequence are freely diffusing. More specifically, in FIG. 11A it may be seen that the calculated $\Delta G$ for the energetically most favorable exemplary hybridization illustrated in box 1A was −9.57 kcal/mole, corresponding to hybridization of all 5 base pairs of the respective tag sequence with the tether sequence, while the calculated $\Delta G$ for the energetically second most favorable exemplary hybridization illustrated in box 1B was −3.07 kcal/mole, corresponding to hybridization of only 2 base pairs of that tag sequence with the tether sequence. In FIG. 11B it may be seen that the calculated $\Delta G$ for the energetically most favorable exemplary hybridization illustrated in box 2A was −10.53 kcal/mole, corresponding to hybridization of all 6 base pairs of the respective tag sequence with the tether sequence, while the calculated $\Delta G$ for the energetically second most favorable exemplary hybridization illustrated in box 2B was −3.2 kcal/mole, corresponding to hybridization of only 3 base pairs of that tag sequence with the tether sequence. In FIG. 11C it may be seen that the calculated $\Delta G$ for the energetically most favorable exemplary hybridization illustrated in box 3A was −12 kcal/mole, corresponding to hybridization of all 7 base pairs of the respective tag sequence with the tether sequence, while the calculated $\Delta G$ for the energetically second most favorable exemplary hybridization illustrated in box 3B was −3.2 kcal/mole, corresponding to hybridization of only 3 base pairs of that tag sequence with the tether sequence. In FIG. 11D it may be seen that the calculated $\Delta G$ for the energetically most favorable exemplary hybridization illustrated in box 4A was −12.96 kcal/mole, corresponding to hybridization of all 8 base pairs of the respective tag sequence with the tether sequence, while the calculated $\Delta G$ for the energetically second most favorable exemplary hybridization illustrated in box 4B was −3.2 kcal/mole, corresponding to hybridization of only 3 base pairs of that tag sequence with the tether sequence. Accordingly, it can be understood from FIGS. 11A-11D that the calculated $\Delta G$ is significantly lower for full hybridization of each of the secondary sequences to the primary sequence than for a partial hybridization of those tag sequences to the tether sequence. It further can be understood from FIGS. 11A-11D that the predicted melting temperatures (Tms) are all less than approximately 11.4° C., including for the moiety with 8 bases. At 150 mM salt (a concentration that suitably can be used in systems configured to measure current or flux through a pore aperture) and 2 mM Mg2+, the moiety with 8 bases has a predicted Tm of approximately 15° C. Thus, it can be expected that freely diffusing nucleotides that encounter the tether will have no meaningful stability at room temperature. Additionally, the highest Tm can be lowered even further, e.g., by approximately 5° C., by using, for example, formamide.

Figures 12A, 12B:
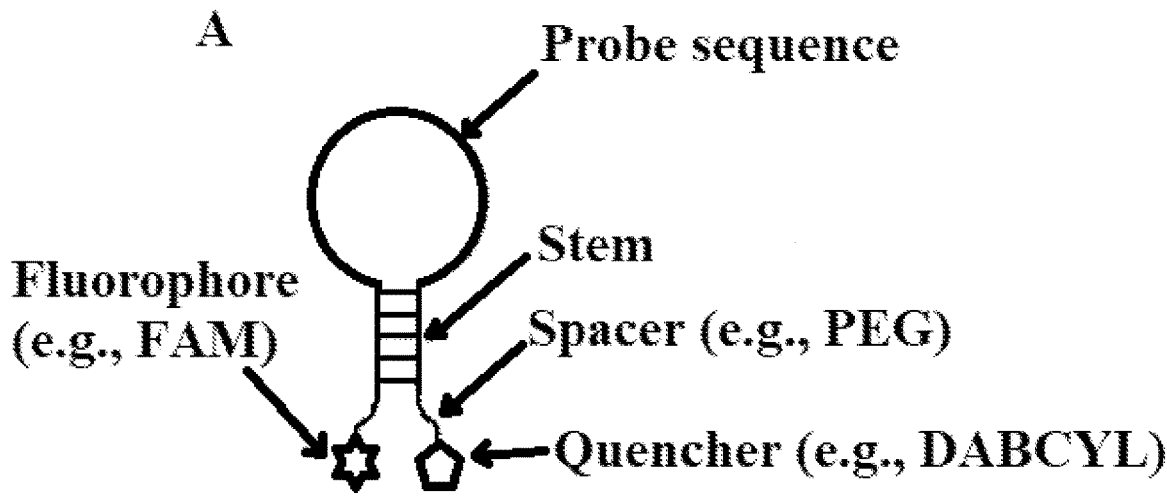
FIG. 12A illustrates a model that can be used to calculate interactions between a tether and moieties, according to some embodiments of the present invention.
FIG. 12B illustrates an exemplary calculation of an interaction between a tether and a moiety, according to some embodiments of the present invention. "Loop" disclosed as SEQ ID NO: 6 and "Full sequence" disclosed as SEQ ID NO: 7.

Additionally, it can be expected that the melting temperatures of duplexes between moieties on nucleotides being acted upon, and moieties on the tether, to be significantly more stable than an otherwise identical pair of freely diffusing oligonucleotides because the tether and the incorporating nucleotide are held in relatively fixed position relative to another, causing an effective increase in the local concentrations of the moieties. The resulting synergistic binding can occur because the nucleotide is held simultaneously to some extent by both the polymerase and the hybridization interaction. Such synergistic binding can significantly increase the effective Tm of a short oligonucleotide duplex. FIG. 12A illustrates a model that can be used to calculate interactions between a tether and moieties. Such a model is based on a molecular beacon, in which two short oligonucleotides of about 5 or 6 bases each are stably hybridized with one another in a stem-loop structure. The loop serves to hold the two stem pieces (the oligonucleotides) in close proximity to one another. Tms>50° C. or >60° C. can be readily achieved with stems of about 5-6 nucleotides and loops on the order of 10 or more nucleotides. Because the oligonucleotides are held in relatively close proximity to one another by the loop ("probe sequence"), their effective concentration is increased and can significantly increase the Tm of hybridization between those nucleotides as compared to freely diffusing nucleotides.

Figure 12C:
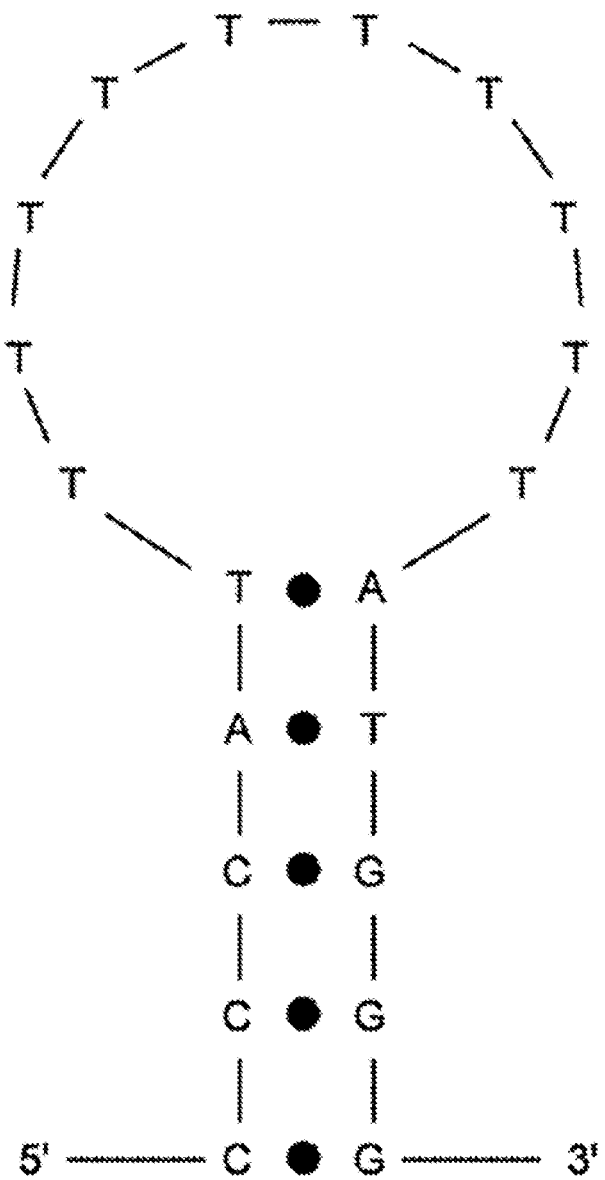
FIG. 12C illustrates a stable structure calculated based on the model of FIG. 12A.

FIG. 12B illustrates exemplary calculations of interactions between a tether and moieties that can be attached to a nucleotide being acted upon by a polymerase, based on the model of FIG. 12A, and FIG. 12C illustrates a stable structure calculated based on the model of FIG. 12A. More specifically, using the example of the sequence encoding the moiety of FIG. 10B for nucleotide "A", the mFold program hosted by the RNA Institute (College of Arts and Sciences, University of Albany, State University of New York at Albany) was used to determine the Tm of this sequence hybridized to its reverse complement in the tether assuming a loop that is 10 nucleotides long. It is anticipated that such a length of the loop is a reasonable approximation for the length of other portions of the elongated tag of the nucleotide being acted upon by the polymerase. As shown in FIG. 12B, the predicted Tm in the presence of 2 mM MgCl$_2$ and 50 mM NaCl is approximately 49° C., indicating that even relatively short 5-mer moieties such as illustrated in FIG. 12C can have relatively high Tms if the effective concentration of the moieties relative to one another is sufficiently high. The exemplary moieties for the other bases (C, G & T) illustrated in FIG. 10B are even longer and range from 6-8 nucleotides, and thus can be expected to have somewhat higher Tms. For example, "G" with an 8-nucleotide moiety is predicted to have a Tm of 59° C. in 2 mM Mg$^{2+}$ and 50 mM NaCl (data not shown) based on the model illustrated in FIG. 12A. In comparison, FIG. 10C illustrates the respective Tm for freely diffusing forms each of the illustrated sequences as predicted by the mFold program in the presence of 1 mM Mg$^{2+}$ and 150 mM NaCl. Note that the mFold program does not report values <10° C. All Tms for freely diffusing forms are well below the expected operating temperature of the system at room temperature (approximately 20° C.), while Tms calculated using the model of FIG. 12A are well above the expected operated temperature of the system.

As noted above, oligonucleotide moieties of different lengths can be used to change the conformation of the tether, e.g., to change the length of the tether, e.g., shorten the tether, by differing amounts. Applying equation (1) above to moieties ranging from 5 to 8 nucleotides yields the results in Table 2. The moiety having 5 nucleotides is anticipated to shorten the tether by approximately 8.5 Angstroms. The moiety having 6 nucleotides is anticipated to shorten the tether by approximately 10.2 Angstroms. The moiety having 7 nucleotides is anticipated to shorten the tether by approximately 11.9 Angstroms. The moiety having 8 nucleotides is expected to shorten the tether by approximately 13.6 Angstroms. Accordingly, moieties shorten the tether by respective amounts that are "spaced" from one another by approximately 1.7 Angstroms.

TABLE 2

Differential shortening from labels of 5-8 bases.

| Label Length | Ds (Ang) | Difference from shortest label (Ang) |
|---|---|---|
| 5 | 8.5 | N/A |
| 6 | 10.2 | 1.7 |
| 7 | 11.9 | 1.7 |
| 8 | 13.6 | 1.7 |

Such conformational movements of the tether responsive to interactions with moieties attached to nucleotides being acted upon by a polymerase can provide signals that facilitate identification of different nucleotides as the polymerase adds such nucleotides to a polynucleotide, e.g., during sequencing by synthesis. FIGS. 13A-13E schematically illustrate movement of an exemplary tether within the aperture of a pore (e.g., nanopore) responsive to interactions with exemplary moieties of respective nucleotides, such as the moieties illustrated in FIGS. 10A-10C. Note that in FIGS. 13A-13E, the polymerase is not specifically illustrated, but can be located adjacent to the first side of the pore in a manner analogous to that described above with reference to FIG. 8A. Additionally, in FIGS. 13B-13E, the nucleotide being acted upon by the polymerase is not specifically illustrated, but can be located within the polymerase in a manner analogous to that described above with reference to FIG. 8A. The dotted line in FIGS. 13B-13E is intended to represent portions of the elongated tag of the nucleotide being acted upon that connect the moiety to the nucleotide. Additionally, in FIGS. 13A-13E, measurement circuitry configured to measure (e.g., optically or electrically measure) movements of the reporter region within the aperture of the pore is not specifically illustrated, but can be configured in a manner analogous to that described above with reference to FIG. 2A or FIG. 2C. In one illustrative embodiment, the measurement circuitry is configured to apply a voltage across the pore and to measure current or flux through the aperture of the pore.

Figure 14:
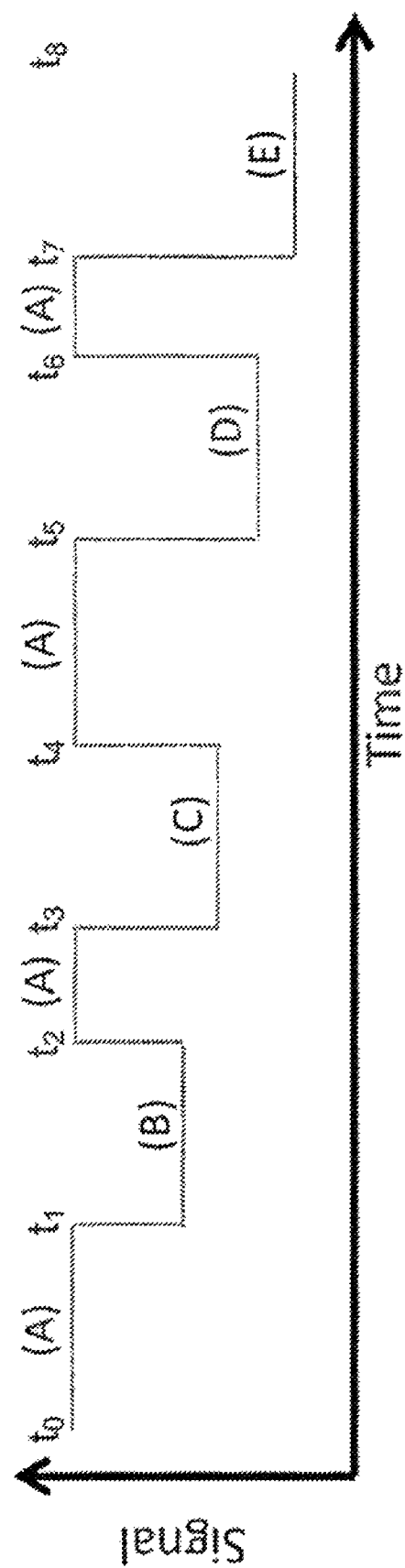
FIG. 14 is a plot of an exemplary signal that can be generated during interactions such as illustrated FIGS. 13A-13E, according to some embodiments of the present invention.

FIG. 13A illustrates the pore and tether in the absence of an event, which can be referred to as their equilibrium state. The reporter region, e.g., one or more abasic residues, denoted by "X," resides within the aperture of the pore, e.g., within the constriction of the pore. FIG. 14 is a plot of an exemplary signal that can be generated during the interactions illustrated in FIG. 13A-13E. As illustrated in FIG. 14, the signal (e.g., optically or electrically measured current or flux) between times $t_0$ and $t_1$ can have a first value (A) corresponding to the location of the reporter region illustrated in FIG. 13A. FIG. 13B illustrates an interaction between an exemplary oligonucleotide moiety attached to a "dA" nucleotide, which is being acted upon by the polymerase, with a corresponding oligonucleotide moiety on the tether at time $t_1$. Based on equation (1), it is anticipated that, responsive to the interaction, the tether can change configuration, e.g., shorten, in such a manner that causes reporter region "X" to move within the aperture of the pore by approximately 8.5 Angstroms toward the first side of the pore, e.g., in the direction of the polymerase. As illustrated in FIG. 14, the signal (e.g., optically or electrically measured current or flux) between times $t_1$ and $t_2$ can have a second value (B) corresponding to the location of the reporter region illustrated in FIG. 13B. At approximately time $t_2$, the polymerase cleaves the elongated tag from the dA nucleotide upon which the polymerase is acting, responsive to which the moiety (formerly) of the dA nucleotide dissociates from the tether, responsive to which the reporter region returns to the state illustrated in FIG. 13A and the signal returns to value (A) until the polymerase acts on another nucleotide. Note that signal changes, e.g., current or flux changes, in FIG. 14 are illustrated as step functions for simplicity, but it should be appreciated that the current or flux changes can have more complex shapes based on the particular manner in which the nucleotide is acted upon by the polymerase, and thus the particular manner in which the reporter region moves within the aperture of the pore. Additionally, noise can be present in signals such as illustrated in FIG. 14 and can manifest as transient spikes (not shown).

FIG. 13C illustrates an interaction between an exemplary oligonucleotide moiety attached to a "dT" nucleotide, which is being acted upon by the polymerase, with the corresponding oligonucleotide moiety on the tether at time $t_3$. Based on equation (1), it is anticipated that, responsive to the interaction, the tether will shorten in such a manner that causes reporter region "X" to move within the aperture of the pore by approximately 10.2 Angstroms toward the first side of the pore, e.g., in the direction of the polymerase. As illustrated in FIG. 14, the signal (e.g., optically or electrically measured current or flux) between times $t_3$ and $t_4$ can have a third value (C) corresponding to the location of the reporter region illustrated in FIG. 13C. At approximately time $t_4$, the polymerase cleaves the elongated tag from the dT nucleotide upon which the polymerase is acting, responsive to which the moiety (formerly) of the dT nucleotide dissociates from the tether, responsive to which the reporter region returns to the state illustrated in FIG. 13A and the signal returns to value (A).

FIG. 13D illustrates an interaction between an exemplary oligonucleotide moiety attached to a "dC" nucleotide, which is being acted upon by the polymerase, with the corresponding oligonucleotide moiety on the tether at time $t_5$. Based on equation (1), it is anticipated that, responsive to the interaction, the tether will shorten in such a manner that causes reporter region "X" to move within the aperture of the pore by approximately 11.9 Angstroms toward the first side of the pore, e.g., in the direction of the polymerase. As illustrated in FIG. 14, the signal (e.g., optically or electrically measured current or flux) between times $t_5$ and $t_6$ can have a fourth value (D) corresponding to the location of the reporter region illustrated in FIG. 13D. At approximately time $t_6$, the polymerase cleaves the elongated tag from the dC nucleotide upon which the polymerase is acting, responsive to which the moiety (formerly) of the dC nucleotide dissociates from the tether, responsive to which the reporter region returns to the state illustrated in FIG. 13A and the signal returns to value (A).

FIG. 13E illustrates an interaction between an exemplary oligonucleotide moiety attached to a "dG" nucleotide, which is being acted upon by the polymerase, with the corresponding oligonucleotide moiety on the tether at time $t_7$. Based on equation (1), it is anticipated that, responsive to the interaction, the tether will shorten in such a manner that causes reporter region "X" to move within the aperture of the pore by approximately 13.6 Angstroms toward the first side of the pore, e.g., in the direction of the polymerase. As illustrated in FIG. 14, the signal (e.g., optically or electrically measured current or flux) beginning at time $t_7$ can have a fifth value (E) corresponding to the location of the reporter region illustrated in FIG. 13E. At approximately time $t_8$, the polymerase cleaves the elongated tag from the dG nucleotide upon which the polymerase is acting, responsive to which the moiety (formerly) of the dC nucleotide dissociates from the tether, responsive to which the reporter region returns to the state illustrated in FIG. 13A and the signal returns to value (A) (not specifically illustrated in FIG. 14).

Table 3 lists exemplary moieties that can be included in the elongated tag of each nucleotide and that interacts with a corresponding moiety along the elongated body of the tether, e.g., the moieties illustrated in FIGS. 13A-13E. Table 3 also lists the number of nucleotides in the moiety that hybridize ("hybed") with the corresponding moiety of the tether. Table 3 also lists the magnitude of the resulting conformational change to the tether, e.g., the amount by which the tether is anticipated to be shortened, in Angstroms. Table 3 also lists the expected differential length of the tether with respect to the exemplary moiety of "dA". Assuming that single stranded DNA has 5 Angstrom spacing between nucleotides, the equivalent shortening length measured in terms of single stranded DNA also is listed in Table 3, as well as the differential distance between nucleotides with respect to "dA", measured in nucleotides ("Delta Bases").

TABLE 3

| Base | Label Seq (5'-3') | Num. Hybed Bases | Ang. Shortening | Delta Ang. | # ssDNA Bases Equiv | Delta Bases |
|---|---|---|---|---|---|---|
| A | CCCAT | 5 | 8.5 | N/A | 1.7 | N/A |
| T | CCCATA | 5 | 10.2 | 1.7 | 2.04 | 0.34 |
| C | CCCATAT | 7 | 11.9 | 1.7 | 2.38 | 0.34 |
| G | CCCATATA | 8 | 13.6 | 1.7 | 2.72 | 0.34 |

Additionally, note that because the moieties of the nucleotides being acted upon can be of different lengths, e.g., ranging from 5 to 8 nucleotides, their Tms can differ somewhat from each other. The Tm and delta G of a given moiety is expected to factor into the rate at which the moiety of the nucleotide dissociates from the moiety of the tether (also referred to as the off rate). Such a rate, or time duration, can potentially be used as another characteristic to ascertain the correct identity of each nucleotide. For example, a signal having a time period corresponding to the difference between $t_1$ and $t_2$ illustrated in FIG. 14 can be correlated to the polymerase acting upon dA in a manner analogous to that illustrated in FIG. 13B, a signal having a time period corresponding to the difference between $t_3$ and $t_4$ can be correlated to the polymerase acting upon dT in a manner analogous to that illustrated in FIG. 13C, a signal having a time period corresponding to the difference between $t_5$ and $t_6$ can be correlated to the polymerase acting upon dC in a manner analogous to that illustrated in FIG. 13D, or a signal having a time period corresponding to the difference between $t_7$ and $t_8$ can be correlated to the polymerase acting upon dG in a manner analogous to that illustrated in FIG. 13E.

Note that the duplex formed between the moiety of the elongated tag and the moiety of the tether can be in thermodynamic equilibrium. It should be appreciated that a duplex in thermodynamic equilibrium can have on and off rates that are based upon the length and character of the nucleic acid sequence, and that the duplex may dissociate from time-to-time. It can be useful for the mean time spent in the duplex state (the inverse of the off rate) to be shorter than the average lifetime of the polymerase-nucleotide complex during the incorporation event, so that after incorporation and tag release from the nucleotide, the tag will diffuse away and not block incoming nucleotide tags. The effective on rate can be sufficiently high to result in relatively fast re-binding as compared with the lifetime of the polymerase-nucleotide complex, so that incorporation events are detected and so that the duplex reforms after any dissociation events occurring during nucleotide incorporation. The on rate will be pseudo-first order in the concentration of the elongated tag of the nucleotide, which can be considered to make such an arrangement a stochastic sensor of the concentration of the elongated tag. Note that freely diffusing elongated tags can have a relatively low concentration (e.g., from 10 nM to 100 nM, or from 100 nM to 250 nM, or from 250 nM to 500 nM, or from 500 nM to 1 uM), whereas the elongated tag of the nucleotide being acted upon will effectively have a relatively high concentration because it is bound to the nucleotide which is held in place by the polymerase during incorporation, and thus is not free to diffuse away.

Accordingly, it should be appreciated that the reporter region of one of the present tethers is movable (e.g., translationally movable) within an aperture by different amounts, or for different amounts of time, or both, responsive to the polymerase acting upon different nucleotides. Such nucleotides can be individually identifiable based on a measured (e.g., optically or electrically measured) magnitude or time duration, or both, of a signal, e.g., of a current or flux through the aperture. For example, first and second nucleotides can be attached to moieties that interact with the tether differently than one another. For example, the tether can include a first oligonucleotide, and the moiety attached to the first nucleotide can include a second oligonucleotide that hybridizes to the first oligonucleotide so as to move the reporter region toward the first side responsive the polymerase acting upon the first oligonucleotide, e.g., to shorten the tether by a first amount. The moiety attached to the second nucleotide can include a third oligonucleotide that hybridizes to the first oligonucleotide so as to move the reporter region toward the first side responsive the polymerase acting upon the second oligonucleotide, e.g., to shorten the tether by a second amount. The first and second nucleotides can be distinguishable from one another, e.g., the first nucleotide can be individually identifiable based on a measured (e.g., optically or electrically measured) magnitude or time duration, or both, of a first signal, e.g., of a first current or flux through the constriction, and the second nucleotide can be individually identifiable based on a measured (e.g., optically or electrically measured) magnitude or time duration, or both, of a second signal, e.g., of a second current or flux through the constriction.

In the exemplary embodiments described above with reference to FIGS. 8A-14, the elongated body of the tether and the elongated tag of the nucleotide being acted upon by the polymerase respectively can include, or can even consist solely of, single-stranded DNA (ssDNA). However, it should be appreciated that other types of molecules suitably can be used. For example, any tether suitably can be used that includes an elongated body having one or more of the following features, and optionally includes all of the following features:

1. The elongated body can include a region that interacts with moieties respectively attached to different types of nucleotides in a manner that the moieties are distinguishable from one another, e.g., via measurement of current or flux through the pore constriction.
2. The elongated body can include a charged region that causes it to be pulled through the constriction of the pore responsive to an applied voltage. The elongated body can be held taut in such a configuration. This charged region can be located adjacent to the pore constriction to result in a net force.
3. The elongated body includes a reporter region that when moved through the pore aperture, e.g., through the pore constriction, yields a clearly distinguishable signal. The reporter region and the charged region can be the same as one another; that is, a single region can be both a reporter region and a charged region.

An exemplary material that can be included in the elongated body of the tether, or the elongated tag of the nucleotide being acted upon, or both, is a polymer. Polymers include biological polymers and synthetic polymers. Exemplary biological polymers that are suitable for use in the elongated body of the tether, or the elongated tag of the nucleotide being acted upon, or both, include polynucleotides, polypeptides, polysaccharides, polynucleotide analogs, and polypeptide analogs. Exemplary polynucleotides and polynucleotide analogs suitable for use in the elongated body of the tether, or the elongated tag of the nucleotide being acted upon, or both, include DNA, enantiomeric DNA, RNA, PNA (peptide-nucleic acid), morpholinos, and LNA (locked nucleic acid). Exemplary synthetic polypeptides can include charged amino acids as well as hydrophilic and neutral residues. In some embodiments, the tether is not a nucleic acid or does not include nucleotides. For example, a tether can exclude naturally occurring nucleotides, non-naturally occurring nucleotide analogs, or both. One or more of the nucleotides set forth herein or otherwise known in the art can be excluded from a tether.

Other exemplary polymers that can be suitable for use in the elongated body of the tether, or the elongated tag of the nucleotide being acted upon, or both, include synthetic polymers such as PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(w-alkenoic acid esters), poly(alkyl methacrylates), and other polymeric chemical and biological linkers such as described in Hermanson, mentioned further above. Additionally, as noted above, the moieties of the elongated body of the tether, or the elongated tag of the nucleotide being acted upon, or both, can be individual short nucleotide sequences that interact with one another. These moieties can be non-interacting with polymerase such as RNA, PNA or LNA labels, morpholinos, or enantiomeric DNA, for example. The moiety need not be formed of the same polymer as other portions of the elongated body of the tether or the elongated tag of the nucleotide being acted upon. Elongated tags can be readily attached to the gamma phosphate of nucleotides, as is well known in the art. Additionally, in one illustrative embodiment, that isoG and isoC bases can be used on the nucleotide elongated tags, or on the tether, or both, so as to inhibit hybridization of the elongated tags or tether with the DNA being sequenced. Additionally, other schemes can be used to induce secondary structure in the tether to shorten it, such as a hairpin.

Additionally, note that the tether can include multiple moieties, each of which respectively interacts with a moiety attached to a given type of nucleotide. The interaction between the moiety of the nucleotide with the corresponding moiety of the tether can move the reporter region of the tether by a corresponding amount that facilitates identification of the corresponding nucleotide via a signal, e.g., via a current or flux through the aperture of the pore.

In one non-limiting, illustrative embodiment, the pore includes MspA, which can provide a satisfactory separation of nucleotide-specific currents or fluxes, e.g., a 3.5-fold greater separation of nucleotide-specific currents or fluxes as compared to alpha-hemolysin. However, it should be appreciated that alpha-hemolysin or other types of pores suitably can be used with the present compositions, systems, and methods.

Additionally, note that in embodiments in which a voltage is applied across the pore and movements of the reporter region are measured (e.g., optically or electrically measured) via current or flux through the pore, the voltage can suitably be applied using either direct current (DC) or alternating current (AC). AC current can help to extend electrode life, help to eject cleaved elongated tags from the pore if the tags become stuck, or can perform part of the work of pulling the tether up against the force of the applied voltage. Additionally, note that a positively charged tether can be used with a reverse bias on the pore so as to inhibit the DNA being sequenced from being drawn into the pore. Additionally, note that a negatively-charged tether can be reverse-threaded through the pore (e.g., with the head region anchored to the second side of the pore and the polymerase disposed adjacent to the first side of the pore) with a reverse bias with negatively charged elongated tags, so as to inhibit the elongated tags from jamming into the constriction, and to inhibit the DNA being sequenced from entering the pore.

Additionally, a stochastic sensing method can be employed. In this arrangement, an AC current can be used to move the hybridized duplex adjacent to the constriction, such as described in greater detail below with reference to FIGS. 18A-18E.

Figure 15:
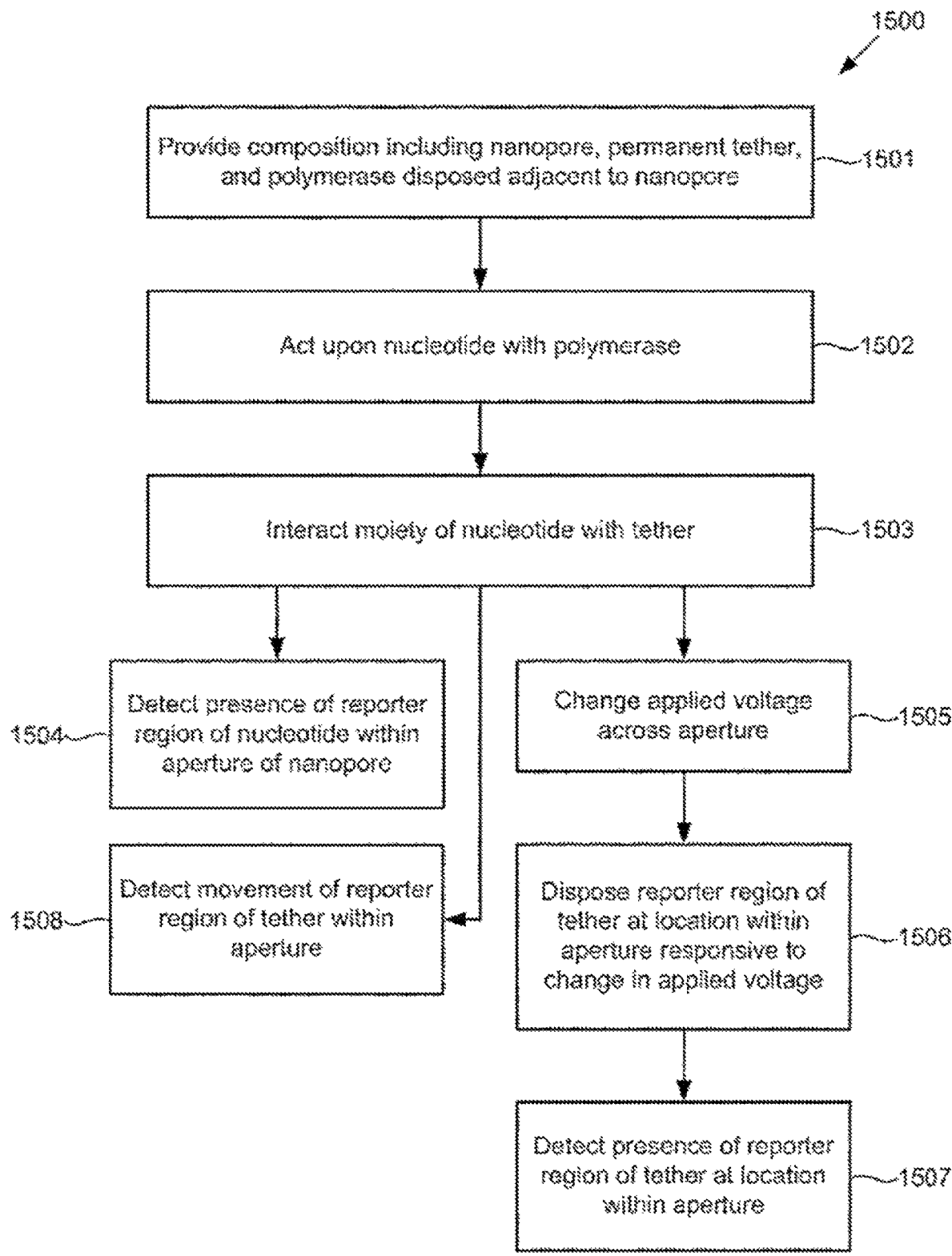
FIG. 15 illustrates an alternative method for detecting action of a polymerase upon a nucleotide using a composition including a tether anchored to or adjacent to a nanopore, according to some embodiments of the present invention.

Exemplary Methods and Compositions for Detecting Action of a Polymerase Upon a Nucleotide It should be understood that alternative methods and compositions can be used to detect action of a polymerase upon a nucleotide. For example, FIG. 15 illustrates an alternative method for detecting action of a polymerase upon a nucleotide using a composition including a tether anchored to or adjacent to a nanopore. For example, a composition can include a nanopore including a first side, a second side, and an aperture extending through the first and second sides; and a permanent tether including a head region, a tail region, and an elongated body disposed therebetween. The head region can be anchored to or adjacent to the first side or second side of the nanopore, and the elongated body can include a moiety. A polymerase can be disposed adjacent to the first side of the nanopore. The composition also includes a first nucleotide including a first elongated tag. The first elongated tag includes a first moiety that interacts with the moiety of the tether responsive to the polymerase acting upon the first nucleotide.

Figure 16:
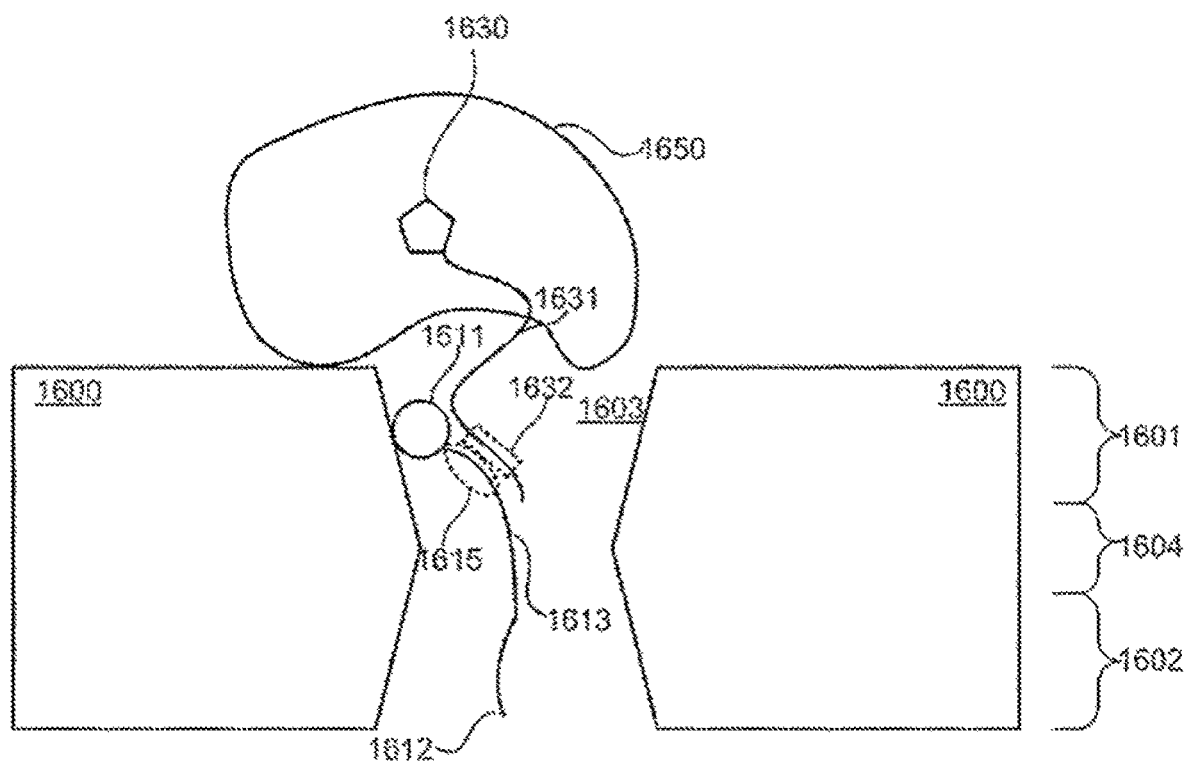
FIG. 16 schematically illustrates an alternative composition including a tether anchored to or adjacent to a nanopore and configured for use in detecting action of a polymerase upon a nucleotide, according to some embodiments of the present invention.

For example, method 1500 illustrated in FIG. 15 includes providing a composition including a nanopore, a permanent tether, and a polymerase disposed adjacent to the nanopore (step 1501). For example, FIG. 16 schematically illustrates an exemplary composition including a tether anchored to a nanopore and configured for use in detecting action of a polymerase upon a nucleotide. In the exemplary embodiment illustrated in FIG. 16, the composition can include nanopore 1600, permanent tether 1610, and polymerase 1650. Nanopore 1600 includes first side 1601, second side 1602, aperture 1603 extending through sides 1601 and 1602, and optionally also includes constriction 1604. Permanent tether 1610 includes head region 1611, tail region 1612, and elongated body 1613 disposed therebetween. Polymerase 1650 is disposed adjacent to first side 1601 of nanopore 1600. For example, polymerase 1650 can be in contact with first side 1601 of nanopore 1600, and optionally can be anchored to or adjacent to the first side of nanopore 1600 via any suitable chemical bond, protein-protein interaction, or any other suitable attachment that is normally irreversible. In the embodiment illustrated in FIG. 16, head region 1611 of tether 1610 is attached to, e.g., anchored to, first side 1601 of nanopore 1600, via any suitable chemical bond, protein-protein interaction, or any other suitable attachment that is normally irreversible.

Head region 1611 can be attached to any suitable portion of nanopore 1600 that places elongated tag 1613 sufficiently close to polymerase 1650 so as to interact with elongated tags of respective nucleotides that can be acted upon by polymerase 1650. For example, nucleotide 1630 can include an elongated tag 1631 including moiety 1632 that interacts with tether 1610. In an illustrative embodiment, elongated tag 1613 of tether 1610 can include a moiety 1615 with which moiety 1632 of tag can interact. Tail region 1612 can extend freely toward the second side of the nanopore, and can be disposed either on the first side of the nanopore, such as described below with reference to FIGS. 17A-17B, or can be disposed on or beyond the second side of the nanopore, such as described above with reference to FIGS. 7A-7B, or can be movable between the first and second sides of the nanopore, such as described below with reference to FIGS. 19-20B. Optionally, tail region 1612 can be attached to another member in a manner such as described with reference to FIGS. 11 and 1M, which other member optionally can be disposed within aperture 1603. Note that polymerase 1650 or nucleotide 1630, or both, can be, but need not necessarily be, considered to be part of the inventive composition, but instead can be considered to be in contact with a composition that includes nanopore 1600 and permanent tether 1610.

Referring again to FIG. 15, method 1500 includes acting upon a nucleotide with the polymerase (step 1502). For example, FIG. 16 schematically illustrates binding of nucleotide 1630 by polymerase 1650, but it should be understood that polymerase 1650 can act upon nucleotide in a variety of ways, e.g., by adding nucleotide 1630 to a polynucleotide, excising nucleotide 1630 from an existing polynucleotide, or sampling nucleotide 1630, e.g., transiently interacting with nucleotide 1630 without binding it. Method 1500 illustrated in FIG. 15 also includes interacting a moiety of the nucleotide with the tether (step 1503). For example, in the embodiment illustrated in FIG. 16, polymerase 1650 acting upon nucleotide 1630 can bring moiety 1632 of nucleotide 1630 into sufficiently close proximity to moiety 1615 that the moieties interact with one another, e.g., bond with one another. Such an interaction can be reversible, e.g., can include formation of a hydrogen bond, ionic bond, dipole-dipole bond, London dispersion forces, reversible covalent bond, or any suitable combination thereof.

Figure 17A:
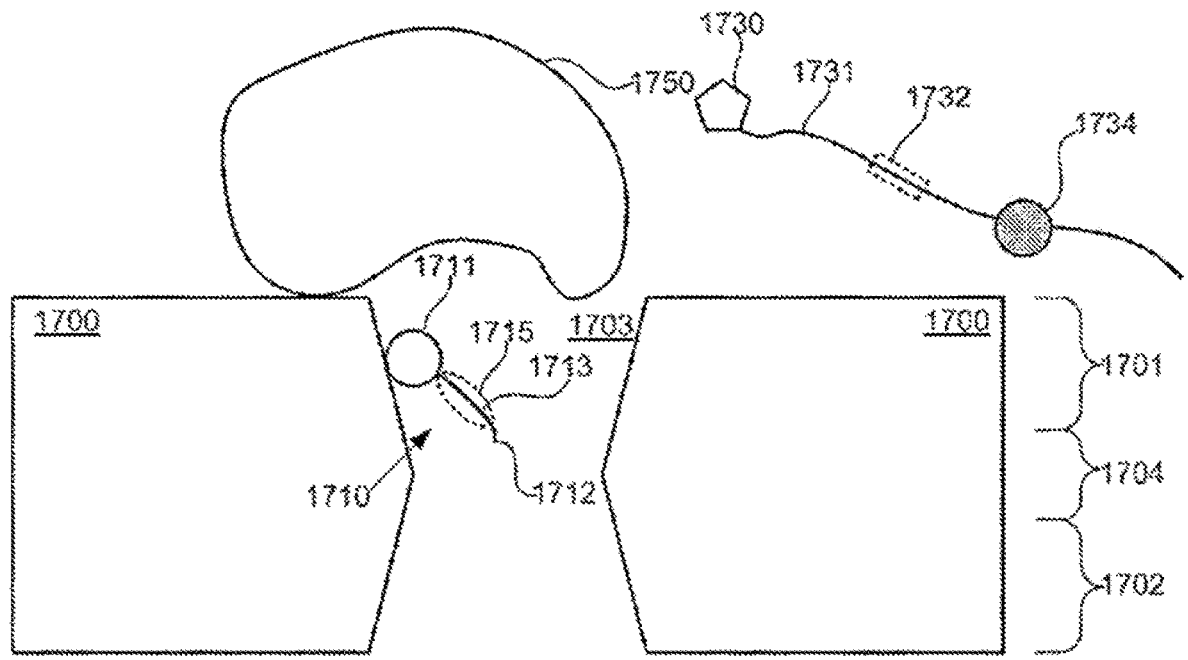
FIGS. 17A-17B schematically illustrate a composition including a tether anchored to or adjacent to a nanopore and configured for use in detecting action of a polymerase upon a nucleotide that includes an elongated tag including a reporter region, according to some embodiments of the present invention.
Figure 17B:
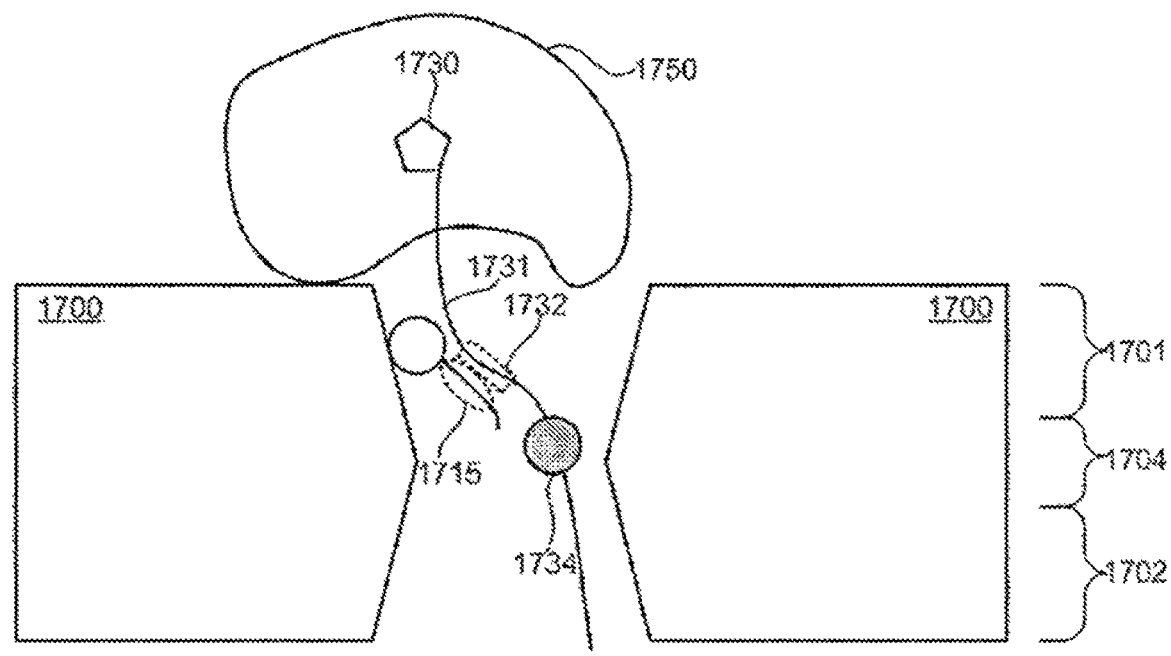

Referring again to FIG. 15, method 1500 also can include detecting the interaction of the moiety with the tether in any suitable manner. For example, the elongated tag of the nucleotide can include a reporter region, and method 1500 can include detecting the presence of the reporter region within the aperture of the nanopore (step 1504). For example, FIGS. 17A-17B schematically illustrate a composition including a tether anchored to or adjacent to a nanopore and configured for use in detecting action of a polymerase upon a nucleotide including an elongated tag including a reporter region. As illustrated in FIG. 17A, the composition can include nanopore 1700, including first side 1701, second side 1702, aperture 1703 extending through the first and second sides, and optional constriction 1704; permanent tether 1710 including head region 1711 anchored to first side 1701 of nanopore 1700, tail region 1712 disposed on first side 1702 of nanopore 1700, and elongated body 1713 that includes moiety 1715 but lacks a reporter region; and nucleotide 1730 including elongated tag 1731 that includes moiety 1732 and reporter region 1734.

As illustrated in FIG. 17B, an interaction between moiety 1732 of nucleotide 1730 and moiety 1715 of tether 1710 can dispose reporter region 1734 within aperture 1703. It should be appreciated that the disposition of reporter region 1734 within aperture 1703 can be detectable in any suitable manner. For example, the composition can be in operable communication with a measurement circuit such as described above with reference to FIG. 2A or FIG. 2C. The measurement circuit can be configured to detect the disposition of reporter region 1734 within aperture 1703. In one illustrative embodiment, nanopore 1700, tether 1710, polymerase 1750, and nucleotide 1730 can be immersed in a conductive fluid, e.g., an aqueous salt solution. A measurement circuit configured analogously to measurement circuit 230 illustrated in FIG. 2A or measurement circuit 240 illustrated in FIG. 2C can be in communication with first and second electrodes and can be configured to apply a voltage between those electrodes so as to apply a voltage across nanopore 1700. The measurement circuit further can be configured to use the electrodes to measure the magnitude of a current or flux through aperture 1703. Reporter region 1734 can have a different electrical or flux blockade property than some or all other regions of elongated tag 1731. For example, reporter region 1734 can include an electrostatic charge, while some or all other regions of elongated tag 1731 can include a different electrostatic charge, or can be uncharged (e.g., can be electrically neutral). Or, for example, reporter region 1734 can be uncharged, while some or all other regions of elongated body 1731 can include an electrostatic charge. The magnitude of the current or flux through aperture 1703 can measurably change responsive to disposition of reporter region 1734 within aperture 1703, and the time period for such a measurable change in the current or flux can be based on the duration of the interaction between moieties 1715 and 1732, which in turn can be based on the duration of the action of polymerase 1750 upon nucleotide 1730. In one illustrative, nonlimiting example, elongated body 1731 includes a polynucleotide that includes one or more abasic nucleotides that define reporter region 1734.

In one illustrative embodiment, the formation of a duplex can be monitored using duplex interrupted sequencing such as described in Derrington et al., "Nanopore DNA sequencing with MspA," Proc. Natl. Acad. Sci. USA, 107:16060-16065 (2010), the entire contents of which are incorporated by reference herein. The present system can uses an AC driving voltage whose temporal period is on the same order of magnitude as the time to duplex formation, which can be expected to be significantly shorter than the polymerase catalytic incorporation event being measured. See also PCT Publication No. WO2011/106459 to Gundlach et al., the entire contents of which are incorporated by reference herein.

The action of polymerase 1750 upon nucleotide 1730 can be individually identifiable based on a measured (e.g., optically or electrically measured) magnitude or time duration, or both, of a signal generated by such a system. For example, the action of polymerase 1750 upon nucleotide 1730 can cause interaction between moieties 1715 and 1732, which in turn causes reporter region 1734 to become disposed at a first location within aperture 1703, and the presence of reporter region 1734 at the first location causes the signal to have a first magnitude. As such, the signal having the first magnitude correlates to the action of polymerase 1750 upon nucleotide 1730 having occurred.

Note that in some embodiments, the respective lengths of elongated body 1713 and elongated tag 1731, the respective locations of moieties 1715 and 1732, and the respective location of reporter region 1734 are co-selected so as to inhibit the application of force to nucleotide 1730 while the nucleotide is being acted upon by polymerase 1750, and thus to inhibit or preclude such a force from modifying the performance of the polymerase. In one illustrative embodiment, the interaction between moiety 1715 and moiety 1713 forms a duplex. The length of elongated body 1713 can be selected such that the elongated body substantially does not extend through the location at which reporter region 1734 is to be disposed. The length of elongated tag 1731 can be selected so as to extend through the location at which reporter region is to be disposed, while providing additional slack such that elongated tag 1731 need not be pulled taut in order to dispose reporter region 1734 at the location. In some embodiments, the respective location of moiety 1715 along elongated body 1713 of tether 1710 and the respective location of moiety 1732 along elongated tag 1731 of nucleotide 1730 are co-selected so as to provide the additional slack in elongated tag 1731 at a location between the duplex of 1715, 1732 and polymerase 1750. Accordingly, the anchoring of head region 1711 to pore 1700 can inhibit movement of the duplex 1715, 1732 through aperture 1703, and can absorb forces that otherwise may have been applied to nucleotide 1730 via elongated tag 1731. Additionally, reporter region 1734 can be disposed at a suitable location along elongated body 1731 so as to be disposed at a suitable location within aperture 1730 to facilitate detection of the reporter region when moieties 1715 and 1732 interact with one another. In one exemplary embodiment, reporter region 1734 is disposed at a suitable location along elongated body 1731 so as to be disposed within, or adjacent to, constriction 1704 of nanopore 1700 when moieties 1715 and 1732 interact with one another responsive to action of polymerase 1750.

Other methods of detecting the action of a polymerase 1750 upon a nucleotide suitably can be used. For example, method 1500 alternatively can include changing an applied voltage across the nanopore aperture (step 1505), disposing a reporter region of a tether at a location within the aperture responsive to the change in applied voltage (step 1506), and detecting the presence of the reporter region of the tether at the location within the aperture (step 1507). For example, FIGS. 18A-18D schematically illustrate a composition including a tether anchored to or adjacent to a nanopore and configured for use in detecting action of a polymerase upon a nucleotide using a tether anchored to or adjacent to a nanopore responsive to a change in electrical potential across the nanopore, and FIG. 18E illustrates an exemplary signal that can be generated during use of such a composition.

The composition illustrated in FIG. 18A includes nanopore 1800 including first side 1801, second side 1802, aperture 1803 extending through the first and second sides, and constriction 1804 disposed between the first and second sides; permanent tether 1810 including a head region (not specifically labeled) anchored to first side 1801 of nanopore 1800, a tail region (not specifically labeled) that is movable between first side 1801 and second side 1802 of nanopore 1800, and an elongated body (not specifically labeled) that includes reporter region 1814 and moiety 1815; and nucleotide 1830 including an elongated tag (not specifically labeled) that includes moiety 1832 but lacks a reporter region. As illustrated in FIG. 18A, an interaction between moiety 1832 of nucleotide 1830 and moiety 1815 of tether 1810 can dispose reporter region 1814 at a predetermined location relative to the moiety 1832. Optionally, more than one reporter region can be provided, e.g., at least two, or three, or four, or five, or more than five reporter regions. Additionally, moiety 1815 can be located at any suitable position along elongated tag 1813, e.g., can be located between head region 1811 and reporter region 1814 and adjacent to reporter region 1814 such as illustrated in FIG. 18A, or can be adjacent to head region 1811, adjacent to tail region 1812, or between tail region 1812 and reporter region 1814.

It should be appreciated that the disposition of reporter region 1814 at the predetermined location relative to moiety 1832 can be detectable in any suitable manner. For example, the composition can be in operable communication with a measurement circuit such as described above with reference to FIG. 2A or FIG. 2C. The measurement circuit can be configured to detect the position of reporter region 1814 relative to moiety 1832. In one illustrative embodiment, nanopore 1800, tether 1810, polymerase 1850, and nucleotide 1830 can be immersed in a conductive fluid, e.g., an aqueous salt solution. A measurement circuit configured analogously to measurement circuit 230 illustrated in FIG. 2A or measurement circuit 240 illustrated in FIG. 2C can be in communication with first and second electrodes and can be configured to apply a first voltage between those electrodes so as to apply a voltage across nanopore 1800, as represented by the "+" and "−" signs illustrated in FIG. 18A, and to use the electrodes to measure the magnitude of a current or flux through aperture 1803 at the first voltage. The portion of FIG. 18E immediately below FIG. 18A illustrates an exemplary current or flux through aperture 1803 at the first voltage. Reporter region 1814 can have a different electrical or flux blockade property than some or all other regions of the elongated body of the tether (not specifically labeled). For example, reporter region 1814 can include an electrostatic charge, while some or all other regions of elongated body can include a different electrostatic charge, or can be uncharged (e.g., can be electrically neutral). Or, for example, reporter region 1814 can be uncharged, while some or all other regions of the elongated body can include an electrostatic charge. In one illustrative, nonlimiting example, the elongated body of the tether includes a polynucleotide that includes one or more abasic nucleotides that define reporter region 1814. The magnitude of the current or flux through aperture 1803 can measurably change responsive to the relative location of reporter region 1814 within aperture 1803, and such relative location can be based upon the applied voltage and on the location of reporter region 1814 relative to moiety 1832, which in turn can be based on the action of polymerase 1850 upon nucleotide 1830.

More specifically, the measurement circuit further can be configured to change the applied voltage across nanopore 1800 to a second voltage, e.g., by reversing the applied voltage such as represented by the reversal of the "+" and "−" signs such as illustrated in FIG. 18B. Such a change in applied voltage can cause movement of interacting moieties 1815, 1832 within aperture 1803 of nanopore 1800. For example, as illustrated in FIG. 18B, the change in applied voltage can move interacting moieties 1815, 1832 adjacent to constriction 1804, and can dispose reporter region 1814 adjacent to or within constriction 1804. The measurement circuit can be configured to use the electrodes to measure the magnitude of a current or flux through aperture 1803 at the second voltage. The portion of FIG. 18E immediately below FIG. 18B illustrates an exemplary current or flux through aperture 1803 at the second voltage. It can be seen that the current or flux at the first voltage is different than the current or flux at the second voltage, and such current or flux can be based upon the second voltage and on the location of reporter region 1814 relative to moiety 1832, which in turn can be based on the action of polymerase 1850 upon nucleotide 1830.

The action of polymerase 1850 upon nucleotide 1830 can be individually identifiable based on a measured (e.g., optically or electrically measured) magnitude or time duration, or both, of a signal generated by such a system. For example, the action of polymerase 1850 upon nucleotide 1830 can cause interaction between moieties 1815 and 1832, which in turn causes reporter region 1814 to become disposed at a first location relative to moiety 1832, and the presence of reporter region 1814 at the first location causes the signal, e.g., current or flux through aperture 1803, to have a first magnitude. As such, the signal having the first magnitude correlates to the action of polymerase 1850 upon nucleotide 1830 having occurred. Note that a duplex formed between moiety 1815 and moiety 1832 can be sufficiently large as to inhibit movement of the duplex through the constriction, e.g., under the second voltage.

As illustrated in FIG. 18C, in some embodiments, continued application of the second voltage can cause moiety 1815 to dissociate from moiety 1832. Such dissociation can be considered to "interrupt" a duplex formed between moiety 1815 and moiety 1832. In some embodiments, reporter region 1814 or moiety 1815, or both, can move through constriction 1804 so as to be disposed on second side 1802 of nanopore 1800. The portion of FIG. 18E immediately below FIG. 18C illustrates an exemplary current or flux through aperture 1803 at the second voltage, following dissociation of moiety 1815 from moiety 1832. Moiety 1832 can be configured so as to remain disposed on the first side of nanopore 1800 even if moiety 1815 becomes disposed on the second side of nanopore 1800, so as to temporarily inhibit interaction between moieties 1815 and 1832. As illustrated in FIG. 18D, following such dissociation, the voltage applied across aperture 1803 can again be changed, e.g., can be changed back to the first voltage, responsive to which moieties 1815 and 1832 can interact with one another. The portion of FIG. 18E immediately below FIG. 18D illustrates an exemplary current or flux through aperture 1803 at the first voltage, following interaction of moiety 1815 from moiety 1832.

Note that in some embodiments, the respective lengths of the elongated body of the tether and the elongated tag of the nucleotide, the respective locations of moieties 1815 and 1832, and the respective location of reporter region 1814 are co-selected so as to inhibit the application of force to nucleotide 1830 while the nucleotide is being acted upon by polymerase 1850, and thus to inhibit or preclude such a force from modifying the performance of the polymerase. In one illustrative embodiment, the interaction between moiety 1815 and moiety 1832 forms a duplex. The length of the elongated body of the tether, and the location of moiety 1815 along the elongated body, can be co-selected such that moiety 1815 can be extended through constriction 1804 responsive to an appropriate applied voltage, e.g., so as to cause dissociation between moiety 1815 and moiety 1832. The length of the elongated tag of the nucleotide, and the location of moiety 1832 along the elongated tag, can be co-selected so as to provide additional slack such that elongated tag need not be pulled taut in order to dispose reporter region 1814 adjacent to constriction 1804 under the second applied voltage. The size of the duplex 1815, 1832 can inhibit movement of the duplex through constriction 1804, and can shield the nucleotide from forces that otherwise may have been applied to nucleotide 1830 via elongated tag 1831. Additionally, the relative locations of reporter region 1814 and moieties 1815 and 1832 can be co-selected so as to dispose reporter region 1814 at a suitable location relative to constriction 1804 under the second voltage so as to facilitate detection of the reporter region when moieties 1815 and 1832 interact with one another. In one exemplary embodiment, reporter region 1814 is disposed at a suitable location along elongated body 1831 so as to be disposed within, or adjacent to, constriction 1804 of nanopore 1800 when moieties 1815 and 1832 interact with one another responsive to action of polymerase 1850.

As yet another alternative method of detecting the action of a polymerase upon a nucleotide, method 1500 alternatively can include detecting the movement of a reporter region of a tether within an aperture (step 1508). Exemplary compositions for detecting the movement of a reporter region of a tether in association with a nucleotide acting upon a polymerase are described further above with reference to FIGS. 7A-14.

Note that following any of steps 1507, 1507, or 1508, method 1500 further can include releasing the moiety of the nucleotide from the tether, in a manner analogous to that described above with reference to FIGS. 7A-14 (step not specifically illustrated in FIG. 15). Additionally, as described in greater detail below with reference to FIGS. 19A-20B, or above with reference to FIGS. 7A-14, the present compositions and methods can be used to individually detect the action of polymerases on different nucleotides.

Sequencing by Synthesis Using Exemplary Methods and Compositions Based on Detecting Action of Polymerases Upon Nucleotides It should be appreciated that method 1500 illustrated in FIG. 15 suitably can be used to detect action of a polymerase upon any type of nucleotide having a suitable moiety attached thereto. In illustrative embodiments described below with reference to FIGS. 18-22F, method 1500 can be used to detect a polymerase's action upon a nucleotide and the use thereof to sequence a first polynucleotide by synthesizing a second polynucleotide that is complementary to the first nucleotide, e.g., using "sequencing by synthesis" (SBS).

FIGS. 19A-19B schematically illustrate a composition including a tether anchored to or adjacent to a nanopore and configured for use in detecting action of a polymerase upon a nucleotide including an elongated tag including a reporter region. The nanopore includes biological pore 1905, which can be disposed in a barrier (not specifically illustrated), e.g., a membrane of biological origin such as a lipid bilayer, or a solid state membrane. Biological pore 1905 includes aperture 1903 and constriction 1904. The permanent tether includes head region 1911, elongated body 1913, and moiety 1915. Polymerase 1950 is disposed adjacent to, and in contact with, biological pore 1905, and optionally can be anchored to biological pore 1905 via a physical or chemical linkage (e.g., using click chemistry or a cysteine-maleimide bond). Polymerase 1950 is configured to receive a template polynucleotide 1970, e.g., circular or linear ssDNA to be sequenced, to synthesize a polynucleotide 1960 having a complementary sequence to that of the ssDNA by sequentially receiving, binding, and adding nucleotides to the polynucleotide in accordance with the sequence of the ssDNA. Head region 1911 of the tether can be anchored to any suitable portion of biological pore 1905 that places moiety 1915 sufficiently close to polymerase 1950 so as to interact with corresponding moieties of nucleotides that can be bound by polymerase 1950. For example, as illustrated in FIG. 19B, nucleotide 1930 can include an elongated tag 1931 including moiety 1932 that interacts with moiety 1915 of the tether, as well as reporter region 1934 configured to be disposed through aperture 1903 of nanopore 1905.

In one example, a voltage can be applied across the nanopore 1905, e.g., using measurement circuit 230 and electrodes 231, 232 such as described further above with reference to FIG. 2A or measurement circuit 240 and electrodes 241, 242 such as described further above with reference to FIG. 2C. Reporter region 1914 or elongated body 1913 optionally includes an electrostatic charge that, responsive to the applied voltage, causes tail region 1912 of elongated body 1913 to extend toward second side 1902 of nanopore 1905. Additionally, elongated tag 1931 of nucleotide 1930 includes an electrostatic charge that, responsive to the applied voltage, causes end region 1933 of tag 1931 to pass through constriction 1904 such that reporter region 1934 is disposed within or adjacent to constriction 1904. Responsive to polymerase 1950 binding nucleotide 1930, moiety 1932 of nucleotide 1930 can reversibly bond to moiety 1915 of tether 1932, which can dispose reporter region 1934 within or adjacent to constriction 1904. As a result, the binding of nucleotide 1930 by polymerase 1950 can be translated or transduced into a measurable change in current or flux through constriction 1904, which also can be referred to as a blockade current or flux. Additionally, the force exerted on tether by the applied voltage is expected to pull on the pore via moiety 1915 rather than on the polymerase, and thus is not expected to significantly disrupt polymerase activity.

In one illustrative embodiment, moiety 1915 includes a first oligonucleotide, and moiety 1932 includes a second oligonucleotide that is complementary to the first oligonucleotide, e.g., that hybridizes to the first oligonucleotide. The hybridization of the second oligonucleotide to the first oligonucleotide can cause reporter region 1934 to become disposed within or adjacent to constriction 1904. The binding of nucleotide 1930 can be individually detected based on a measured (e.g., optically or electrically measured) magnitude or time duration, or both, of a current or flux through constriction 1904. For example, FIG. 19B schematically illustrates an exemplary nucleotide 1930, e.g., T, including an elongated tag 1931 including an oligonucleotide moiety 1932 that can be attached to the gamma phosphate of the nucleotide 1930, e.g., via a delta phosphate linkage. Oligonucleotide moiety 1932 can include any suitable sequence of nucleotides selected to hybridize to a corresponding sequence of nucleotides within moiety 1915 of the tether. For example, oligonucleotide moiety 1932 illustrated in FIG. 19B can include the exemplary sequence TACG, and moiety 1915 can include the complementary sequence ATGC. In a manner analogous to that described above with reference to FIGS. 8A-14, the action of polymerase 1905 upon nucleotide 1930 can maintain moiety 1932 in relatively close proximity to moiety 1915 of the tether, resulting in a transient increase in the local concentration of oligonucleotide moiety 1932 that can induce hybridization between moieties 1932 and 1915 preferentially to moieties that are attached to nucleotides not presently being acted upon by polymerase 1905. The resulting hybridization causes disposition of reporter region 1934 adjacent to or within constriction 1904. Polymerase 1950 can release elongated tag 1931 upon incorporating nucleotide 1930 into a polynucleotide, responsive to which moiety 1932 can dissociate from moiety 1915.

Each different type of nucleotide can include a corresponding elongated tag that is attached to its gamma phosphate in a manner analogous to that illustrated in FIG. 19B. For example, FIG. 19C schematically illustrates exemplary nucleotides including elongated tags that include respective reporter regions and moieties that bond to an exemplary tether during use in detecting action of a nucleotide by a polymerase disposed adjacent to a nanopore. As shown in FIGS. 19C, A, T, C, and G nucleotides can include respectively elongated tags that include different reporter regions than one another, e.g., as respectively represented by the triangle, diamond, square, and circle. For further information about reporter regions that can be attached to nucleotides so as to permit distinguishing the nucleotides from one another, see U.S. Pat. No. 8,652,779 to Turner et al., the entire contents of which are incorporated by reference herein. Additionally, elongated tags include moieties that can be suitably selected so as to hybridize to a corresponding moiety of the permanent tether. However, the moieties need not be different than one another, and indeed can be the same as one another because the nucleotides can be distinguishable from one another based on differences between their respective reporter regions. In one illustrative embodiment, the moieties have lengths of 5 to 8 nucleotides. It is expected that the melting temperatures of duplexes between moieties on incorporating nucleotides and moieties on the tether to be significantly more stable than an otherwise identical pair of freely diffusing oligonucleotides because the tether and the incorporating nucleotide are held in relatively fixed position relative to another, causing an effective increase in the local concentrations of the moieties, as discussed above with reference to FIGS. 8A-14.

Other compositions suitably can be used to perform sequencing by synthesis based on detection action of a polymerase upon nucleotides. For example, FIGS. 20A-20D schematically illustrate a composition including a tether anchored to or adjacent to a nanopore and configured for use in detecting action of a polymerase upon a first nucleotide using a tether anchored to or adjacent to a nanopore responsive to a change in electrical potential across the nanopore, and FIG. 20E illustrates an exemplary signal that can be generated during use of such a composition.

The composition illustrated in FIG. 20A includes nanopore 2000 including first side 2001, second side 2002, aperture 2003 extending through the first and second sides, and constriction 2004 disposed between the first and second sides; a permanent tether (not specifically labeled) including a head region (not specifically labeled) anchored to second side 2002 of nanopore 2000, a tail region (not specifically labeled) that is movable between first side 2001 and second side 2002 of nanopore 2000, and an elongated body (not specifically labeled) that includes a plurality of reporter regions 2014, 2024, 2034, and moiety 2015; and nucleotide 2030 including an elongated tag (not specifically labeled) that includes moiety 2032 but lacks a reporter region. As illustrated in FIG. 20A, an interaction between moiety 2032 of nucleotide 2030 and moiety 2015 of tether 2010 can dispose each reporter region 2014, 2024, 2034 at a predetermined location relative to the moiety 2032. Any suitable number of reporter regions can be provided, e.g., at least two reporter regions, three reporter regions, four reporter regions, five reporter regions, or more than five reporter regions. Additionally, moiety 2015 can be located at any suitable position along elongated tag 2013, e.g., can be located between and adjacent to each of tail region 2012 and first reporter region 2014 such as illustrated in FIG. 20A, or can be adjacent to head region 2011, or between head region 2011 and third reporter region 2034, or between any of reporter regions 2014, 2024, or 2034.

It should be appreciated that the relative position of moiety 2032 and one or more of the reporter regions, e.g., reporter region 2014 can be detectable in any suitable manner. For example, the composition can be in operable communication with a measurement circuit such as described above with reference to FIG. 2A or FIG. 2C. The measurement circuit can be configured to detect the position of reporter region 2014 relative to moiety 2032. In one illustrative embodiment, nanopore 2000, tether 2010, polymerase 2050, and nucleotide 2030 can be immersed in a conductive fluid, e.g., an aqueous salt solution. A measurement circuit configured analogously to measurement circuit 230 illustrated in FIG. 2A or measurement circuit 240 illustrated in FIG. 2C can be in communication with first and second electrodes and can be configured to apply a first voltage between those electrodes so as to apply a voltage across nanopore 2000, as represented by the "+" and "−" signs illustrated in FIG. 20A, and to use the electrodes to measure the magnitude of a current or flux through aperture 2003 at the first voltage. The portion of FIG. 20E immediately below FIG. 20A illustrates an exemplary current or flux through aperture 2003 at the first voltage. Reporter region 2014 can have a different electrical or flux blockade property than some or all other regions of the elongated body of the tether (not specifically labeled), as well as than some or all other reporter regions 2024, 2034. The magnitude of the current or flux through aperture 2003 can measurably change responsive to the relative location of reporter region 2014 within aperture 2003, and such relative location can be based upon the applied voltage and on the location of reporter region 2014 relative to moiety 2032, which in turn can be based on the action of polymerase 2050 upon nucleotide 2030.

More specifically, the measurement circuit further can be configured to change the applied voltage across nanopore 2000 to a second voltage, e.g., by reversing the applied voltage such as represented by the reversal of the "+" and "−" signs such as illustrated in FIG. 20B. Such a change in applied voltage can cause movement of interacting moieties 2015, 2032 within aperture 2003 of nanopore 2000. For example, as illustrated in FIG. 20B, the change in applied voltage can move interacting moieties 2015, 2032 adjacent to constriction 2004, and can dispose reporter region 2014 adjacent to or within constriction 2004 selectively relative to reporter regions 2024, 2034. The measurement circuit can be configured to use the electrodes to measure the magnitude of a current or flux through aperture 2003 at the second voltage. The portion of FIG. 20E immediately below FIG. 20B illustrates an exemplary current or flux through aperture 2003 at the second voltage. It can be seen that the current or flux at the first voltage is different than the current or flux at the second voltage, and such current or flux can be based upon the second voltage and on the location of reporter region 2014 relative to moiety 2032, which in turn can be based on the action of polymerase 2050 upon nucleotide 2030.

The action of polymerase 2050 upon nucleotide 2030 can be individually identifiable based on a measured (e.g., optically or electrically measured) magnitude or time duration, or both, of a signal generated by such a system. For example, the action of polymerase 2050 upon nucleotide 2030 can cause interaction between moieties 2015 and 2032, which in turn causes reporter region 2014 to become disposed at a first location relative to moiety 2032, and the presence of reporter region 2014 at the first location causes the signal, e.g., current or flux through aperture 2003, to have a first magnitude. As such, the signal having the first magnitude correlates to the action of polymerase 2050 upon nucleotide 2030 having occurred. Note that a duplex formed between moiety 2015 and moiety 2032 can be sufficiently large as to inhibit movement of the duplex through the constriction, e.g., under the second voltage.

As illustrated in FIG. 20C, in some embodiments, continued application of the second voltage can cause moiety 2015 to dissociate from moiety 2032. Such dissociation can be considered to "interrupt" a duplex formed between moiety 2015 and moiety 2032. In some embodiments, reporter region 2014 or moiety 2015, or both, can move through constriction 2004 so as to be disposed on second side 2002 of nanopore 2000. The portion of FIG. 20E immediately below FIG. 20C illustrates an exemplary current or flux through aperture 2003 at the second voltage, following dissociation of moiety 2015 from moiety 2032. Moiety 2032 can be configured so as to remain disposed on the first side of nanopore 2000 even if moiety 2015 becomes disposed on the second side of nanopore 2000, so as to temporarily inhibit interaction between moieties 2015 and 2032. As illustrated in FIG. 20D, following such dissociation, the voltage applied across aperture 2003 can again be changed, e.g., can be changed back to the first voltage, responsive to which moieties 2015 and 2032 can interact with one another. The portion of FIG. 20E immediately below FIG. 20D illustrates an exemplary current or flux through aperture 2003 at the first voltage, following interaction of moiety 2015 from moiety 2032.

Figures 21A, 21B, 21C, 21D, 21E:
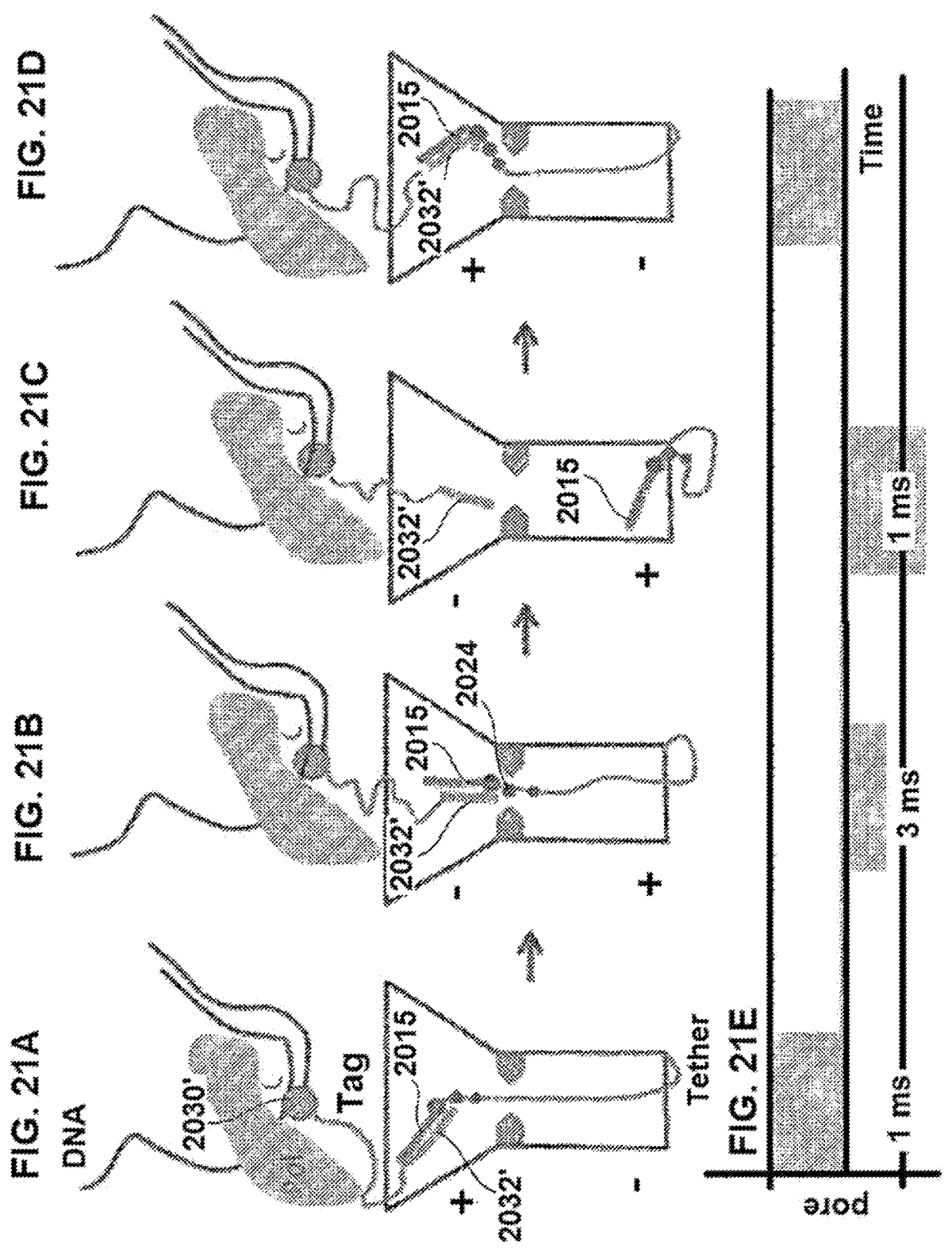

As part of the action of polymerase 2050 upon nucleotide 2030, polymerase 2050 can, for example, cleave the elongated tag from nucleotide 2030, causing dissociation of moiety 2032 from moiety 2015, and can add nucleotide 2030 to polynucleotide 2060 in accordance with the sequence of template 2070. Polymerase 2050 then can act upon a second nucleotide. For example, FIGS. 21A-21D schematically illustrate the composition of FIGS. 20A-20D configured for use in detecting action of the polymerase upon a second nucleotide using the tether anchored to or adjacent to a nanopore responsive to a change in electrical potential across the nanopore, and FIG. 21E illustrates an exemplary signal that can be generated during use of such a composition. More specifically, FIG. 21 illustrates polymerase 2050 acting upon second nucleotide 2030' having second moiety 2032'. Second moiety 2032' of second nucleotide 2030' interacts with moiety 2015 in a different manner than does moiety 2032 of first nucleotide 2030.

For example, as illustrated in FIG. 21A, an interaction between moiety 2032' of second nucleotide 2030' and moiety 2015 of the tether can dispose each reporter region 2014, 2024, 2034 at a predetermined location relative to the moiety 2032' that is different than the predetermined locations illustrated in FIG. 21A because moiety 2032' is different than moiety 2032, e.g., interacts with a different portion of moiety 2015 than does moiety 2023. The measurement circuit can be configured to detect the position of reporter region 2024 relative to moiety 2032' responsive to first and second applied voltages in a manner analogous to that described above with reference to FIGS. 20A-20E. For example, the portion of FIG. 21E immediately below FIG. 21A illustrates an exemplary current or flux through aperture 2003 at the first voltage. Reporter region 2024 can have a different electrical or flux blockade property than some or all other regions of the elongated body of the tether (not specifically labeled), as well as than some or all other reporter regions 2014, 2034.

The magnitude of the current or flux through aperture 2003 can measurably change responsive to the relative location of reporter region 2014 within aperture 2003, and such relative location can be based upon the applied voltage and on the location of reporter region 2014 relative to moiety 2032', which in turn can be based on the action of polymerase 2050 upon nucleotide 2030'. More specifically, the measurement circuit further can be configured to change the applied voltage across nanopore 2000 to a second voltage, e.g., by reversing the applied voltage such as represented by the reversal of the "+" and "−" signs such as illustrated in FIG. 21B. Such a change in applied voltage can cause movement of interacting moieties 2015, 2032' within aperture 2003 of nanopore 2000. For example, as illustrated in FIG. 21B, the change in applied voltage can move interacting moieties 2015, 2032' adjacent to constriction 2004, and can dispose reporter region 2024 adjacent to or within constriction 2004 selectively relative to reporter regions 2014, 2034. The measurement circuit can be configured to use the electrodes to measure the magnitude of a current or flux through aperture 2003 at the second voltage. The portion of FIG. 21E immediately below FIG. 21B illustrates an exemplary current or flux through aperture 2003 at the second voltage. It can be seen that the current or flux at the first voltage is different than the current or flux at the second voltage, and such current or flux can be based upon the second voltage and on the location of reporter region 2024 relative to moiety 2032', which in turn can be based on the action of polymerase 2050 upon nucleotide 2030'. For example, it can be seen that the current or flux illustrated in FIG. 21E as corresponding to FIG. 21B is greater than the current or flux illustrated in FIG. 20E as corresponding to FIG. 20B, because reporter region 2024 has a measurably different characteristic than does reporter region 2014. As such, the magnitude of the signal, e.g., current or flux, correlates to the particular type of nucleotide upon which polymerase 2050 is acting.

As illustrated in FIG. 21C, in some embodiments, continued application of the second voltage can cause moiety 2015 to dissociate from moiety 2032' in a manner analogous to that described above with reference to FIG. 20C. The portion of FIG. 21E immediately below FIG. 21C illustrates an exemplary current or flux through aperture 2003 at the first voltage, following interaction of moiety 2015 from moiety 2032'. As illustrated in FIG. 21D, following such dissociation, the voltage applied across aperture 2003 can again be changed, e.g., can be changed back to the first voltage, responsive to which moieties 2015 and 2032' can interact with one another in a manner described above with reference to FIG. 20D. The portion of FIG. 21E immediately below FIG. 21D illustrates an exemplary current or flux through aperture 2003 at the first voltage, following interaction of moiety 2015 from moiety 2032'.

Note that in some embodiments, the respective lengths of the elongated body of the tether and the elongated tag of the nucleotide, the respective locations of moieties 2015 and 2032 and 2032', and the respective locations of reporter regions 2014, 2024, and 2034 are co-selected so as to inhibit the application of force to nucleotide 2030 or 2030' while the nucleotide respectively is being acted upon by polymerase 2050, and thus to inhibit or preclude such a force from modifying the performance of the polymerase, as well as to permit different nucleotides to be individually distinguishable from one another. In one illustrative embodiment, the interaction between moiety 2015 and moiety 2032 or 2032' forms a duplex. The length of the elongated body of the tether, and the location of moiety 2015 along the elongated body, can be co-selected such that moiety 2015 can be extended through constriction 2004 responsive to an appropriate applied voltage, e.g., so as to permit interaction between moiety 2015 and moiety 2032 or moiety 2032'. The length of the elongated tag of the nucleotide, and the location of moiety 2032 or 2032' along the elongated tag, can be co-selected so as to provide additional slack such that elongated tag need not be pulled taut in order to respectively dispose one of reporter regions 2014, 2024, or 2034 within or adjacent to constriction 2004 under the second applied voltage. The size of the duplex 2015, 2032 or 2015, 2032' can inhibit movement of the duplex through constriction 2004, and can shield the respective nucleotide 2030, 2030' from forces that otherwise may have been applied to that nucleotide 2030 or 2030' via elongated tag 2031. Additionally, the relative locations of reporter regions 2014, 2024, and 2034 and moieties 2015 and 2032 and 2032' can be co-selected so as to dispose one of those reporter regions at a suitable location relative to constriction 2004 under the second voltage so as to facilitate detection of that reporter region when moieties 2015 and 2032 or moieties 2015 and 2032' respectively interact with one another. In one exemplary embodiment, reporter region 2014 is disposed at a first location along elongated body 2031 so as to be disposed within, or adjacent to, constriction 2004 of nanopore 2000 when moieties 2015 and 2032 interact with one another responsive to action of polymerase 2050, reporter region 2024 is disposed at a second location along elongated body 2031 so as to be disposed within, or adjacent to, constriction 2004 of nanopore 2000 when moieties 2015 and 2032' interact with one another responsive to action of polymerase 2050, and reporter region 2034 is disposed at a suitable location along elongated body 2031 so as to be disposed within, or adjacent to, constriction 2004 of nanopore 2000 when moiety 2015 interacts with a moiety of yet another nucleotide responsive to action of polymerase 2050. Accordingly, it should be understood that any suitable number of reporter regions can be provided so as to provide detectable signals corresponding to particular nucleotides being acted upon by the polymerase.

Note that the embodiment described further above with reference to FIGS. 18A-18E, in which the head region of the tether is anchored to the first side of the nanopore rather than to the second side of the nanopore, can be used in a manner analogous to that of FIGS. 20A-21E so as to individually identify nucleotides being acted upon by a polymerase.

Still other configurations suitably can be used. For example, FIGS. 22A-22F schematically illustrate a composition including a tether anchored adjacent to a nanopore and configured for use in detecting action of a polymerase upon a first nucleotide using a change in applied voltage across the nanopore, according to some embodiments of the present invention.

Figure 22A:
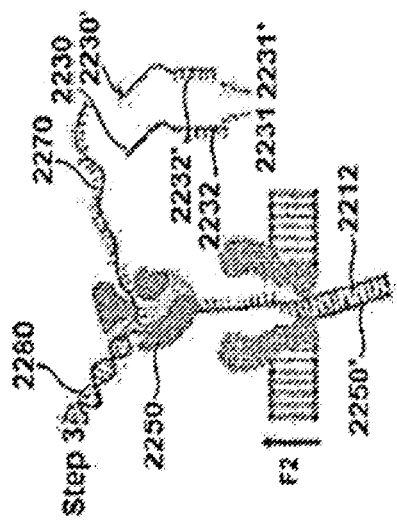
FIGS. 22A 22F schematically illustrate a composition including a tether anchored adjacent to a nanopore and configured for use in detecting action of a polymerase upon a first nucleotide using a change in applied voltage across the nanopore, according to some embodiments of the present invention.
Figure 22B:
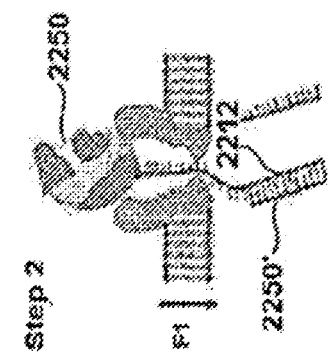

More specifically, FIG. 22A illustrates a composition including nanopore 2300 including first side 2201, second side 2202, aperture 2203 extending through the first and second sides, and constriction 2204 disposed between the first and second sides. Illustratively, nanopore 2200 can include a biological pore, such as a MspA nanopore (e.g., M2-NNN MspA mutant), disposed in a barrier, such as a membrane of biological origin (e.g., a lipid bilayer) or a solid state membrane. The composition illustrated in FIG. 22A further includes tether 2210 including head region 2211, tail region 2212, and elongated body 2213 disposed therebetween. Head region 2211 is suitably anchored to polymerase 2250, e.g., using any suitable attachment provided herein or otherwise known in the art. Elongated body 2213 of tether 2210 can include a moiety 2214. Illustratively, elongated body 2213 can include a polynucleotide, and a first subset of the nucleic acids of the polynucleotide can define moiety 2214. Additionally, tail region 2212 can include at least one charged atom such that, based upon a voltage being applied across nanopore 2200 illustrated in FIG. 22A during step 1, such voltage generates a first directional force F1 that causes translocation of tail region 2212 through aperture 2203 and past constriction 2204 such that a portion of elongated tail 2213 becomes disposed within aperture 2203 and tail region becomes disposed beyond second side 2202 of nanopore 2200 in a manner such as illustrated in FIG. 22B. For example, such voltage can be applied using a system such as described herein with reference to FIGS. 2A-2C. Such directional force F1 also causes translocation of polymerase 2250 towards second side 2202 of nanopore 2200 until polymerase 2250 comes to rest on or adjacent to first side 2201 of nanopore 2200 in a manner such as illustrated in FIG. 22B, preventing or inhibiting further movement of polymerase 2250 under directional force F1. Note that polymerase optionally can be partially disposed within aperture 2203 of nanopore 2200.

The composition illustrated in FIG. 22A also can include another member 2250' to which tail region 2212 of tether 210 can attach in a manner analogous to that described above with reference to FIG. 1M. For example, the composition illustrated in FIG. 22A can include one or more polynucleotides 2250' having a sequence that suitably can hybridize to corresponding nucleic acids on elongated body 2213 or on tail region 2212 of tether 2210. For example, as illustrated in FIG. 22B, under directional force F1 that is applied during step 1 (FIG. 22A) and can continue during step 2 (FIG. 22B), tail region 2212 becomes disposed beyond second side 2202 of nanopore 2200 and becomes attached to, e.g., hybridizes with member 2250', e.g., a complimentary piece of DNA ("capture-DNA") present adjacent to second side 2202 (e.g., on the trans side) of nanopore 2200. The bond between tail region 2212 and member 2250', e.g., hybridization between one or more first nucleic acids of tail region 2212 and one or more second nucleic acids of member 2250' so as to form a duplex 2212, 2250', e.g., double stranded DNA, is sufficiently strong so that upon application of a reverse directional force F2 (e.g., during step 3 illustrated in FIG. 22C), e.g., reversal of the voltage, the duplex inhibits separation of the polymerase from the nanopore and, as such, the polymerase remains captured at the nanopore. For example, duplex 2212, 2250' can include a sufficient number of hybridized nucleic acids such that the duplex does not dissociate under application of force F2. Additionally, the duplex 2212, 2250' can be sufficiently large as to inhibit movement of the duplex through constriction 2204. Additionally, in some embodiments, the lateral dimensions of constriction 2204 of nanopore 2200 are selected such that only a single elongated body 2213 of a single tether 2210 can be disposed therethrough, thus assuring that only one polymerase 2250 becomes captured at the nanopore.

In particular embodiments, a quality assessment step can be utilized to evaluate the nanopore or the capture of polymerase at the nanopore. A nanopore that is properly embedded in a membrane can produce a characteristic current or flux pattern that is distinguishable from the current or flux pattern that results when no nanopore is present in the membrane or when a nanopore is not fully functional. In the event that a quality assessment indicates that a nanopore is not properly embedded in a membrane, the steps used to load the nanopore can be repeated.

A polymerase that is properly captured by a nanopore can also produce a characteristic current or flux pattern. For example, a bias voltage that is applied to a nanopore that has captured a polymerase via a tether can produce a current or flux pattern that is indicative of interaction between the nanopore aperture and signature bases in a nucleic acid tether. Bias voltages can be applied in opposite directions to determine whether the tether has desired mobility in the nanopore lumen such that signature bases interact with the aperture as predicted. In the event that a quality assessment indicates that a polymerase has not been properly captured by a nanopore, the polymerase can be stripped, for example by application of a strong reverse bias, and steps used to capture the polymerase at the nanopore can be repeated.

In another optional quality assessment routine, a relatively large reverse bias voltage can be applied to the system to determine if the polymerase and tether are removed from the nanopore. Typically, the duplex formed between member 2250' and 2212 will be sufficiently strong to prevent removal of the tether. This quality assessment routine will indicate if this is the case. Similarly, bias voltages can be applied at this stage and the resulting current or flux patterns detected to determine if corking or uncorking occurs as set forth previously herein. In the event that a quality assessment indicates that a polymerase has not been captured by a nanopore with sufficient stability, steps used to capture the polymerase at the nanopore can be repeated.

Several embodiments set forth herein relate to multiplex devices that are loaded with multiple nanopores each of which is desired to attach to a polymerase. Quality assessment steps, such as those set forth above, can be carried out for the multiplex population. If a desired number of functional nanopores have not been formed in a multiplex nanopore apparatus or if the fractional loading is not sufficient, then the apparatus can be treated in bulk to repeat nanopore (or polymerase) loading. Optionally, the nanopores (or polymerases) can be removed prior to repeating the loading step, for example, if faulty nanopores or polymerases are present. For example, repetition of loading (and optionally removal of nanopores or polymerases) can be carried out if the multiplex apparatus is loaded at fewer than 90%, 75%, 50%, 30% or fewer of the expected sites.

Figure 22C:
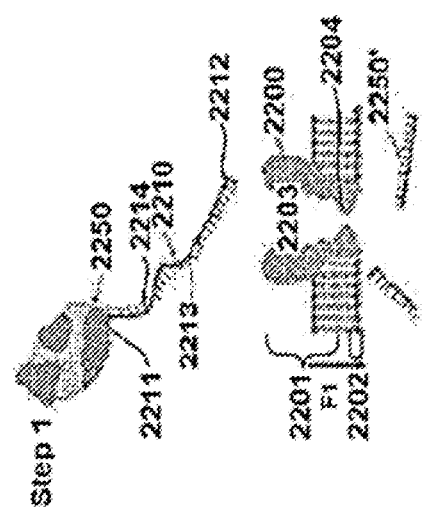

At step 3 illustrated in FIG. 22C, the composition illustrated in FIG. 22B further can be subjected to a reverse directional force F2, e.g., reversal of the voltage relative to that of steps 1 and 2, based upon which polymerase 2250 can come out of contact with first side 2201 of nanopore 2200, and can be contacted with sequencing primer 2280, target single stranded DNA 2270 (target), and a plurality of nucleotides 2230, 2230', each of which includes a corresponding elongated tag 2231, 2231' including a corresponding moiety 2232, 2232' that interacts with the moiety of tether 2213 responsive to polymerase 2250 acting upon that nucleotide 2230 or 230'.

Figure 22D:
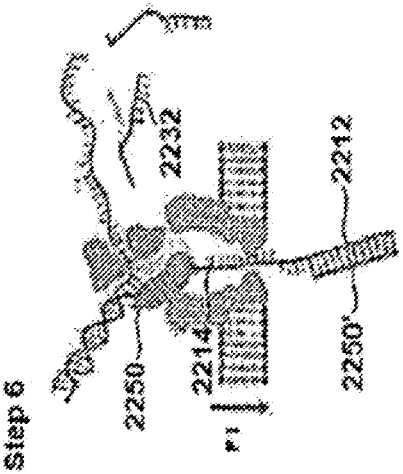

At step 4 illustrated in FIG. 22D, based upon the sequence of target 2270, polymerase 2250 acts upon first nucleotide 2230, based upon which the corresponding moiety 2232 of elongated tag 2231 of nucleotide 2230 interacts with moiety 2214 of tether 2310. For example, polymerase 2250 can preferentially bind first nucleotide 2230 relative to second nucleotide 2230' based upon first nucleotide 2230 being complementary to a next nucleotide in the sequence of target 2270. Additionally, elongated tag 2231 can include a first nucleotide sequence, and moiety 2214 of elongated body 2213 can include a second nucleotide sequence that is complementary to the first nucleotide sequence of elongated tag 2231, such that the first nucleotide sequence and the second nucleotide sequence hybridize to one another. Note that step 4 can be performed under reverse directional force F2, e.g., reversal of the voltage relative to that of steps 1 and 2, so that polymerase 2250 need not be disposed against first side 2201 of nanopore 2200.

Figure 22E:
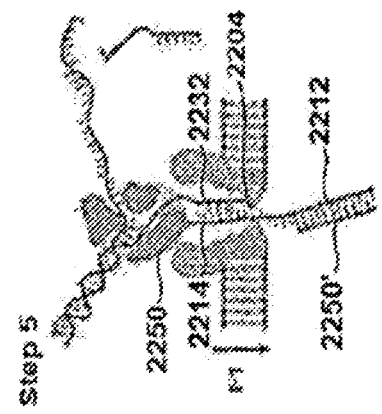

At step 5 illustrated in FIG. 22E, directional force F1 again can be applied, which can cause translocation of tail region 2212 in a direction away from first side 2201 of nanopore 220 and translocation of polymerase 2250 towards second side 2202 of nanopore 2200. For example, a voltage across nanopore 2200 again can be reversed, e.g., using a system such as described herein with reference to FIGS. 2A-2C. However, application of force F1 at step 5 may not necessarily cause polymerase 2250 to come to rest on or adjacent to first side 2201 of nanopore 2200 in a manner such as illustrated in FIG. 22B. Instead, application of force F1 (pulling towards trans) can cause a duplex defined by the interaction (e.g., binding or hybridization) between moiety 2214 and 2232 to come to rest on or adjacent to constriction 2204. Illustratively, the composition can be included in a system that includes measurement circuitry configured to measure a current or flux through constriction 2204. During step 5, the current or flux can be based on first moiety 2232, e.g., based upon the particular sequence of moiety 2232, and first nucleotide 2230 can be identifiable based upon the current or flux. For example, moiety 2232 of first nucleotide 2230 can have a different sequence than does moiety 2232' of second nucleotide 2230', and can bind to a different portion (moiety) of elongated body 2213 of tether 2210. Illustratively, the elongated tags can include any suitable polynucleotide sequence that facilitates distinguishing from one another nucleotides to which such tags are attached, e.g., such as described herein with reference to FIGS. 19A-21D.

Figure 22F:
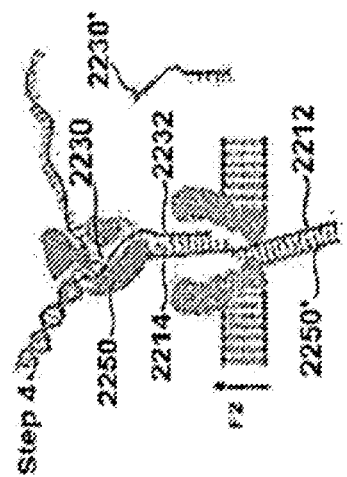

At step 6 illustrated in FIG. 22F, under continued application of directional force F1, after a stochastic time the duplex between moiety 2214 of tether 2210 and moiety 2232 of elongated tag 2231 of nucleotide 2230 dissociates in a manner analogous to that described in Derrington et al., PNAS 2010, cited elsewhere herein. Following such dissociation, directional force F1 can cause polymerase 2250 to come to rest on or adjacent to first side 2201 of nanopore 2200 in a manner such as illustrated in FIG. 22B.

Note that other configurations suitably can be used. For example, alternatively to steps 5 and 6 respectively illustrated in FIGS. 22E and 22F, elongated tag 2231 instead can be sufficiently short that the duplex between moiety 2214 of tether 2210 and moiety 2232 of elongated tag 2231 of nucleotide 2230 does not reach the constriction under application of directional force F1, and instead polymerase 2250 comes to rest on or adjacent to first side 2201 of nanopore 2200 in a manner such as illustrated in FIG. 22B. In such embodiments, the elongated tags 2231, 2231' attached to different nucleotides 2230, 2230' that can be bound by polymerase 2250 can include moieties 2232, 2232' that are different sequences or lengths than one another and thus interact differently with, e.g., hybridize differently with, moiety 2214 of tether 2210 than one another so as to cause different changes in the length of tether 2214 in a manner analogous to that described herein with reference to FIGS. 7A-14. The corresponding nucleotides 2230, 2230' can be identified based on changes in current or flux based on the length of tether 2210 caused by interactions between moiety 2214 and the corresponding moiety 2232, 2232'. Steps 4-6 analogous to those illustrated in FIGS. 22D-22F can be repeated, therefore applying AC-voltage preserving the electrodes. In yet another embodiment, the elongated tag or the elongated body can include a reporter region such as provided elsewhere herein, and the current or flux through aperture 2203 can be based on the reporter region being disposed within the aperture, and nucleotide 2230 can be identifiable based on the current or flux.

Additionally, note that should a dysfunctional polymerase be captured, one can reverse the voltage to a very high voltage so that the capture DNA comes off and a new polymerase can be captured (repeating steps 1-3).

Voltage, current, or optical waveforms can be measured for various states of a tether that passes through a nanopore. The voltage, current, or optical waveforms can be useful for determining results of an analytical method carried out on a nanopore system. For example, the waveforms can be fit to data to increase accuracy of sequencing reads.

FIGS. 24A through 24C shows three potential states for a tether that simulate states experienced in a nucleic acid sequencing method set forth herein. The resulting optical or electrical signals, e.g., voltage waveforms, are shown in FIG. 24D. A protein-DNA tether conjugate is captured in an MspA nanopore and locked into place using a trans-side lock oligonucleotide. An oligonucleotide complementary to a region of the DNA tether is then added to the cis side. Voltage is cycled between 120 mV and −60 mV with approximately a 200 msec period. FIG. 24A shows the conjugate upon the application of forward voltage and the resulting signal is indicated at 102 of FIG. 24D. FIG. 24B shows the conjugate upon the application of the negative voltage and the resulting signal is indicated at 2400 of FIG. 24D. FIG. 24C shows hybridization of an oligonucleotide conjugate that is pulled up to the pore constriction. The duplex signal is seen prior to stripping at 2401 of FIG. 24D.

After stripping, the system returns to the state shown in FIG. 24A while the voltage is still at 120 mV, resulting in signal 2402.

In embodiments such as those described above with reference to FIGS. 20A-22F and 24A-24D, note that the moiety of the elongated tag on the nucleotide is designed to interact with the moiety of the elongated body of the tether. For example, the elongated tag of the nucleotide and the elongated body of tether can include polynucleotides that hybridize (anneal) with one another, e.g., can include DNA. In such embodiments, the elongated tag of the nucleotide can include nucleotide analogs that substantially do not interact with the polymerase. Discrimination between nucleotides can be achieved by using four different moieties that anneal at slightly different locations within the tether sequence. For example, in one illustrative embodiment, the 3-4 nucleotides adjacent to the nascent duplex create maximally different blockade currents or fluxes corresponding to the four different nucleotides. If the duplex is present, the tether can stall adjacent to the constriction, in a manner analogous to that illustrated in FIGS. 18B, 20B, or 21B, for a period of time, e.g., for a few milliseconds, as the duplex is being dissociated (stripped) and a current or flux blockade reading proportional to the 3-4 nucleotides adjacent to the duplex region is recorded. Upon stripping, the AC voltage resets the duplex via its stochastic interaction with the DNA tag on the labeled nucleotide locked into a tertiary closed state complex. The frequency of the AC voltage can be tuned such that for a given AC cycle, there is a relatively low probability of detecting a diffusive event (free nucleotides), and a relatively high probability of detecting an incorporation event (nucleotide bound in a closed tertiary structure). Moreover, the number of AC cycles per nucleotide incorporation event can be on the order of 5× to 100× oversampling to adequately distinguish between incorporation vs. diffusive events. Note that in such a mode of interaction, instead of relying on the intrinsic off-rate of the elongated tag of the nucleotide from the tether, the moieties of the elongated tag and the tether interact with one another and then can be actively stripped apart under AC voltage control, in a manner analogous to that illustrated in FIGS. 18C, 20C, or 21C. The frequency of the AC voltage (i.e. ~100-200 Hz) can tuned to be just long enough to detect binding of "mM concentration" tags, but significantly shorter than the dwell time of incorporation. This active stripping of the duplex can remove dependency on the exponential distribution of the off-rate.

As noted elsewhere herein, a variety of compositions suitably can be included in the elongated tag of the nucleotide or the elongated body of the tether, or both. Such compositions can include DNA, PNA, LNA, RNA, morpholinos, PEG (polyethylene glycol), and the like, and can have any suitable length. An oligonucleotide label including an appropriately modified nucleotide suitably can be linked to such different compositions, for example, using click chemistry compatible precursors are ideal. In one example, the nucleotide is azide-labeled, which would facilitate the use of alkyne-labeled oligonucleotides which are easily synthesized. Exemplary molecules include tetraphosphate-labeled nucleotides such as shown below, in which (A) corresponds to Azide-$P_4O_{13}$-dTTP, and (B) corresponds to Alkyne-$P_4O_{13}$-dTTP. These nucleotides can be modified with any desired tag by using standard click chemistry:

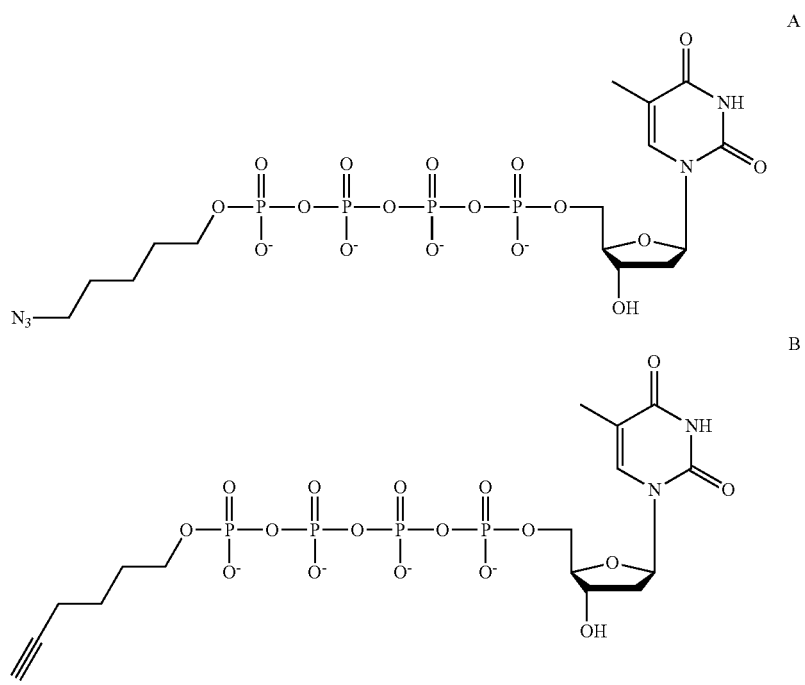

References on making and labeling tetraphosphate nucleotides include the following, the entire contents of each of which are incorporated by reference herein:

Kumar, S., A. Sood, J. Wegener, P. J. Finn, S. Nampalli, J. R. Nelson, A. Sekher, P. Mitsis, J. Macklin and C. W. Fuller, "Terminal phosphate labeled nucleotides: synthesis, applications, and linker effect on incorporation by DNA polymerases," *Nucleosides Nucleotides Nucleic Acids* 24(5-7): 401-408 (2005);

Sood, A., S. Kumar, S. Nampalli, J. R. Nelson, J. Macklin and C. W. Fuller, "Terminal phosphate-labeled nucleotides with improved substrate properties for homogeneous nucleic acid assays," *J Am Chem Soc* 127(8): 2394-2395 (2005);

Kumar, S., C. Tao, M. Chien, B. Hellner, A. Balijepalli, J. W. Robertson, Z. Li, J. J. Russo, J. E. Reiner, J. J. Kasianowicz and J. Ju, "PEG-labeled nucleotides and nanopore detection for single molecule DNA sequencing by synthesis," *Sci Rep* 2: 684 (8 pages) (2012);

Bonnac, L., S. E. Lee, G. T. Giuffredi, L. M. Elphick, A. A. Anderson, E. S. Child, D. J. Mann and V. Gouverneur, "Synthesis and O-phosphorylation of 3,3,4,4-tetrafluoro-aryl-C-nucleoside analogues," *Org Biomol Chem* 8(6): 1445-1454 (2010); and Lee, S. E., L. M. Elphick, A. A. Anderson, L. Bonnac, E. S. Child, D. J. Mann and V. Gouverneur, "Synthesis and reactivity of novel gamma-phosphate modified ATP analogues," *Bioorg Med Chem Lett* 19(14): 3804-3807 (2009).

As noted elsewhere herein, any suitable detection method or system can be used to detect action of a polymerase upon a nucleotide. For example, fluorescent resonance energy transfer (FRET) is an optical-based detection method that suitably can be used with the present compositions so as to detect action of a polymerase upon a nucleotide. In an exemplary method, the first elongated tag of the first nucleotide further includes a first fluorescent resonant energy transfer (FRET) pair partner, such as a FRET acceptor or donor, and the tether further includes a second FRET pair partner, such as a FRET donor or acceptor. The first FRET pair partner and the second FRET pair partner can interact with one another responsive to the polymerase acting upon the first nucleotide. The method further can include detecting a first wavelength emitted responsive to the interaction between the first FRET pair partner and the second FRET pair partner. The method further can include providing a second nucleotide including a second elongated tag, the second elongated tag including a third fluorescent resonant energy transfer (FRET) pair partner, e.g., a FRET acceptor or donor. The third FRET pair partner and the second FRET pair partner can interact with one another responsive to the polymerase acting upon the second nucleotide. The method further can include detecting a second wavelength emitted responsive to the interaction between the third FRET pair partner and the second FRET pair partner. The first and second nucleotides are individually distinguishable from one another based on the first and second wavelengths.

As one illustrative example, FIG. 23A schematically illustrates exemplary nucleotides including elongated tags including respective reporter regions and moieties that can bond to an exemplary tether during use in detecting action of a polymerase upon the nucleotides, according to some embodiments of the present invention. Each different type of nucleotide can include a corresponding elongated tag that is attached to its gamma phosphate in a manner analogous to that described above with reference to FIGS. 19B-19C, and that includes a corresponding fluorescent resonant energy transfer (FRET) pair partner, e.g., a FRET acceptor or donor, that can be used as a reporter region. For example, FIG. 23A schematically illustrates exemplary nucleotides 2330 including elongated tags 2331 that include respective FRET acceptor-based reporter regions 2334 and optionally also include moieties 2332 that can bond to an exemplary tether during use in detecting action of a nucleotide by a polymerase disposed adjacent to a nanopore. As shown in FIGS. 23A, A, T, C, and G nucleotides can include respectively elongated tags that include different FRET acceptor-based reporter regions than one another, e.g., as respectively represented by the triangle, diamond, square, and circle. Alternatively, the A, T, C, and G nucleotides can include respectively elongated tags that include different FRET donor-based reporter regions than one another, e.g., as respectively represented by the triangle, diamond, square, and circle. For further information about FRET pair partners, e.g., acceptors and donors, and systems and methods for detecting emissions from interactions between FRET pair partners, see US Patent Publication No. 2014/0087474 to Huber and PCT Patent Publication No. WO 2014/066902 to Huber et al., the entire contents of both of which are incorporated by reference herein.

Optionally, elongated tags 2331 of nucleotides 2330 include moieties that can be suitably selected so as to hybridize to a corresponding moiety of the permanent tether as described in greater detail below with reference to FIGS. 23B-23C. However, optional moieties 2332 of the nucleotides need not be different than one another, and indeed can be the same as one another because the nucleotides can be distinguishable from one another based on differences between their FRET pair partner-based respective reporter regions. In one illustrative embodiment, optional moieties 2315 and 2332 have lengths of 5 to 8 nucleotides. It is expected that the melting temperatures of duplexes between moieties on incorporating nucleotides and moieties on the tether to be significantly more stable than an otherwise identical pair of freely diffusing oligonucleotides because the tether and the incorporating nucleotide are held in relatively fixed position relative to another, causing an effective increase in the local concentrations of the moieties, as discussed above with reference to FIGS. 8A-14. Exemplary oligonucleotides that can be used as moieties are described further herein, e.g., with reference to FIGS. 19A-19C.

In one example, FIG. 23B schematically illustrates a composition including a tether anchored to or adjacent to a nanopore and configured for use in detecting action of a polymerase upon a first nucleotide based on an interaction between the tether and a reporter region of a nucleotide, according to some embodiments of the present invention. The tether can include a FRET pair partner that interacts with the respective FRET pair partners of nucleotides 2331. In one illustrative embodiment, the FRET pair partner of the tether is a FRET donor, and the respective FRET pair partners of the nucleotides are FRET acceptors. In another illustrative embodiment, the FRET pair partner of the tether is a FRET acceptor, and the respective FRET pair partners of the nucleotides are FRET donors.

The nanopore includes biological pore 2305, which can be disposed in a barrier (not specifically illustrated), e.g., a membrane of biological origin such as a lipid bilayer, or a solid state membrane. Biological pore 2305 includes aperture 2303 and constriction 2304. The permanent tether includes head region 2311, elongated body 2313, optional moiety 2315, and FRET pair partner 2316, e.g., donor or acceptor, optionally which can be located at or adjacent to tail region 2312 of the permanent tether. Polymerase 2350 is disposed adjacent to, and in contact with, biological pore 2305, and optionally can be anchored to biological pore 2305 via a physical or chemical linkage (e.g., using click chemistry or a cysteine-maleimide bond). Polymerase 2350 is configured to receive a template polynucleotide 2370, e.g., circular or linear ssDNA to be sequenced, to synthesize a polynucleotide 2360 having a complementary sequence to that of the ssDNA by sequentially receiving, binding, and adding nucleotides to the polynucleotide in accordance with the sequence of the ssDNA. Head region 2311 of the tether can be anchored to any suitable portion of biological pore 2305 that places FRET pair partner 2316 sufficiently close to polymerase 2350 so as to interact with FRET pair partner-based reporter regions 2334 of nucleotides 2330 that can be bound by polymerase 2350. For example, based upon FRET donor 2316 and FRET acceptor-based reporter region 2334 being within approximately 70 Angstroms of one another, a characteristic wavelength of light can be emitted based upon which nucleotide 2330 can be identified. In another example, based upon FRET acceptor 2316 and FRET donor-based reporter region 2334 being within approximately 70 Angstroms of one another, a characteristic wavelength of light can be emitted based upon which nucleotide 2330 can be identified.

For example, FIG. 23C schematically illustrates a detectable interaction between one of the reporter regions of FIG. 23A with the tether of FIG. 23B during action of a polymerase upon a first nucleotide, according to some embodiments of the present invention. As illustrated in FIG. 23C, nucleotide 2330 can include an elongated tag 2331 including first FRET pair partner-based reporter region 2334 that interacts with second FRET pair partner 2316 of the tether. In certain embodiments in which the permanent tether includes moiety 2315 and elongated tag 2331 of the nucleotide includes moiety 2332, moieties 2315 and 2332 can interact with one another.

In some embodiments, first FRET pair partner-based reporter region 2334 and second FRET pair partner 2316 interact with one another responsive to polymerase 2350 acting upon nucleotide 2330, and a first wavelength emitted responsive to the interaction between first FRET partner-based reporter region 2334 and second FRET pair partner 2316 can be detectable. For example, as illustrated in FIG. 23C, an exemplary nucleotide 2330, e.g., T, includes an elongated tag 2331 including FRET acceptor-based reporter region 2334 and optionally oligonucleotide moiety 2332 that can be attached to the gamma phosphate of the nucleotide 2330, e.g., via a delta phosphate linkage. Interaction between FRET acceptor-based reporter region 2334 and FRET donor 2316 of the tether causes light of a selected wavelength "$\lambda_T$" to be emitted. A suitable measurement circuit such as described further above with reference to FIG. 2A can be used to detect wavelength "$\lambda_T$," based upon which nucleotide 2330 can be identified, e.g., as T. Optionally, in one illustrative embodiment, moiety 2315 includes a first oligonucleotide, and moiety 2332 includes a second oligonucleotide that is complementary to the first oligonucleotide, e.g., that hybridizes to the first oligonucleotide. The hybridization of the second oligonucleotide to the first oligonucleotide can cause FRET acceptor-based reporter region 2334 to become disposed adjacent to FRET donor 2316. The action of polymerase 2350 upon nucleotide 2330 can be individually detected based on emission of light having wavelength "$\lambda_T$" responsive to the interaction between FRET acceptor-based reporter region 2334 and FRET donor 2316. It should be understood that region 2334 instead can be based on a FRET donor and region 2316 instead can be based on a FRET acceptor.

Additionally, as illustrated in FIG. 23A, each different type of nucleotide can include a corresponding elongated tag 2331 that includes a corresponding FRET pair partner-based reporter region 2334. Each such reporter region 2334 can be configured such that interaction between that reporter region and FRET pair partner 2316 emits a corresponding wavelength based upon which the corresponding nucleotide can be identified. For example, interaction of the FRET pair partner-based reporter region 2334 attached to the A nucleotide 2330 (represented with a triangle) with FRET pair partner 2316 can cause emission of light having wavelength "$\lambda_A$"; interaction of the FRET pair partner-based reporter region 2334 attached to the C nucleotide 2330 (represented with a square) with FRET pair partner 2316 can cause emission of light having wavelength "$\lambda_C$"; and interaction of the FRET pair partner-based reporter region 2334 attached to the G nucleotide 2330 (represented with a circle) with FRET pair partner 2316 can cause emission of light having wavelength "$\lambda_G$". Accordingly, the interaction of each such reporter region 2334 with FRET pair partner 2316 can facilitate identification of the corresponding nucleotide. For example, a first FRET pair partner of a first nucleotide and the second FRET pair partner of the tether can interact with one another responsive to the polymerase acting upon the first nucleotide. A first wavelength emitted responsive to the interaction between the first FRET pair partner and the second FRET pair partner can be detected. A second nucleotide can include a second elongated tag including a third FRET pair partner. The third FRET pair partner and the second FRET pair partner of the tether can interact with one another responsive to the polymerase acting upon the second nucleotide. An optical detection system can be configured to detect a second wavelength emitted responsive to the interaction between the third FRET pair partner and the second FRET pair partner. The first and second nucleotides can be individually distinguishable from one another based on the first and second wavelengths.

Elongated tags 2331 of nucleotides 2330 can be cleaved following incorporation of such nucleotides into polynucleotide 2360 in a manner such as described elsewhere herein.

Additionally, note that the roles of FRET donor and acceptor suitably can be interchanged. For example, the permanent tether can include a FRET acceptor, and the elongated tag 2331 of nucleotides 2330 can include FRET donor-based reporter regions 2334. Or, for example, the permanent tether can include a FRET donor, and the elongated tag 2331 of nucleotides 2330 can include FRET acceptor-based reporter regions 2334. Interactions between such FRET pair partners can cause light to be emitted based upon which each corresponding nucleotide can be identified.

Exemplary Modification of Statistical Distribution of Signals

It should be noted that the dissociation of a duplex such as may be formed based on an interaction between a first moiety of an elongated body and a second moiety of an elongated tag responsive to an applied voltage can be characterized as defining a first pathway that is characterized by two or more kinetic constants. Additionally, the action of a polymerase upon a nucleotide, e.g., a conformational change of the polymerase, release of pyrophosphate, or release of the elongated tag of the nucleotide, can be characterized as defining a second pathway that is characterized by two or more kinetic constants. The statistical distribution of signals measured (e.g., optically or electrically measured) during the course of obtaining measurements of the first pathway or the second pathway can be based on the relative values of these kinetic constants corresponding to that pathway. For example, based upon a given kinetic constant for the first pathway or for the second pathway being significantly greater than other kinetic constants for that pathway, the kinetics of that pathway can be dominated by that given kinetic constant, and the resulting statistical distribution of signals can be described by an exponential function. In comparison, two or more of the kinetic constants for the first pathway or for the second pathway can be selected so as to be of the same order of magnitude as one another, or even so as to be substantially the same as one another (e.g., to differ from one another by a factor of five or less, or four or less, or three or less, or two or less), such that the kinetics of that pathway not dominated by either kinetic constant, and the resulting statistical distribution of signals can be described by a gamma function, in which there is substantially no probability of zero-time or very short events that are substantially non-observable. In comparison, with an exponential distribution, there is a high probability of very short or zero-time events that are substantially non-observable.

One or more of the kinetic constants of the first or second pathway can be modified in any suitable manner so as to be of the same order as one or more other of the kinetic constants of that pathway, or even so as to be substantially the same as one or more other of the kinetic constants of that pathway. For example, the polymerase of any of the compositions provided herein can be modified so as to delay release of pyrophosphate responsive to incorporation of a nucleotide into the first nucleotide, thus modifying at least one kinetic constant of the second pathway. For example, in some embodiments, the polymerase can include a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, the polymerase can include a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, the polymerase can include a modified recombinant Φ29 DNA polymerase having at least one amino acid substitution or combination of substitutions selected from the group consisting of E375Y, K512Y, T368F, A484E, A484Y, N387L, T372Q, T372L, K478Y, I370W, F198W, and L381A. For further details regarding exemplary modified polymerases that can delay release of pyrophosphate responsive to incorporation of a nucleotide into a polynucleotide, see U.S. Pat. No. 8,133,672 to Bjornson et al., the entire contents of which are incorporated by reference herein.

Figure 26A:
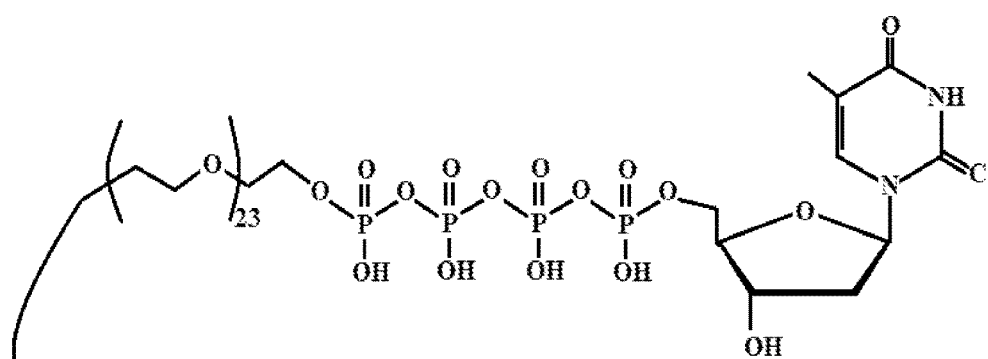
FIGS. 26A-26D illustrate exemplary structures for use in modifying a kinetic constant in a reaction scheme in which a nucleotide is being acted upon by a polymerase, according to some embodiments of the present invention.
Figure 26B:
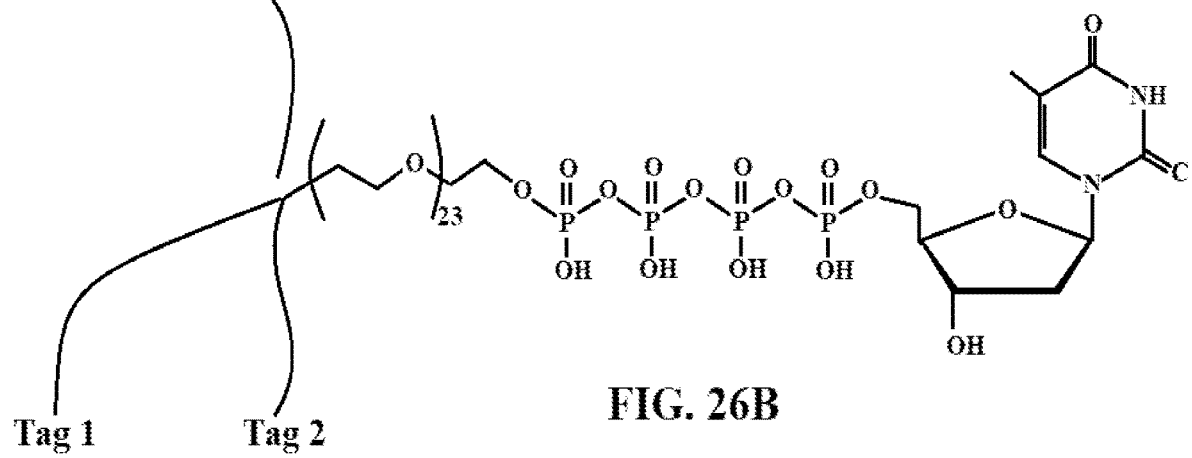
Figure 26C:
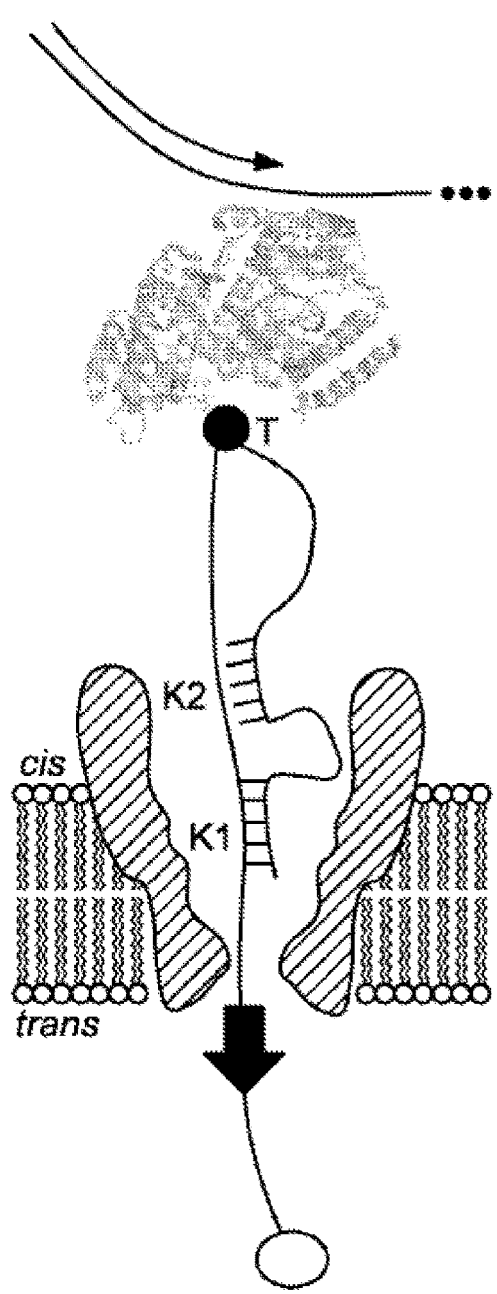
Figure 26D:
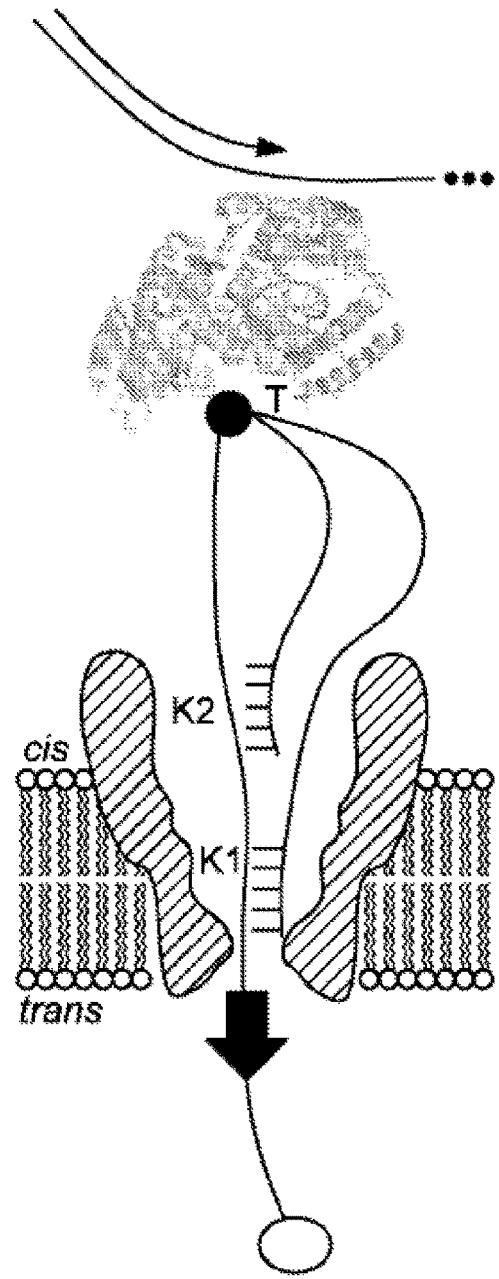

As another example, one or more of the kinetic constants of the first pathway can be modified by including along any of the present tethers a second moiety that hybridizes with the first moiety so as to form a hairpin structure. The first and second moieties of the tether can be configured to dehybridize from one another in a two-step process responsive to a voltage applied across the nanopore. An exemplary tetraphosphate modified nucleotide with a label configured to form a hairpin structure is shown in FIG. 26A. Upon hybridization with the tether, a hairpin is formed as shown in FIG. 26C. This hairpin can be expected to have two stripping rate constants, k1 and k2, that are shown in FIG. 26C. These rate constants can be designed to be of a similar magnitude as one another, so that when added together, they can form a gamma distribution. A second exemplary tetraphosphate modified nucleotide with two labels is shown in FIG. 26B. There are two labels, each configured to interact with the tether, as shown in FIG. 26D. Each label has its own stripping rate constant, k1 and k2 respectively, and the sum of these two rate constants for the entire stripping event can yield a gamma function. Note that any suitable phosphate moieties can be used, e.g., moieties including three, four, or six phosphates.

Illustratively, in some embodiments, a composition includes a nanopore including a first side, a second side, and an aperture extending through the first and second sides; and a permanent tether including a head region, a tail region, and an elongated body disposed therebetween, the head region being anchored to or adjacent to the first side or second side of the nanopore, and the elongated body including a reporter region being movable within the aperture responsive to a first event occurring adjacent to the first side of the nanopore. Exemplary embodiments of such compositions are provided above with reference at least to FIGS. 1C, 1D, 1E-1M, 5A-5B, 6C-6D, 7A-7B, 8A-8B, 9A-9B, 10A-10C, 11A-11D, 12A-12C, 13A-13E, 20A-20E, 22A-22E, 23A-23C, and 24A-24D.

In some embodiments, such a composition further includes a polymerase disposed on the first side, the head region being anchored to the polymerase. The composition further can include a first nucleotide and first and second polynucleotides each in contact with the polymerase, the polymerase configured to add the first nucleotide to the first polynucleotide based on a sequence of the second polynucleotide. The polymerase optionally can be modified so as to delay release of pyrophosphate responsive to addition of the first nucleotide to the first polynucleotide. For example, the polymerase can include a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. For example, the polymerase can include a modified recombinant Φ29 DNA polymerase having at least one amino acid substitution or combination of substitutions selected from the group consisting of: an amino acid substitution at position 484, an amino acid substitution at position 198, and an amino acid substitution at position 381. Or, for example, the polymerase can include a modified recombinant Φ29 DNA polymerase having at least one amino acid substitution or combination of substitutions selected from the group consisting of E375Y, K512Y, T368F, A484E, A484Y, N387L, T372Q, T372L, K478Y, 1370W, F198 W, and L381A.

Illustratively, in some embodiments, a method can include providing a nanopore including a first side, a second side, and an aperture extending through the first and second sides; providing a permanent tether including a head region, a tail region, and an elongated body disposed therebetween, the head region being anchored to or adjacent to the first or second side of the nanopore, the elongated body including a reporter region; and moving the reporter within the aperture responsive to a first event occurring adjacent to the first side of the nanopore. Exemplary embodiments of such methods are provided above with reference at least to FIGS. 3A, 4A-4B, and 15.

In some embodiments, the method further can include disposing a polymerase on the first side, the head region being anchored to the polymerase. The method further can include contacting the polymerase with a first nucleotide and with first and second polynucleotides, the polymerase adding the first nucleotide to the first polynucleotide based on a sequence of the second polynucleotide. The polymerase optionally can be modified so as to delay release of pyrophosphate responsive to addition of the first nucleotide to the first polynucleotide. For example, the polymerase can include a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. For example, the polymerase can include a modified recombinant Φ29 DNA polymerase having at least one amino acid substitution or combination of substitutions selected from the group consisting of: an amino acid substitution at position 484, an amino acid substitution at position 198, and an amino acid substitution at position 381. Or, for example, the polymerase can include a modified recombinant Φ29 DNA polymerase having at least one amino acid substitution or combination of substitutions selected from the group consisting of E375Y, K512Y, T368F, A484E, A484Y, N387L, T372Q, T372L, K478Y, 1370 W, F198W, and L381A.

Illustratively, in some embodiments, a composition can include a nanopore including a first side, a second side, and an aperture extending through the first and second sides; a permanent tether including a head region, a tail region, and an elongated body disposed therebetween, the head region being anchored to or adjacent to the first side or second side of the nanopore, the elongated body including a moiety; a polymerase disposed adjacent to the first side of the nanopore; and a first nucleotide including a first elongated tag, the first elongated tag including a first moiety that interacts with the moiety of the tether responsive to the polymerase acting upon the first nucleotide. Exemplary embodiments of such compositions are provided above with reference at least to FIGS. 7A-7B, 8A-8B, 9A-9B, 10A-10C, 11A-11D, 12A-12C, 13A-13E, 16, 17A-17B, 18A-18E, 19A-19C, 20A-20E, 21A-21E, 22A-22F, 23A-23C, and 24A-24D.

In some embodiments, the composition further includes first and second polynucleotides in contact with the polymerase, the polymerase configured to add the first nucleotide to the first polynucleotide based on a sequence of the second polynucleotide. Optionally, the polymerase can be modified so as to delay release of pyrophosphate responsive to addition of the first nucleotide to the first polynucleotide. For example, the polymerase can include a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. For example, the polymerase can include a modified recombinant Φ29 DNA polymerase having at least one amino acid substitution or combination of substitutions selected from the group consisting of: an amino acid substitution at position 484, an amino acid substitution at position 198, and an amino acid substitution at position 381. Or, for example, the polymerase can include a modified recombinant Φ29 DNA polymerase having at least one amino acid substitution or combination of substitutions selected from the group consisting of E375Y, K512Y, T368F, A484E, A484Y, N387L, T372Q, T372L, K478Y, 1370W, F198W, and L381A.

Additionally, or alternatively, in some embodiments, the first moiety and the moiety of the tether are configured to hybridize with one another so as to form a hairpin structure. A system can include such a composition and a voltage source configured to apply a voltage across the first and second sides. Non-limiting examples of hairpin structures are described above with reference to FIGS. 26A and 26C. Exemplary systems are described above with reference to at least FIGS. 2A and 2C, and exemplary signals that can be produced using such systems are described above with reference to at least FIGS. 2B, 14, 18E, 20E, 21E, and 24D. In some embodiments, the first moiety and the moiety of the tether are configured to dehybridize from one another responsive to the voltage in a two-step process.

Additionally, or alternatively, in some embodiments, the first elongated tag further includes a second moiety, the composition further including a third moiety anchored to or adjacent to the first side or second side of the nanopore, the second moiety and the third moiety interacting responsive to addition of the first nucleotide to the first polynucleotide. A system can include such a composition and a voltage source configured to apply a voltage across the first and second sides. Non-limiting examples of third moieties are described above with reference to FIGS. 26B and 26D. Exemplary systems are described above with reference to at least FIGS. 2A and 2C, and exemplary signals that can be produced using such systems are described above with reference to at least FIGS. 2B, 14, 18E, 20E, 21E, and 24D. In some embodiments, the first moiety and the moiety of the tether are configured to separate from one another responsive to the voltage in a first process, and the second moiety and the third moiety are configured to separate from one another responsive to the voltage in a second process.

Illustratively, in some embodiments, a method includes providing a nanopore including a first side, a second side, and an aperture extending through the first and second sides; providing a permanent tether including a head region, a tail region, and an elongated body disposed therebetween, the head region being anchored to or adjacent to the first side or second side of the nanopore, the elongated body including a moiety; providing a polymerase disposed adjacent to the first side of the nanopore; providing a first nucleotide including a first elongated tag, the first elongated tag including a moiety; acting upon the first nucleotide with the polymerase; and interacting the first moiety with the moiety of the tether responsive to the polymerase acting upon the first nucleotide. Exemplary methods are described above with reference at least to FIGS. 4B and 15.

In some embodiments, the method includes disposing a polymerase on the first side, the head region being anchored to the polymerase. The method further can include contacting the polymerase with a first nucleotide and with first and second polynucleotides, the polymerase adding the first nucleotide to the first polynucleotide based on a sequence of the second polynucleotide. The polymerase optionally can be modified so as to delay release of pyrophosphate responsive to addition of the first nucleotide to the first polynucleotide. For example, the polymerase can include a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. For example, the polymerase can include a modified recombinant Φ29 DNA polymerase having at least one amino acid substitution or combination of substitutions selected from the group consisting of: an amino acid substitution at position 484, an amino acid substitution at position 198, and an amino acid substitution at position 381. For example, the polymerase can include a modified recombinant Φ29 DNA polymerase having at least one amino acid substitution or combination of substitutions selected from the group consisting of E375Y, K512Y, T368F, A484E, A484Y, N387L, T372Q, T372L, K478Y, 1370W, F198W, and L381A.

Additionally, or alternatively, in some embodiments, the first moiety and the moiety of the tether hybridize with one another so as to form a hairpin structure. Some embodiments further include applying a voltage across the first and second sides. The first moiety and the moiety of the tether can dehybridize from one another responsive to the voltage in a two-step process.

Additionally, or alternatively, in some embodiments, the first elongated tag further can include a second moiety, the composition further including a third moiety anchored to or adjacent to the first side or second side of the nanopore, the second moiety and the third moiety interacting responsive to addition of the first nucleotide to the first polynucleotide. Some embodiments further include applying a voltage across the first and second sides. The first moiety and the moiety of the tether can separate from one another responsive to the voltage in a first process, and the second moiety and the third moiety can separate from one another responsive to the voltage in a second process.

Optional Modifications for Sequencing by Synthesis

In embodiments in which a polymerase adds a first nucleotide to a polynucleotide, e.g., to a first polynucleotide that is complementary to a second polynucleotide being sequenced, as in sequencing-by-synthesis (SBS), note that the first nucleotide can be coupled to any suitable reversible terminator that inhibits the polymerase from adding a second nucleotide to the first polynucleotide until a "deblock" step is performed.

For example, the SBS can be performed by disposing any suitable inventive composition in a flow cell, and fluid reagents for each step in the SBS protocol can be delivered to the flow cell. For example, in SBS, extension of a nucleic acid primer along a nucleic acid template (e.g., a target polynucleotide or amplicon thereof) is monitored to determine the sequence of nucleotides in the template. The underlying chemical process can include polymerization (e.g., as catalyzed by a polymerase enzyme). In a particular polymerase-based SBS embodiment, nucleotides are added to a primer (thereby extending the primer) in a template dependent fashion such that detection of the order and type of nucleotides added to the primer can be used to determine the sequence of the template. As provided herein, the nucleotides can include tags that facilitate identification of those nucleotides, for example, using a nanopore composition set forth herein.

Flow cells provide a convenient format for housing an array of polymerase-attached nanopores that are subjected to an SBS technique that involves repeated delivery of reagents in cycles. To initiate a first SBS cycle, one or more labeled nucleotides can be flowed into/through a flow cell that houses an array of polymerase-attached nanopores that have formed a complex with a template nucleic acid that is hybridized to a sequencing primer. Those sites of an array where primer extension causes a labeled nucleotide to be incorporated can be detected using compositions, systems, and methods such as provided herein. Optionally, the nucleotides can further include a reversible terminator that terminates further primer extension once a nucleotide has been added to a primer. For example, the nucleotide that is contacted with a complex can include a reversible terminator moiety that gets added to a primer in such a manner that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection system components that can be readily adapted for use in a system of method of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, the entire contents of each of which are incorporated herein by reference.

In some embodiments, the tag can be provided on the 3' sugar position of the nucleotide so that the tag can be used both to identify the nucleotide and as a reversible terminator to inhibit the polymerase from adding a second nucleotide to the first polynucleotide until a "deblock" step is performed.

In some embodiments, a reversible terminator can be provided on the 3' sugar position of the nucleotide and a tag can be provided on the base, or vice versa, to as to enhance control over, and confidence in, a homopolymer sequencing process. For example, in embodiments in which the reversible terminator is provided on the 3' sugar position and the tag is provided on the base, a first "deblock" process can be performed so as to remove the reversible terminator and expose the 3' OH, and a second "deblock" process can be performed so as to remove the tag, with any suitable order of the first and second "deblock" processes. For example, the tag first can be removed, based upon which the signal associated with such a tag no longer may be observed, and the presence of the 3' reversible terminator can inhibit the polymerase from adding a second nucleotide to the first polynucleotide until a second "deblock" step is performed for that reversible terminator. In such a manner, based upon the same signal being observed in a second cycle prior to the second deblock step being performed, the absence of signal between the first and second cycles can confirm that the tag was released at the end of the first cycle and added back during the second cycle, thus increasing confidence that the polynucleotide is a a homopolymer. Or, for example, in embodiments in which the reversible terminator is provided on the base and the tag is provided on the 3' sugar position, the polymerase can remove the tag upon incorporation of the nucleotide into a polynucleotide without the need for a separate chemistry step.

Additionally, note that a deblocking agent can be delivered from the trans side (the side of the barrier opposite that of the nucleotides) in a manner that can be controlled by the selective application of a voltage gradient across the nanopore. The deblocking agent can be expected to have an effective concentration substantially only in the vicinity of the first side of the nanopore, and can be expected to have a low concentration as it diffuses out into the bulk where the pool of nucleotides resides so as not to deblock the nucleotides in the bulk. Alternatively, an agent that is configured to neutralize or deactivate the deblocking agent can be present on the first side of the nanopore. This agent can be locally depleted by transport of the deblocking agent across the nanopore, and can be expected to neutralize or deactivate the deblocking agent further away from the nanopore, e.g., in the bulk of the first side, so as to inhibit deblocking of the nucleotides in the bulk.

In particular embodiments a 3' OH blocking group can include one or more moieties such as disclosed in PCT Publication No. WO 2004/018497, the entire contents of which are incorporated herein by reference. For example, the blocking group can include azidomethyl ($CH_2N_3$) or allyl, and the deblocking agent can include a strong reducing agent, such as THP (tris(hydroxypropyl)phosphine). Further examples of useful blocking groups are described, for example, in the following references, the entire contents of each of which is incorporated by reference in its entirety: U.S. Pat. Nos. 7,816,503, 7,771,903, U.S. Patent Publication No. 2008/0108082, U.S. Patent Publication No. 2010/00317531, PCT Publication No. WO 91/06678, PCT Publication No. WO 04/018497, and PCT Publication No. WO 07/123744.

Illustratively, in some embodiments, a composition includes a nanopore including a first side, a second side, and an aperture extending through the first and second sides; and a permanent tether including a head region, a tail region, and an elongated body disposed therebetween, the head region being anchored to or adjacent to the first side or second side of the nanopore, and the elongated body including a reporter region being movable within the aperture responsive to a first event occurring adjacent to the first side of the nanopore. The composition further can include a polymerase disposed on the first side, the head region being anchored to the polymerase. The composition further can include a first nucleotide and first and second polynucleotides each in contact with the polymerase, the polymerase configured to add the first nucleotide to the first polynucleotide based on a sequence of the second polynucleotide. Exemplary embodiments of such compositions are provided above with reference to at least FIGS. 1F, 1M, 5A-5B, 6C-6D, 7A-7B, 8A-8B, 9A-9B, 10A-10C, 11A-11D, 12A-12C, 13A-13E, 20A-20E, 22A-22E, 23A-23C, and 24A-24D.

Optionally, the first nucleotide is coupled to a reversible terminator that inhibits the polymerase from adding a second nucleotide to the first polynucleotide, optionally in a manner that is controlled by the selective application of a voltage gradient across the nanopore. The deblocking agent can be expected to have an effective concentration substantially only in the vicinity of the first side of the nanopore, and can be expected to have a low concentration as it diffuses out into the bulk where the pool of nucleotides resides. Alternatively, an agent that is configured to neutralize or deactivate the deblocking agent can be present on the first side of the nanopore. This agent can be locally depleted by transport of the deblocking agent across the nanopore, and can be expected to neutralize or deactivate the deblocking agent further away from the nanopore, e.g., in the bulk of the first side, so as to inhibit deblocking of the nucleotides in the bulk. In some embodiments, the reversible terminator is cleavable by exposure to light or heat. For example, the reversible terminator can be cleavable by absorption of heat from the light. In one non-limiting example, the reversible terminator can include a gold nanoparticle that is sufficiently heated by the light as to cleave the reversible terminator. Or, for example, the reversible terminator can be cleavable by a photochemical reaction induced by the light. Or, for example, the reversible terminator can be cleavable by reaction with a chemical agent. The composition further can include a source of the chemical agent. In some embodiments, the reversible terminator is disposed on the first side, and the source of the chemical agent is disposed on the second side such that the chemical agent moves from the second side to the first side through the aperture. In one non-limiting example, the reversible terminator includes azidomethyl ($CH_2N_3$), and the chemical agent includes THP.

In some embodiments, an apparatus includes any of such compositions, the composition is present in a flow cell, and the flow cell is configured to replenish reagents that are in contact with the polymerase.

Illustratively, in some embodiments, a method can include providing a nanopore including a first side, a second side, and an aperture extending through the first and second sides; providing a permanent tether including a head region, a tail region, and an elongated body disposed therebetween, the head region being anchored to or adjacent to the first or second side of the nanopore, the elongated body including a reporter region; and moving the reporter within the aperture responsive to a first event occurring adjacent to the first side of the nanopore. A polymerase can be disposed on the first side, the head region being anchored to the polymerase. The method further can include contacting the polymerase with a first nucleotide and with first and second polynucleotides, the polymerase adding the first nucleotide to the first polynucleotide based on a sequence of the second polynucleotide. Exemplary embodiments of such methods are provided above with reference at least to FIG. 15.

Optionally, the first nucleotide can be coupled to a reversible terminator, and the method further can include inhibiting, by the reversible terminator, the polymerase from adding a second nucleotide to the first polynucleotide. In some embodiments, the method can include cleaving the reversible terminator by exposure to light or heat. For example, the method can include cleaving the reversible terminator by absorption of heat from the light. Or, for example, the method can include cleaving the reversible terminator by a photochemical reaction induced by the light. Or, for example, the method can include cleaving the reversible terminator by reaction with a chemical agent. The method optionally can include providing a source of the chemical agent. The method optionally can include flowing fluid past the polymerase to remove the chemical agent. The method optionally can include supplying new reagents to the polymerase by fluid flow. In some embodiments, the reversible terminator is disposed on the first side and the source of the chemical agent is disposed on the second side, and the method includes moving the chemical agent from the second side to the first side through the aperture. In one non-limiting example, the reversible terminator includes azidomethyl ($CH_2N_3$), and the chemical agent includes THP.

Illustratively, in some embodiments, a composition can include a nanopore including a first side, a second side, and an aperture extending through the first and second sides; a permanent tether including a head region, a tail region, and an elongated body disposed therebetween, the head region being anchored to or adjacent to the first side or second side of the nanopore, the elongated body including a moiety; a polymerase disposed adjacent to the first side of the nanopore; and a first nucleotide including a first elongated tag, the first elongated tag including a first moiety that interacts with the moiety of the tether responsive to the polymerase acting upon the first nucleotide. The composition also can include first and second polynucleotides in contact with the polymerase, the polymerase configured to add the first nucleotide to the first polynucleotide based on a sequence of the second polynucleotide. Exemplary embodiments of such compositions are provided above with reference at least to FIGS. 7A-7B, 8A-8B, 9A-9B, 10A-10C, 11A-11D, 12A-12C, 13A-13E, 16, 17A-17B, 18A-18E, 19A-19C, 20A-20E, 21A-21E, 22A-22F, 23A-23C, and 24A-24D.

Optionally, the first elongated tag further can be a moiety of a reversible terminator that inhibits the polymerase from adding a second nucleotide to the first polynucleotide. For example, the reversible terminator can be cleavable to remove the elongated tag from the polymerase-nucleic acid complex. The cleavage can be, for example, by exposure to light or heat. For example, the reversible terminator can be cleavable by absorption of heat from the light. Or, for example, the reversible terminator can be cleavable by a photochemical reaction induced by the light. Or, for example, the reversible terminator can be cleavable by reaction with a chemical agent. In some embodiments, the composition further includes a source of the chemical agent. In some embodiments, the reversible terminator is disposed on the first side, and the source of the chemical agent is disposed on the second side such that the chemical agent moves from the second side to the first side through the aperture. In one non-limiting example, the reversible terminator includes azidomethyl ($CH_2N_3$), and the chemical agent includes THP.

In some embodiments, an apparatus includes any of such compositions, the composition is present in a flow cell, and the flow cell is configured to replenish reagents that are in contact with the polymerase.

Illustratively, in some embodiments, a method includes providing a nanopore including a first side, a second side, and an aperture extending through the first and second sides; providing a permanent tether including a head region, a tail region, and an elongated body disposed therebetween, the head region being anchored to or adjacent to the first side or second side of the nanopore, the elongated body including a moiety; providing a polymerase disposed adjacent to the first side of the nanopore; providing a first nucleotide including a first elongated tag, the first elongated tag including a moiety; acting upon the first nucleotide with the polymerase; and interacting the first moiety with the moiety of the tether responsive to the polymerase acting upon the first nucleotide. The method further can include disposing a polymerase on the first side, the head region being anchored to the polymerase. The method further can include contacting the polymerase with a first nucleotide and with first and second polynucleotides, the polymerase adding the first nucleotide to the first polynucleotide based on a sequence of the second polynucleotide. Exemplary methods are described above with reference at least to FIG. 15.

Optionally, the first elongated tag can include a reversible terminator, and the method further can include inhibiting, by the reversible terminator, the polymerase from adding a second nucleotide to the first polynucleotide. For example, the method can include cleaving the reversible terminator by exposure to light or heat. For example, the method can include cleaving the reversible terminator by absorption of heat from the light. Or, for example, the method can include cleaving the reversible terminator by a photochemical reaction induced by the light. Or, for example, the method can include cleaving the reversible terminator by reaction with a chemical agent. The method also can include providing a source of the chemical agent. In some embodiments, the reversible terminator is disposed on the first side and the source of the chemical agent is disposed on the second side, the method including moving the chemical agent from the second side to the first side through the aperture. In one non-limiting example, the reversible terminator includes azidomethyl ($CH_2N_3$), and the chemical agent includes THP. In some embodiments, the method includes flowing fluid past the polymerase to remove the chemical agent. The method also can include supplying new reagents to the polymerase by fluid flow.

Other Alternative Embodiments

While various illustrative embodiments of the invention are described above, it will be apparent to one skilled in the art that various changes and modifications may be made therein without departing from the invention. For example, although certain compositions, systems, and methods are discussed above with reference to detecting events associated with sequencing polynucleotides such as DNA or RNA, it should be understood that the present compositions, systems, and methods suitably can be adapted for use in detecting any type of event, e.g., the motion of a molecule, or a portion thereof, that can be linked to the presence or motion of a reporter region adjacent to a constriction of a nanopore. The appended claims are intended to cover all such changes and modifications that fall within the true spirit and scope of the invention.

What is claimed is:

1. A system comprising:
a measurement device; and
a chamber comprising a barrier, a first liquid medium, and a second liquid medium separated from the first liquid medium by the barrier wherein the barrier has a first side, and a second side and comprise at least one nanopore comprising a first opening on the first side of the barrier and in contact with the first liquid medium, a second opening on the second side and in contact with the second liquid medium, and an aperture extending through the first side and the second side wherein the first liquid medium includes a polymerase enzyme comprising
a permanent tether comprising a head, a tail, and an elongated body disposed between the head and the tail, wherein the head is anchored to the polymerase enzyme and the elongated body comprises a first reporter movable within the aperture wherein the permanent tether is retained in a corresponding nanopore of the at least one nanopore by a capture moiety attached to the tail of the permanent tether; and wherein
the measurement device is configured to measure a current through the aperture, a flux through the aperture or an optical signal provided by the first reporter.

2. The system of claim 1, wherein the barrier prevents molecules from passing from the first side to the second side or from the second side to the first side.

3. The system of claim 2, wherein the barrier is a biological barrier.

4. The system of claim 3, wherein the biological barrier is a lipid membrane.

5. The system of claim 1, wherein the barrier is a solid-state membrane.

6. The system of claim 5, wherein the solid-state membrane comprises silicon or graphene.

7. The system of claim 1, wherein the at least one nanopore is one or more biological nanopores or one or more solid state nanopores.

8. The system of claim 1, wherein each nanopore of the at least one nanopore comprises a constriction disposed between a corresponding first opening and a corresponding second opening.

9. The system of claim 1, wherein the tail comprises a first nucleic acid sequence.

10. The system of claim 9, wherein the capture moiety comprises a second nucleic acid sequence complementary to the first nucleic acid sequence.

11. The system of claim 1, wherein the elongated body comprises a synthetic polymer.

12. The system of claim 1, wherein the elongated body comprises a second reporter.

13. The system of claim 11, wherein the synthetic polymer is selected from the group consisting of a polynucleotide, a polypeptide, a polysaccharide, a polynucleotide analog, and a polypeptide analog or a combination thereof.

14. The system of claim 12, wherein the first reporter and the second reporter enables a measurement of a translation, a rotational or a conformational movement of the elongated body.

15. The system of claim 1, wherein the current, the flux or the optical signal is based on an electrical blockade or on a flux blockade characteristic of the reporter and on a predetermined location of the first reporter.

* * * * *

SEQUENCE LISTING

```
<160> NUMBER OF SEQ ID NOS: 7

<210> SEQ ID NO 1
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 1
tttttttttt tttttttttt tttttttttt tttttttttt tt                          42

<210> SEQ ID NO 2
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 2
aaaaaaaaaa aaaaaaaaaa aaaaaaaaaa aaaaaaaaaa aa                          42

<210> SEQ ID NO 3
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 3
gggggggggg gggggggggg gggggggggg gggggggggg gg                          42

<210> SEQ ID NO 4
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 4
cccccccccc cccccccccc cccccccccc cccccccccc cc                          42

<210> SEQ ID NO 5
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 12
<223> OTHER INFORMATION: Any abasic amino acid

<400> SEQUENCE: 5
tttttttttt tnttttttta tatggg                                            26

<210> SEQ ID NO 6
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 6
tttttttttt                                                              10
```

```
<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
cccatttttt tttttatggg                                              20
```

UNITED STATES PATENT AND TRADEMARK OFFICE
CERTIFICATE OF CORRECTION

| | | |
|---|---|---|
| PATENT NO. | : 12,365,939 B2 | Page 1 of 1 |
| APPLICATION NO. | : 17/675264 | |
| DATED | : July 22, 2025 | |
| INVENTOR(S) | : Jeffrey G. Mandell, Kevin L. Gunderson and Jens H. Gundlach | |

It is certified that error appears in the above-identified patent and that said Letters Patent is hereby corrected as shown below:

In the Specification

In Column 1, Line 9, delete "continuation" and insert --divisional--.

Signed and Sealed this
Twenty-third Day of December, 2025

John A. Squires
*Director of the United States Patent and Trademark Office*